(12) United States Patent
Romero

(10) Patent No.: US 10,919,900 B2
(45) Date of Patent: Feb. 16, 2021

(54) ARYL HYDROCARBON RECEPTOR ANTAGONISTS AND USES THEREOF

(71) Applicant: Magenta Therapeutics Inc., Cambridge, MA (US)

(72) Inventor: Arthur Glenn Romero, Chesterfield, MO (US)

(73) Assignee: Magenta Therapeutics Inc., Cambridge, MA (US)

( * ) Notice: Subject to any disclaimer, the term of this patent is extended or adjusted under 35 U.S.C. 154(b) by 0 days.

(21) Appl. No.: 16/570,045

(22) Filed: Sep. 13, 2019

(65) Prior Publication Data

US 2020/0123161 A1   Apr. 23, 2020

Related U.S. Application Data

(63) Continuation of application No. 15/951,585, filed on Apr. 12, 2018, now Pat. No. 10,457,683.

(60) Provisional application No. 62/625,896, filed on Feb. 2, 2018, provisional application No. 62/613,382, filed on Jan. 3, 2018, provisional application No. 62/484,692, filed on Apr. 12, 2017.

(51) Int. Cl.
| | |
|---|---|
| C07D 487/04 | (2006.01) |
| A61K 35/28 | (2015.01) |
| C07D 519/00 | (2006.01) |
| C07D 471/04 | (2006.01) |
| C12N 5/0789 | (2010.01) |
| A61K 35/12 | (2015.01) |

(52) U.S. Cl.
CPC .......... C07D 487/04 (2013.01); A61K 35/28 (2013.01); C07D 471/04 (2013.01); C07D 519/00 (2013.01); C12N 5/0647 (2013.01); A61K 2035/124 (2013.01); C12N 2501/999 (2013.01); Y02A 50/401 (2018.01); Y02A 50/414 (2018.01)

(58) Field of Classification Search
CPC .............................. C07D 487/04; A61K 35/28
See application file for complete search history.

(56) References Cited

U.S. PATENT DOCUMENTS

| | | | |
|---|---|---|---|
| 4,873,191 A | 10/1989 | Wagner et al. |
| 5,233,044 A | 8/1993 | Hudson |
| 5,512,421 A | 4/1996 | Burns et al. |
| 5,547,892 A | 8/1996 | Wuu et al. |
| 5,670,354 A | 9/1997 | Burns et al. |
| 5,801,030 A | 9/1998 | McVey et al. |
| 6,028,172 A | 2/2000 | Stepaniuk et al. |
| 6,080,398 A | 6/2000 | Pelus et al. |
| 6,447,766 B1 | 9/2002 | Pelus et al. |
| 7,442,386 B2 | 10/2008 | Diamond et al. |
| 8,021,867 B2 | 9/2011 | Smith et al. |
| 8,445,251 B2 | 5/2013 | Smith et al. |
| 8,518,701 B2 | 8/2013 | Fahrenkrug et al. |
| 8,546,350 B2 | 10/2013 | Bennett et al. |
| 8,673,905 B2 | 3/2014 | Luk et al. |
| 8,697,359 B1 | 4/2014 | Zhang |
| 9,169,287 B2 | 10/2015 | Simon et al. |
| 9,206,222 B2 | 12/2015 | Caussil-Amblard et al. |
| 9,388,212 B2 | 7/2016 | Barlos |
| 9,580,426 B2 | 2/2017 | Boitano et al. |
| 10,196,369 B2 | 2/2019 | Pinkerton et al. |
| 10,351,572 B2 | 7/2019 | Romero et al. |
| 10,457,683 B2 | 10/2019 | Romero et al. |
| 2005/0112764 A1 | 5/2005 | Ivics et al. |
| 2006/0035829 A1 | 2/2006 | Bridger et al. |
| 2010/0227406 A1 | 9/2010 | Andreou et al. |
| 2010/0251395 A1 | 9/2010 | Harris et al. |
| 2010/0317114 A1 | 12/2010 | Poppe et al. |
| 2012/0222143 A1 | 8/2012 | Fahrenkrug et al. |
| 2014/0187548 A1 | 7/2014 | Koppitz et al. |
| 2019/0314407 A1 | 10/2019 | Boitano et al. |
| 2019/0343885 A1 | 11/2019 | Boitano et al. |

FOREIGN PATENT DOCUMENTS

| | | |
|---|---|---|
| EP | 2 460 805 A1 | 6/2012 |
| EP | 2 651 944 A1 | 10/2013 |
| WO | WO 94/11026 A2 | 5/1994 |
| WO | WO 99/050461 A1 | 10/1999 |
| WO | WO 00/056729 A1 | 9/2000 |
| WO | WO 01/085196 A2 | 11/2001 |
| WO | WO 01/094420 A1 | 12/2001 |

(Continued)

OTHER PUBLICATIONS

Araki, H. et al., "Expansion of human umbilical cord blood SCID-repopulating cells using chromatin-modifying agents," Experimental Hematology, 34:140-149 (2006).
Bachleda, P. et al., "Examination of Zolpidem effects on AhR- and PXR-dependent expression of drug-metabolizing cytochromes P450 in primary cultures of human hepatocytes," Toxicology Letters, 191(1):74-78 (2009).
Bailey, N. et al., "Orally active C-6 heteroaryl- and heterocyclyl-substituted imidazo[1,2-a]pyridine acid pump antagonists (APAs)," Bioorganic & Medicinal Chemistry Letters, 19:3602-3606 (2009).
Boitano, A. E. et al., "Aryl Hydrocarbon Receptor Antagonists Promote the Expansion of Human Hematopoietic Stem Cells," Science, 329(5997):1345-1348 (2010).

(Continued)

*Primary Examiner* — Golam M Shameem
(74) *Attorney, Agent, or Firm* — Cooley LLP; Heidi A. Erlacher; Xixi Sun

(57) ABSTRACT

The disclosure relates to aryl hydrocarbon receptor antagonists, such as substituted imidazopyridines and imidazopyrazines, as well as methods of expanding hematopoietic stem cells by culturing hematopoietic stem or progenitor cells in the presence of these agents. Additionally, the disclosure provides methods of treating various pathologies in a patient by administration of expanded hematopoietic stem cells. The disclosure further provides methods of synthesizing aryl hydrocarbon receptor antagonists, such as substituted imidazopyridines and imidazopyrazines, as well as kits containing aryl hydrocarbon receptor antagonists that can be used for the expansion of hematopoietic stem cells.

16 Claims, 15 Drawing Sheets

(56) References Cited

FOREIGN PATENT DOCUMENTS

| WO | WO 03/090512 A2 | 11/2003 |
|----|----|----|
| WO | WO 2007/095594 A2 | 8/2007 |
| WO | WO 2010/059401 A2 | 5/2010 |
| WO | WO 2010/085699 A2 | 7/2010 |
| WO | WO 2012/080234 A1 | 6/2012 |
| WO | WO 2012/080236 A1 | 6/2012 |
| WO | WO 2013/086436 A1 | 6/2013 |
| WO | WO 2015/057976 A1 | 4/2015 |
| WO | WO 2016/164502 A1 | 10/2016 |
| WO | WO 2017/161001 A1 | 9/2017 |
| WO | WO 2018/191476 A1 | 10/2018 |

OTHER PUBLICATIONS

Boitano, A. E. et al., "Aryl Hydrocarbon Receptor Antagonists Promote the Expansion of Human Hematopoietic Stem Cells," Science, 329(5997):1345-1348 (2010), 64 pages; Supporting Online Materials.

Brunstein, C. G. et al., "Allogeneic hematopoietic cell transplantation for hematologic malignancy: relative risks and benefits of double umbilical cord blood," Blood, 116(22):4693-4699 (2010).

Chaurasia, P. et al., "Epigenetic reprogramming induces the expansion of cord blood stem cells," J Clin Invest., 124(6):2378-2395 (2014); doi:10.1172/JCI70313.

Chu, G. et al., "Electroporation for the efficient transfection of mammalian cells with DNA," Nucleic Acids Research, 15(3):1311-1326 (1987).

Database Accession No. 1349345-91-0, Database Registry [Online], Dec. 6, 2011, 1 page.

Dennig, J., "Gene Transfer in Eukaryotic Cells Using Activated Dendrimers," Top Curr Chem, 228:227-236 (2003).

Distler, J. H. W. et al., "Nucleofection: a new, highly efficient transfection method for primary human keratinocytes," Experimental Dermatology, 14:315-320 (2005).

Eapen, M. et al., "Effect of graft source on unrelated donor haemopoietic stem-cell transplantation in adults with acute leukaemia: a retrospective analysis," Lancet Oncol, 11:653-60 (2010); doi:10.1016/S1470-2045(10)70127-3.

Eapen, M. et al., "Umbilical Cord Blood Transplantation in Children with Acute Leukemia: Impact of Conditioning on Transplantation Outcomes," Biol Blood Marrow Transplant, 23:1714-1721 (2017).

Fares, I. et al., "Pyrimidoindole derivatives are agonists of human hematopoietic stem cell self-renewal," Science, 345(6203):1509-1512 (2014); doi: 10.1126/science.1256337.

Gulick, T., "Transfection Using DEAE-Dextran," Current Protocols in Molecular Biology, 9.2.1-9.2.10, S40-S63 (1997).

Hoban, M. D. et al., "Aryl Hydrocarbon Receptor Antagonists Expand Adult Hematopoietic Stem Cells from Mobilized Peripheral Blood and Bone Marrow and Increase the Dose of CRISPR/Cas9 Gene-Edited NSG-Repopulating Cells," Blood, 130:3341 (2017), 5 pages.

Hwang, W. Y. et al., "Efficient genome editing in zebrafish using a CRISPR-Cas system," Nature Biotechnology, 31(3):227-229 (2013).

Jesberger, M. et al., "Applications of Lawesson's Reagent in Organic and Organometallic Syntheses," Synthesis, 13:1929-1958 (2003).

Joung, J. K. & Sander, J. D., "TALENs: a widely applicable technology for targeted genome editing," Nature Reviews Molecular Cell Biology, 14:49-55 (2013).

Lavitrano, M. et al., "Efficient production by sperm-mediated gene transfer of human decay accelerating factor (hDAF) transgenic pigs for xenotransplantation," PNAS, 99(22):14230-14235 (2002).

Lavitrano, M. et al., "Sperm-mediated gene transfer," Reproduction, Fertility and Development, 18:19-23 (2006).

Li, T. W. & Jones, P. A., "Methylation changes in early embryonic genes in cancer," Abstract, In: Proceedings of the 18th Annual Meeting of the American Society of Gene and Cell Therapy; May 13, 2015 Abstract No. 22.

Lo, C. W., "Transformation by Iontophoretic Microinjection of DNA: Multiple Integrations Without Tandem Insertions," Molecular and Cell Biology, 3(10):1803-1814 (1983).

Mandal, P. K, "Efficient Ablation of Genes in Human Hematopoietic Stem and Effector Cells using CRISPR/Cas9," Cell Stem Cell, 15(5):643-652 (2014).

Psatha, N. et al., "Optimizing autologous cell grafts to improve stem cell gene therapy," Experimental Hematology, 44(7):528-539 (2016).

Quinn, T. P. et al., "Genetic Modification of Target Cells by Direct Delivery of Active Protein," Abstract, Molecular Therapy, 23:S50-S51 (2015).

Rhodes, K. et al., "Cellular Laserfection," Methods in Cell Biology, 82:309-333 (2007).

Shelburne, N. & Bevans, M., Non-Myeloablative Allogeneic Hematopoietic Stem Cell Transplantation, Seminars in Oncology Nursing, 25(2):120-128 (2009).

Sullivan, K. M. et al., "Bone Marrow Transplantation for Non-Malignant Disease," American Society of Hematology, ASH Education Book, 1:319-338 (2000).

Thompson, S. et al., "Germ Line Transmission and Expression of a Corrected HPRT Gene Produced by Gene Targeting in Embryonic Stem Cells," Cell, 56:313-321 (1989).

Urnov, F. D. et al., "Genome editing with engineered zinc finger nucleases," Nature Reviews Genetics, 11:636-646 (2010).

Van Der Putten, H. et al., "Efficient insertion of genes into the mouse germ line via retroviral vectors," Proc. Natl. Acad. Sci. USA, 82:6148-6152 (1985).

Wagner, J. E. et al., "Phase I/II Trial of StemRegenin-1 Expanded Umbilical Cord Blood Hematopoietic Stem Cells Supports Testing as a Stand-Alone Graft," Cell Stem Cell, 18:144-155 (2016).

Wakayama, T. et al., "Full-term development of mice from enucleated oocytes injected with cumulus cell nuclei," Nature, 394:369-374 (1998).

Wang, X. & Rivière, I., "Genetic Engineering and Manufacturing of Hematopoietic Stem Cells," Molecular Therapy, Methods & Clinical Development, 5:96-105 (2017).

Wilmut, I. et al., "Viable offspring derived from fetal and adult mammalian cells," Nature, 385:810-813 (1997).

Wynn, R., "Stem Cell Transplantation in Inherited Metabolic Disorders," Hematology, 2011(1):285-291 (2011).

Yaniv, M., "Enhancing elements for activation of eukaryotic promoters," Nature, 297:17-18 (1982).

Zonari, E. et al., "Efficient Ex Vivo Engineering and Expansion of Highly Purified Human Hematopoietic Stem and Progenitor Cell Populations for Gene Therapy," Stem Cell Reports, 8(4):977-990 (2017).

ARYL HYDROCARBON RECEPTOR ANTAGONISTS AND USES THEREOF

CROSS-REFERENCE TO RELATED APPLICATIONS

This application is a continuation of U.S. application Ser. No. 15/951,585, filed Apr. 12, 2018, which claims priority to, and the benefit of, U.S. Application Nos. 62/484,692, filed Apr. 12, 2017, 62/613,382, filed Jan. 3, 2018, and 62/625,896, filed Feb. 2, 2018, the entire contents of each of which are incorporated herein by reference.

FIELD

The present disclosure relates to aryl hydrocarbon receptor antagonists useful, for example, for ex vivo expansion, enrichment, and maintenance of hematopoietic stem cells, as well as methods of treating various hematopoietic pathologies by administration of the expanded hematopoietic stem cells.

BACKGROUND

While hematopoietic stem cells have significant therapeutic potential, a limitation that has hindered their clinical use has been the difficulty associated with obtaining sufficient numbers of these cells. In particular, hematopoietic stem cells are resistant to maintenance, propagation, and expansion ex vivo. Another challenge to be overcome in order to further develop the use of hematopoietic stem cells (HSCs) as a therapeutic modality is the loss of multi-potency that can occur when these cells are cultured ex vivo.

There is currently a need for compositions and methods for the ex vivo maintenance, propagation, and expansion of HSCs that preserve the multi-potency and hematopoietic functionality of such cells.

SUMMARY

The present disclosure features aryl hydrocarbon receptor antagonists, such as substituted imidazopyridines and imidazopyrazines, as well as methods of expanding hematopoietic stem cells by culturing hematopoietic stem cells in the presence of such agents. Additionally described herein are methods of chemically synthesizing aryl hydrocarbon receptor antagonists, such as substituted imidazopyridines and imidazopyrazines, as well as kits containing aryl hydrocarbon receptor antagonists that can be used for the expansion of hematopoietic stem cells. Additionally, the disclosure provides methods of treating various hematopoietic pathologies in a patient by administration of expanded hematopoietic stem cells. The patient may be suffering, for example, from a hemoglobinopathy or another disease of a cell in the hematopoietic lineage, and is thus in need of hematopoietic stem cell transplantation. As described herein, hematopoietic stem cells are capable of differentiating into a multitude of cell types in the hematopoietic family, and can be administered to a patient in order to populate or reconstitute a blood cell type that is deficient in the patient. The disclosure thus provides methods of treating a variety of hematopoietic conditions, such as sickle cell anemia, thalassemia, Fanconi anemia, Wiskott-Aldrich syndrome, adenosine deaminase deficiency-severe combined immunodeficiency, metachromatic leukodystrophy, Diamond-Blackfan anemia and Schwachman-Diamond syndrome, human immunodeficiency virus infection, and acquired immune deficiency syndrome, among others.

In a first aspect, the disclosure features a compound represented by formula (I)

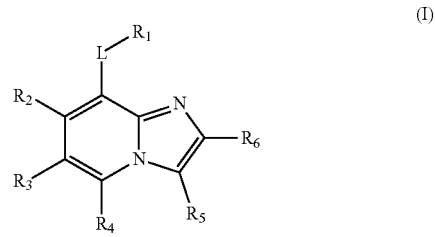

(I)

wherein L is a linker selected from the group consisting of —$NR_{7a}(CR_{8a}R_{8b})_n$—, —$O(CR_{8a}R_{8b})_n$—, —$C(O)(CR_{8a}R_{8b})_n$—, —$C(S)(CR_{8a}R_{8b})_n$—, —$S(O)_{0\text{-}2}(CR_{8a}R_{8b})_n$—, —$(CR_{8a}R_{8b})_n$—, —$NR_{7a}C(O)(CR_{8a}R_{8b})_n$—, —$NR_{7a}C(S)(CR_{8a}R_{8b})_n$—, —$OC(O)(CR_{8a}R_{8b})_n$—, —$OC(S)(CR_{8a}R_{8b})_n$—, —$C(O)NR_{7a}(CR_{8a}R_{8b})_n$—, —$C(S)NR_{7a}(CR_{8a}R_{8b})_n$—, —$C(O)O(CR_{8a}R_{8b})_n$—, —$C(S)O(CR_{8a}R_{8b})_n$—, —$S(O)_2NR_{7a}(CR_{8a}R_{8b})_n$—, —$NR_{7a}S(O)_2(CR_{8a}R_{8b})_n$—, —$NR_{7a}C(O)NR_{7b}(CR_{8a}R_{8b})_n$—, —$NR_{7a}(CR_{8a}R_{8b})_nNR_{7a}$—, —$NR_{7a}(CR_{8a}R_{8b})_nO$—, —$NR_{7a}(CR_{8a}R_{8b})_nS$—, —$O(CR_{8a}R_{8b})_nNR_{7a}$—, —$O(CR_{8a}R_{8b})_nO$—, —$O(CR_{8a}R_{8b})_nS$—, —$S(CR_{8a}R_{8b})_nNR_{7a}$—, —$S(CR_{8a}R_{8b})_nO$—, —$S(CR_{8a}R_{8b})_nS$—, and —$NR_{7a}C(O)O(CR_{8a}R_{8b})_n$—, wherein $R_{7a}$, $R_{7b}$, $R_{8a}$, and $R_{8b}$ are each independently selected from the group consisting of hydrogen and optionally substituted C1-4 alkyl, and each n is independently an integer from 2 to 6;

$R_1$ is selected from the group consisting of —$S(O)_2NR_{9a}R_{9b}$, —$NR_{9a}C(O)R_{9b}$, —$NR_{9a}C(S)R_{9b}$, —$NR_{9a}C(O)NR_{9b}R_{9c}$, —$C(O)R_{9a}$, —$C(S)R_{9a}$, —$S(O)_{0\text{-}2}R_{9a}$, —$C(O)OR_{9a}$, —$C(S)OR_{9a}$, —$C(O)NR_{9a}R_{9b}$, —$C(S)NR_{9a}R_{9b}$, —$NR_{9a}S(O)_2R_{9b}$, —$NR_{9a}C(O)OR_{9b}$, —$OC(O)CR_{9a}R_{9b}R_{9c}$, —$OC(S)CR_{9a}R_{9b}R_{9c}$, optionally substituted aryl, optionally substituted heteroaryl, optionally substituted cycloalkyl, and optionally substituted heterocycloalkyl, wherein $R_{9a}$, $R_{9b}$, and $R_{9c}$ are each independently selected from the group consisting of hydrogen, optionally substituted aryl, optionally substituted heteroaryl, optionally substituted alkyl, optionally substituted heteroalkyl, optionally substituted cycloalkyl, and optionally substituted heterocycloalkyl;

$R_2$ is selected from the group consisting of hydrogen and optionally substituted C1-4 alkyl;

$R_3$ is selected from the group consisting of optionally substituted aryl, optionally substituted heteroaryl, optionally substituted cycloalkyl, and optionally substituted heterocycloalkyl;

$R_4$ is selected from the group consisting of hydrogen and optionally substituted C1-4 alkyl;

$R_5$ is selected from the group consisting of optionally substituted aryl, optionally substituted heteroaryl, optionally substituted alkyl, optionally substituted heteroalkyl, optionally substituted cycloalkyl, and optionally substituted heterocycloalkyl; and $R_6$ is selected from the group consisting of hydrogen, optionally substituted aryl, optionally substituted heteroaryl, optionally substituted alkyl, optionally substituted heteroalkyl, optionally substituted cycloalkyl, and optionally substituted heterocycloalkyl;

or a salt thereof.

As used herein to describe linkers (represented by "L" in formulas (I), (II), and the like), the notation "-(Linker)-"

(wherein "linker" is represented using chemical symbols such as NR$_{7a}$(CR$_{8a}$R$_{8b}$)$_n$, O(CR$_{8a}$R$_{8b}$)$_n$, C(O)(CR$_{8a}$R$_{8b}$)$_n$, C(S)(CR$_{8a}$R$_{8b}$)$_n$, S(O)$_{0-2}$(CR$_{8a}$R$_{8b}$)$_n$, (CR$_{8a}$R$_{8b}$)$_n$, NR$_{7a}$C(O)(CR$_{8a}$R$_{8b}$)$_n$, NR$_{7a}$C(S)(CR$_{8a}$R$_{8b}$)$_n$, OC(O)(CR$_{8a}$R$_{8b}$)$_n$, OC(S)(CR$_{8a}$R$_{8b}$)$_n$, C(O)NR$_{7a}$(CR$_{8a}$R$_{8b}$)$_n$, C(S)NR$_{7a}$(CR$_{8a}$R$_{8b}$)$_n$, C(O)O(CR$_{8a}$R$_{8b}$)$_n$, C(S)O(CR$_{8a}$R$_{8b}$)$_n$, S(O)$_2$NR$_{7a}$(CR$_{8a}$R$_{8b}$)$_n$, NR$_{7a}$S(O)$_2$(CR$_{8a}$R$_{8b}$)$_n$, and NR$_{7a}$C(O)NR$_{7b}$(CR$_{8a}$R$_{8b}$)$_n$) designates that the left hyphen represents a covalent bond to the indicated position on the imidazopyridine or imidazopyrazine ring system, while the right hyphen represents a covalent bond to R$_1$.

In some embodiments, R$_1$ is selected from the group consisting of —S(O)$_2$NR$_{9a}$R$_{9b}$, —NR$_{9a}$C(O)R$_{9b}$, —NR$_{9a}$C(S)R$_{9b}$, —NR$_{9a}$C(O)NR$_{9b}$R$_{9c}$, —C(O)R$_{9a}$, —C(S)R$_{9a}$, —S(O)$_{0-2}$R$_{9a}$, —C(O)OR$_{9a}$, —C(S)OR$_{9a}$, —C(O)NR$_{9a}$R$_{9b}$, —C(S)NR$_{9a}$R$_{9b}$, —NR$_{9a}$S(O)$_2$R$_{9b}$, —NR$_{9a}$C(O)OR$_{9b}$, —OC(O)CR$_{9a}$R$_{9b}$R$_{9c}$, —OC(S)CR$_{9a}$R$_{9b}$R$_{9c}$, phenyl, 1H-pyrrolopyridinyl, 1H-pyrrolopyridinyl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl, and 1H-indazolyl, wherein the phenyl, 1H-pyrrolopyridinyl, 1H-pyrrolopyridinyl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl, or 1H-indazolyl is optionally substituted, for example, with from 1 to 3 substituents independently selected from the group consisting of cyano, hydroxy, C1-4 alkyl, C1-4 alkoxy, halo, halo-substituted-C1-4 alkyl, halo-substituted-C1-4 alkoxy, amino, —O(CH$_2$)$_2$NR$_{10a}$R$_{10b}$, —S(O)$_2$NR$_{10a}$R$_{10b}$, —OS(O)$_2$NR$_{10a}$R$_{10b}$, and —NR$_{10a}$S(O)$_2$R$_{10b}$, wherein R$_{10a}$ and R$_{10b}$ are each independently selected from the group consisting of hydrogen, optionally substituted aryl, optionally substituted heteroaryl, optionally substituted alkyl, optionally substituted heteroalkyl, optionally substituted cycloalkyl, and optionally substituted heterocycloalkyl.

In some embodiments, R$_1$ is selected from the group consisting of —S(O)$_2$NR$_{9a}$R$_{9b}$, —NR$_{9a}$C(O)R$_{9b}$, —NR$_{9a}$C(S)R$_{9b}$, —NR$_{9a}$C(O)NR$_{9b}$R$_{9c}$, —C(O)R$_{9a}$, —C(S)R$_{9a}$, —S(O)$_{0-2}$R$_{9a}$, —C(O)OR$_{9a}$, —C(S)OR$_{9a}$, —C(O)NR$_{9a}$R$_{9b}$, —C(S)NR$_{9a}$R$_{9b}$, —NR$_{9a}$S(O)$_2$R$_{9b}$, —NR$_{9a}$C(O)OR$_{9b}$, —OC(O)CR$_{9a}$R$_{9b}$R$_{9c}$, and —OC(S)CR$_{9a}$R$_{9b}$R$_{9c}$.

In some embodiments, R$_1$ is selected from the group consisting of phenyl, 1H-pyrrolopyridinyl, 1H-pyrrolopyridinyl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl, and 1H-indazolyl, wherein the phenyl, 1H-pyrrolopyridinyl, 1H-pyrrolopyridinyl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl, or 1H-indazolyl is optionally substituted, for example, with from 1 to 3 substituents independently selected from the group consisting of cyano, hydroxy, C1-4 alkyl, C$_{1-4}$ alkoxy, halo, halo-substituted-C1-4 alkyl, halo-substituted-C1-4 alkoxy, amino, —O(CH$_2$)$_2$NR$_{10a}$R$_{10b}$, —S(O)$_2$NR$_{10a}$R$_{10b}$, —OS(O)$_2$NR$_{10a}$R$_{10b}$, and —NR$_{10a}$S(O)$_2$R$_{10b}$.

In some embodiments, R$_1$ is selected from the group consisting of phenyl, 1H-indol-2-yl, 1H-indol-3-yl, thiophen-3-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, and 2-oxo-2,3-dihydro-1H-benzo[d]imidazol-5-yl, wherein the phenyl, 1H-indol-2-yl, 1H-indol-3-yl, thiophen-3-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, or 2-oxo-2,3-dihydro-1H-benzo[d]imidazol-5-yl is optionally substituted, for example, with from 1 to 3 substituents independently selected from the group consisting of cyano, hydroxy, C1-4 alkyl, C1-4 alkoxy, halo, halo-substituted-C1-4 alkyl, halo-substituted-C1-4 alkoxy, amino, —O(CH$_2$)$_2$NR$_{10a}$R$_{10b}$, —S(O)$_2$NR$_{10a}$R$_{10b}$, —OS(O)$_2$NR$_{10a}$R$_{10b}$, and —NR$_{10a}$S(O)$_2$R$_{10b}$.

In some embodiments, R$_1$ is selected from the group consisting of phenyl, phenol-4-yl, 1H-indol-2-yl, 1H-indol-3-yl, thiophen-3-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, and 2-oxo-2,3-dihydro-1H-benzo[d]imidazol-5-yl.

In some embodiments, R$_1$ is selected from the group consisting of:

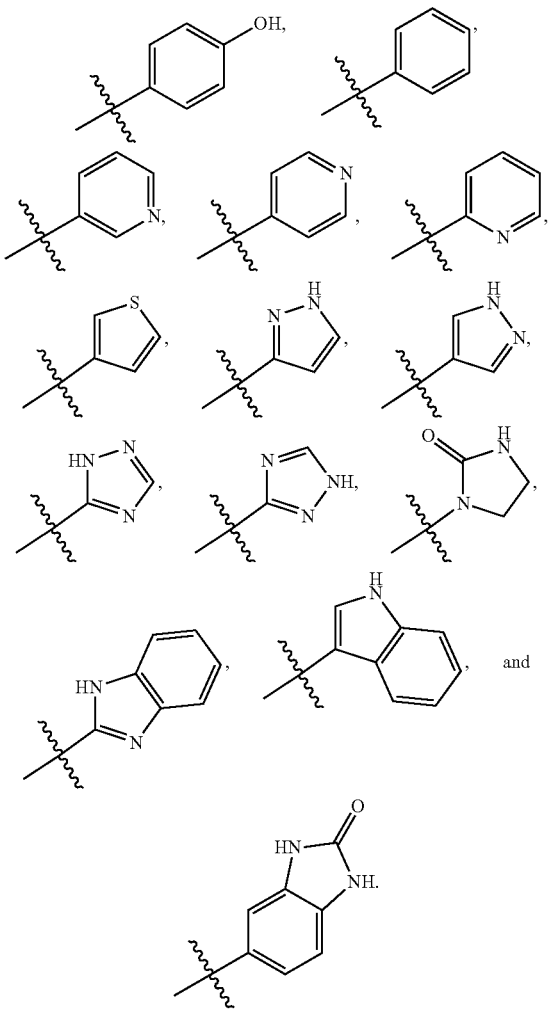

In some embodiments, R$_1$ is selected from the group consisting of:

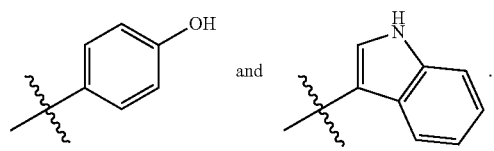 [SMILES: *c1ccc(O)cc1 ; *c1c[nH]c2ccccc12]

In some embodiments, R$_1$ is selected from the group consisting of phenol-4-yl and 1H-indol-3-yl.

In some embodiments, L is selected from the group consisting of —NR$_{7a}$(CR$_{8a}$R$_{8b}$)$_n$— and —O(CR$_{8a}$R$_{8b}$)$_n$—.

In some embodiments, L is selected from the group consisting of —NH(CH$_2$)$_2$— and —O(CH$_2$)$_2$—.

In some embodiments, R$_2$ is hydrogen.

In some embodiments, R$_3$ is selected from the group consisting of optionally substituted aryl and optionally substituted heteroaryl.

In some embodiments, R$_3$ is selected from the group consisting of phenyl, thiophenyl, furanyl, 1H-benzoimidazolyl, quinolinyl, isoquinolinyl, imidazopyridinyl, benzothiophenyl, pyrimidinyl, pyridinyl, 1H-imidazolyl, pyrazinyl, pyridazinyl, 1H-pyrrolyl, and thiazolyl, wherein the phenyl, thiophenyl, furanyl, 1H-benzoimidazolyl, quinolinyl, isoquinolinyl, imidazopyridinyl, benzothiophenyl, pyrimidinyl, pyridinyl, 1H-imidazolyl, pyrazinyl, pyridazinyl, 1H-pyrrolyl, or thiazolyl is optionally substituted, for example, with from 1 to 3 substituents independently selected from the group consisting of cyano, hydroxy, C$_1$-4 alkyl, C1-4 alkenyl, C1-4 alkynyl, C2-6 cycloalkyl, C1-4 alkoxy, halo, halo-substituted-C1-4 alkyl, halo-substituted-C1-4 alkoxy, amino, —C(O)R$_{11a}$, —S(O)$_{0-2}$R$_{11a}$, —C(O)OR$_{11a}$, and —C(O)NR$_{11a}$R$_{11b}$, and wherein R$_{11a}$ and R$_{11b}$ are each independently selected from the group consisting of hydrogen and C$_{1-4}$ alkyl.

In some embodiments, R$_3$ is selected from the group consisting of thiophen-2-yl, thiophen-3-yl, furan-3-yl, 1H-benzo[d]imidazol-1-yl, isoquinolin-4-yl, 1H-imidazo[4,5-b]pyridin-1-yl, imidazo[1,2-a]pyridin-3-yl, benzo[b]thiophen-3-yl, pyrimidin-5-yl, pyridin-2-yl, pyridin-3-yl, pyridin-4-yl, 1H-imidazol-1-yl, pyrazin-2-yl, pyridazin-4-yl, 1H-pyrrol-2-yl and thiazol-5-yl, wherein the thiophen-2-yl, thiophen-3-yl, furan-3-yl, 1H-benzo[d]imidazol-1-yl, isoquinolin-4-yl, 1H-imidazo[4,5-b]pyridin-1-yl, benzo[b]thiophen-3-yl, pyrimidin-5-yl, pyridin-2-yl, pyridin-3-yl, pyridin-4-yl, 1H-imidazol-1-yl, pyrazin-2-yl, pyridazin-4-yl, 1H-pyrrol-2-yl, or thiazol-5-yl is optionally substituted, for example, with from 1 to 3 substituents independently selected from the group consisting of cyano, hydroxy, C$_1$-4 alkyl, C1-4 alkenyl, C1-4 alkynyl, C2-6 cycloalkyl, C1-4 alkoxy, halo, halo-substituted-C1-4 alkyl, halo-substituted-C1-4 alkoxy, amino, —C(O)R$_{11a}$, —S(O)$_{0-2}$R$_{11a}$, —C(O)OR$_{11a}$, and —C(O)NR$_{11a}$R$_{11b}$.

In some embodiments, R$_3$ is selected from the group consisting of thiophen-3-yl, benzo[b]thiophen-3-yl, pyridin-3-yl, pyrimidin-5-yl, 1H-imidazol-1-yl, 1H-benzo[d]imidazol-1-yl, isoquinolin-4-yl, 1H-imidazo[4,5-b]pyridin-1-yl, and imidazo[1,2-a]pyridin-3-yl, wherein the thiophen-3-yl, benzo[b]thiophen-3-yl, pyridin-3-yl, pyrimidin-5-yl, 1H-imidazol-1-yl, 1H-benzo[d]imidazol-1-yl, isoquinolin-4-yl, 1H-imidazo[4,5-b]pyridin-1-yl, or imidazo[1,2-a]pyridin-3-yl is optionally substituted, for example, with from 1 to 3 substituents independently selected from the group consisting of cyano, hydroxy, C1-4 alkyl, C1-4 alkenyl, C1-4 alkynyl, C2-6 cycloalkyl, C1-4 alkoxy, halo, halo-substituted-C1-4 alkyl, halo-substituted-C1-4 alkoxy, amino, —C(O)R$_{11a}$, —S(O)$_{0-2}$R$_{11a}$, —C(O)OR$_{11a}$, and —C(O)NR$_{11a}$R$_{11b}$.

In some embodiments, R$_3$ is selected from the group consisting of optionally substituted:

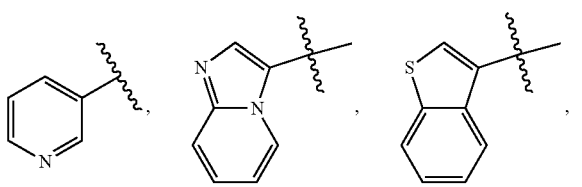

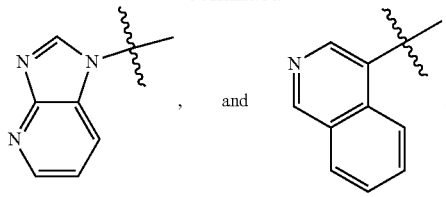

In some embodiments, R$_3$ is pyridin-3-yl, wherein the pyridin-3-yl is optionally substituted at C5, for example, with a substituent selected from the group consisting of C1-4 alkyl, halo, halo-substituted-C1-4 alkyl, C1-4 alkenyl, C1-4 alkynyl, C2-6 cycloalkyl, C1-4 alkoxy, cyano, amino, C(O)R$_{11a}$, —S(O)$_{0-2}$R$_{11a}$, —C(O)OR$_{11a}$, and —C(O)NR$_{11a}$R$_{11b}$.

In some embodiments, the pyridin-3-yl is substituted at C5 with a substituent selected from the group consisting of ethoxycarbonyl, methoxy, cyano, methyl, methylsulfonyl, fluoro, chloro, trifluoromethyl, ethynyl, and cyclopropyl.

In some embodiments, R$_3$ is selected from the group consisting of:

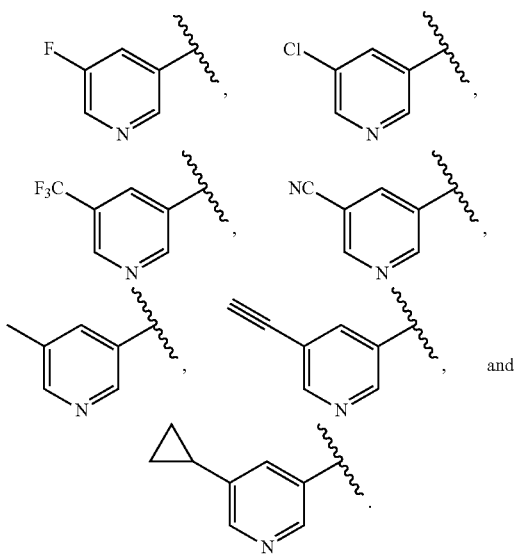

In some embodiments, R$_3$ is imidazo[1,2-a]pyridin-3-yl, wherein the imidazo[1,2-a]pyridin-3-yl is optionally substituted, for example, with a substituent selected from the group consisting of C1-4 alkyl, halo, halo-substituted-C1-4 alkyl, C1-4 alkenyl, C1-4 alkynyl, C2-6 cycloalkyl, C1-4 alkoxy, cyano, amino, C(O)R$_{11a}$, —S(O)$_{0-2}$R$_{11a}$, —C(O)OR$_{11a}$, and —C(O)NR$_{11a}$R$_{11b}$.

In some embodiments, R$_3$ is benzo[b]thiophen-3-yl, wherein the benzo[b]thiophen-3-yl is optionally substituted, for example, with a substituent selected from the group consisting of C1-4 alkyl, halo, halo-substituted-C1-4 alkyl, C1-4 alkenyl, C1-4 alkynyl, C2-6 cycloalkyl, C1-4 alkoxy, cyano, amino, C(O)R$_{11a}$, —S(O)$_{0-2}$R$_{11a}$, —C(O)OR$_{11a}$, and —C(O)NR$_{11a}$R$_{11b}$.

In some embodiments, R$_3$ is 1H-imidazo[4,5-b]pyridin-1-yl, wherein the 1H-imidazo[4,5-b]pyridin-1-yl is optionally substituted, for example, with a substituent selected from the group consisting of C1-4 alkyl, halo, halo-substituted-C1-4 alkyl, C1-4 alkenyl, C1-4 alkynyl, C2-6 cycloalkyl, C1-4 alkoxy, cyano, amino, C(O)R$_{11a}$, —S(O)$_{0-2}$R$_{11a}$, —C(O)OR$_{11a}$, and —C(O)NR$_{11a}$R$_{11b}$.

In some embodiments, R$_3$ is isoquinolin-4-yl, wherein the isoquinolin-4-yl is optionally substituted, for example, with a substituent selected from the group consisting of C1-4 alkyl, halo, halo-substituted-C1-4 alkyl, C1-4 alkenyl, C1-4 alkynyl, C2-6 cycloalkyl, C1-4 alkoxy, cyano, amino, C(O)R$_{11a}$, —S(O)$_{0-2}$R$_{11a}$, —C(O)OR$_{11a}$, and —C(O)NR$_{11a}$R$_{11b}$.

In some embodiments, R$_4$ is hydrogen.

In some embodiments, R$_5$ is selected from the group consisting of C1-10 alkyl, prop-1-en-2-yl, cyclohexyl, cyclopropyl, 2-(2-oxopyrrolidin-1-yl)ethyl, oxetan-2-yl, oxetan-3-yl, benzhydryl, tetrahydro-2H-pyran-2-yl, tetrahydro-2H-pyran-3-yl, phenyl, tetrahydrofuran-3-yl, benzyl, (4-pentylphenyl)(phenyl)methyl, and 1-(1-(2-oxo-6,9,12-trioxa-3-azatetradecan-14-yl)-1H-1,2,3-triazol-4-yl)ethyl, wherein the C1-10 alkyl, prop-1-en-2-yl, cyclohexyl, cyclopropyl, 2-(2-oxopyrrolidin-1-yl)ethyl, oxetan-2-yl, oxetan-3-yl, benzhydryl, tetrahydro-2H-pyran-2-yl, tetrahydro-2H-pyran-3-yl, phenyl, tetrahydrofuran-3-yl, benzyl, (4-pentylphenyl)(phenyl)methyl, or 1-(1-(2-oxo-6,9,12-trioxa-3-azatetradecan-14-yl)-1H-1,2,3-triazol-4-yl)ethyl is optionally substituted, for example, with from 1 to 3 substituents independently selected from the group consisting of hydroxy, C1-4 alkyl, and halo-substituted-C1-4alkyl.

In some embodiments, R$_5$ is selected from the group consisting of isopropyl, methyl, ethyl, prop-1-en-2-yl, isobutyl, cyclohexyl, sec-butyl, (S)-sec-butyl, (R)-sec-butyl, 1-hydroxypropan-2-yl, (S)-1-hydroxypropan-2-yl, (R)-1-hydroxypropan-2-yl, and nonan-2-yl.

In some embodiments, R$_5$ is (S)-1-hydroxypropan-2-yl.
In some embodiments, R$_5$ is (R)-1-hydroxypropan-2-yl
In some embodiments, R$_5$ is (S)-sec-butyl.
In some embodiments, R$_5$ is (R)-sec-butyl.
In some embodiments, R$_5$ is selected from the group consisting of (i), (ii), (iii), (iv), and (v)

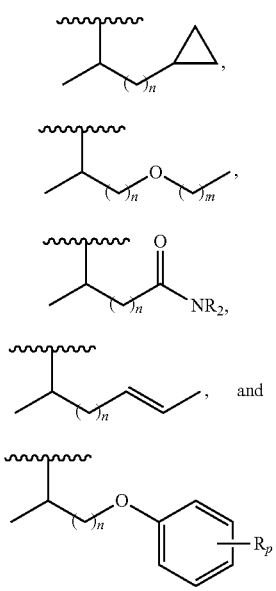

wherein n is an integer from 1 to 6, m is an integer from 0 to 6, p is an integer from 0 to 5, and each R is independently selected from the group consisting of cyano, hydroxy, C$_{1-4}$ alkyl, C1-4 alkenyl, C1-4 alkynyl, C2-6 cycloalkyl, C1-4 alkoxy, halo, halo-substituted-C1-4 alkyl, halo-substituted-C1-4 alkoxy, amino, —C(O)R$_{12a}$, —S(O)$_{0-2}$R$_{12a}$, —C(O)OR$_{12a}$, and —C(O)NR$_{12a}$R$_{12b}$, and wherein R$_{12a}$ and R$_{12b}$ are each independently selected from the group consisting of hydrogen and C$_{1-4}$ alkyl.

In some embodiments, R$_5$ is selected from the group consisting of:

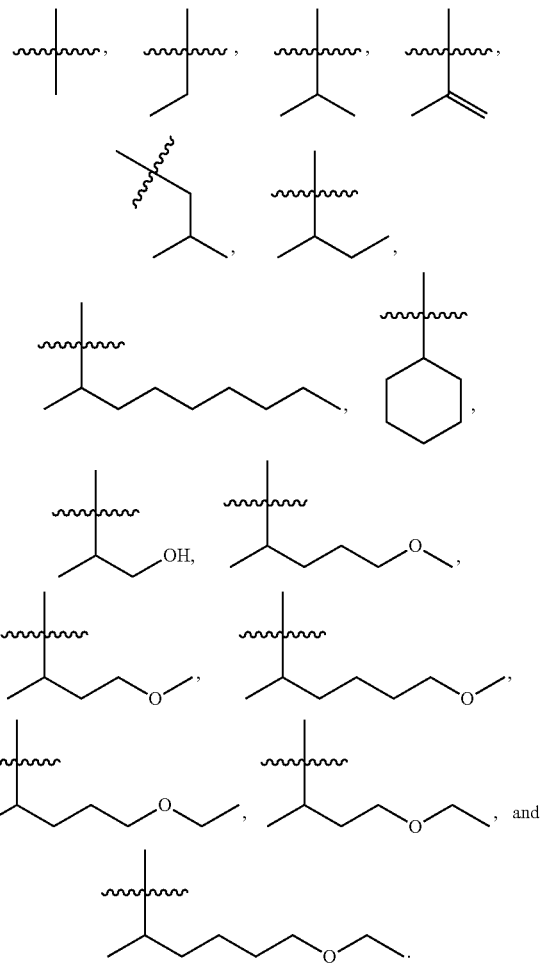

In some embodiments, R$_5$ is (ii).

In some embodiments, R$_5$ is selected from the group consisting of 4-methoxybutan-2-yl, (S)-4-methoxybutan-2-yl, (R)-4-methoxybutan-2-yl, 4-ethoxybutan-2-yl, (S)-4-ethoxybutan-2-yl, (R)-4-ethoxybutan-2-yl, 5-methoxypentan-2-yl, (S)-5-methoxypentan-2-yl, (R)-5-methoxypentan-2-yl, 5-ethoxypentan-2-yl, (S)-5-ethoxypentan-2-yl, (R)-5-ethoxypentan-2-yl, 6-methoxyhexan-2-yl, (S)-6-methoxyhexan-2-yl, (R)-6-methoxyhexan-2-yl, 6-ethoxyhexan-2-yl, (S)-6-ethoxyhexan-2-yl, and (R)-6-ethoxyhexan-2-yl.

In some embodiments, R$_5$ is (S)-4-methoxybutan-2-yl.
In some embodiments, R$_5$ is (R)-4-methoxybutan-2-yl.
In some embodiments, R$_5$ is (S)-5-methoxypentan-2-yl.
In some embodiments, R$_5$ is (R)-5-methoxypentan-2-yl.
In some embodiments, R$_5$ is (S)-4-ethoxybutan-2-yl.
In some embodiments, R$_5$ is (R)-4-ethoxybutan-2-yl.
In some embodiments, R$_6$ is hydrogen.

In some embodiments, the disclosure features a compound represented by formula (I-a)

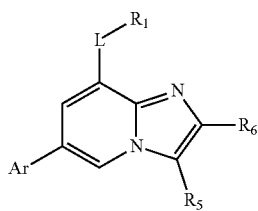

(I-a)

wherein L is a linker selected from the group consisting of —NR$_{7a}$(CR$_{8a}$R$_{8b}$)$_n$—, —O(CR$_{8a}$R$_{8b}$)$_n$—, —C(O)(CR$_{8a}$R$_{8b}$)$_n$—, —C(S)(CR$_{8a}$R$_{8b}$)$_n$—, —S(O)$_{0-2}$(CR$_{8a}$R$_{8b}$)$_n$—, —(CR$_{8a}$R$_{8b}$)$_n$—, —NR$_{7a}$C(O)(CR$_{8a}$R$_{8b}$)$_n$—, —NR$_{7a}$C(S)(CR$_{8a}$R$_{8b}$)$_n$—, —OC(O)(CR$_{8a}$R$_{8b}$)$_n$—, —OC(S)(CR$_{8a}$R$_{8b}$)$_n$—, —C(O)NR$_{7a}$(CR$_{8a}$R$_{8b}$)$_n$—, —C(S)NR$_{7a}$(CR$_{8a}$R$_{8b}$)$_n$—, —C(O)O(CR$_{8a}$R$_{8b}$)$_n$—, —C(S)O(CR$_{8a}$R$_{8b}$)$_n$—, —S(O)$_2$NR$_{7a}$(CR$_{8a}$R$_{8b}$)$_n$—, —NR$_{7a}$S(O)$_2$(CR$_{8a}$R$_{8b}$)$_n$—, —NR$_{7a}$C(O)NR$_{7b}$(CR$_{8a}$R$_{8b}$)$_n$—, and —NR$_{7a}$C(O)O(CR$_{8a}$R$_{8b}$)$_n$—, wherein R$_{7a}$, R$_{7b}$, R$_{8a}$, and R$_{8b}$ are each independently selected from the group consisting of hydrogen and optionally substituted C1-4 alkyl, and each n is independently an integer from 2 to 6;

R$_1$ is selected from the group consisting of —S(O)$_2$NR$_{9a}$R$_{9b}$, —NR$_{9a}$C(O)R$_{9b}$, —NR$_{9a}$C(S)R$_{9b}$, —NR$_{9a}$C(O)NR$_{9b}$R$_{9c}$, —C(O)R$_{9a}$, —C(S)R$_{9a}$, —S(O)$_{0-2}$R$_{9a}$, —C(O)OR$_{9a}$, —C(S)OR$_{9a}$, —C(O)NR$_{9a}$R$_{9b}$, —C(S)NR$_{9a}$R$_{9b}$, —NR$_{9a}$S(O)$_2$R$_{9b}$, —NR$_{9a}$C(O)OR$_{9b}$, —OC(O)CR$_{9a}$R$_{9b}$R$_{9c}$, —OC(S)CR$_{9a}$R$_{9b}$R$_{9c}$, optionally substituted aryl, optionally substituted heteroaryl, optionally substituted cycloalkyl, and optionally substituted heterocycloalkyl, wherein R$_{9a}$, R$_{9b}$, and R$_{9c}$ are each independently selected from the group consisting of hydrogen, optionally substituted aryl, optionally substituted heteroaryl, optionally substituted alkyl, optionally substituted heteroalkyl, optionally substituted cycloalkyl, and optionally substituted heterocycloalkyl (for example, R$_1$ may be selected from the group consisting of phenyl, 1H-pyrrolopyridinyl, 1H-pyrrolopyridinyl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl, and 1H-indazolyl, wherein the phenyl, 1H-pyrrolopyridinyl, 1H-pyrrolopyridinyl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl, or 1H-indazolyl is optionally substituted, for example, with from 1 to 3 substituents independently selected from the group consisting of cyano, hydroxy, C1-4 alkyl, C$_{1-4}$ alkoxy, halo, halo-substituted-C1-4 alkyl, halo-substituted-C1-4 alkoxy, amino, —O(CH$_2$)$_2$NR$_{10a}$R$_{10b}$, —S(O)$_2$NR$_{10a}$R$_{10b}$, —OS(O)$_2$NR$_{10a}$R$_{10b}$, and —NR$_{10a}$S(O)$_2$R$_{10b}$, wherein R$_{10a}$ and R$_{10b}$ are each independently selected from the group consisting of hydrogen, optionally substituted aryl, optionally substituted heteroaryl, optionally substituted alkyl, optionally substituted heteroalkyl, optionally substituted cycloalkyl, and optionally substituted heterocycloalkyl);

Ar is selected from the group consisting of optionally substituted monocyclic aryl and heteroaryl, such as optionally substituted thiophenyl, furanyl, 1H-benzoimidazolyl, isoquinolinyl, imidazopyridinyl, benzothiophenyl, pyrimidinyl, pyridinyl, 1H-imidazolyl, pyrazinyl, pyridazinyl, 1H-pyrrolyl, and thiazolyl;

R$_5$ is selected from the group consisting of optionally substituted aryl, optionally substituted heteroaryl, optionally substituted alkyl, optionally substituted heteroalkyl, optionally substituted cycloalkyl, and optionally substituted heterocycloalkyl; and R$_6$ is selected from the group consisting of hydrogen, optionally substituted aryl, optionally substituted heteroaryl, optionally substituted alkyl, optionally substituted heteroalkyl, optionally substituted cycloalkyl, and optionally substituted heterocycloalkyl;

or a salt thereof.

In some embodiments, Ar is pyridin-3-yl, wherein the pyridin-3-yl is optionally substituted at C5, for example, with a substituent selected from the group consisting of ethoxycarbonyl, methoxy, cyano, methyl, methylsulfonyl, fluoro, chloro, trifluoromethyl, ethynyl, and cyclopropyl.

In some embodiments, the disclosure features a compound represented by formula (I-b)

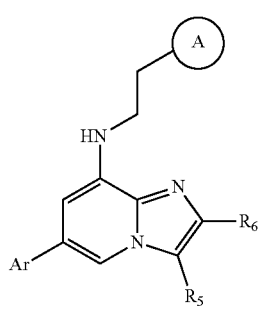

(I-b)

wherein A is an optionally substituted ring system selected from the group consisting of phenyl, 1H-pyrrolopyridinyl, 1H-pyrrolopyridinyl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl, and 1H-indazolyl, wherein the phenyl, 1H-pyrrolopyridinyl, 1H-pyrrolopyridinyl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl, or 1H-indazolyl is optionally substituted with from 1 to 3 substituents independently selected from the group consisting of cyano, hydroxy, C1-4 alkyl, C$_{1-4}$ alkoxy, halo, halo-substituted-C1-4 alkyl, halo-substituted-C1-4 alkoxy, amino, —O(CH$_2$)$_2$NR$_{10a}$R$_{10b}$, —S(O)$_2$NR$_{10a}$R$_{10b}$, —OS(O)$_2$NR$_{10a}$R$_{10b}$, and —NR$_{10a}$S(O)$_2$R$_{10b}$, wherein R$_{10a}$ and R$_{10b}$ are each independently selected from the group consisting of hydrogen, optionally substituted aryl, optionally substituted heteroaryl, optionally substituted alkyl, optionally substituted heteroalkyl, optionally substituted cycloalkyl, and optionally substituted heterocycloalkyl;

Ar is selected from the group consisting of optionally substituted monocyclic aryl and heteroaryl, such as optionally substituted thiophenyl, furanyl, 1H-benzoimidazolyl, isoquinolinyl, imidazopyridinyl, benzothiophenyl, pyrimidinyl, pyridinyl, 1H-imidazolyl, pyrazinyl, pyridazinyl, 1H-pyrrolyl, and thiazolyl;

R$_5$ is selected from the group consisting of optionally substituted aryl, optionally substituted heteroaryl, optionally substituted alkyl, optionally substituted heteroalkyl, optionally substituted cycloalkyl, and optionally substituted heterocycloalkyl; and R$_6$ is selected from the group consisting of hydrogen, optionally substituted aryl, optionally substituted heteroaryl, optionally substituted alkyl, optionally substituted heteroalkyl, optionally substituted cycloalkyl, and optionally substituted heterocycloalkyl;

or a salt thereof.

In some embodiments, A is selected from the group consisting of phenyl, phenol-4-yl, 1H-indol-2-yl, 1H-indol-3-yl, thiophen-3-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, and 2-oxo-2,3-dihydro-1H-benzo[d]imidazol-5-yl.

In some embodiments, A is selected from the group consisting of phenol-4-yl and 1H-indol-3-yl.

In some embodiments, the disclosure features a compound represented by formula (I-c)

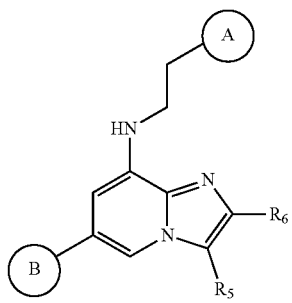

(I-c)

wherein A is an optionally substituted ring system selected from the group consisting of phenyl, 1H-pyrrolopyridinyl, 1H-pyrrolopyridinyl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl, and 1H-indazolyl, wherein the phenyl, 1H-pyrrolopyridinyl, 1H-pyrrolopyridinyl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl, or 1H-indazolyl is optionally substituted with from 1 to 3 substituents independently selected from the group consisting of cyano, hydroxy, C1-4 alkyl, $C_{1-4}$ alkoxy, halo, halo-substituted-C1-4 alkyl, halo-substituted-C1-4 alkoxy, amino, —O(CH$_2$)$_2$NR$_{10a}$R$_{10b}$, —S(O)$_2$NR$_{10a}$R$_{10b}$, —OS(O)$_2$NR$_{10a}$R$_{10b}$, and —NR$_{10a}$S(O)$_2$R$_{10b}$, wherein R$_{10a}$ and R$_{10b}$ are each independently selected from the group consisting of hydrogen, optionally substituted aryl, optionally substituted heteroaryl, optionally substituted alkyl, optionally substituted heteroalkyl, optionally substituted cycloalkyl, and optionally substituted heterocycloalkyl;

B is an optionally substituted ring system selected from the group consisting of thiophenyl, furanyl, 1H-benzoimidazolyl, isoquinolinyl, imidazopyridinyl, benzothiophenyl, pyrimidinyl, pyridinyl, 1H-imidazolyl, pyrazinyl, pyridazinyl, 1H-pyrrolyl, and thiazolyl, wherein the thiophenyl, furanyl, 1H-benzoimidazolyl, isoquinolinyl, 1H-imidazopyridinyl, benzothiophenyl, pyrimidinyl, pyridinyl, 1H-imidazolyl, pyrazinyl, pyridazinyl, 1H-pyrrolyl, or thiazolyl is optionally substituted with from 1 to 3 substituents independently selected from the group consisting of cyano, hydroxy, $C_1$-4 alkyl, C1-4 alkenyl, C1-4 alkynyl, C2-6 cycloalkyl, C1-4 alkoxy, halo, halo-substituted-C1-4 alkyl, halo-substituted-C1-4 alkoxy, amino, —C(O)R$_{11a}$, —S(O)$_{0-2}$R$_{11a}$, —C(O)OR$_{11a}$, and —C(O)NR$_{11a}$R$_{11b}$, wherein R$_{11a}$ and R$_{11b}$ are each independently selected from the group consisting of hydrogen and $C_{1-4}$ alkyl;

R$_5$ is selected from the group consisting of optionally substituted aryl, optionally substituted heteroaryl, optionally substituted alkyl, optionally substituted heteroalkyl, optionally substituted cycloalkyl, and optionally substituted heterocycloalkyl; and R$_6$ is selected from the group consisting of hydrogen, optionally substituted aryl, optionally substituted heteroaryl, optionally substituted alkyl, optionally substituted heteroalkyl, optionally substituted cycloalkyl, and optionally substituted heterocycloalkyl;

or a salt thereof.

In some embodiments, B is pyridin-3-yl, wherein the pyridin-3-yl is optionally substituted at C5, for example, with a substituent selected from the group consisting of ethoxycarbonyl, methoxy, cyano, methyl, methylsulfonyl, fluoro, chloro, trifluoromethyl, ethynyl, and cyclopropyl.

In some embodiments, the disclosure features a compound represented by formula (I-d)

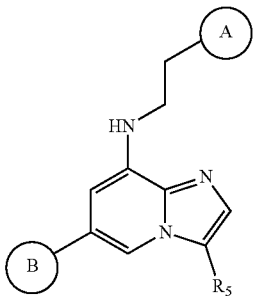

(I-d)

wherein A is an optionally substituted ring system selected from the group consisting of phenyl, 1H-pyrrolopyridinyl, 1H-pyrrolopyridinyl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl, and 1H-indazolyl, wherein the phenyl, 1H-pyrrolopyridinyl, 1H-pyrrolopyridinyl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl, or 1H-indazolyl is optionally substituted with from 1 to 3 substituents independently selected from the group consisting of cyano, hydroxy, C1-4 alkyl, $C_{1-4}$ alkoxy, halo, halo-substituted-C1-4 alkyl, halo-substituted-C1-4 alkoxy, amino, —O(CH$_2$)$_2$NR$_{10a}$R$_{10b}$, —S(O)$_2$NR$_{10a}$R$_{10b}$, —OS(O)$_2$NR$_{10a}$R$_{10b}$, and —NR$_{10a}$S(O)$_2$R$_{10b}$, wherein R$_{10a}$ and R$_{10b}$ are each independently selected from the group consisting of hydrogen, optionally substituted aryl, optionally substituted heteroaryl, optionally substituted alkyl, optionally substituted heteroalkyl, optionally substituted cycloalkyl, and optionally substituted heterocycloalkyl;

B is an optionally substituted ring system selected from the group consisting of thiophenyl, furanyl, 1H-benzoimidazolyl, isoquinolinyl, imidazopyridinyl, benzothiophenyl, pyrimidinyl, pyridinyl, 1H-imidazolyl, pyrazinyl, pyridazinyl, 1H-pyrrolyl, and thiazolyl, wherein the thiophenyl, furanyl, 1H-benzoimidazolyl, isoquinolinyl, 1H-imidazopyridinyl, benzothiophenyl, pyrimidinyl, pyridinyl, 1H-imidazolyl, pyrazinyl, pyridazinyl, 1H-pyrrolyl, or thiazolyl is optionally substituted with from 1 to 3 substituents independently selected from the group consisting of cyano, hydroxy, $C_1$-4 alkyl, C1-4 alkenyl, C1-4 alkynyl, C2-6 cycloalkyl, C1-4 alkoxy, halo, halo-substituted-C1-4 alkyl, halo-substituted-C1-4 alkoxy, amino, —C(O)R$_{11a}$, —S(O)$_{0-2}$R$_{11a}$, —C(O)OR$_{11a}$, and —C(O)NR$_{11a}$R$_{11b}$, wherein R$_{11a}$ and R$_{11b}$ are each independently selected from the group consisting of hydrogen and C$_{1-4}$ alkyl; and R$_5$ is selected from the group consisting of optionally substituted aryl, optionally substituted heteroaryl, optionally substituted alkyl, optionally substituted heteroalkyl, optionally substituted cycloalkyl, and optionally substituted heterocycloalkyl;

or a salt thereof.

In some embodiments, the disclosure features a compound represented by formula (I-e)

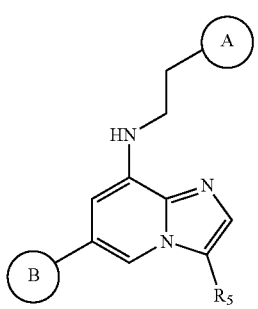

(I-e)

wherein A is an optionally substituted ring system selected from the group consisting of phenyl, 1H-indol-2-yl, 1H-indol-3-yl, thiophen-3-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, and 2-oxo-2,3-dihydro-1H-benzo[d]imidazol-5-yl, wherein the phenyl, 1H-indol-2-yl, 1H-indol-3-yl, thiophen-3-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, or 2-oxo-2,3-dihydro-1H-benzo[d]imidazol-5-yl is optionally substituted with from 1 to 3 substituents independently selected from the group consisting of cyano, hydroxy, C1-4 alkyl, C1-4 alkoxy, halo, halo-substituted-C1-4 alkyl, halo-substituted-C1-4 alkoxy, amino, —O(CH$_2$)$_2$NR$_{10a}$R$_{10b}$, —S(O)$_2$NR$_{10a}$R$_{10b}$, —OS(O)$_2$NR$_{10a}$R$_{10b}$, and —NR$_{10a}$S(O)$_2$R$_{10b}$, wherein R$_{10a}$ and R$_{10b}$ are each independently selected from the group consisting of hydrogen, optionally substituted aryl, optionally substituted heteroaryl, optionally substituted alkyl, optionally substituted heteroalkyl, optionally substituted cycloalkyl, and optionally substituted heterocycloalkyl;

B is an optionally substituted ring system selected from the group consisting of thiophen-2-yl, thiophen-3-yl, furan-3-yl, 1H-benzo[d]imidazol-1-yl, isoquinolin-4-yl, 1H-imidazo[4,5-b]pyridin-1-yl, imidazo[1,2-a]pyridin-3-yl, benzo[b]thiophen-3-yl, pyrimidin-5-yl, pyridin-2-yl, pyridin-3-yl, pyridin-4-yl, 1H-imidazol-1-yl, pyrazin-2-yl, pyridazin-4-yl, 1H-pyrrol-2-yl and thiazol-5-yl, wherein the thiophen-2-yl, thiophen-3-yl, furan-3-yl, 1H-benzo[d]imidazol-1-yl, isoquinolin-4-yl, 1H-imidazo[4,5-b]pyridin-1-yl, benzo[b]thiophen-3-yl, pyrimidin-5-yl, pyridin-2-yl, pyridin-3-yl, pyridin-4-yl, 1H-imidazol-1-yl, pyrazin-2-yl, pyridazin-4-yl, 1H-pyrrol-2-yl, or thiazol-5-yl is optionally substituted with from 1 to 3 substituents independently selected from the group consisting of cyano, hydroxy, C$_1$-4 alkyl, C1-4 alkenyl, C1-4 alkynyl, C2-6 cycloalkyl, C1-4 alkoxy, halo, halo-substituted-C1-4 alkyl, halo-substituted-C1-4 alkoxy, amino, —C(O)R$_{11a}$, —S(O)$_{0-2}$R$_{11a}$, —C(O)OR$_{11a}$, and —C(O)NR$_{11a}$R$_{11b}$, wherein R$_{11a}$ and R$_{11b}$ are each independently selected from the group consisting of hydrogen and C$_{1-4}$ alkyl; and R$_5$ is selected from the group consisting of C1-10 alkyl, prop-1-en-2-yl, cyclohexyl, cyclopropyl, 2-(2-oxopyrrolidin-1-yl)ethyl, oxetan-2-yl, oxetan-3-yl, benzhydryl, tetrahydro-2H-pyran-2-yl, tetrahydro-2H-pyran-3-yl, phenyl, tetrahydrofuran-3-yl, benzyl, (4-pentylphenyl)(phenyl)methyl, and 1-(1-(2-oxo-6,9,12-trioxa-3-azatetradecan-14-yl)-1H-1,2,3-triazol-4-yl)ethyl, wherein the C1-10 alkyl, prop-1-en-2-yl, cyclohexyl, cyclopropyl, 2-(2-oxopyrrolidin-1-yl)ethyl, oxetan-2-yl, oxetan-3-yl, benzhydryl, tetrahydro-2H-pyran-2-yl, tetrahydro-2H-pyran-3-yl, phenyl, tetrahydrofuran-3-yl, benzyl, (4-pentylphenyl)(phenyl)methyl, or 1-(1-(2-oxo-6,9,12-trioxa-3-azatetradecan-14-yl)-1H-1,2,3-triazol-4-yl)ethyl is optionally substituted with from 1 to 3 substituents independently selected from the group consisting of hydroxy, C1-4 alkyl, and halo-substituted-C1-4alkyl, or R$_5$ is selected from the group consisting of (i), (ii), (iii), (iv), and (v)

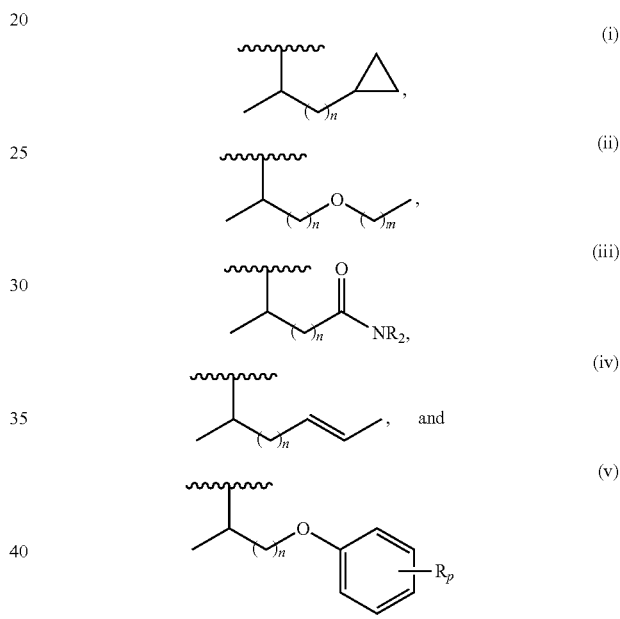

wherein n is an integer from 1 to 6, m is an integer from 0 to 6, p is an integer from 0 to 5, and each R is independently selected from the group consisting of cyano, hydroxy, C$_1$-4 alkyl, C1-4 alkenyl, C1-4 alkynyl, C2-6 cycloalkyl, C1-4 alkoxy, halo, halo-substituted-C1-4 alkyl, halo-substituted-C1-4 alkoxy, amino, —C(O)R$_{12a}$, —S(O)$_{0-2}$R$_{12a}$, —C(O)OR$_{12a}$, and —C(O)NR$_{12a}$R$_{12b}$, and wherein R$_{12a}$ and R$_{12b}$ are each independently selected from the group consisting of hydrogen and C$_{1-4}$ alkyl;

In some embodiments, R$_5$ is selected from the group consisting of:

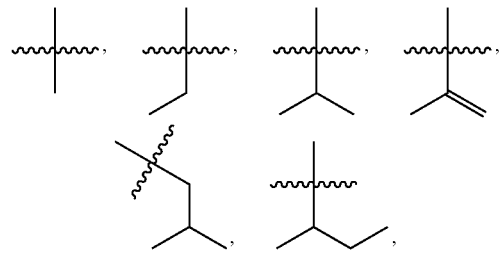

-continued

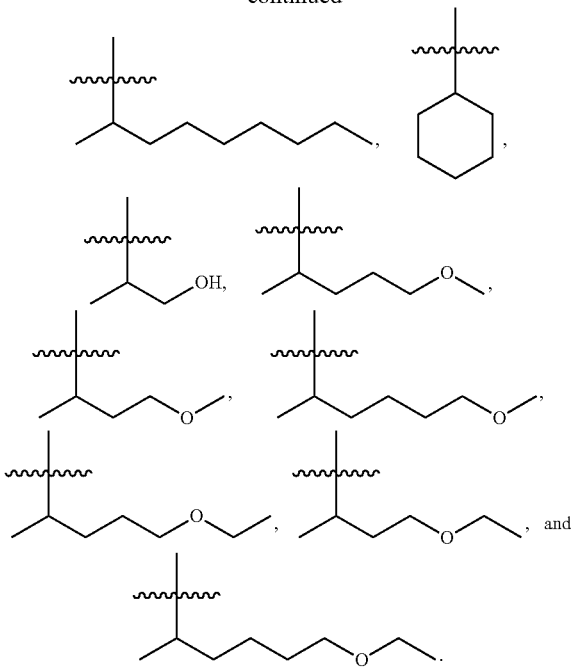

in some embodiments, $R_5$ is (ii);

in some embodiments, $R_5$ is selected from the group consisting of 4-methoxybutan-2-yl, (S)-4-methoxybutan-2-yl, (R)-4-methoxybutan-2-yl, 4-ethoxybutan-2-yl, (S)-4-ethoxybutan-2-yl, (R)-4-ethoxybutan-2-yl, 5-methoxypentan-2-yl, (S)-5-methoxypentan-2-yl, (R)-5-methoxypentan-2-yl, 5-ethoxypentan-2-yl, (S)-5-ethoxypentan-2-yl, (R)-5-ethoxypentan-2-yl, 6-methoxyhexan-2-yl, (S)-6-methoxyhexan-2-yl, (R)-6-methoxyhexan-2-yl, 6-ethoxyhexan-2-yl, (S)-6-ethoxyhexan-2-yl, and (R)-6-ethoxyhexan-2-yl; or a salt thereof.

In some embodiments, the disclosure features a compound represented by formula (I-f)

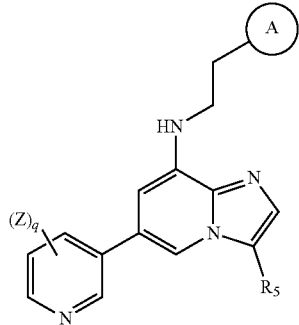

(I-f)

wherein A is an optionally substituted ring system selected from the group consisting of phenol-4-yl and 1H-indol-3-yl;

q is an integer from 0 to 4;

each Z is independently a substituent selected from the group consisting of C1-4 alkyl, halo, halo-substituted-C1-4 alkyl, C1-4 alkenyl, C1-4 alkynyl, C2-6 cycloalkyl, C1-4 alkoxy, cyano, amino, $C(O)R_{11a}$, $-S(O)_{0-2}R_{11a}$, $-C(O)OR_{11a}$, and $-C(O)NR_{11a}R_{11b}$, wherein $R_{11a}$ and $R_{11b}$ are each independently selected from the group consisting of hydrogen and $C_{1-4}$ alkyl; and $R_5$ is selected from the group consisting of isopropyl, methyl, ethyl, prop-1-en-2-yl, isobutyl, cyclohexyl, sec-butyl, (S)-sec-butyl, (R)-sec-butyl, 1-hydroxypropan-2-yl, (S)-1-hydroxypropan-2-yl, (R)-1-hydroxypropan-2-yl, and nonan-2-yl, or $R_5$ is selected from the group consisting of (i), (ii), (iii), (iv), and (v)

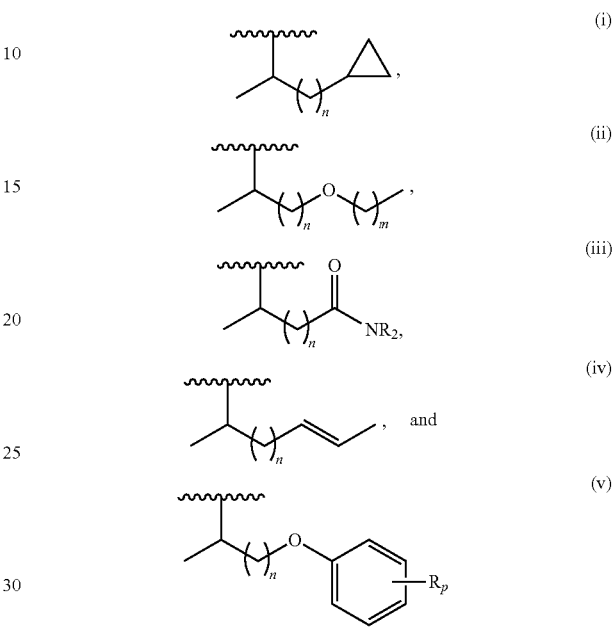

wherein n is an integer from 1 to 6, m is an integer from 0 to 6, p is an integer from 0 to 5, and each R is independently selected from the group consisting of cyano, hydroxy, $C_1$-4 alkyl, C1-4 alkenyl, C1-4 alkynyl, C2-6 cycloalkyl, C1-4 alkoxy, halo, halo-substituted-C1-4 alkyl, halo-substituted-C1-4 alkoxy, amino, $-C(O)R_{12a}$, $-S(O)_{0-2}R_{12a}$, $-C(O)OR_{12a}$, and $-C(O)NR_{12a}R_{12b}$, and wherein $R_{12a}$ and $R_{12b}$ are each independently selected from the group consisting of hydrogen and $C_{1-4}$ alkyl;

In some embodiments, $R_5$ is selected from the group consisting of:

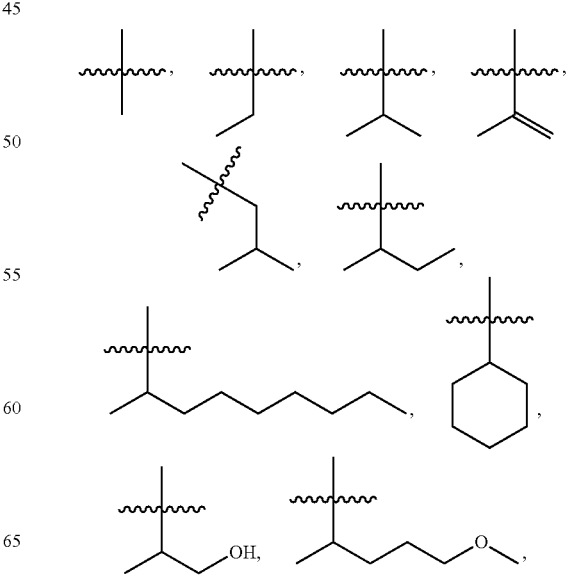

-continued

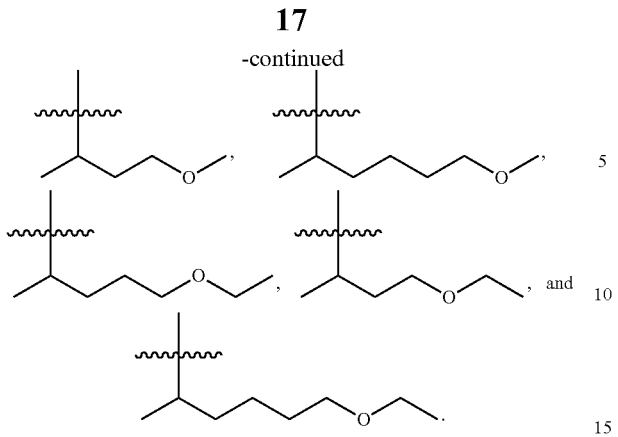

in some embodiments, $R_5$ is (ii);

in some embodiments, $R_5$ is selected from the group consisting of 4-methoxybutan-2-yl, (S)-4-methoxybutan-2-yl, (R)-4-methoxybutan-2-yl, 4-ethoxybutan-2-yl, (S)-4-ethoxybutan-2-yl, (R)-4-ethoxybutan-2-yl, 5-methoxypentan-2-yl, (S)-5-methoxypentan-2-yl, (R)-5-methoxypentan-2-yl, 5-ethoxypentan-2-yl, (S)-5-ethoxypentan-2-yl, (R)-5-ethoxypentan-2-yl, 6-methoxyhexan-2-yl, (S)-6-methoxyhexan-2-yl, (R)-6-methoxyhexan-2-yl, 6-ethoxyhexan-2-yl, (S)-6-ethoxyhexan-2-yl, and (R)-6-ethoxyhexan-2-yl;

or a salt thereof.

In some embodiments, each Z is independently a substituent selected from the group consisting of ethoxycarbonyl, methoxy, cyano, methyl, methylsulfonyl, fluoro, chloro, trifluoromethyl, ethynyl, and cyclopropyl.

In some embodiments, the disclosure features a compound represented by formula (I-g)

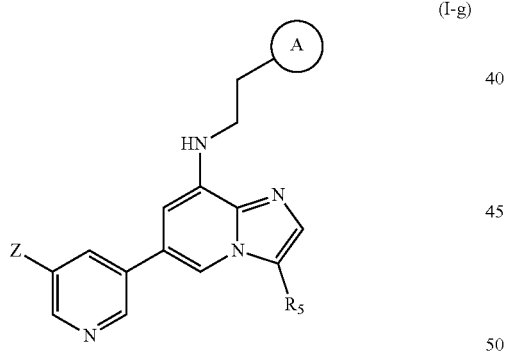

(I-g)

wherein A is an optionally substituted ring system selected from the group consisting of phenol-4-yl and 1H-indol-3-yl;

Z is a substituent selected from the group consisting of C1-4 alkyl, halo, halo-substituted-C1-4 alkyl, C1-4 alkenyl, C1-4 alkynyl, C2-6 cycloalkyl, C1-4 alkoxy, cyano, amino, $C(O)R_{11a}$, $-S(O)_{0-2}R_{11a}$, $-C(O)OR_{11a}$, and $-C(O)NR_{11a}R_{11b}$, wherein $R_{11a}$ and $R_{11b}$ are each independently selected from the group consisting of hydrogen and $C_{1-4}$ alkyl; and $R_5$ is selected from the group consisting of isopropyl, methyl, ethyl, prop-1-en-2-yl, isobutyl, cyclohexyl, sec-butyl, (S)-sec-butyl, (R)-sec-butyl, 1-hydroxypropan-2-yl, (S)-1-hydroxypropan-2-yl, (R)-1-hydroxypropan-2-yl, and nonan-2-yl, or $R_5$ is selected from the group consisting of (i), (ii), (iii), (iv), and (v)

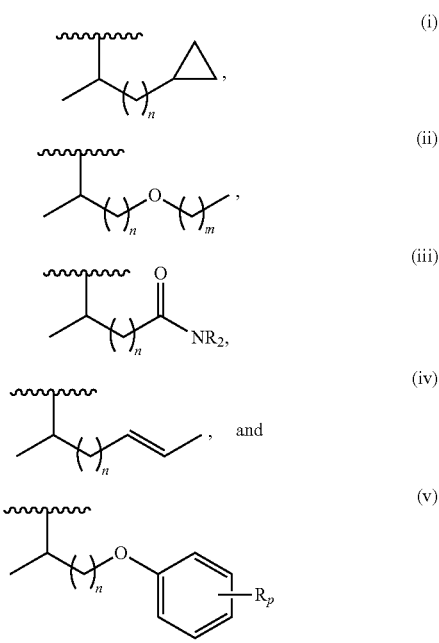

wherein n is an integer from 1 to 6, m is an integer from 0 to 6, p is an integer from 0 to 5, and each R is independently selected from the group consisting of cyano, hydroxy, $C_1$-4 alkyl, C1-4 alkenyl, C1-4 alkynyl, C2-6 cycloalkyl, C1-4 alkoxy, halo, halo-substituted-C1-4 alkyl, halo-substituted-C1-4 alkoxy, amino, $-C(O)R_{12a}$, $-S(O)_{0-2}R_{12a}$, $-C(O)OR_{12a}$, and $-C(O)NR_{12a}R_{12b}$, and wherein $R_{12a}$ and $R_{12b}$ are each independently selected from the group consisting of hydrogen and $C_{1-4}$ alkyl;

In some embodiments, $R_5$ is selected from the group consisting of:

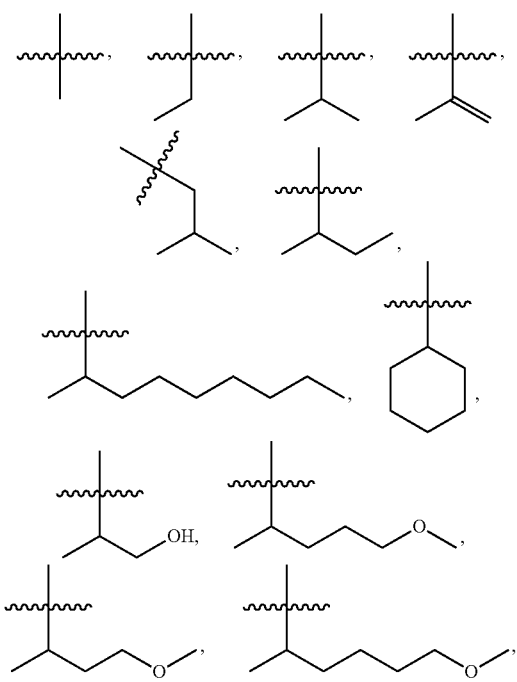

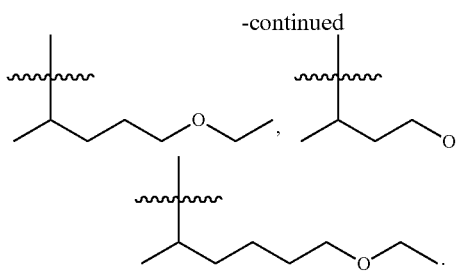

in some embodiments, $R_5$ is (ii);

in some embodiments, $R_5$ is selected from the group consisting of 4-methoxybutan-2-yl, (S)-4-methoxybutan-2-yl, (R)-4-methoxybutan-2-yl, 4-ethoxybutan-2-yl, (S)-4-ethoxybutan-2-yl, (R)-4-ethoxybutan-2-yl, 5-methoxypentan-2-yl, (S)-5-methoxypentan-2-yl, (R)-5-methoxypentan-2-yl, 5-ethoxypentan-2-yl, (S)-5-ethoxypentan-2-yl, (R)-5-ethoxypentan-2-yl, 6-methoxyhexan-2-yl, (S)-6-methoxyhexan-2-yl, (R)-6-methoxyhexan-2-yl, 6-ethoxyhexan-2-yl, (S)-6-ethoxyhexan-2-yl, and (R)-6-ethoxyhexan-2-yl;

or a salt thereof.

In some embodiments, the disclosure features a compound represented by formula (I-h)

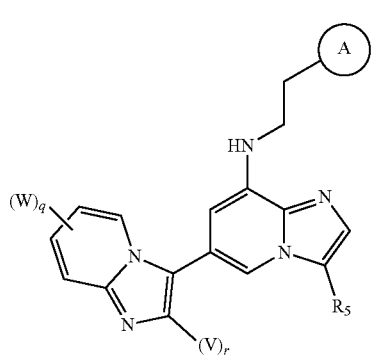

(I-h)

wherein A is an optionally substituted ring system selected from the group consisting of phenol-4-yl and 1H-indol-3-yl;

q is an integer from 0 to 4;

r is 0 or 1;

W and V are each independently a substituent selected from the group consisting of C1-4 alkyl, halo, halo-substituted-C1-4 alkyl, C1-4 alkenyl, C1-4 alkynyl, C2-6 cycloalkyl, C1-4 alkoxy, cyano, amino, $C(O)R_{11a}$, $—S(O)_{0-2}R_{11a}$, $—C(O)OR_{11a}$, and $—C(O)NR_{11a}R_{11b}$, wherein $R_{11a}$ and $R_{11b}$ are each independently selected from the group consisting of hydrogen and $C_{1-4}$ alkyl; and $R_5$ is selected from the group consisting of C1-10 alkyl, prop-1-en-2-yl, cyclohexyl, cyclopropyl, 2-(2-oxopyrrolidin-1-yl)ethyl, oxetan-2-yl, oxetan-3-yl, benzhydryl, tetrahydro-2H-pyran-2-yl, tetrahydro-2H-pyran-3-yl, phenyl, tetrahydrofuran-3-yl, benzyl, (4-pentylphenyl)(phenyl)methyl, and 1-(1-(2-oxo-6,9,12-trioxa-3-azatetradecan-14-yl)-1H-1,2,3-triazol-4-yl)ethyl, wherein the C1-10 alkyl, prop-1-en-2-yl, cyclohexyl, cyclopropyl, 2-(2-oxopyrrolidin-1-yl)ethyl, oxetan-2-yl, oxetan-3-yl, benzhydryl, tetrahydro-2H-pyran-2-yl, tetrahydro-2H-pyran-3-yl, phenyl, tetrahydrofuran-3-yl, benzyl, (4-pentylphenyl)(phenyl)methyl, and 1-(1-(2-oxo-6,9,12-trioxa-3-azatetradecan-14-yl)-1H-1,2,3-triazol-4-yl)ethyl is optionally substituted with from 1 to 3 substituents independently selected from the group consisting of hydroxy, C1-4 alkyl, and halo-substituted-C1-4alkyl, or $R_5$ is selected from the group consisting of (i), (ii), (iii), (iv), and (v)

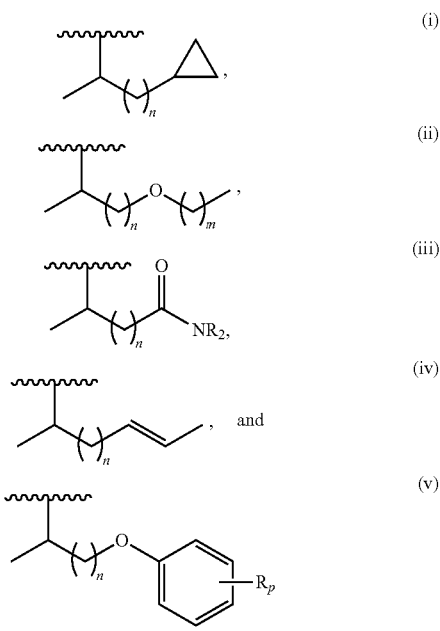

wherein n is an integer from 1 to 6, m is an integer from 0 to 6, p is an integer from 0 to 5, and each R is independently selected from the group consisting of cyano, hydroxy, $C_1$-4 alkyl, C1-4 alkenyl, C1-4 alkynyl, C2-6 cycloalkyl, C1-4 alkoxy, halo, halo-substituted-C1-4 alkyl, halo-substituted-C1-4 alkoxy, amino, $—C(O)R_{12a}$, $—S(O)_{0-2}R_{12a}$, $—C(O)OR_{12a}$, and $—C(O)NR_{12a}R_{12b}$, and wherein $R_{12a}$ and $R_{12b}$ are each independently selected from the group consisting of hydrogen and $C_{1-4}$ alkyl;

In some embodiments, $R_5$ is selected from the group consisting of:

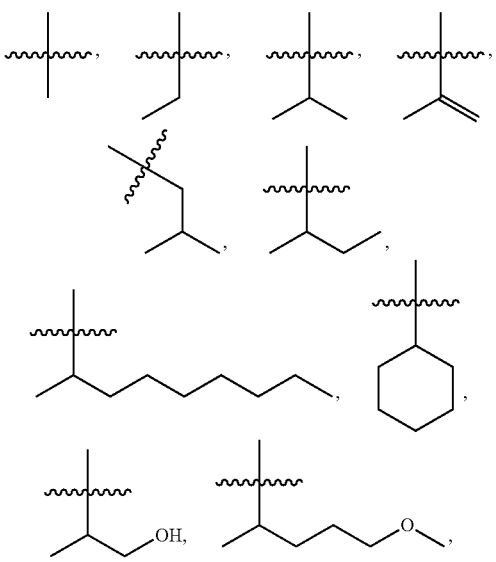

-continued

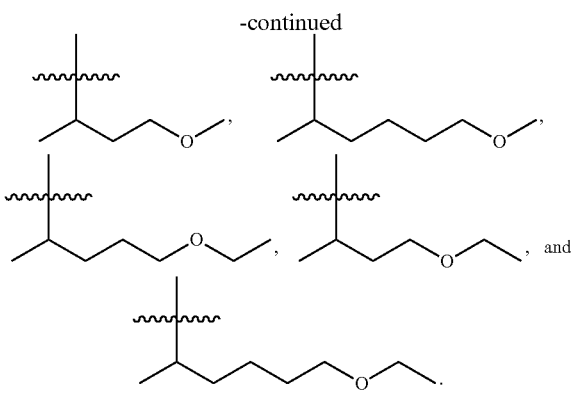

in some embodiments, $R_5$ is (ii);

in some embodiments, $R_5$ is selected from the group consisting of 4-methoxybutan-2-yl, (S)-4-methoxybutan-2-yl, (R)-4-methoxybutan-2-yl, 4-ethoxybutan-2-yl, (S)-4-ethoxybutan-2-yl, (R)-4-ethoxybutan-2-yl, 5-methoxypentan-2-yl, (S)-5-methoxypentan-2-yl, (R)-5-methoxypentan-2-yl, 5-ethoxypentan-2-yl, (S)-5-ethoxypentan-2-yl, (R)-5-ethoxypentan-2-yl, 6-methoxyhexan-2-yl, (S)-6-methoxyhexan-2-yl, (R)-6-methoxyhexan-2-yl, 6-ethoxyhexan-2-yl, (S)-6-ethoxyhexan-2-yl, and (R)-6-ethoxyhexan-2-yl;

or a salt thereof.

In some embodiments, the disclosure features a compound represented by formula (I-i)

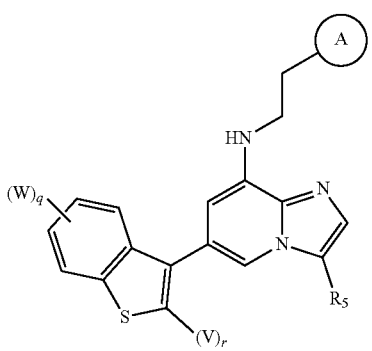

(I-i)

wherein A is an optionally substituted ring system selected from the group consisting of phenol-4-yl and 1H-indol-3-yl;

q is an integer from 0 to 4;

r is 0 or 1;

W and V are each independently a substituent selected from the group consisting of C1-4 alkyl, halo, halo-substituted-C1-4 alkyl, C1-4 alkenyl, C1-4 alkynyl, C2-6 cycloalkyl, C1-4 alkoxy, cyano, amino, $C(O)R_{11a}$, $—S(O)_{0-2}R_{11a}$, $—C(O)OR_{11a}$, and $—C(O)NR_{11a}R_{11b}$, wherein $R_{11a}$ and $R_{11b}$ are each independently selected from the group consisting of hydrogen and $C_{1-4}$ alkyl; and $R_5$ is selected from the group consisting of C1-10 alkyl, prop-1-en-2-yl, cyclohexyl, cyclopropyl, 2-(2-oxopyrrolidin-1-yl)ethyl, oxetan-2-yl, oxetan-3-yl, benzhydryl, tetrahydro-2H-pyran-2-yl, tetrahydro-2H-pyran-3-yl, phenyl, tetrahydrofuran-3-yl, benzyl, (4-pentylphenyl)(phenyl)methyl, and 1-(1-(2-oxo-6,9,12-trioxa-3-azatetradecan-14-yl)-1H-1,2,3-triazol-4-yl)ethyl, wherein the C1-10 alkyl, prop-1-en-2-yl, cyclohexyl, cyclopropyl, 2-(2-oxopyrrolidin-1-yl)ethyl, oxetan-2-yl, oxetan-3-yl, benzhydryl, tetrahydro-2H-pyran-2-yl, tetrahydro-2H-pyran-3-yl, phenyl, tetrahydrofuran-3-yl, benzyl, (4-pentylphenyl)(phenyl)methyl, or 1-(1-(2-oxo-6,9,12-trioxa-3-azatetradecan-14-yl)-1H-1,2,3-triazol-4-yl)ethyl is optionally substituted with from 1 to 3 substituents independently selected from the group consisting of hydroxy, C1-4 alkyl, and halo-substituted-C1-4alkyl, or $R_5$ is selected from the group consisting of (i), (ii), (iii), (iv), and (v)

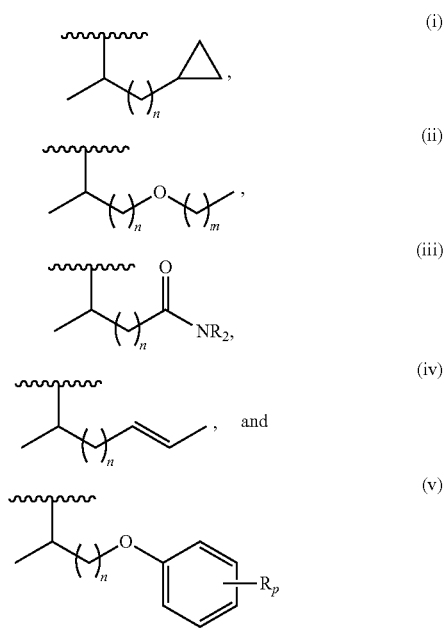

wherein n is an integer from 1 to 6, m is an integer from 0 to 6, p is an integer from 0 to 5, and each R is independently selected from the group consisting of cyano, hydroxy, $C_{1}$-4 alkyl, C1-4 alkenyl, C1-4 alkynyl, C2-6 cycloalkyl, C1-4 alkoxy, halo, halo-substituted-C1-4 alkyl, halo-substituted-C1-4 alkoxy, amino, $—C(O)R_{12a}$, $—S(O)_{0-2}R_{12a}$, $—C(O)OR_{12a}$, and $—C(O)NR_{12a}R_{12b}$, and wherein $R_{12a}$ and $R_{12b}$ are each independently selected from the group consisting of hydrogen and $C_{1-4}$ alkyl;

In some embodiments, $R_5$ is selected from the group consisting of:

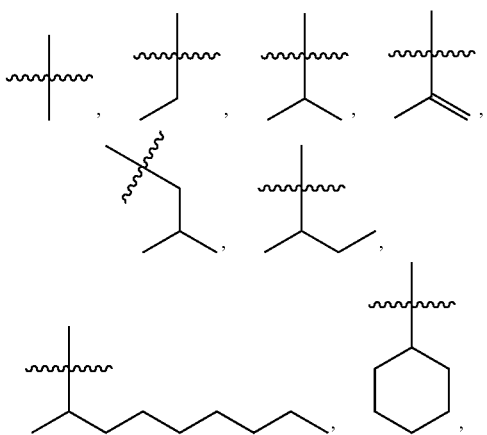

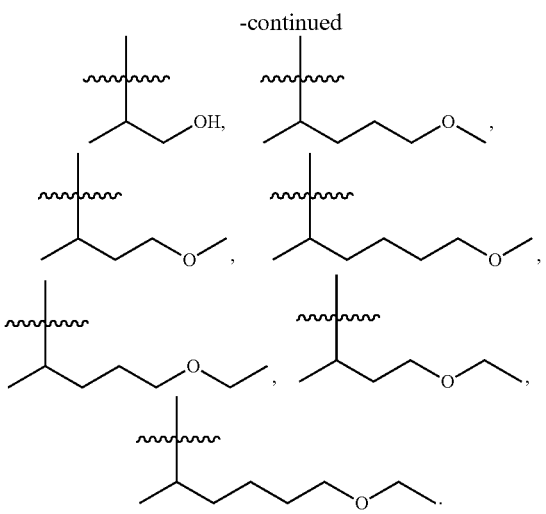

in some embodiments, $R_5$ is (ii);

in some embodiments, $R_5$ is selected from the group consisting of 4-methoxybutan-2-yl, (S)-4-methoxybutan-2-yl, (R)-4-methoxybutan-2-yl, 4-ethoxybutan-2-yl, (S)-4-ethoxybutan-2-yl, (R)-4-ethoxybutan-2-yl, 5-methoxypentan-2-yl, (S)-5-methoxypentan-2-yl, (R)-5-methoxypentan-2-yl, 5-ethoxypentan-2-yl, (S)-5-ethoxypentan-2-yl, (R)-5-ethoxypentan-2-yl, 6-methoxyhexan-2-yl, (S)-6-methoxyhexan-2-yl, (R)-6-methoxyhexan-2-yl, 6-ethoxyhexan-2-yl, (S)-6-ethoxyhexan-2-yl, and (R)-6-ethoxyhexan-2-yl;

or a salt thereof.

In some embodiments, the disclosure features a compound represented by formula (I-j)

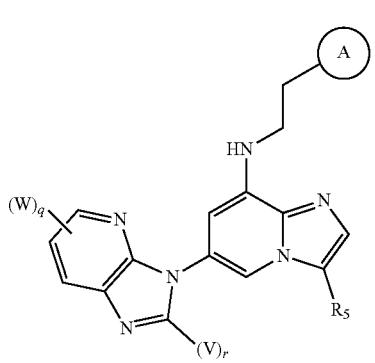

(I-j)

wherein A is an optionally substituted ring system selected from the group consisting of phenol-4-yl and 1H-indol-3-yl;

q is an integer from 0 to 4;

r is 0 or 1;

W and V are each independently a substituent selected from the group consisting of C1-4 alkyl, halo, halo-substituted-C1-4 alkyl, C1-4 alkenyl, C1-4 alkynyl, C2-6 cycloalkyl, C1-4 alkoxy, cyano, amino, $C(O)R_{11a}$, $—S(O)_{0-2}R_{11a}$, $—C(O)OR_{11a}$, and $—C(O)NR_{11a}R_{11b}$, wherein $R_{11a}$ and $R_{11b}$ are each independently selected from the group consisting of hydrogen and $C_{1-4}$ alkyl; and $R_5$ is selected from the group consisting of C1-10 alkyl, prop-1-en-2-yl, cyclohexyl, cyclopropyl, 2-(2-oxopyrrolidin-1-yl)ethyl, oxetan-2-yl, oxetan-3-yl, benzhydryl, tetrahydro-2H-pyran-2-yl, tetrahydro-2H-pyran-3-yl, phenyl, tetrahydrofuran-3-yl, benzyl, (4-pentylphenyl)(phenyl)methyl, and 1-(1-(2-oxo-6,9,12-trioxa-3-azatetradecan-14-yl)-1H-1,2,3-triazol-4-yl)ethyl, wherein the C1-10 alkyl, prop-1-en-2-yl, cyclohexyl, cyclopropyl, 2-(2-oxopyrrolidin-1-yl)ethyl, oxetan-2-yl, oxetan-3-yl, benzhydryl, tetrahydro-2H-pyran-2-yl, tetrahydro-2H-pyran-3-yl, phenyl, tetrahydrofuran-3-yl, benzyl, (4-pentylphenyl)(phenyl)methyl, or 1-(1-(2-oxo-6,9,12-trioxa-3-azatetradecan-14-yl)-1H-1,2,3-triazol-4-yl)ethyl is optionally substituted with from 1 to 3 substituents independently selected from the group consisting of hydroxy, C1-4 alkyl, and halo-substituted-C1-4alkyl, or $R_5$ is selected from the group consisting of (i), (ii), (iii), (iv), and (v)

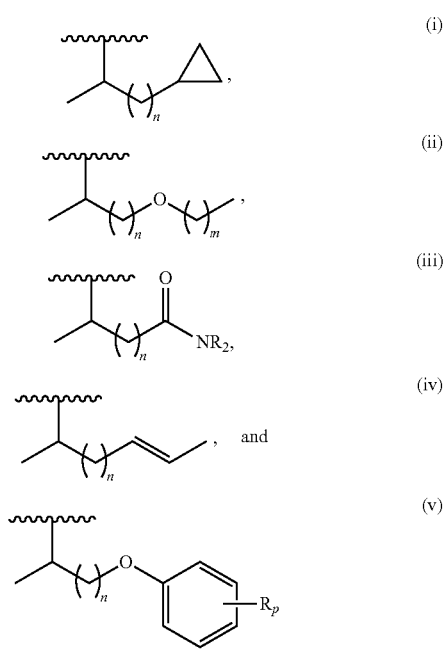

wherein n is an integer from 1 to 6, m is an integer from 0 to 6, p is an integer from 0 to 5, and each R is independently selected from the group consisting of cyano, hydroxy, $C_1$-4 alkyl, C1-4 alkenyl, C1-4 alkynyl, C2-6 cycloalkyl, C1-4 alkoxy, halo, halo-substituted-C1-4 alkyl, halo-substituted-C1-4 alkoxy, amino, $—C(O)R_{12a}$, $—S(O)_{0-2}R_{12a}$, $—C(O)OR_{12a}$, and $—C(O)NR_{12a}R_{12b}$, and wherein $R_{12a}$ and $R_{12b}$ are each independently selected from the group consisting of hydrogen and $C_{1-4}$ alkyl;

In some embodiments, $R_5$ is selected from the group consisting of:

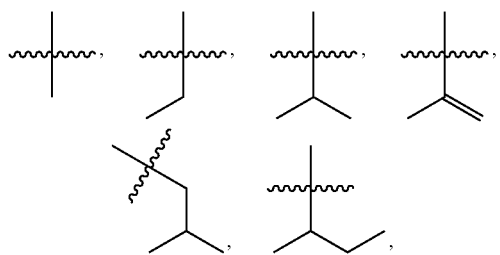

-continued

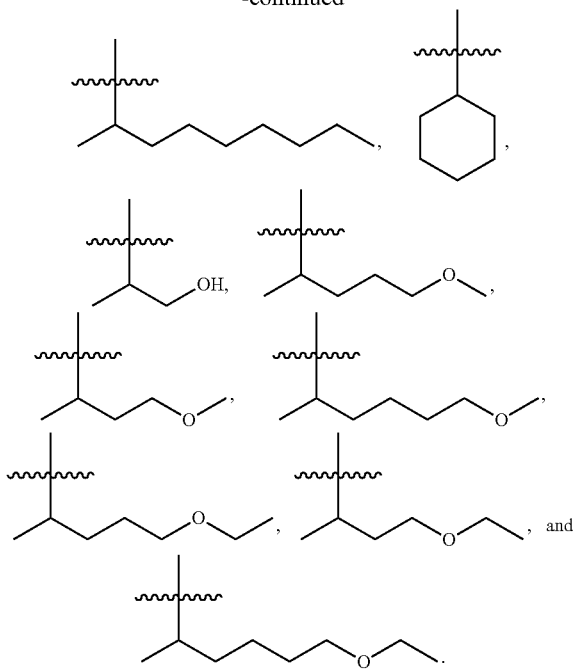

in some embodiments, R₅ is (ii);

in some embodiments, R₅ is selected from the group consisting of 4-methoxybutan-2-yl, (S)-4-methoxybutan-2-yl, (R)-4-methoxybutan-2-yl, 4-ethoxybutan-2-yl, (S)-4-ethoxybutan-2-yl, (R)-4-ethoxybutan-2-yl, 5-methoxypentan-2-yl, (S)-5-methoxypentan-2-yl, (R)-5-methoxypentan-2-yl, 5-ethoxypentan-2-yl, (S)-5-ethoxypentan-2-yl, (R)-5-ethoxypentan-2-yl, 6-methoxyhexan-2-yl, (S)-6-methoxyhexan-2-yl, (R)-6-methoxyhexan-2-yl, 6-ethoxyhexan-2-yl, (S)-6-ethoxyhexan-2-yl, and (R)-6-ethoxyhexan-2-yl;

or a salt thereof.

In some embodiments, the disclosure features a compound represented by formula (I-k)

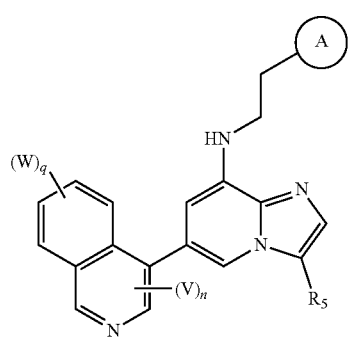

(I-k)

wherein A is an optionally substituted ring system selected from the group consisting of phenol-4-yl and 1H-indol-3-yl;

q is an integer from 0 to 4;

r is 0 or 1;

W and V are each independently a substituent selected from the group consisting of C1-4 alkyl, halo, halo-substituted-C1-4 alkyl, C1-4 alkenyl, C1-4 alkynyl, C2-6 cycloalkyl, C1-4 alkoxy, cyano, amino, $C(O)R_{11a}$, $-S(O)_{0-2}R_{11a}$, $-C(O)OR_{11a}$, and $-C(O)NR_{11a}R_{11b}$, wherein $R_{11a}$ and $R_{11b}$ are each independently selected from the group consisting of hydrogen and $C_{1-4}$ alkyl; and R₅ is selected from the group consisting of C1-10 alkyl, prop-1-en-2-yl, cyclohexyl, cyclopropyl, 2-(2-oxopyrrolidin-1-yl)ethyl, oxetan-2-yl, oxetan-3-yl, benzhydryl, tetrahydro-2H-pyran-2-yl, tetrahydro-2H-pyran-3-yl, phenyl, tetrahydrofuran-3-yl, benzyl, (4-pentylphenyl)(phenyl)methyl, and 1-(1-(2-oxo-6,9,12-trioxa-3-azatetradecan-14-yl)-1H-1,2,3-triazol-4-yl)ethyl, wherein the C1-10 alkyl, prop-1-en-2-yl, cyclohexyl, cyclopropyl, 2-(2-oxopyrrolidin-1-yl)ethyl, oxetan-2-yl, oxetan-3-yl, benzhydryl, tetrahydro-2H-pyran-2-yl, tetrahydro-2H-pyran-3-yl, phenyl, tetrahydrofuran-3-yl, benzyl, (4-pentylphenyl)(phenyl)methyl, or 1-(1-(2-oxo-6,9,12-trioxa-3-azatetradecan-14-yl)-1H-1,2,3-triazol-4-yl)ethyl is optionally substituted with from 1 to 3 substituents independently selected from the group consisting of hydroxy, C1-4 alkyl, and halo-substituted-C1-4alkyl, or R₅ is selected from the group consisting of (i), (ii), (iii), (iv), and (v)

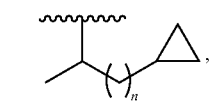 (i)

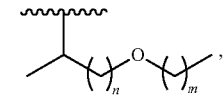 (ii)

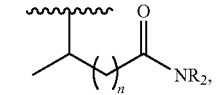 (iii)

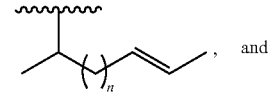 (iv)

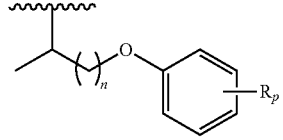 (v)

wherein n is an integer from 1 to 6, m is an integer from 0 to 6, p is an integer from 0 to 5, and each R is independently selected from the group consisting of cyano, hydroxy, C1-4 alkyl, C1-4 alkenyl, C1-4 alkynyl, C2-6 cycloalkyl, C1-4 alkoxy, halo, halo-substituted-C1-4 alkyl, halo-substituted-C1-4 alkoxy, amino, $-C(O)R_{12a}$, $-S(O)_{0-2}R_{12a}$, $-C(O)OR_{12a}$, and $-C(O)NR_{12a}R_{12b}$, and wherein $R_{12a}$ and $R_{12b}$ are each independently selected from the group consisting of hydrogen and $C_{1-4}$ alkyl;

In some embodiments, R₅ is selected from the group consisting of:

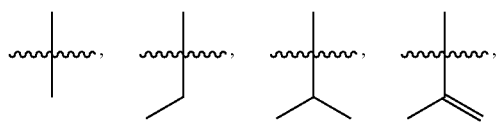

-continued

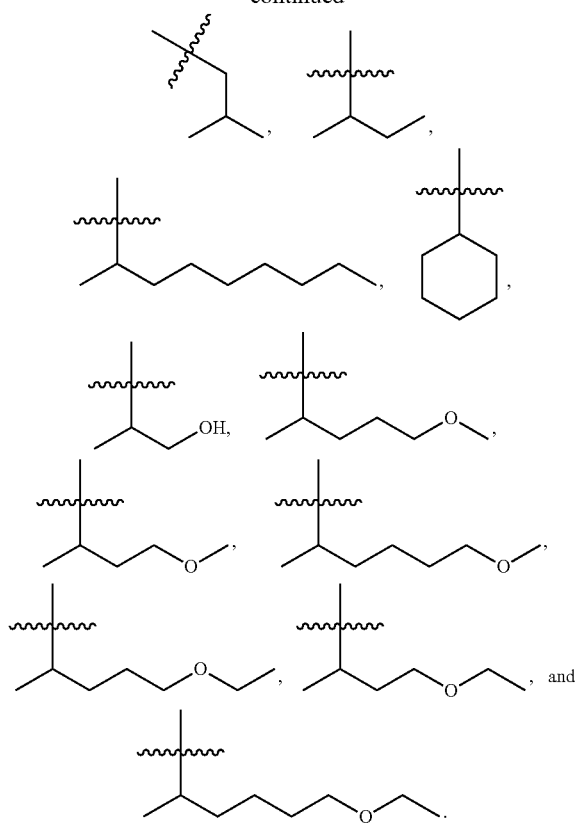

in some embodiments, R₅ is (ii);

in some embodiments, R₅ is selected from the group consisting of 4-methoxybutan-2-yl, (S)-4-methoxybutan-2-yl, (R)-4-methoxybutan-2-yl, 4-ethoxybutan-2-yl, (S)-4-ethoxybutan-2-yl, (R)-4-ethoxybutan-2-yl, 5-methoxypentan-2-yl, (S)-5-methoxypentan-2-yl, (R)-5-methoxypentan-2-yl, 5-ethoxypentan-2-yl, (S)-5-ethoxypentan-2-yl, (R)-5-ethoxypentan-2-yl, 6-methoxyhexan-2-yl, (S)-6-methoxyhexan-2-yl, (R)-6-methoxyhexan-2-yl, 6-ethoxyhexan-2-yl, (S)-6-ethoxyhexan-2-yl, and (R)-6-ethoxyhexan-2-yl;

or a salt thereof.

In some embodiments, the compound is compound (1)

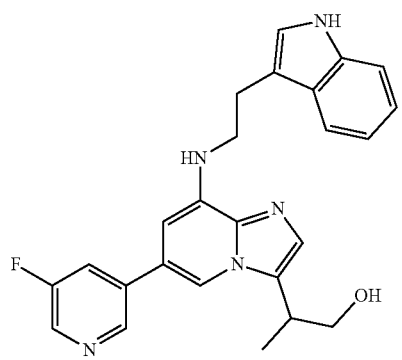

(1)

or a salt thereof.

In some embodiments, the compound is compound (2)

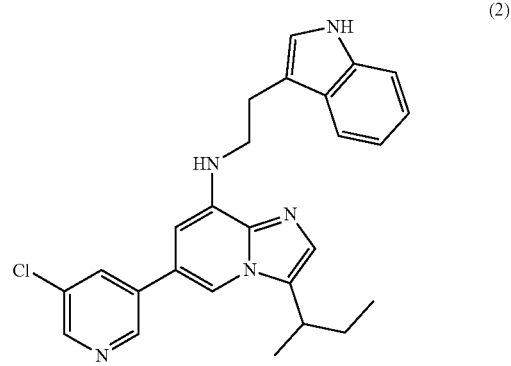 [SMILES: CCC(C)c1cnc2c(NCCc3c[nH]c4ccccc34)cc(-c3cncc(Cl)c3)cn12]

(2)

or a salt thereof.

In some embodiments, the compound is compound (3)

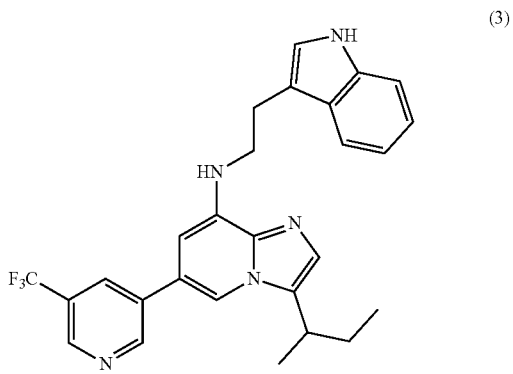 [SMILES: CCC(C)c1cnc2c(NCCc3c[nH]c4ccccc34)cc(-c3cncc(C(F)(F)F)c3)cn12]

(3)

or a salt thereof.

In some embodiments, the compound is compound (4)

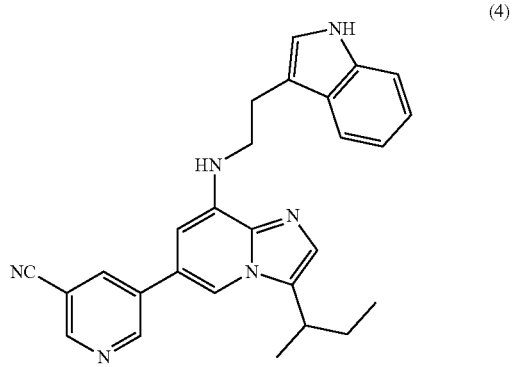 [SMILES: CCC(C)c1cnc2c(NCCc3c[nH]c4ccccc34)cc(-c3cncc(C#N)c3)cn12]

(4)

or a salt thereof.

In some embodiments, the compound is compound (5)

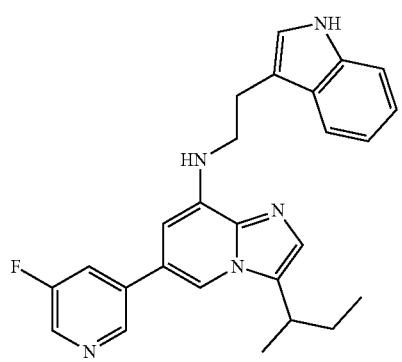

(5)

or a salt thereof.
In some embodiments, the compound is compound (6)

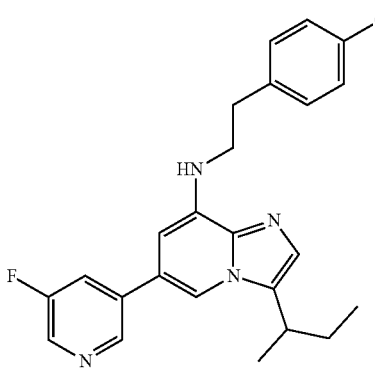

(6)

or a salt thereof.
In some embodiments, the compound is compound (7)

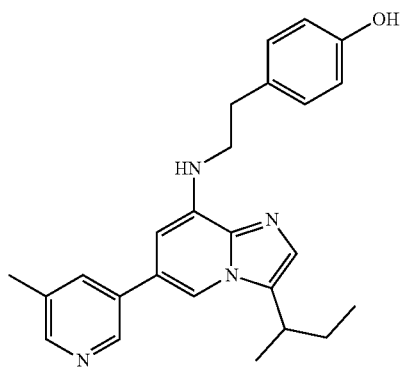

(7)

or a salt thereof.

In some embodiments, the compound is compound (8)

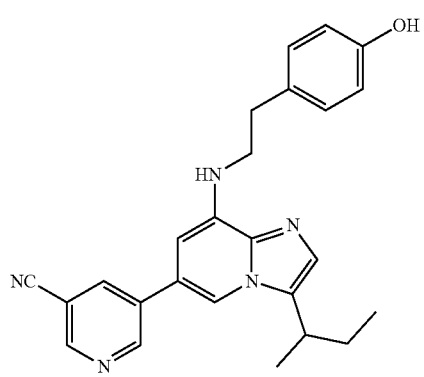

(8)

or a salt thereof.
In some embodiments, the compound is compound (9)

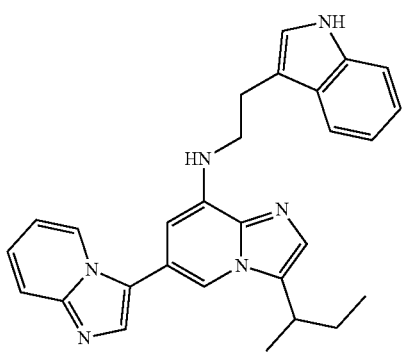

(9)

or a salt thereof.
In some embodiments, the compound is compound (10)

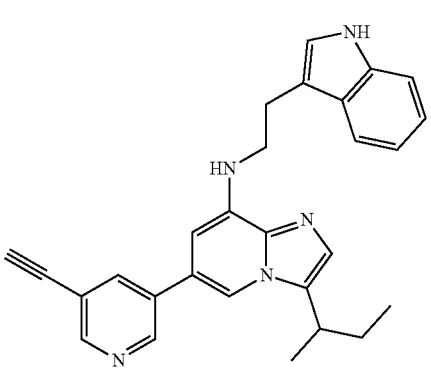

(10)

or a salt thereof.

In some embodiments, the compound is compound (11)

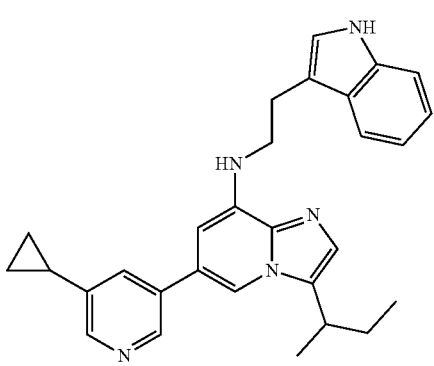

(11)

or a salt thereof.
In some embodiments, the compound is compound (23)

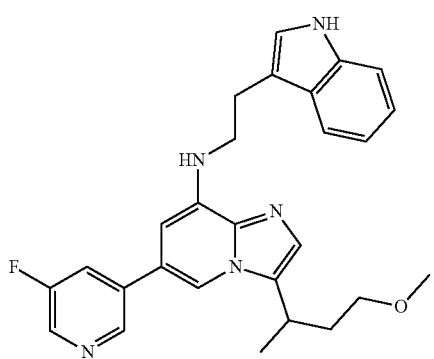

(23)

or a salt thereof.
In some embodiments, the compound is compound (25)

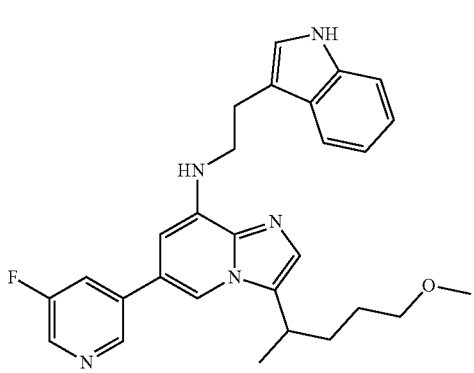

(25)

or a salt thereof.

In some embodiments, the compound is compound (26)

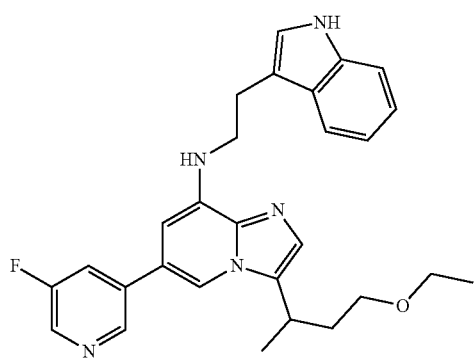

(26)

or a salt thereof.
In another aspect, the disclosure features a compound represented by formula (II)

$$\underset{R_3}{\overset{R_4}{\vphantom{X}}}\text{(II)}$$

wherein L is a linker selected from the group consisting of —NR$_{7a}$(CR$_{8a}$R$_{8b}$)$_n$—, —O(CR$_{8a}$R$_{8b}$)$_n$—, —C(O)(CR$_{8a}$R$_{8b}$)$_n$—, —C(S)(CR$_{8a}$R$_{8b}$)$_n$—, —S(O)$_{0-2}$(CR$_{8a}$R$_{8b}$)$_n$—, —(CR$_{8a}$R$_{8b}$)$_n$—, —NR$_{7a}$C(O)(CR$_{8a}$R$_{8b}$)$_n$—, —NR$_{7a}$C(S)(CR$_{8a}$R$_{8b}$)$_n$—, —OC(O)(CR$_{8a}$R$_{8b}$)$_n$—, —OC(S)(CR$_{8a}$R$_{8b}$)$_n$—, —C(O)NR$_{7a}$(CR$_{8a}$R$_{8b}$)$_n$—, —C(S)NR$_{7a}$(CR$_{8a}$R$_{8b}$)$_n$—, —C(O)O(CR$_{8a}$R$_{8b}$)$_n$—, —C(S)O(CR$_{8a}$R$_{8b}$)$_n$—, —S(O)$_2$NR$_{7a}$(CR$_{8a}$R$_{8b}$)$_n$—, —NR$_{7a}$S(O)$_2$(CR$_{8a}$R$_{8b}$)$_n$—, —NR$_{7a}$C(O)NR$_{7b}$(CR$_{8a}$R$_{8b}$)$_n$—, —NR$_{7a}$(CR$_{8a}$R$_{8b}$)$_n$NR$_{7a}$—, —NR$_{7a}$(CR$_{8a}$R$_{8b}$)$_n$O—, —NR$_{7a}$(CR$_{8a}$R$_{8b}$)$_n$S—, —O(CR$_{8a}$R$_{8b}$)$_n$NR$_{7a}$—, —O(CR$_{8a}$R$_{8b}$)$_n$O—, —O(CR$_{8a}$R$_{8b}$)$_n$S—, —S(CR$_{8a}$R$_{8b}$)$_n$NR$_{7a}$—, —S(CR$_{8a}$R$_{8b}$)$_n$O—, —S(CR$_{8a}$R$_{8b}$)$_n$S—, and —NR$_{7a}$C(O)O(CR$_{8a}$R$_{8b}$)$_n$—, wherein R$_{7a}$, R$_{7b}$, R$_{8a}$, and R$_{8b}$ are each independently selected from the group consisting of hydrogen and optionally substituted C1-4 alkyl, and each n is independently an integer from 2 to 6;

R$_1$ is selected from the group consisting of —S(O)$_2$NR$_{9a}$R$_{9b}$, —NR$_{9a}$C(O)R$_{9b}$, —NR$_{9a}$C(S)R$_{9b}$, —NR$_{9a}$C(O)NR$_{9b}$R$_{9c}$, —C(O)R$_{9a}$, —C(S)R$_{9a}$, —S(O)$_{0-2}$R$_{9a}$, —C(O)OR$_{9a}$, —C(S)OR$_{9a}$, —C(O)NR$_{9a}$R$_{9b}$, —C(S)NR$_{9a}$R$_{9b}$, —NR$_{9a}$S(O)$_2$R$_{9b}$, —NR$_{9a}$C(O)OR$_{9b}$, —OC(O)CR$_{9a}$R$_{9b}$R$_{9c}$, —OC(S)CR$_{9a}$R$_{9b}$R$_{9c}$, optionally substituted aryl, optionally substituted heteroaryl, optionally substituted cycloalkyl, and optionally substituted heterocycloalkyl, wherein R$_{9a}$, R$_{9b}$, and R$_{9c}$ are each independently selected from the group consisting of hydrogen, optionally substituted aryl, optionally substituted heteroaryl, optionally substituted alkyl, optionally substituted heteroalkyl, optionally substituted cycloalkyl, and optionally substituted heterocycloalkyl;

R$_3$ is selected from the group consisting of optionally substituted aryl, optionally substituted heteroaryl, optionally substituted cycloalkyl, and optionally substituted heterocycloalkyl;

R₄ is selected from the group consisting of hydrogen and optionally substituted C1-4 alkyl;

R₅ is selected from the group consisting of optionally substituted aryl, optionally substituted heteroaryl, optionally substituted alkyl, optionally substituted heteroalkyl, optionally substituted cycloalkyl, and optionally substituted heterocycloalkyl; and R₆ is selected from the group consisting of hydrogen, optionally substituted aryl, optionally substituted heteroaryl, optionally substituted alkyl, optionally substituted heteroalkyl, optionally substituted cycloalkyl, and optionally substituted heterocycloalkyl;

or a salt thereof.

In some embodiments, R₁ is selected from the group consisting of —S(O)₂NR₉ₐR₉ᵦ, —NR₉ₐC(O)R₉ᵦ, —NR₉ₐC(S)R₉ᵦ, —NR₉ₐC(O)NR₉ᵦR₉ᵧ, —C(O)R₉ₐ, —C(S)R₉ₐ, —S(O)₀₋₂R₉ₐ, —C(O)OR₉ₐ, —C(S)OR₉ₐ, —C(O)NR₉ₐR₉ᵦ, —C(S)NR₉ₐR₉ᵦ, —NR₉ₐS(O)₂R₉ᵦ, —NR₉ₐC(O)OR₉ᵦ, —OC(O)CR₉ₐR₉ᵦR₉ᵧ, —OC(S)CR₉ₐR₉ᵦR₉ᵧ, phenyl, 1H-pyrrolopyridinyl, 1H-pyrrolopyridinyl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl, and 1H-indazolyl, wherein the phenyl, 1H-pyrrolopyridinyl, 1H-pyrrolopyridinyl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl, or 1H-indazolyl is optionally substituted, for example, with from 1 to 3 substituents independently selected from the group consisting of cyano, hydroxy, C1-4 alkyl, C1-4 alkoxy, halo, halo-substituted-C1-4 alkyl, halo-substituted-C1-4 alkoxy, amino, —O(CH₂)₂NR₁₀ₐR₁₀ᵦ, —S(O)₂NR₁₀ₐR₁₀ᵦ, —OS(O)₂NR₁₀ₐR₁₀ᵦ, and —NR₁₀ₐS(O)₂R₁₀ᵦ; wherein R₁₀ₐ and R₁₀ᵦ are each independently selected from the group consisting of hydrogen, optionally substituted aryl, optionally substituted heteroaryl, optionally substituted alkyl, optionally substituted heteroalkyl, optionally substituted cycloalkyl, and optionally substituted heterocycloalkyl.

In some embodiments, R₁ is selected from the group consisting of —S(O)₂NR₉ₐR₉ᵦ, —NR₉ₐC(O)R₉ᵦ, —NR₉ₐC(S)R₉ᵦ, —NR₉ₐC(O)NR₉ᵦR₉ᵧ, —C(O)R₉ₐ, —C(S)R₉ₐ, —S(O)₀₋₂R₉ₐ, —C(O)OR₉ₐ, —C(S)OR₉ₐ, —C(O)NR₉ₐR₉ᵦ, —C(S)NR₉ₐR₉ᵦ, —NR₉ₐS(O)₂R₉ᵦ, —NR₉ₐC(O)OR₉ᵦ, —OC(O)CR₉ₐR₉ᵦR₉ᵧ, and —OC(S)CR₉ₐR₉ᵦR₉ᵧ.

In some embodiments, R₁ is selected from the group consisting of phenyl, 1H-pyrrolopyridinyl, 1H-pyrrolopyridinyl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl, and 1H-indazolyl, wherein the phenyl, 1H-pyrrolopyridinyl, 1H-pyrrolopyridinyl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl, or 1H-indazolyl is optionally substituted, for example, with from 1 to 3 substituents independently selected from the group consisting of cyano, hydroxy, C1-4 alkyl, C₁₋₄ alkoxy, halo, halo-substituted-C1-4 alkyl, halo-substituted-C1-4 alkoxy, amino, —O(CH₂)₂NR₁₀ₐR₁₀ᵦ, —S(O)₂NR₁₀ₐR₁₀ᵦ, —OS(O)₂NR₁₀ₐR₁₀ᵦ, and —NR₁₀ₐS(O)₂R₁₀ᵦ.

In some embodiments, R₁ is selected from the group consisting of phenyl, 1H-indol-2-yl, 1H-indol-3-yl, thiophen-3-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, and 2-oxo-2,3-dihydro-1H-benzo[d]imidazol-5-yl, wherein the phenyl, 1H-indol-2-yl, 1H-indol-3-yl, thiophen-3-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, or 2-oxo-2,3-dihydro-1H-benzo[d]imidazol-5-yl is optionally substituted, for example, with from 1 to 3 substituents independently selected from the group consisting of cyano, hydroxy, C1-4 alkyl, C1-4 alkoxy, halo, halo-substituted-C1-4 alkyl, halo-substituted-C1-4 alkoxy, amino, —O(CH₂)₂NR₁₀ₐR₁₀ᵦ, —S(O)₂NR₁₀ₐR₁₀ᵦ, —OS(O)₂NR₁₀ₐR₁₀ᵦ, and —NR₁₀ₐS(O)₂R₁₀ᵦ.

In some embodiments, R₁ is selected from the group consisting of phenyl, phenol-4-yl, 1H-indol-2-yl, 1H-indol-3-yl, thiophen-3-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, and 2-oxo-2,3-dihydro-1H-benzo[d]imidazol-5-yl.

In some embodiments, R₁ is selected from the group consisting of:

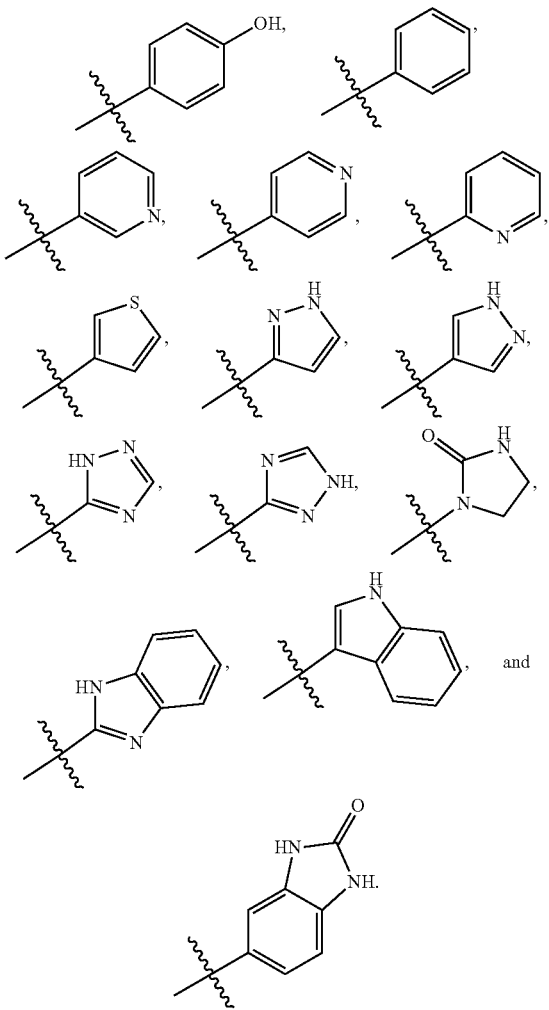

In some embodiments, R₁ is selected from the group consisting of:

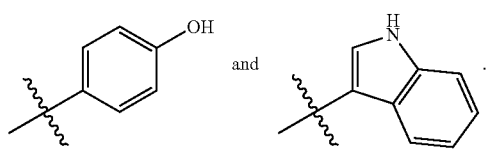 [SMILES: *c1ccc(O)cc1 ; *c1c[nH]c2ccccc12]

In some embodiments, R₁ is selected from the group consisting of phenol-4-yl and 1H-indol-3-yl.

In some embodiments, L is selected from the group consisting of —NR₇ₐ(CR₈ₐR₈ᵦ)ₙ— and —O(CR₈ₐR₈ᵦ)ₙ—.

In some embodiments, L is selected from the group consisting of —NH(CH₂)₂— and —O(CH₂)₂—.

In some embodiments, R₃ is selected from the group consisting of optionally substituted aryl and optionally substituted heteroaryl.

In some embodiments, R₃ is selected from the group consisting of phenyl, thiophenyl, furanyl, 1H-benzoimidazolyl, quinolinyl, isoquinolinyl, imidazopyridinyl, benzothiophenyl, pyrimidinyl, pyridinyl, 1H-imidazolyl, pyrazinyl, pyridazinyl, 1H-pyrrolyl, and thiazolyl, wherein the phenyl, thiophenyl, furanyl, 1H-benzoimidazolyl, quinolinyl, isoquinolinyl, imidazopyridinyl, benzothiophenyl, pyrimidinyl, pyridinyl, 1H-imidazolyl, pyrazinyl, pyridazinyl, 1H-pyrrolyl, or thiazolyl is optionally substituted, for example, with from 1 to 3 substituents independently selected from the group consisting of cyano, hydroxy, C1-4 alkyl, C1-4 alkenyl, C1-4 alkynyl, C2-6 cycloalkyl, C1-4 alkoxy, halo, halo-substituted-C1-4 alkyl, halo-substituted-C1-4 alkoxy, amino, —C(O)R₁₁ₐ, —S(O)₀₋₂R₁₁ₐ, —C(O)OR₁₁ₐ, and —C(O)NR₁₁ₐR₁₁ᵦ, and wherein R₁₁ₐ and R₁₁ᵦ are each independently selected from the group consisting of hydrogen and C₁₋₄ alkyl.

In some embodiments, R₃ is selected from the group consisting of thiophen-2-yl, thiophen-3-yl, furan-3-yl, 1H-benzo[d]imidazol-1-yl, isoquinolin-4-yl, 1H-imidazo[4,5-b]pyridin-1-yl, imidazo[1,2-a]pyridin-3-yl, benzo[b]thiophen-3-yl, pyrimidin-5-yl, pyridin-2-yl, pyridin-3-yl, pyridin-4-yl, 1H-imidazol-1-yl, pyrazin-2-yl, pyridazin-4-yl, 1H-pyrrol-2-yl and thiazol-5-yl, wherein the thiophen-2-yl, thiophen-3-yl, furan-3-yl, 1H-benzo[d]imidazol-1-yl, isoquinolin-4-yl, 1H-imidazo[4,5-b]pyridin-1-yl, benzo[b]thiophen-3-yl, pyrimidin-5-yl, pyridin-2-yl, pyridin-3-yl, pyridin-4-yl, 1H-imidazol-1-yl, pyrazin-2-yl, pyridazin-4-yl, 1H-pyrrol-2-yl, or thiazol-5-yl is optionally substituted, for example, with from 1 to 3 substituents independently selected from the group consisting of cyano, hydroxy, C₁-4 alkyl, C1-4 alkenyl, C1-4 alkynyl, C2-6 cycloalkyl, C1-4 alkoxy, halo, halo-substituted-C1-4 alkyl, halo-substituted-C1-4 alkoxy, amino, —C(O)R₁₁ₐ, —S(O)₀₋₂R₁₁ₐ, —C(O)OR₁₁ₐ, and —C(O)NR₁₁ₐR₁₁ᵦ.

In some embodiments, R₃ is selected from the group consisting of thiophen-3-yl, benzo[b]thiophen-3-yl, pyridin-3-yl, pyrimidin-5-yl, 1H-imidazol-1-yl, 1H-benzo[d]imidazol-1-yl, isoquinolin-4-yl, 1H-imidazo[4,5-b]pyridin-1-yl, and imidazo[1,2-a]pyridin-3-yl, wherein the thiophen-3-yl, benzo[b]thiophen-3-yl, pyridin-3-yl, pyrimidin-5-yl, 1H-imidazol-1-yl, 1H-benzo[d]imidazol-1-yl, isoquinolin-4-yl, 1H-imidazo[4,5-b]pyridin-1-yl, or imidazo[1,2-a]pyridin-3-yl is optionally substituted, for example, with from 1 to 3 substituents independently selected from the group consisting of cyano, hydroxy, C1-4 alkyl, C1-4 alkenyl, C1-4 alkynyl, C2-6 cycloalkyl, C1-4 alkoxy, halo, halo-substituted-C1-4 alkyl, halo-substituted-C1-4 alkoxy, amino, —C(O)R₁₁ₐ, —S(O)₀₋₂R₁₁ₐ, —C(O)OR₁₁ₐ, and —C(O)NR₁₁ₐR₁₁ᵦ.

In some embodiments, R₃ is selected from the group consisting of optionally substituted:

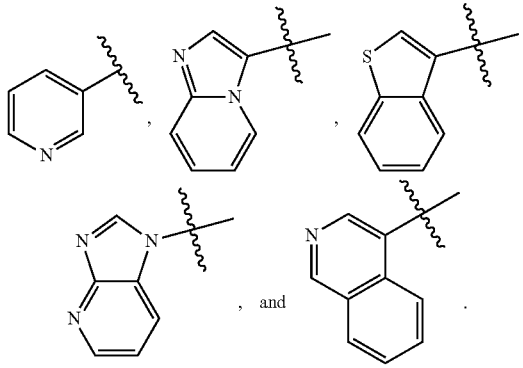

, and .

In some embodiments, R₃ is pyridin-3-yl, wherein the pyridin-3-yl is optionally substituted at C5, for example, with a substituent selected from the group consisting of C1-4 alkyl, halo, halo-substituted-C1-4 alkyl, C1-4 alkenyl, C1-4 alkynyl, C2-6 cycloalkyl, C1-4 alkoxy, cyano, amino, C(O)R₁₁ₐ, —S(O)₀₋₂R₁₁ₐ, —C(O)OR₁₁ₐ, and —C(O)NR₁₁ₐR₁₁ᵦ.

In some embodiments, the pyridin-3-yl is substituted at C5 with a substituent selected from the group consisting of ethoxycarbonyl, methoxy, cyano, methyl, methylsulfonyl, fluoro, chloro, trifluoromethyl, ethynyl, and cyclopropyl.

In some embodiments, R₃ is selected from the group consisting of:

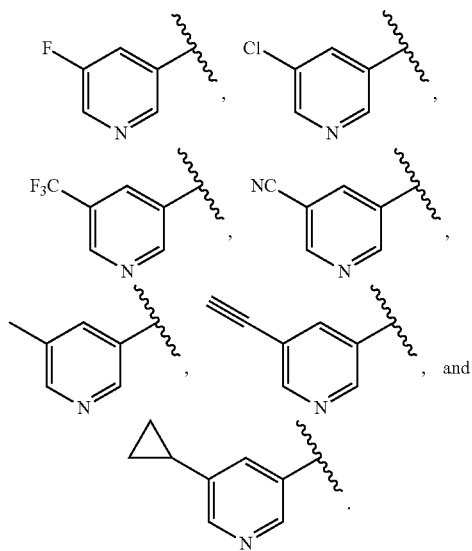

, and .

In some embodiments, R₃ is imidazo[1,2-a]pyridin-3-yl, wherein the imidazo[1,2-a]pyridin-3-yl is optionally substituted, for example, with a substituent selected from the group consisting of C1-4 alkyl, halo, halo-substituted-C1-4 alkyl, C1-4 alkenyl, C1-4 alkynyl, C2-6 cycloalkyl, C1-4 alkoxy, cyano, amino, C(O)R₁₁ₐ, —S(O)₀₋₂R₁₁ₐ, —C(O)OR₁₁ₐ, and —C(O)NR₁₁ₐR₁₁ᵦ.

In some embodiments, R₃ is benzo[b]thiophen-3-yl, wherein the benzo[b]thiophen-3-yl is optionally substituted, for example, with a substituent selected from the group consisting of C1-4 alkyl, halo, halo-substituted-C1-4 alkyl, C1-4 alkenyl, C1-4 alkynyl, C2-6 cycloalkyl, C1-4 alkoxy, cyano, amino, $C(O)R_{11a}$, $—S(O)_{0-2}R_{11a}$, $—C(O)OR_{11a}$, and $—C(O)NR_{11a}R_{11b}$.

In some embodiments, $R_3$ is 1H-imidazo[4,5-b]pyridin-1-yl, wherein the 1H-imidazo[4,5-b]pyridin-1-yl is optionally substituted, for example, with a substituent selected from the group consisting of C1-4 alkyl, halo, halo-substituted-C1-4 alkyl, C1-4 alkenyl, C1-4 alkynyl, C2-6 cycloalkyl, C1-4 alkoxy, cyano, amino, $C(O)R_{11a}$, $—S(O)_{0-2}R_{11a}$, $—C(O)OR_{11a}$, and $—C(O)NR_{11a}R_{11b}$.

In some embodiments, $R_3$ is isoquinolin-4-yl, wherein the isoquinolin-4-yl is optionally substituted, for example, with a substituent selected from the group consisting of C1-4 alkyl, halo, halo-substituted-C1-4 alkyl, C1-4 alkenyl, C1-4 alkynyl, C2-6 cycloalkyl, C1-4 alkoxy, cyano, amino, $C(O)R_{11a}$, $—S(O)_{0-2}R_{11a}$, $—C(O)OR_{11a}$, and $—C(O)NR_{11a}R_{11b}$.

In some embodiments, $R_4$ is hydrogen.

In some embodiments, $R_5$ is selected from the group consisting of C1-10 alkyl, prop-1-en-2-yl, cyclohexyl, cyclopropyl, 2-(2-oxopyrrolidin-1-yl)ethyl, oxetan-2-yl, oxetan-3-yl, benzhydryl, tetrahydro-2H-pyran-2-yl, tetrahydro-2H-pyran-3-yl, phenyl, tetrahydrofuran-3-yl, benzyl, (4-pentylphenyl)(phenyl)methyl, and 1-(1-(2-oxo-6,9,12-trioxa-3-azatetradecan-14-yl)-1H-1,2,3-triazol-4-yl)ethyl, wherein the C1-10 alkyl, prop-1-en-2-yl, cyclohexyl, cyclopropyl, 2-(2-oxopyrrolidin-1-yl)ethyl, oxetan-2-yl, oxetan-3-yl, benzhydryl, tetrahydro-2H-pyran-2-yl, tetrahydro-2H-pyran-3-yl, phenyl, tetrahydrofuran-3-yl, benzyl, (4-pentylphenyl)(phenyl)methyl, or 1-(1-(2-oxo-6,9,12-trioxa-3-azatetradecan-14-yl)-1H-1,2,3-triazol-4-yl)ethyl is optionally substituted, for example, with from 1 to 3 substituents independently selected from the group consisting of hydroxy, C1-4 alkyl, and halo-substituted-C1-4alkyl.

In some embodiments, $R_5$ is selected from the group consisting of isopropyl, methyl, ethyl, prop-1-en-2-yl, isobutyl, cyclohexyl, sec-butyl, (S)-sec-butyl, (R)-sec-butyl, 1-hydroxypropan-2-yl, (S)-1-hydroxypropan-2-yl, (R)-1-hydroxypropan-2-yl, and nonan-2-yl.

In some embodiments, $R_5$ is (S)-1-hydroxypropan-2-yl.

In some embodiments, $R_5$ is (R)-1-hydroxypropan-2-yl.

In some embodiments, $R_5$ is (S)-sec-butyl.

In some embodiments, $R_5$ is (R)-sec-butyl.

In some embodiments, $R_5$ is selected from the group consisting of (i), (ii), (iii), (iv), and (v)

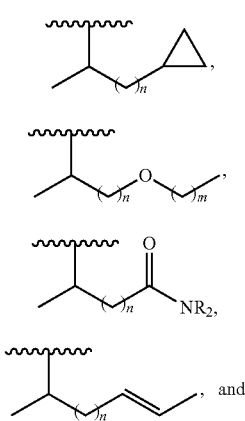

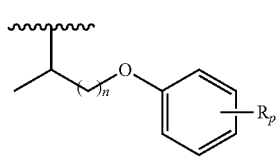

wherein n is an integer from 1 to 6, m is an integer from 0 to 6, p is an integer from 0 to 5, and each R is independently selected from the group consisting of cyano, hydroxy, C1-4 alkyl, C1-4 alkenyl, C1-4 alkynyl, C2-6 cycloalkyl, C1-4 alkoxy, halo, halo-substituted-C1-4 alkyl, halo-substituted-C1-4 alkoxy, amino, $—C(O)R_{12a}$, $—S(O)_{0-2}R_{12a}$, $—C(O)OR_{12a}$, and $—C(O)NR_{12a}R_{12b}$, and wherein $R_{12a}$ and $R_{12b}$ are each independently selected from the group consisting of hydrogen and $C_{1-4}$ alkyl.

In some embodiments, $R_5$ is selected from the group consisting of:

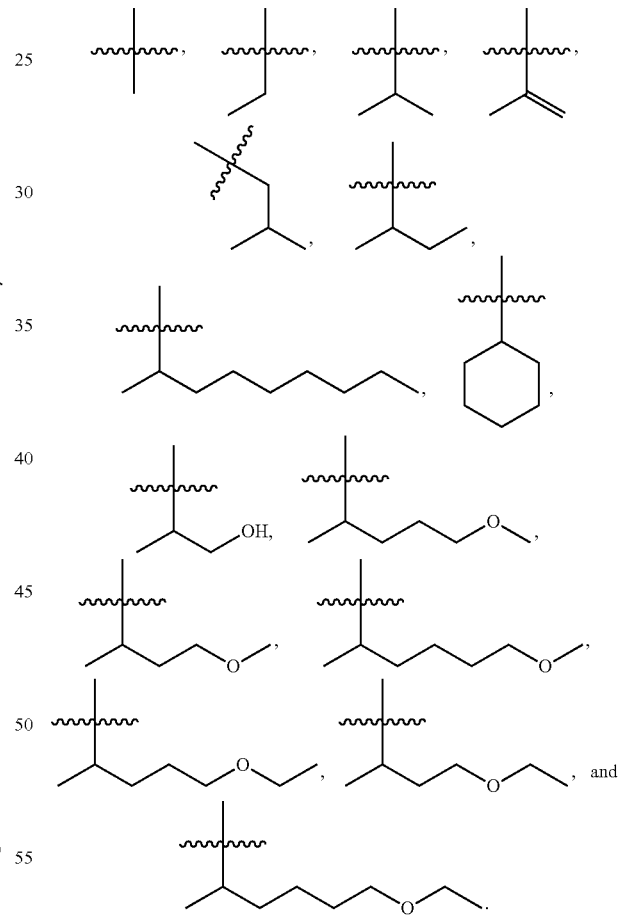

In some embodiments, $R_5$ is (ii).

In some embodiments, $R_5$ is selected from the group consisting of 4-methoxybutan-2-yl, (S)-4-methoxybutan-2-yl, (R)-4-methoxybutan-2-yl, 4-ethoxybutan-2-yl, (S)-4-ethoxybutan-2-yl, (R)-4-ethoxybutan-2-yl, 5-methoxypentan-2-yl, (S)-5-methoxypentan-2-yl, (R)-5-methoxypentan-2-yl, 5-ethoxypentan-2-yl, (S)-5-ethoxypentan-2-yl, (R)-5-ethoxypentan-2-yl, 6-methoxyhexan-2-yl, (S)-6- methoxyhexan-2-yl, (R)-6-methoxyhexan-2-yl, 6-ethoxyhexan-2-yl, (S)-6-ethoxyhexan-2-yl, and (R)-6-ethoxyhexan-2-yl.

In some embodiments, $R_5$ is (S)-4-methoxybutan-2-yl.
In some embodiments, $R_5$ is (R)-4-methoxybutan-2-yl.
In some embodiments, $R_5$ is (S)-5-methoxypentan-2-yl.
In some embodiments, $R_5$ is (R)-5-methoxypentan-2-yl.
In some embodiments, $R_5$ is (S)-4-ethoxybutan-2-yl.
In some embodiments, $R_5$ is (R)-4-ethoxybutan-2-yl.
In some embodiments, $R_6$ is hydrogen.

In some embodiments, the disclosure features a compound represented by formula (II-a)

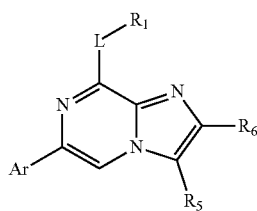

(II-a)

wherein L is a linker selected from the group consisting of —$NR_{7a}(CR_{8a}R_{8b})_n$—, —$O(CR_{8a}R_{8b})_n$—, —$C(O)(CR_{8a}R_{8b})_n$—, —$C(S)(CR_{8a}R_{8b})_n$—, —$S(O)_{0-2}(CR_{8a}R_{8b})_n$—, —$(CR_{8a}R_{8b})_n$—, —$NR_{7a}C(O)(CR_{8a}R_{8b})_n$—, —$NR_{7a}C(S)(CR_{8a}R_{8b})_n$—, —$OC(O)(CR_{8a}R_{8b})_n$—, —$OC(S)(CR_{8a}R_{8b})_n$—, —$C(O)NR_{7a}(CR_{8a}R_{8b})_n$—, —$C(S)NR_{7a}(CR_{8a}R_{8b})_n$—, —$C(O)O(CR_{8a}R_{8b})_n$—, —$C(S)O(CR_{8a}R_{8b})_n$—, —$S(O)_2NR_{7a}(CR_{8a}R_{8b})_n$—, —$NR_{7a}S(O)_2(CR_{8a}R_{8b})_n$—, —$NR_{7a}C(O)NR_{7b}(CR_{8a}R_{8b})_n$—, and —$NR_{7a}C(O)O(CR_{8a}R_{8b})_n$—, wherein $R_{7a}$, $R_{7b}$, $R_{8a}$, and $R_{8b}$ are each independently selected from the group consisting of hydrogen and optionally substituted C1-4 alkyl, and each n is independently an integer from 2 to 6;

$R_1$ is selected from the group consisting of —$S(O)_2NR_{9a}R_{9b}$, —$NR_{9a}C(O)R_{9b}$, —$NR_{9a}C(S)R_{9b}$, —$NR_{9a}C(O)NR_{9b}R_{9c}$, —$C(O)R_{9a}$, —$C(S)R_{9a}$, —$S(O)_{0-2}R_{9a}$, —$C(O)OR_{9a}$, —$C(S)OR_{9a}$, —$C(O)NR_{9a}R_{9b}$, —$C(S)NR_{9a}R_{9b}$, —$NR_{9a}S(O)_2R_{9b}$, —$NR_{9a}C(O)OR_{9b}$, —$OC(O)CR_{9a}R_{9b}R_{9c}$, —$OC(S)CR_{9a}R_{9b}R_{9c}$, optionally substituted aryl, optionally substituted heteroaryl, optionally substituted cycloalkyl, and optionally substituted heterocycloalkyl, wherein $R_{9a}$, $R_{9b}$, and $R_{9c}$ are each independently selected from the group consisting of hydrogen, optionally substituted aryl, optionally substituted heteroaryl, optionally substituted alkyl, optionally substituted heteroalkyl, optionally substituted cycloalkyl, and optionally substituted heterocycloalkyl (for example, $R_1$ may be selected from the group consisting of phenyl, 1H-pyrrolopyridinyl, 1H-pyrrolopyridinyl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl, and 1H-indazolyl, wherein the phenyl, 1H-pyrrolopyridinyl, 1H-pyrrolopyridinyl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl, or 1H-indazolyl is optionally substituted, for example, with from 1 to 3 substituents independently selected from the group consisting of cyano, hydroxy, C1-4 alkyl, $C_{1-4}$ alkoxy, halo, halo-substituted-C1-4 alkyl, halo-substituted-C1-4 alkoxy, amino, —$O(CH_2)_2NR_{10a}R_{10b}$, —$S(O)_2NR_{10a}R_{10b}$, —$OS(O)_2NR_{10a}R_{10b}$, and —$NR_{10a}S(O)_2R_{10b}$, wherein $R_{10a}$ and $R_{10b}$ are each independently selected from the group consisting of hydrogen, optionally substituted aryl, optionally substituted heteroaryl, optionally substituted alkyl, optionally substituted heteroalkyl, optionally substituted cycloalkyl, and optionally substituted heterocycloalkyl);

Ar is selected from the group consisting of optionally substituted monocyclic aryl and heteroaryl, such as optionally substituted thiophenyl, furanyl, 1H-benzoimidazolyl, isoquinolinyl, imidazopyridinyl, benzothiophenyl, pyrimidinyl, pyridinyl, 1H-imidazolyl, pyrazinyl, pyridazinyl, 1H-pyrrolyl, and thiazolyl;

$R_5$ is selected from the group consisting of optionally substituted aryl, optionally substituted heteroaryl, optionally substituted alkyl, optionally substituted heteroalkyl, optionally substituted cycloalkyl, and optionally substituted heterocycloalkyl; and $R_6$ is selected from the group consisting of hydrogen, optionally substituted aryl, optionally substituted heteroaryl, optionally substituted alkyl, optionally substituted heteroalkyl, optionally substituted cycloalkyl, and optionally substituted heterocycloalkyl;

or a salt thereof.

In some embodiments, Ar is pyridin-3-yl, wherein the pyridin-3-yl is optionally substituted at C5, for example, with a substituent selected from the group consisting of ethoxycarbonyl, methoxy, cyano, methyl, methylsulfonyl, fluoro, chloro, trifluoromethyl, ethynyl, and cyclopropyl.

In some embodiments, the disclosure features a compound represented by formula (II-b)

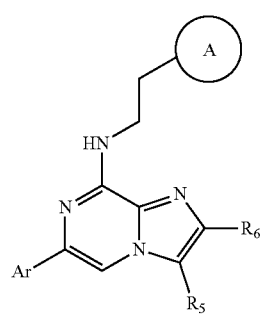

(II-b)

wherein A is an optionally substituted ring system selected from the group consisting of phenyl, 1H-pyrrolopyridinyl, 1H-pyrrolopyridinyl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl, and 1H-indazolyl, wherein the phenyl, 1H-pyrrolopyridinyl, 1H-pyrrolopyridinyl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl, or 1H-indazolyl is optionally substituted with from 1 to 3 substituents independently selected from the group consisting of cyano, hydroxy, C1-4 alkyl, $C_{1-4}$ alkoxy, halo, halo-substituted-C1-4 alkyl, halo-substituted-C1-4 alkoxy, amino, —$O(CH_2)_2NR_{10a}R_{10b}$, —$S(O)_2NR_{10a}R_{10b}$, —$OS(O)_2NR_{10a}R_{10b}$, and —$NR_{10a}S(O)_2R_{10b}$, wherein $R_{10a}$ and $R_{10b}$ are each independently selected from the group consisting of hydrogen, optionally substituted aryl, optionally substituted heteroaryl, optionally substituted alkyl, optionally substituted heteroalkyl, optionally substituted cycloalkyl, and optionally substituted heterocycloalkyl;

Ar is selected from the group consisting of optionally substituted monocyclic aryl and heteroaryl, such as optionally substituted thiophenyl, furanyl, 1H-benzoimidazolyl, isoquinolinyl, imidazopyridinyl, benzothiophenyl, pyrimidinyl, pyridinyl, 1H-imidazolyl, pyrazinyl, pyridazinyl, 1H-pyrrolyl, and thiazolyl;

$R_5$ is selected from the group consisting of optionally substituted aryl, optionally substituted heteroaryl, optionally substituted alkyl, optionally substituted heteroalkyl, optionally substituted cycloalkyl, and optionally substituted heterocycloalkyl; and $R_6$ is selected from the group consisting of hydrogen, optionally substituted aryl, optionally substituted heteroaryl, optionally substituted alkyl, optionally substituted heteroalkyl, optionally substituted cycloalkyl, and optionally substituted heterocycloalkyl;

or a salt thereof.

In some embodiments, A is selected from the group consisting of phenyl, phenol-4-yl, 1H-indol-2-yl, 1H-indol-3-yl, thiophen-3-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, and 2-oxo-2,3-dihydro-1H-benzo[d]imidazol-5-yl.

In some embodiments, A is selected from the group consisting of phenol-4-yl and 1H-indol-3-yl.

In some embodiments, the disclosure features a compound represented by formula (II-c)

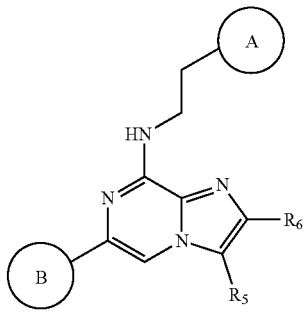

(II-c)

wherein A is an optionally substituted ring system selected from the group consisting of phenyl, 1H-pyrrolopyridinyl, 1H-pyrrolopyridinyl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl, and 1H-indazolyl, wherein the phenyl, 1H-pyrrolopyridinyl, 1H-pyrrolopyridinyl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl, or 1H-indazolyl is optionally substituted with from 1 to 3 substituents independently selected from the group consisting of cyano, hydroxy, C1-4 alkyl, $C_{1-4}$ alkoxy, halo, halo-substituted-C1-4 alkyl, halo-substituted-C1-4 alkoxy, amino, —O(CH$_2$)$_2$NR$_{10a}$R$_{10b}$, —S(O)$_2$NR$_{10a}$R$_{10b}$, —OS(O)$_2$NR$_{10a}$R$_{10b}$, and —NR$_{10a}$S(O)$_2$R$_{10b}$, wherein R$_{10a}$ and R$_{10b}$ are each independently selected from the group consisting of hydrogen, optionally substituted aryl, optionally substituted heteroaryl, optionally substituted alkyl, optionally substituted heteroalkyl, optionally substituted cycloalkyl, and optionally substituted heterocycloalkyl;

B is an optionally substituted ring system selected from the group consisting of thiophenyl, furanyl, 1H-benzoimidazolyl, isoquinolinyl, imidazopyridinyl, benzothiophenyl, pyrimidinyl, pyridinyl, 1H-imidazolyl, pyrazinyl, pyridazinyl, 1H-pyrrolyl, and thiazolyl, wherein the thiophenyl, furanyl, 1H-benzoimidazolyl, isoquinolinyl, 1H-imidazopyridinyl, benzothiophenyl, pyrimidinyl, pyridinyl, 1H-imidazolyl, pyrazinyl, pyridazinyl, 1H-pyrrolyl, or thiazolyl is optionally substituted with from 1 to 3 substituents independently selected from the group consisting of cyano, hydroxy, $C_1$-4 alkyl, C1-4 alkenyl, C1-4 alkynyl, C2-6 cycloalkyl, C1-4 alkoxy, halo, halo-substituted-C1-4 alkyl, halo-substituted-C1-4 alkoxy, amino, —C(O)R$_{11a}$, —S(O)$_{0-2}$R$_{11a}$, —C(O)OR$_{11a}$, and —C(O)NR$_{11a}$R$_{11b}$, wherein R$_{11a}$ and R$_{11b}$ are each independently selected from the group consisting of hydrogen and $C_{1-4}$ alkyl;

$R_5$ is selected from the group consisting of optionally substituted aryl, optionally substituted heteroaryl, optionally substituted alkyl, optionally substituted heteroalkyl, optionally substituted cycloalkyl, and optionally substituted heterocycloalkyl; and $R_6$ is selected from the group consisting of hydrogen, optionally substituted aryl, optionally substituted heteroaryl, optionally substituted alkyl, optionally substituted heteroalkyl, optionally substituted cycloalkyl, and optionally substituted heterocycloalkyl;

or a salt thereof.

In some embodiments, B is pyridin-3-yl, wherein the pyridin-3-yl is optionally substituted at C5, for example, with a substituent selected from the group consisting of ethoxycarbonyl, methoxy, cyano, methyl, methylsulfonyl, fluoro, chloro, trifluoromethyl, ethynyl, and cyclopropyl.

In some embodiments, the disclosure features a compound represented by formula (II-d)

(II-d)

wherein A is an optionally substituted ring system selected from the group consisting of phenyl, 1H-pyrrolopyridinyl, 1H-pyrrolopyridinyl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl, and 1H-indazolyl, wherein the phenyl, 1H-pyrrolopyridinyl, 1H-pyrrolopyridinyl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl, or 1H-indazolyl is optionally substituted with from 1 to 3 substituents independently selected from the group consisting of cyano, hydroxy, C1-4 alkyl, $C_{1-4}$ alkoxy, halo, halo-substituted-C1-4 alkyl, halo-substituted-C1-4 alkoxy, amino, —O(CH$_2$)$_2$NR$_{10a}$R$_{10b}$, —S(O)$_2$NR$_{10a}$R$_{10b}$, —OS(O)$_2$NR$_{10a}$R$_{10b}$, and —NR$_{10a}$S(O)$_2$R$_{10b}$, wherein R$_{10a}$ and R$_{10b}$ are each independently selected from the group consisting of hydrogen, optionally substituted aryl, optionally substituted heteroaryl, optionally substituted alkyl, optionally substituted heteroalkyl, optionally substituted cycloalkyl, and optionally substituted heterocycloalkyl;

B is an optionally substituted ring system selected from the group consisting of thiophenyl, furanyl, 1H-benzoimidazolyl, isoquinolinyl, imidazopyridinyl, benzothiophenyl, pyrimidinyl, pyridinyl, 1H-imidazolyl, pyrazinyl, pyridazinyl, 1H-pyrrolyl, and thiazolyl, wherein the thiophenyl, furanyl, 1H-benzoimidazolyl, isoquinolinyl, 1H-imidazopyridinyl, benzothiophenyl, pyrimidinyl, pyridinyl, 1H-imidazolyl, pyrazinyl, pyridazinyl, 1H-pyrrolyl, or thiazolyl is optionally substituted with from 1 to 3 substituents independently selected from the group consisting of cyano, hydroxy, $C_1$-4 alkyl, C1-4 alkenyl, C1-4 alkynyl, C2-6 cycloalkyl, C1-4 alkoxy, halo, halo-substituted-C1-4 alkyl, halo-substituted-C1-4 alkoxy, amino, —C(O)$R_{11a}$, —S(O)$_{0-2}R_{11a}$, —C(O)O$R_{11a}$, and —C(O)N$R_{11a}R_{11b}$, wherein $R_{11a}$ and $R_{11b}$ are each independently selected from the group consisting of hydrogen and $C_{1-4}$ alkyl; and $R_5$ is selected from the group consisting of optionally substituted aryl, optionally substituted heteroaryl, optionally substituted alkyl, optionally substituted heteroalkyl, optionally substituted cycloalkyl, and optionally substituted heterocycloalkyl;

or a salt thereof.

In some embodiments, the disclosure features a compound represented by formula (II-e)

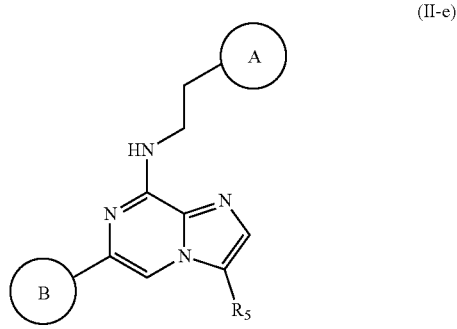

(II-e)

wherein A is an optionally substituted ring system selected from the group consisting of phenyl, 1H-indol-2-yl, 1H-indol-3-yl, thiophen-3-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, and 2-oxo-2,3-dihydro-1H-benzo[d]imidazol-5-yl, wherein the phenyl, 1H-indol-2-yl, 1H-indol-3-yl, thiophen-3-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, or 2-oxo-2,3-dihydro-1H-benzo[d]imidazol-5-yl is optionally substituted with from 1 to 3 substituents independently selected from the group consisting of cyano, hydroxy, C1-4 alkyl, C1-4 alkoxy, halo, halo-substituted-C1-4 alkyl, halo-substituted-C1-4 alkoxy, amino, —O(CH$_2$)$_2$N$R_{10a}R_{10b}$, —S(O)$_2$N$R_{10a}R_{10b}$, —OS(O)$_2$N$R_{10a}R_{10b}$, and —N$R_{10a}$S(O)$_2R_{10b}$, wherein $R_{10a}$ and $R_{10b}$ are each independently selected from the group consisting of hydrogen, optionally substituted aryl, optionally substituted heteroaryl, optionally substituted alkyl, optionally substituted heteroalkyl, optionally substituted cycloalkyl, and optionally substituted heterocycloalkyl;

B is an optionally substituted ring system selected from the group consisting of thiophen-2-yl, thiophen-3-yl, furan-3-yl, 1H-benzo[d]imidazol-1-yl, isoquinolin-4-yl, 1H-imidazo[4,5-b]pyridin-1-yl, imidazo[1,2-a]pyridin-3-yl, benzo[b]thiophen-3-yl, pyrimidin-5-yl, pyridin-2-yl, pyridin-3-yl, pyridin-4-yl, 1H-imidazol-1-yl, pyrazin-2-yl, pyridazin-4-yl, 1H-pyrrol-2-yl and thiazol-5-yl, wherein the thiophen-2-yl, thiophen-3-yl, furan-3-yl, 1H-benzo[d]imidazol-1-yl, isoquinolin-4-yl, 1H-imidazo[4,5-b]pyridin-1-yl, benzo[b]thiophen-3-yl, pyrimidin-5-yl, pyridin-2-yl, pyridin-3-yl, pyridin-4-yl, 1H-imidazol-1-yl, pyrazin-2-yl, pyridazin-4-yl, 1H-pyrrol-2-yl, or thiazol-5-yl is optionally substituted with from 1 to 3 substituents independently selected from the group consisting of cyano, hydroxy, $C_1$-4 alkyl, C1-4 alkenyl, C1-4 alkynyl, C2-6 cycloalkyl, C1-4 alkoxy, halo, halo-substituted-C1-4 alkyl, halo-substituted-C1-4 alkoxy, amino, —C(O)$R_{11a}$, —S(O)$_{0-2}R_{11a}$, —C(O)O$R_{11a}$, and —C(O)N$R_{11a}R_{11b}$, wherein $R_{11a}$ and $R_{11b}$ are each independently selected from the group consisting of hydrogen and $C_{1-4}$ alkyl; and $R_5$ is selected from the group consisting of C1-10 alkyl, prop-1-en-2-yl, cyclohexyl, cyclopropyl, 2-(2-oxopyrrolidin-1-yl)ethyl, oxetan-2-yl, oxetan-3-yl, benzhydryl, tetrahydro-2H-pyran-2-yl, tetrahydro-2H-pyran-3-yl, phenyl, tetrahydrofuran-3-yl, benzyl, (4-pentylphenyl)(phenyl)methyl, and 1-(1-(2-oxo-6,9,12-trioxa-3-azatetradecan-14-yl)-1H-1,2,3-triazol-4-yl)ethyl, wherein the C1-10 alkyl, prop-1-en-2-yl, cyclohexyl, cyclopropyl, 2-(2-oxopyrrolidin-1-yl)ethyl, oxetan-2-yl, oxetan-3-yl, benzhydryl, tetrahydro-2H-pyran-2-yl, tetrahydro-2H-pyran-3-yl, phenyl, tetrahydrofuran-3-yl, benzyl, (4-pentylphenyl)(phenyl)methyl, and 1-(1-(2-oxo-6,9,12-trioxa-3-azatetradecan-14-yl)-1H-1,2,3-triazol-4-yl)ethyl is optionally substituted with from 1 to 3 substituents independently selected from the group consisting of hydroxy, C1-4 alkyl, and halo-substituted-C1-4alkyl, or $R_5$ is selected from the group consisting of (i), (ii), (iii), (iv), and (v)

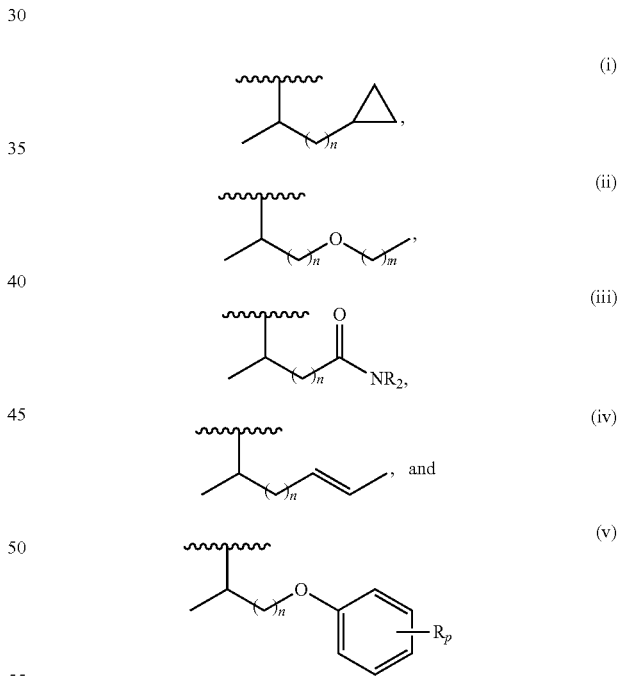

wherein n is an integer from 1 to 6, m is an integer from 0 to 6, p is an integer from 0 to 5, and each R is independently selected from the group consisting of cyano, hydroxy, C1-4 alkyl, C1-4 alkenyl, C1-4 alkynyl, C2-6 cycloalkyl, C1-4 alkoxy, halo, halo-substituted-C1-4 alkyl, halo-substituted-C1-4 alkoxy, amino, —C(O)$R_{12a}$, —S(O)$_{0-2}R_{12a}$, —C(O)O$R_{12a}$, and —C(O)N$R_{12a}R_{12b}$, and wherein $R_{12a}$ and $R_{12b}$ are each independently selected from the group consisting of hydrogen and C1-4 alkyl;

In some embodiments, R₅ is selected from the group consisting of:

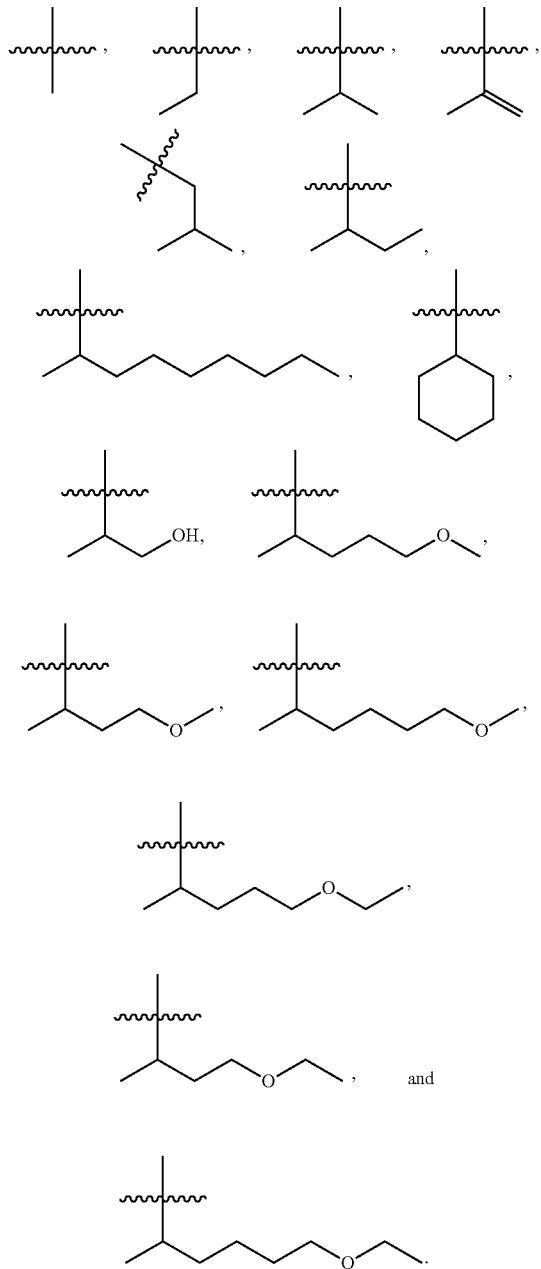

in some embodiments, R₅ is (ii);

in some embodiments, R₅ is selected from the group consisting of 4-methoxybutan-2-yl, (S)-4-methoxybutan-2-yl, (R)-4-methoxybutan-2-yl, 4-ethoxybutan-2-yl, (S)-4-ethoxybutan-2-yl, (R)-4-ethoxybutan-2-yl, 5-methoxypentan-2-yl, (S)-5-methoxypentan-2-yl, (R)-5-methoxypentan-2-yl, 5-ethoxypentan-2-yl, (S)-5-ethoxypentan-2-yl, (R)-5-ethoxypentan-2-yl, 6-methoxyhexan-2-yl, (S)-6-methoxyhexan-2-yl, (R)-6-methoxyhexan-2-yl, 6-ethoxyhexan-2-yl, (S)-6-ethoxyhexan-2-yl, and (R)-6-ethoxyhexan-2-yl;

or a salt thereof.

In some embodiments, the disclosure features a compound represented by formula (II-f)

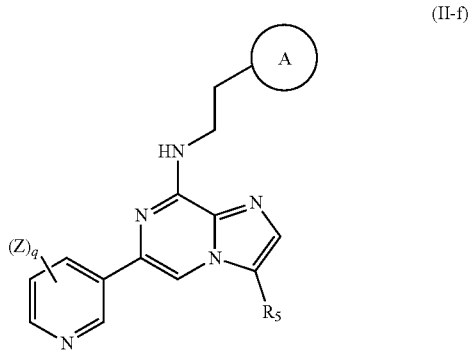

(II-f)

wherein A is an optionally substituted ring system selected from the group consisting of phenol-4-yl and 1H-indol-3-yl;

q is an integer from 0 to 4;

each Z is independently a substituent selected from the group consisting of C1-4 alkyl, halo, halo-substituted-C1-4 alkyl, C1-4 alkenyl, C1-4 alkynyl, C2-6 cycloalkyl, C1-4 alkoxy, cyano, amino, $C(O)R_{11a}$, $-S(O)_{0-2}R_{11a}$, $-C(O)OR_{11a}$, and $-C(O)NR_{11a}R_{11b}$, wherein $R_{11a}$ and $R_{11b}$ are each independently selected from the group consisting of hydrogen and $C_{1-4}$ alkyl; and R₅ is selected from the group consisting of isopropyl, methyl, ethyl, prop-1-en-2-yl, isobutyl, cyclohexyl, sec-butyl, (S)-sec-butyl, (R)-sec-butyl, 1-hydroxypropan-2-yl, (S)-1-hydroxypropan-2-yl, (R)-1-hydroxypropan-2-yl, and nonan-2-yl, or R₅ is selected from the group consisting of (i), (ii), (iii), (iv), and (v)

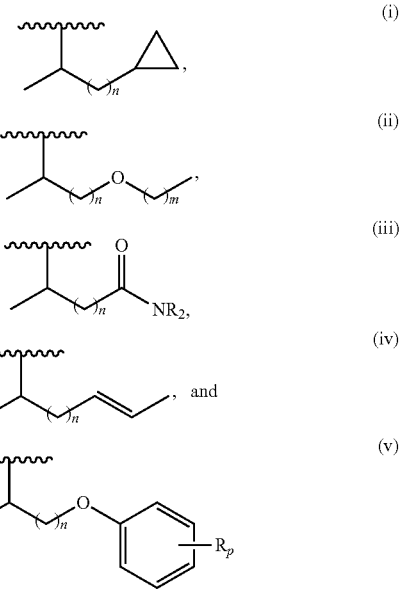

wherein n is an integer from 1 to 6, m is an integer from 0 to 6, p is an integer from 0 to 5, and each R is independently selected from the group consisting of cyano, hydroxy, $C_{1-4}$ alkyl, C1-4 alkenyl, C1-4 alkynyl, C2-6 cycloalkyl, C1-4 alkoxy, halo, halo-substituted-C1-4 alkyl, halo-substituted-C1-4 alkoxy, amino, —C(O)R$_{12a}$, —S(O)$_{0-2}$R$_{12a}$, —C(O)OR$_{12a}$, and —C(O)NR$_{12a}$R$_{12b}$, and wherein R$_{12a}$ and R$_{12b}$ are each independently selected from the group consisting of hydrogen and C$_{1-4}$ alkyl;

In some embodiments, R$_5$ is selected from the group consisting of:

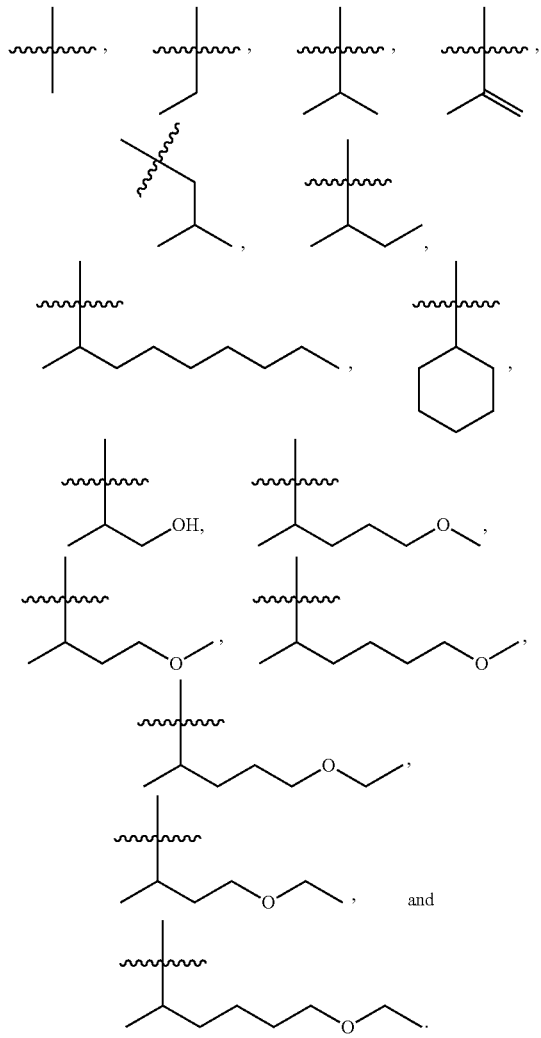

in some embodiments, R$_5$ is (ii);

in some embodiments, R$_5$ is selected from the group consisting of 4-methoxybutan-2-yl, (S)-4-methoxybutan-2-yl, (R)-4-methoxybutan-2-yl, 4-ethoxybutan-2-yl, (S)-4-ethoxybutan-2-yl, (R)-4-ethoxybutan-2-yl, 5-methoxypentan-2-yl, (S)-5-methoxypentan-2-yl, (R)-5-methoxypentan-2-yl, 5-ethoxypentan-2-yl, (S)-5-ethoxypentan-2-yl, (R)-5-ethoxypentan-2-yl, 6-methoxyhexan-2-yl, (S)-6-methoxyhexan-2-yl, (R)-6-methoxyhexan-2-yl, 6-ethoxyhexan-2-yl, (S)-6-ethoxyhexan-2-yl, and (R)-6-ethoxyhexan-2-yl;

or a salt thereof.

In some embodiments, each Z is independently a substituent selected from the group consisting of ethoxycarbonyl, methoxy, cyano, methyl, methylsulfonyl, fluoro, chloro, trifluoromethyl, ethynyl, and cyclopropyl.

In some embodiments, the disclosure features a compound represented by formula (II-g)

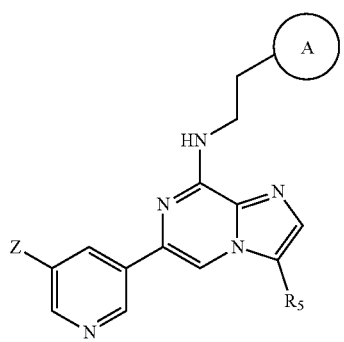

(II-g)

wherein A is an optionally substituted ring system selected from the group consisting of phenol-4-yl and 1H-indol-3-yl;

Z is a substituent selected from the group consisting of C1-4 alkyl, halo, halo-substituted-C1-4 alkyl, C1-4 alkenyl, C1-4 alkynyl, C2-6 cycloalkyl, C1-4 alkoxy, cyano, amino, C(O)R$_{11a}$, —S(O)$_{0-2}$R$_{11a}$, —C(O)OR$_{11a}$, and —C(O)NR$_{11a}$R$_{11b}$, wherein R$_{11a}$ and R$_{11b}$ are each independently selected from the group consisting of hydrogen and C$_{1-4}$ alkyl; and R$_5$ is selected from the group consisting of isopropyl, methyl, ethyl, prop-1-en-2-yl, isobutyl, cyclohexyl, sec-butyl, (S)-sec-butyl, (R)-sec-butyl, 1-hydroxypropan-2-yl, (S)-1-hydroxypropan-2-yl, (R)-1-hydroxypropan-2-yl, and nonan-2-yl, or R$_5$ is selected from the group consisting of (i), (ii), (iii), (iv), and (v)

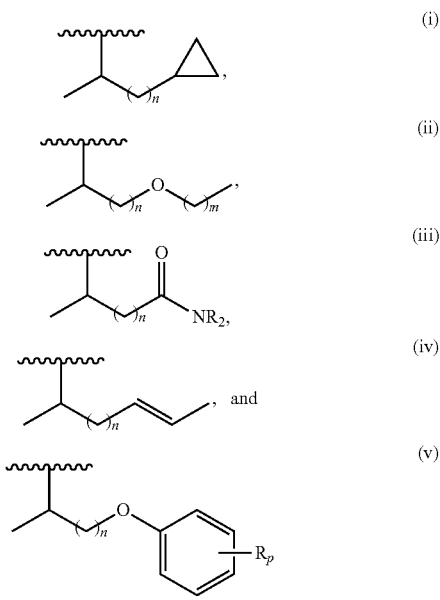

wherein n is an integer from 1 to 6, m is an integer from 0 to 6, p is an integer from 0 to 5, and each R is independently selected from the group consisting of cyano, hydroxy, C1-4 alkyl, C1-4 alkenyl, C1-4 alkynyl, C2-6 cycloalkyl, C1-4 alkoxy, halo, halo-substituted-C1-4 alkyl, halo-substituted-C1-4 alkoxy, amino, —C(O)R$_{12a}$, —S(O)$_{0-2}$R$_{12a}$, —C(O)OR$_{12a}$, and —C(O)NR$_{12a}$R$_{12b}$, and wherein R$_{11a}$ and R$_{11b}$ are each independently selected from the group consisting of hydrogen and C$_{1-4}$ alkyl;

In some embodiments, R$_5$ is selected from the group consisting of:

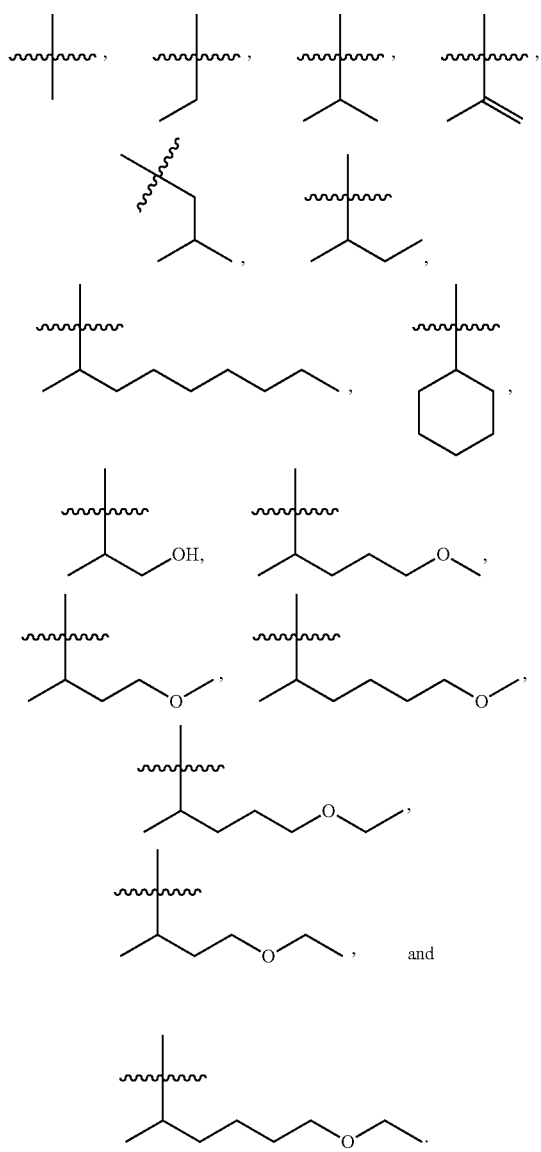

in some embodiments, R$_5$ is (ii);

in some embodiments, R$_5$ is selected from the group consisting of 4-methoxybutan-2-yl, (S)-4-methoxybutan-2-yl, (R)-4-methoxybutan-2-yl, 4-ethoxybutan-2-yl, (S)-4-ethoxybutan-2-yl, (R)-4-ethoxybutan-2-yl, 5-methoxypentan-2-yl, (S)-5-methoxypentan-2-yl, (R)-5-methoxypentan-2-yl, 5-ethoxypentan-2-yl, (S)-5-ethoxypentan-2-yl, (R)-5-ethoxypentan-2-yl, 6-methoxyhexan-2-yl, (S)-6-methoxyhexan-2-yl, (R)-6-methoxyhexan-2-yl, 6-ethoxyhexan-2-yl, (S)-6-ethoxyhexan-2-yl, and (R)-6-ethoxyhexan-2-yl;

or a salt thereof.

In some embodiments, the disclosure features a compound represented by formula (II-h)

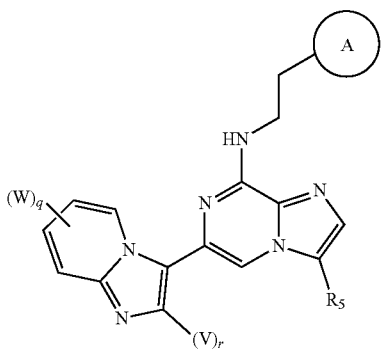

(II-h)

wherein A is an optionally substituted ring system selected from the group consisting of phenol-4-yl and 1H-indol-3-yl;

q is an integer from 0 to 4;

r is 0 or 1;

W and V are each independently a substituent selected from the group consisting of C1-4 alkyl, halo, halo-substituted-C1-4 alkyl, C1-4 alkenyl, C1-4 alkynyl, C2-6 cycloalkyl, C1-4 alkoxy, cyano, amino, C(O)R$_{11a}$, —S(O)$_{0-2}$R$_{11a}$, —C(O)OR$_{11a}$, and —C(O)NR$_{11a}$R$_{11b}$, wherein R$_{11a}$ and R$_{11b}$ are each independently selected from the group consisting of hydrogen and C$_{1-4}$ alkyl; and R$_5$ is selected from the group consisting of C1-10 alkyl, prop-1-en-2-yl, cyclohexyl, cyclopropyl, 2-(2-oxopyrrolidin-1-yl)ethyl, oxetan-2-yl, oxetan-3-yl, benzhydryl, tetrahydro-2H-pyran-2-yl, tetrahydro-2H-pyran-3-yl, phenyl, tetrahydrofuran-3-yl, benzyl, (4-pentylphenyl)(phenyl)methyl, and 1-(1-(2-oxo-6,9,12-trioxa-3-azatetradecan-14-yl)-1H-1,2,3-triazol-4-yl)ethyl, wherein the C1-10 alkyl, prop-1-en-2-yl, cyclohexyl, cyclopropyl, 2-(2-oxopyrrolidin-1-yl)ethyl, oxetan-2-yl, oxetan-3-yl, benzhydryl, tetrahydro-2H-pyran-2-yl, tetrahydro-2H-pyran-3-yl, phenyl, tetrahydrofuran-3-yl, benzyl, (4-pentylphenyl)(phenyl)methyl, or 1-(1-(2-oxo-6,9,12-trioxa-3-azatetradecan-14-yl)-1H-1,2,3-triazol-4-yl)ethyl is optionally substituted with from 1 to 3 substituents independently selected from the group consisting of hydroxy, C1-4 alkyl, and halo-substituted-C1-4alkyl, or R$_5$ is selected from the group consisting of (i), (ii), (iii), (iv), and (v)

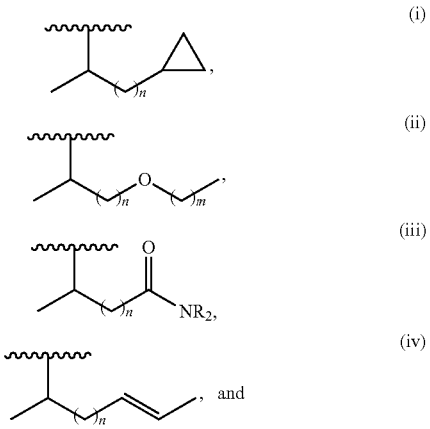

-continued

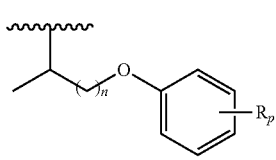
(v)

wherein n is an integer from 1 to 6, m is an integer from 0 to 6, p is an integer from 0 to 5, and each R is independently selected from the group consisting of cyano, hydroxy, C1-4 alkyl, C1-4 alkenyl, C1-4 alkynyl, C2-6 cycloalkyl, C1-4 alkoxy, halo, halo-substituted-C1-4 alkyl, halo-substituted-C1-4 alkoxy, amino, —C(O)$R_{12a}$, —S(O)$_{0-2}R_{12a}$, —C(O)O$R_{12a}$, and —C(O)N$R_{12a}R_{12b}$, and wherein $R_{12a}$ and $R_{12b}$ are each independently selected from the group consisting of hydrogen and $C_{1-4}$ alkyl;

In some embodiments, $R_5$ is selected from the group consisting of:

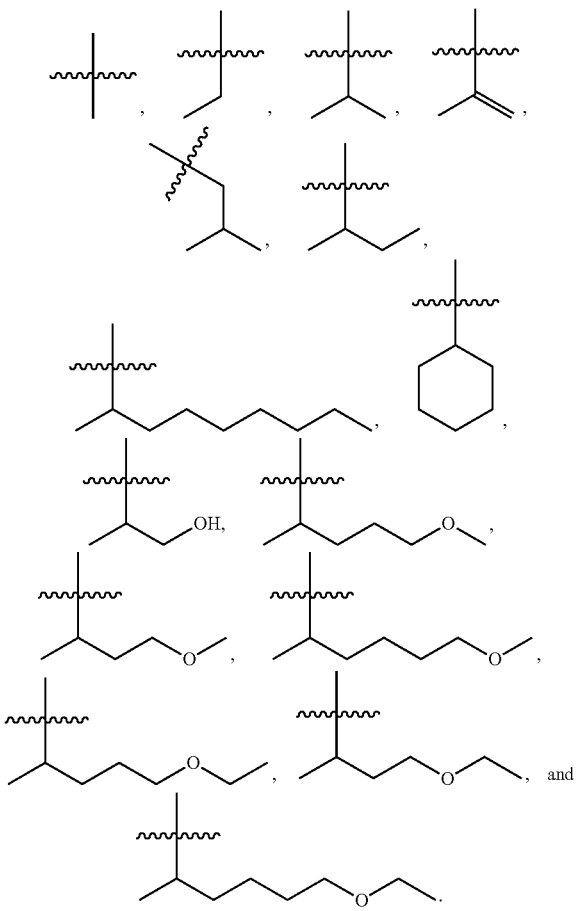

in some embodiments, $R_5$ is (ii);

in some embodiments, $R_5$ is selected from the group consisting of 4-methoxybutan-2-yl, (S)-4-methoxybutan-2-yl, (R)-4-methoxybutan-2-yl, 4-ethoxybutan-2-yl, (S)-4-ethoxybutan-2-yl, (R)-4-ethoxybutan-2-yl, 5-methoxypentan-2-yl, (S)-5-methoxypentan-2-yl, (R)-5-methoxypentan-2-yl, 5-ethoxypentan-2-yl, (S)-5-ethoxypentan-2-yl, (R)-5-ethoxypentan-2-yl, 6-methoxyhexan-2-yl, (S)-6-methoxyhexan-2-yl, (R)-6-methoxyhexan-2-yl, 6-ethoxyhexan-2-yl, (S)-6-ethoxyhexan-2-yl, and (R)-6-ethoxyhexan-2-yl;

or a salt thereof.

In some embodiments, the disclosure features a compound represented by formula (II-i)

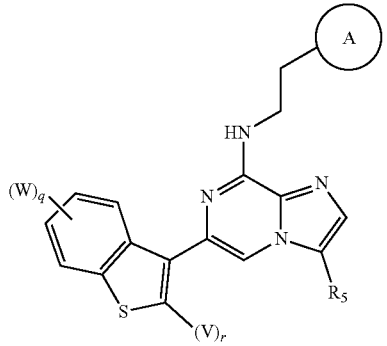
(II-i)

wherein A is an optionally substituted ring system selected from the group consisting of phenol-4-yl and 1H-indol-3-yl;

q is an integer from 0 to 4;

r is 0 or 1;

W and V are each independently a substituent selected from the group consisting of C1-4 alkyl, halo, halo-substituted-C1-4 alkyl, C1-4 alkenyl, C1-4 alkynyl, C2-6 cycloalkyl, C1-4 alkoxy, cyano, amino, C(O)$R_{11a}$, —S(O)$_{0-2}R_{11a}$, —C(O)O$R_{11a}$, and —C(O)N$R_{11a}R_{11b}$, wherein $R_{11a}$ and $R_{11b}$ are each independently selected from the group consisting of hydrogen and $C_{1-4}$ alkyl; and $R_5$ is selected from the group consisting of C1-10 alkyl, prop-1-en-2-yl, cyclohexyl, cyclopropyl, 2-(2-oxopyrrolidin-1-yl)ethyl, oxetan-2-yl, oxetan-3-yl, benzhydryl, tetrahydro-2H-pyran-2-yl, tetrahydro-2H-pyran-3-yl, phenyl, tetrahydrofuran-3-yl, benzyl, (4-pentylphenyl)(phenyl)methyl, and 1-(1-(2-oxo-6,9,12-trioxa-3-azatetradecan-14-yl)-1H-1,2,3-triazol-4-yl)ethyl, wherein the C1-10 alkyl, prop-1-en-2-yl, cyclohexyl, cyclopropyl, 2-(2-oxopyrrolidin-1-yl)ethyl, oxetan-2-yl, oxetan-3-yl, benzhydryl, tetrahydro-2H-pyran-2-yl, tetrahydro-2H-pyran-3-yl, phenyl, tetrahydrofuran-3-yl, benzyl, (4-pentylphenyl)(phenyl)methyl, or 1-(1-(2-oxo-6,9,12-trioxa-3-azatetradecan-14-yl)-1H-1,2,3-triazol-4-yl)ethyl is optionally substituted with from 1 to 3 substituents independently selected from the group consisting of hydroxy, C1-4 alkyl, and halo-substituted-C1-4alkyl, or $R_5$ is selected from the group consisting of (i), (ii), (iii), (iv), and (v)

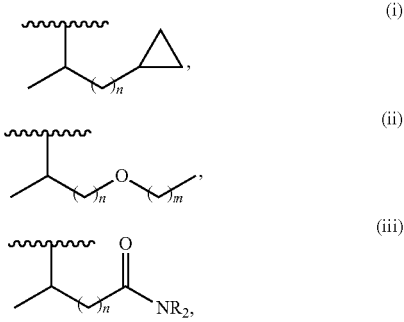

-continued

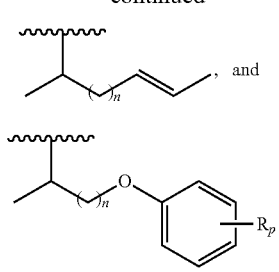

wherein n is an integer from 1 to 6, m is an integer from 0 to 6, p is an integer from 0 to 5, and each R is independently selected from the group consisting of cyano, hydroxy, C1-4 alkyl, C1-4 alkenyl, C1-4 alkynyl, C2-6 cycloalkyl, C1-4 alkoxy, halo, halo-substituted-C1-4 alkyl, halo-substituted-C1-4 alkoxy, amino, —C(O)R$_{12a}$, —S(O)$_{0-2}$R$_{12a}$, —C(O)OR$_{12a}$, and —C(O)NR$_{12a}$R$_{12b}$, and wherein R$_{12a}$ and R$_{12b}$ are each independently selected from the group consisting of hydrogen and C$_{1-4}$ alkyl;

In some embodiments, R$_5$ is selected from the group consisting of:

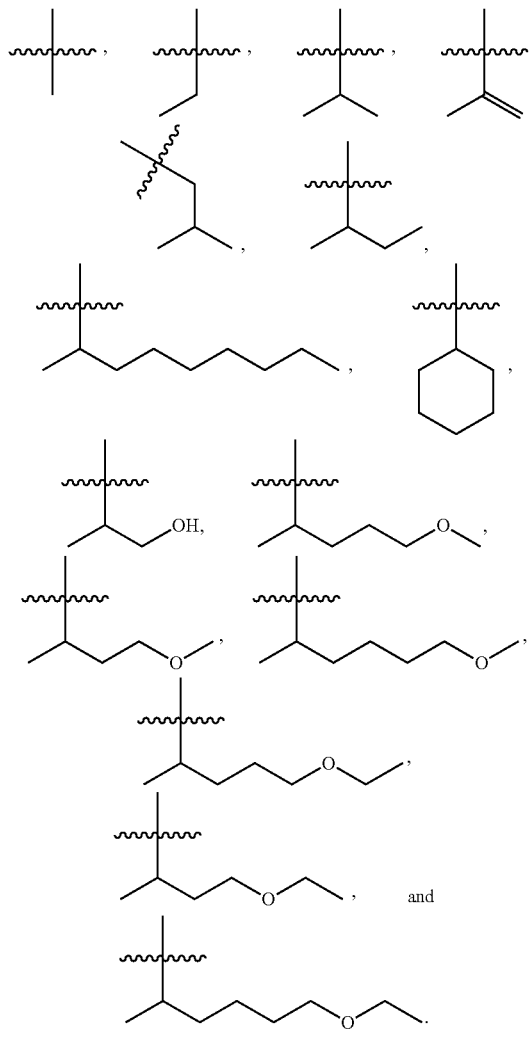

in some embodiments, R$_5$ is (ii);

in some embodiments, R$_5$ is selected from the group consisting of 4-methoxybutan-2-yl, (S)-4-methoxybutan-2-yl, (R)-4-methoxybutan-2-yl, 4-ethoxybutan-2-yl, (S)-4-ethoxybutan-2-yl, (R)-4-ethoxybutan-2-yl, 5-methoxypentan-2-yl, (S)-5-methoxypentan-2-yl, (R)-5-methoxypentan-2-yl, 5-ethoxypentan-2-yl, (S)-5-ethoxypentan-2-yl, (R)-5-ethoxypentan-2-yl, 6-methoxyhexan-2-yl, (S)-6-methoxyhexan-2-yl, (R)-6-methoxyhexan-2-yl, 6-ethoxyhexan-2-yl, (S)-6-ethoxyhexan-2-yl, and (R)-6-ethoxyhexan-2-yl;

or a salt thereof.

In some embodiments, the disclosure features a compound represented by formula (II-j)

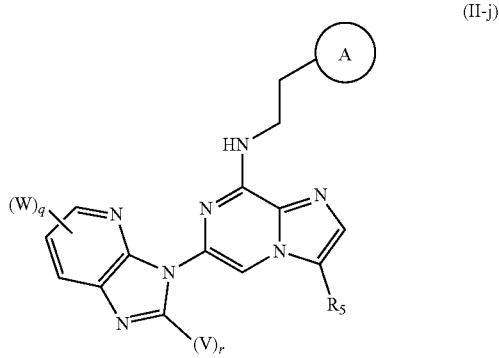

(II-j)

wherein A is an optionally substituted ring system selected from the group consisting of phenol-4-yl and 1H-indol-3-yl;

q is an integer from 0 to 4;

r is 0 or 1;

W and V are each independently a substituent selected from the group consisting of C1-4 alkyl, halo, halo-substituted-C1-4 alkyl, C1-4 alkenyl, C1-4 alkynyl, C2-6 cycloalkyl, C1-4 alkoxy, cyano, amino, C(O)R$_{11a}$, —S(O)$_{0-2}$R$_{11a}$, —C(O)OR$_{11a}$, and —C(O)NR$_{11a}$R$_{11b}$, wherein R$_{11a}$ and R$_{11b}$ are each independently selected from the group consisting of hydrogen and C$_{1-4}$ alkyl; and R$_5$ is selected from the group consisting of C1-10 alkyl, prop-1-en-2-yl, cyclohexyl, cyclopropyl, 2-(2-oxopyrrolidin-1-yl)ethyl, oxetan-2-yl, oxetan-3-yl, benzhydryl, tetrahydro-2H-pyran-2-yl, tetrahydro-2H-pyran-3-yl, phenyl, tetrahydrofuran-3-yl, benzyl, (4-pentylphenyl)(phenyl)methyl, and 1-(1-(2-oxo-6,9,12-trioxa-3-azatetradecan-14-yl)-1H-1,2,3-triazol-4-yl)ethyl, wherein the C1-10 alkyl, prop-1-en-2-yl, cyclohexyl, cyclopropyl, 2-(2-oxopyrrolidin-1-yl)ethyl, oxetan-2-yl, oxetan-3-yl, benzhydryl, tetrahydro-2H-pyran-2-yl, tetrahydro-2H-pyran-3-yl, phenyl, tetrahydrofuran-3-yl, benzyl, (4-pentylphenyl)(phenyl)methyl, or 1-(1-(2-oxo-6,9,12-trioxa-3-azatetradecan-14-yl)-1H-1,2,3-triazol-4-yl)ethyl is optionally substituted with from 1 to 3 substituents independently selected from the group consisting of hydroxy, C1-4 alkyl, and halo-substituted-C1-4alkyl, or R$_5$ is selected from the group consisting of (i), (ii), (iii), (iv), and (v)

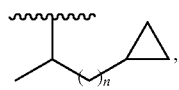

(i)

-continued

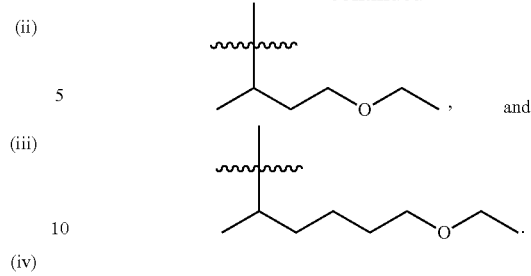

in some embodiments, $R_5$ is (ii);

in some embodiments, $R_5$ is selected from the group consisting of 4-methoxybutan-2-yl, (S)-4-methoxybutan-2-yl, (R)-4-methoxybutan-2-yl, 4-ethoxybutan-2-yl, (S)-4-ethoxybutan-2-yl, (R)-4-ethoxybutan-2-yl, 5-methoxypentan-2-yl, (S)-5-methoxypentan-2-yl, (R)-5-methoxypentan-2-yl, 5-ethoxypentan-2-yl, (S)-5-ethoxypentan-2-yl, (R)-5-ethoxypentan-2-yl, 6-methoxyhexan-2-yl, (S)-6-methoxyhexan-2-yl, (R)-6-methoxyhexan-2-yl, 6-ethoxyhexan-2-yl, (S)-6-ethoxyhexan-2-yl, and (R)-6-ethoxyhexan-2-yl;

or a salt thereof.

In some embodiments, the disclosure features a compound represented by formula (II-k)

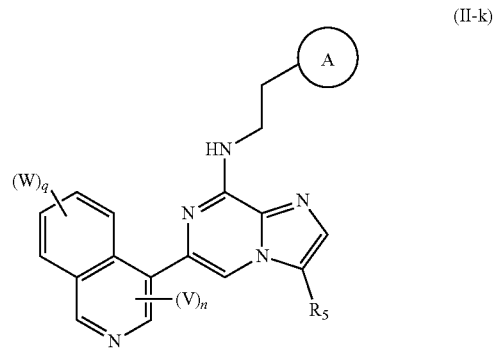

wherein A is an optionally substituted ring system selected from the group consisting of phenol-4-yl and 1H-indol-3-yl;

q is an integer from 0 to 4;

r is 0 or 1;

W and V are each independently a substituent selected from the group consisting of C1-4 alkyl, halo, halo-substituted-C1-4 alkyl, C1-4 alkenyl, C1-4 alkynyl, C2-6 cycloalkyl, C1-4 alkoxy, cyano, amino, $C(O)R_{11a}$, $—S(O)_{0-2}R_{11a}$, $—C(O)OR_{11a}$, and $—C(O)NR_{11a}R_{11b}$, wherein $R_{11a}$ and $R_{11b}$ are each independently selected from the group consisting of hydrogen and $C_{1-4}$ alkyl; and $R_5$ is selected from the group consisting of C1-10 alkyl, prop-1-en-2-yl, cyclohexyl, cyclopropyl, 2-(2-oxopyrrolidin-1-yl)ethyl, oxetan-2-yl, oxetan-3-yl, benzhydryl, tetrahydro-2H-pyran-2-yl, tetrahydro-2H-pyran-3-yl, phenyl, tetrahydrofuran-3-yl, benzyl, (4-pentylphenyl)(phenyl)methyl, and 1-(1-(2-oxo-6,9,12-trioxa-3-azatetradecan-14-yl)-1H-1,2,3-triazol-4-yl)ethyl, wherein the C1-10 alkyl, prop-1-en-2-yl, cyclohexyl, cyclopropyl, 2-(2-oxopyrrolidin-1-yl)ethyl, oxetan-2-yl, oxetan-3-yl, benzhydryl, tetrahydro-2H-pyran-2-yl, tetrahydro-2H-pyran-3-yl, phenyl, tetrahydrofuran-3-yl, benzyl, (4-pentylphenyl)(phenyl)methyl, or 1-(1-(2-oxo-6,9,12-trioxa-3-azatetradecan-14-

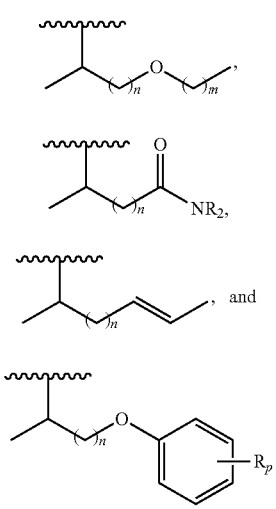

wherein n is an integer from 1 to 6, m is an integer from 0 to 6, p is an integer from 0 to 5, and each R is independently selected from the group consisting of cyano, hydroxy, C1-4 alkyl, C1-4 alkenyl, C1-4 alkynyl, C2-6 cycloalkyl, C1-4 alkoxy, halo, halo-substituted-C1-4 alkyl, halo-substituted-C1-4 alkoxy, amino, $—C(O)R_{12a}$, $—S(O)_{0-2}R_{12a}$, $—C(O)OR_{12a}$, and $—C(O)NR_{12a}R_{12b}$, and wherein $R_{12a}$ and $R_{12b}$ are each independently selected from the group consisting of hydrogen and $C_{1-4}$ alkyl;

In some embodiments, $R_5$ is selected from the group consisting of:

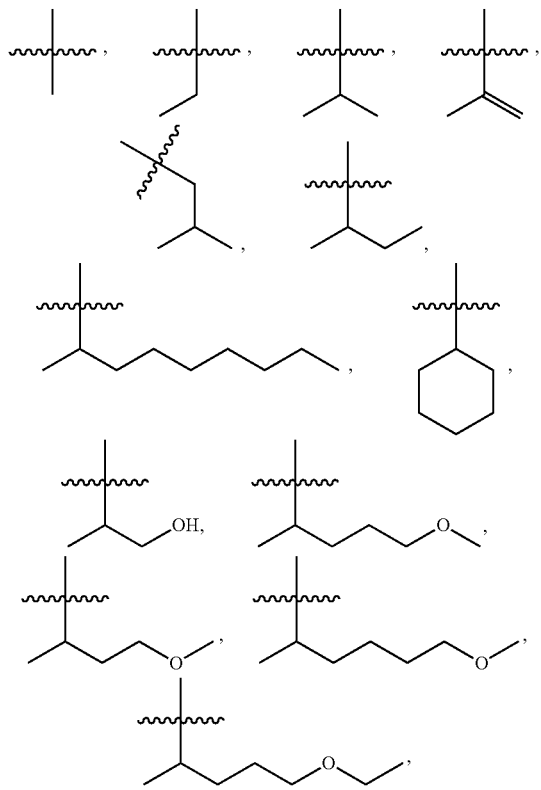

yl)-1H-1,2,3-triazol-4-yl)ethyl is optionally substituted with from 1 to 3 substituents independently selected from the group consisting of hydroxy, C1-4 alkyl, and halo-substituted-C1-4alkyl, or $R_5$ is selected from the group consisting of (i), (ii), (iii), (iv), and (v)

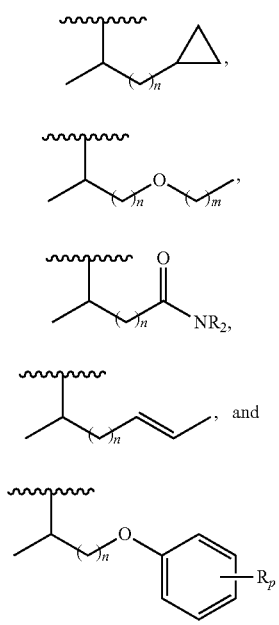

wherein n is an integer from 1 to 6, m is an integer from 0 to 6, p is an integer from 0 to 5, and each R is independently selected from the group consisting of cyano, hydroxy, $C_{1-4}$ alkyl, C1-4 alkenyl, C1-4 alkynyl, C2-6 cycloalkyl, C1-4 alkoxy, halo, halo-substituted-C1-4 alkyl, halo-substituted-C1-4 alkoxy, amino, —C(O)$R_{12a}$, —S(O)$_{0-2}R_{12a}$, —C(O)O$R_{12a}$, and —C(O)N$R_{12a}R_{12b}$, and wherein $R_{12a}$ and $R_{12b}$ are each independently selected from the group consisting of hydrogen and $C_{1-4}$ alkyl;

In some embodiments, $R_5$ is selected from the group consisting of:

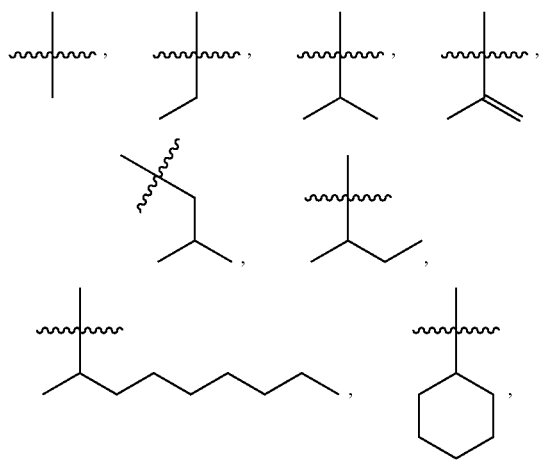

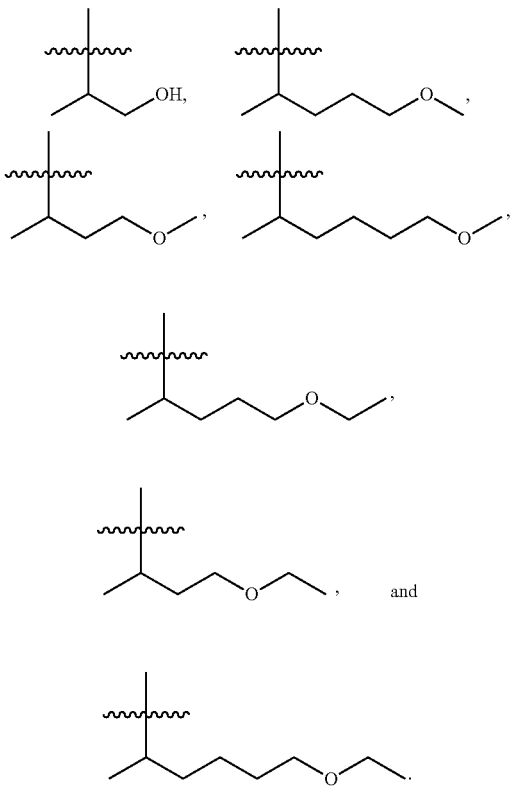

in some embodiments, $R_5$ is (ii);

in some embodiments, $R_5$ is selected from the group consisting of 4-methoxybutan-2-yl, (S)-4-methoxybutan-2-yl, (R)-4-methoxybutan-2-yl, 4-ethoxybutan-2-yl, (S)-4-ethoxybutan-2-yl, (R)-4-ethoxybutan-2-yl, 5-methoxypentan-2-yl, (S)-5-methoxypentan-2-yl, (R)-5-methoxypentan-2-yl, 5-ethoxypentan-2-yl, (S)-5-ethoxypentan-2-yl, (R)-5-ethoxypentan-2-yl, 6-methoxyhexan-2-yl, (S)-6-methoxyhexan-2-yl, (R)-6-methoxyhexan-2-yl, 6-ethoxyhexan-2-yl, (S)-6-ethoxyhexan-2-yl, and (R)-6-ethoxyhexan-2-yl;

or a salt thereof.

In some embodiments, the compound is compound (12)

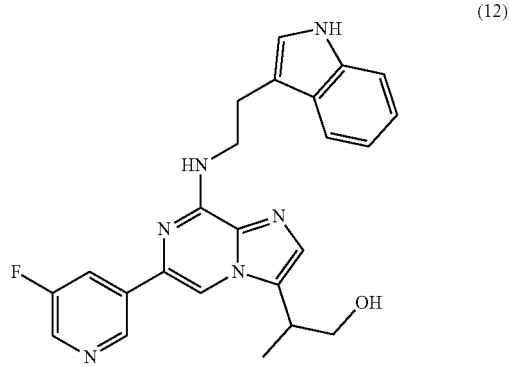 [SMILES: CC(CO)c1cnc2c(NCCc3c[nH]c4ccccc34)nc(-c3cncc(F)c3)cn12]

or a salt thereof.

In some embodiments, the compound is compound (13)

(13)

or a salt thereof.

In some embodiments, the compound is compound (14)

(14)

or a salt thereof.

In some embodiments, the compound is compound (15)

(15)

or a salt thereof.

In some embodiments, the compound is compound (16)

(16)

or a salt thereof.

In some embodiments, the compound is compound (17)

(17)

or a salt thereof.

In some embodiments, the compound is compound (18)

(18)

or a salt thereof.

In some embodiments, the compound is compound (19)

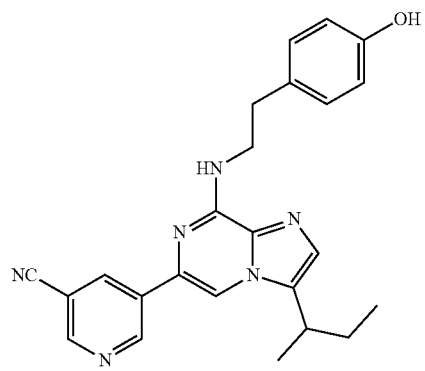

(19)

or a salt thereof.

In some embodiments, the compound is compound (20)

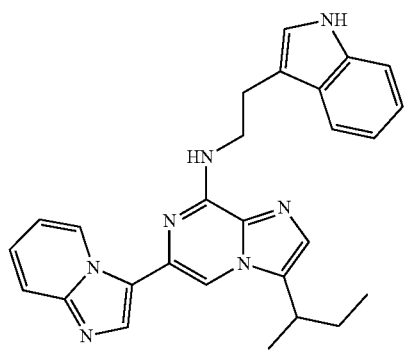

(20)

or a salt thereof.

In some embodiments, the compound is compound (21)

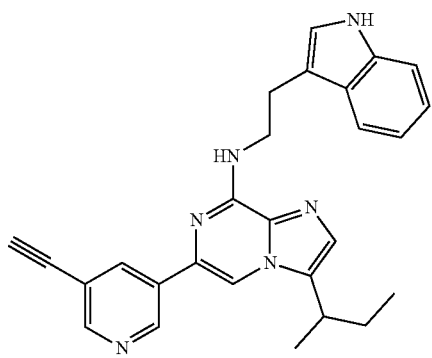

(21)

or a salt thereof.

In some embodiments, the compound is compound (22)

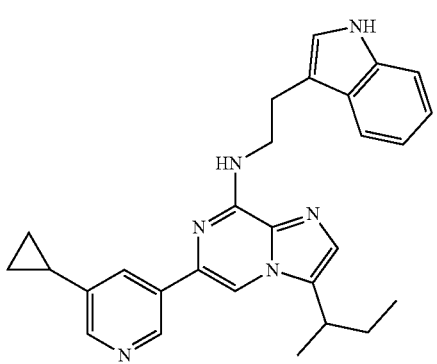

(22)

or a salt thereof.

In some embodiments, the compound is compound (24)

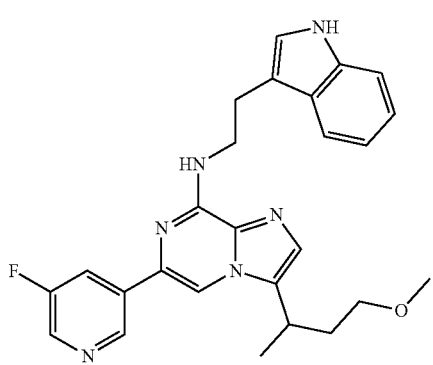

(24)

or a salt thereof.

In some embodiments, the compound is compound (27)

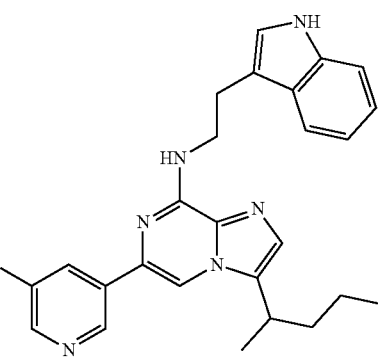

(27)

or a salt thereof.

In some embodiments, the compound is compound (28)

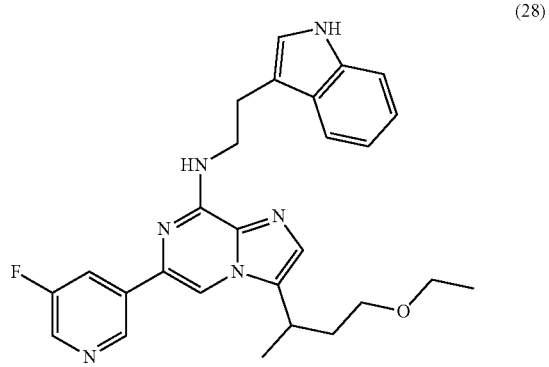 [SMILES: CCOCCC(C)c1cnc2c(NCCc3c[nH]c4ccccc34)nc(-c3cncc(F)c3)cn12]

(28)

or a salt thereof.

In another aspect, the disclosure features a method of producing an expanded population of hematopoietic stem cells ex vivo, the method including contacting a population of hematopoietic stem cells with the compound of any one of the above aspects or embodiments in an amount sufficient to produce an expanded population of hematopoietic stem cells.

In another aspect, the disclosure features a method of enriching a population of cells with hematopoietic stem cells ex vivo, the method including contacting a population of hematopoietic stem cells with the compound of any one of the above aspects or embodiments in an amount sufficient to produce a population of cells enriched with hematopoietic stem cells.

In another aspect, the disclosure features a method of maintaining the hematopoietic stem cell functional potential of a population of hematopoietic stem cells ex vivo for two or more days, the method including contacting a first population of hematopoietic stem cells with the compound of any one of the above aspects or embodiments, wherein the first population of hematopoietic stem cells exhibits a hematopoietic stem cell functional potential after two or more days that is greater than that of a control population of hematopoietic stem cells cultured under the same conditions and for the same time as the first population of hematopoietic stem cells but not contacted with the compound.

In some embodiments, the first population of hematopoietic stem cells exhibits a hematopoietic stem cell functional potential after three or more days (for example, three days, ten days, thirty days, sixty days, or more) of culture that is greater than that of the control population of hematopoietic stem cells.

In some embodiments, the hematopoietic stem cells are mammalian cells, such as human cells. In some embodiments, the human cells are CD34+ cells, such as CD34+ cells are CD34+, CD34+ CD38−, CD34+CD38−CD90+, CD34+CD38−CD90+CD45RA−, CD34+CD38−CD90+CD45RA−CD49F+, or CD34+CD90+CD45RA− cells.

In some embodiments, the hematopoietic stem cells are CD34+ hematopoietic stem cells. In some embodiments, the hematopoietic stem cells are CD90+ hematopoietic stem cells. In some embodiments, the hematopoietic stem cells are CD45RA− hematopoietic stem cells. In some embodiments, the hematopoietic stem cells are CD34+CD90+ hematopoietic stem cells. In some embodiments, the hematopoietic stem cells are CD34+CD45RA− hematopoietic stem cells. In some embodiments, the hematopoietic stem cells are CD90+CD45RA− hematopoietic stem cells. In some embodiments, the hematopoietic stem cells are CD34+CD90+CD45RA− hematopoietic stem cells.

In some embodiments, the hematopoietic stem cells are obtained from human cord blood, mobilized human peripheral blood, or human bone marrow. The hematopoietic stem cells may, for example, be freshly isolated from the human or may have been previously cryopreserved.

In some embodiments, the hematopoietic stem cells or progeny thereof maintain hematopoietic stem cell functional potential after two or more days upon transplantation of the hematopoietic stem cells into a human subject.

In some embodiments, the hematopoietic stem cells or progeny thereof are capable of localizing to hematopoietic tissue and reestablishing hematopoiesis upon transplantation of the hematopoietic stem cells into a human subject.

In some embodiments, upon transplantation into a human subject, the hematopoietic stem cells give rise to a population of cells selected from the group consisting of megakaryocytes, thrombocytes, platelets, erythrocytes, mast cells, myoblasts, basophils, neutrophils, eosinophils, microglia, granulocytes, monocytes, osteoclasts, antigen-presenting cells, macrophages, dendritic cells, natural killer cells, T-lymphocytes, and B-lymphocytes.

In another aspect, the disclosure features a method of treating a patient (e.g., a human patient) suffering from a stem cell disorder, the method including administering to the patient a population of hematopoietic stem cells, wherein the hematopoietic stem cells were produced by contacting the hematopoietic stem cells or progenitors thereof with a compound of any of the above aspects or embodiments.

In another aspect, the disclosure features a method of preparing an expanded population of hematopoietic stem cells for transplantation into a patient (e.g., a human patient) suffering from a stem cell disorder, the method including contacting a first population of hematopoietic stem cells with a compound of any of the above aspects or embodiments for a time sufficient to produce the expanded population of hematopoietic stem cells.

In another aspect, the disclosure features a method of treating a patient (e.g., a human patient) suffering from a stem cell disorder, the method including:
a. preparing an expanded population of hematopoietic stem cells by contacting a first population of hematopoietic stem cells with a compound of any of the above aspects or embodiments; and
b. administering the expanded population of hematopoietic stem cells to the patient.

In yet another aspect, provided herein is a method of treating a stem cell disorder in a patient (e.g., a human patient) in need thereof, comprising administering an expanded population of hematopoietic stem cells to the patient, wherein the expanded population of hematopoietic stem cells is prepared by contacting a first population of hematopoietic stem cells with a compound of any of the above aspects or embodiments for a time sufficient to produce the expanded population of hematopoietic stem cells.

In some embodiments, the stem cell disorder is a hemoglobinopathy.

In some embodiments, the stem cell disorder is selected from the group consisting of sickle cell anemia, thalassemia, Fanconi anemia, and Wiskott-Aldrich syndrome.

In some embodiments, the stem cell disorder is Fanconi anemia.

In some embodiments, the stem cell disorder is a myelodysplastic disorder.

In some embodiments, the stem cell disorder is an immunodeficiency disorder, such as a congenital immunodeficiency or an acquired immunodeficiency. The acquired immunodeficiency may be, for example, human immunodeficiency virus (HIV) or acquired immune deficiency syndrome (AIDS).

In some embodiments, the stem cell disorder is a metabolic disorder, such as a glycogen storage disease, a mucopolysaccharidose, Gaucher's Disease, Hurlers Disease, a sphingolipidose, or metachromatic leukodystrophy.

In some embodiments, the stem cell disorder is cancer, such as a hematological cancer. The cancer may be, for example, leukemia, lymphoma, multiple myeloma, or neuroblastoma. In some embodiments, the cancer is acute myeloid leukemia, acute lymphoid leukemia, chronic myeloid leukemia, chronic lymphoid leukemia, multiple myeloma, diffuse large B-cell lymphoma, or non-Hodgkin's lymphoma.

In some embodiments, the stem cell disorder is a disorder selected from the group consisting of adenosine deaminase deficiency and severe combined immunodeficiency, hyper immunoglobulin M syndrome, Chediak-Higashi disease, hereditary lymphohistiocytosis, osteopetrosis, osteogenesis imperfecta, storage diseases, thalassemia major, systemic sclerosis, systemic lupus erythematosus, multiple sclerosis, and juvenile rheumatoid arthritis.

In some embodiments, the stem cell disorder is an autoimmune disorder. For example, the stem cell disorder may be multiple sclerosis, human systemic lupus, rheumatoid arthritis, inflammatory bowel disease, treating psoriasis, Type 1 diabetes mellitus, acute disseminated encephalomyelitis, Addison's disease, alopecia universalis, ankylosing spondylitisis, antiphospholipid antibody syndrome, aplastic anemia, autoimmune hemolytic anemia, autoimmune hepatitis, autoimmune inner ear disease, autoimmune lymphoproliferative syndrome, autoimmune oophoritis, Balo disease, Behcet's disease, bullous pemphigoid, cardiomyopathy, Chagas' disease, chronic fatigue immune dysfunction syndrome, chronic inflammatory demyelinating polyneuropathy, Crohn's disease, cicatrical pemphigoid, coeliac sprue-dermatitis herpetiformis, cold agglutinin disease, CREST syndrome, Degos disease, discoid lupus, dysautonomia, endometriosis, essential mixed cryoglobulinemia, fibromyalgia-fibromyositis, Goodpasture's syndrome, Grave's disease, Guillain-Barre syndrome, Hashimoto's thyroiditis, Hidradenitis suppurativa, idiopathic and/or acute thrombocytopenic purpura, idiopathic pulmonary fibrosis, IgA neuropathy, interstitial cystitis, juvenile arthritis, Kawasaki's disease, lichen planus, Lyme disease, Meniere disease, mixed connective tissue disease, myasthenia gravis, neuromyotonia, opsoclonus myoclonus syndrome, optic neuritis, Ord's thyroiditis, pemphigus vulgaris, pernicious anemia, polychondritis, polymyositis and dermatomyositis, primary biliary cirrhosis, polyarteritis nodosa, polyglandular syndromes, polymyalgia rheumatica, primary agammaglobulinemia, Raynaud phenomenon, Reiter's syndrome, rheumatic fever, sarcoidosis, scleroderma, Sjögren's syndrome, stiff person syndrome, Takayasu's arteritis, temporal arteritis, ulcerative colitis, uveitis, vasculitis, vitiligo, vulvodynia, or Wegener's granulomatosis.

In some embodiments, the stem cell disorder is a neurological disorder, such as Parkinson's disease, Alzheimer's disease, multiple sclerosis, Amyotrophic lateral sclerosis, Huntington's disease, mild cognitive impairment, amyloidosis, AIDS-related dementia, encephalitis, stroke, head trauma, epilepsy, mood disorders, or dementia.

In another aspect, provided herein is a method of producing microglia in the central nervous system of a patient (e.g., a human patient) in need thereof, comprising administering an expanded population of hematopoietic stem cells to the patient, wherein the expanded population of hematopoietic stem cells is prepared by contacting a first population of hematopoietic stem cells with a compound of any of the above aspects or embodiments for a time sufficient to produce the expanded population of hematopoietic stem cells, and wherein administration of the expanded population of hematopoietic stem cells results in formation of microglia in the central nervous system of the patient.

In another aspect, the disclosure features a composition comprising a population of hematopoietic stem cells, wherein the hematopoietic stem cells or progenitors thereof have been contacted with the compound of any one of the above aspects or embodiments, thereby expanding the hematopoietic stem cells or progenitors thereof.

In another aspect, the disclosure features a kit including the compound of any one of the above aspects or embodiments and a package insert, wherein the package insert instructs a user of the kit to contact a population of hematopoietic stem cells with the compound for a time sufficient to produce an expanded population of hematopoietic stem cells.

In another aspect, the disclosure features a kit including the compound of any one of the above aspects or embodiments and a package insert, wherein the package insert instructs a user of the kit to contact a population of cells including hematopoietic stem cells with the compound for a time sufficient to produce a population of cells enriched with hematopoietic stem cells.

In another aspect, the disclosure features a kit including the compound of any one of the above aspects or embodiments and a package insert, wherein the package insert instructs a user of the kit to contact a population of hematopoietic stem cells with the compound for a time sufficient to maintain the hematopoietic stem cell functional potential of the population of hematopoietic stem cells ex vivo for two or more days. In some embodiments, the kit further includes a population of cells including hematopoietic stem cells.

In another aspect, the disclosure features a compound of any of the above aspects or embodiments for use in producing an expanded population of hematopoietic stem cells ex vivo.

In another aspect, the disclosure features a compound of any of the above aspects or embodiments for use in enriching a population of cells with hematopoietic stem cells ex vivo.

In another aspect, the disclosure features a compound of any of the above aspects or embodiments for use in maintaining the hematopoietic stem cell functional potential of a population of hematopoietic stem cells ex vivo for two or more days.

In another aspect, the disclosure features use of a compound of any of the above aspects or embodiments in producing an expanded population of hematopoietic stem cells ex vivo.

In another aspect, the disclosure features use of a compound of any of the above aspects or embodiments in enriching a population of cells with hematopoietic stem cells ex vivo.

In another aspect, the disclosure features use of a compound of any of the above aspects or embodiments in maintaining the hematopoietic stem cell functional potential of a population of hematopoietic stem cells ex vivor for two or more days.

In another aspect, the disclosure features a composition for use in treating a human patient suffering from a disorder, said composition comprising a population of hematopoietic stem cells, wherein said hematopoietic stem cells were produced by contacting said hematopoietic stem cells or progenitors thereof with a compound of any of the above aspects or embodiments.

In another aspect, the disclosure features a composition for use in treating a human patient suffering from a disorder, said composition comprising an expanded population of hematopoietic stem cells prepared by contacting a first population of hematopoietic stem cells with a compound of any of the above aspects or embodiments for a time sufficient to produce said expanded population of hematopoietic stem cells.

In another aspect, the disclosure features use of a compound of any of the above aspects or embodiments in preparing a medicament for treating a human patient suffering from a disorder.

In some embodiments, the disorder is selected from hemoglobinopathy, sickle cell anemia, thalassemia, Fanconi anemia, Wiskott-Aldrich syndrome, a myelodysplastic disorder, an immunodeficiency disorder, a metabolic disorder, cancer, adenosine deaminase deficiency and severe combined immunodeficiency, hyper immunoglobulin M syndrome, Chediak-Higashi disease, hereditary lymphohistiocytosis, osteopetrosis, osteogenesis imperfecta, storage diseases, thalassemia major, systemic sclerosis, systemic lupus erythematosus, multiple sclerosis, juvenile rheumatoid arthritis, an autoimmune disorder, and a neurological disorder.

In some embodiments, the immunodeficiency disorder is a congenital immunodeficiency.

In some embodiments, the immunodeficiency disorder is an acquired immunodeficiency.

In some embodiments, the acquired immunodeficiency is human immunodeficiency virus or acquired immune deficiency syndrome.

In some embodiments, the metabolic disorder is selected from the group consisting of glycogen storage diseases, mucopolysaccharidoses, Gauchers Disease, Hurlers Disease, sphingolipidoses, and metachromatic leukodystrophy.

In some embodiments, the cancer is a hematological cancer.

In some embodiments, the cancer is selected from the group consisting of leukemia, lymphoma, multiple myeloma, and neuroblastoma.

In some embodiments, the cancer is acute myeloid leukemia, acute lymphoid leukemia, chronic myeloid leukemia, chronic lymphoid leukemia, multiple myeloma, diffuse large B-cell lymphoma, or non-Hodgkin's lymphoma.

In some embodiments, the autoimmune disorder is selected from the group consisting of multiple sclerosis, human systemic lupus, rheumatoid arthritis, inflammatory bowel disease, treating psoriasis, Type 1 diabetes mellitus, acute disseminated encephalomyelitis, Addison's disease, alopecia universalis, ankylosing spondylitisis, antiphospholipid antibody syndrome, aplastic anemia, autoimmune hemolytic anemia, autoimmune hepatitis, autoimmune inner ear disease, autoimmune lymphoproliferative syndrome, autoimmune oophoritis, Balo disease, Behcet's disease, bullous pemphigoid, cardiomyopathy, Chagas' disease, chronic fatigue immune dysfunction syndrome, chronic inflammatory demyelinating polyneuropathy, Crohn's disease, cicatrical pemphigoid, coeliac sprue-dermatitis herpetiformis, cold agglutinin disease, CREST syndrome, Degos disease, discoid lupus, dysautonomia, endometriosis, essential mixed cryoglobulinemia, fibromyalgia-fibromyositis, Goodpasture's syndrome, Grave's disease, Guillain-Barre syndrome, Hashimoto's thyroiditis, Hidradenitis suppurativa, idiopathic and/or acute thrombocytopenic purpura, idiopathic pulmonary fibrosis, IgA neuropathy, interstitial cystitis, juvenile arthritis, Kawasaki's disease, lichen planus, Lyme disease, Meniere disease, mixed connective tissue disease, myasthenia gravis, neuromyotonia, opsoclonus myoclonus syndrome, optic neuritis, Ord's thyroiditis, pemphigus vulgaris, pernicious anemia, polychondritis, polymyositis and dermatomyositis, primary biliary cirrhosis, polyarteritis nodosa, polyglandular syndromes, polymyalgia rheumatica, primary agammaglobulinemia, Raynaud phenomenon, Reiter s syndrome, rheumatic fever, sarcoidosis, scleroderma, Sjögren's syndrome, stiff person syndrome, Takayasu's arteritis, temporal arteritis, ulcerative colitis, uveitis, vasculitis, vitiligo, vulvodynia, and Wegener's granulomatosis.

In some embodiments, the neurological disorder is selected from the group consisting of Parkinson's disease, Alzheimer's disease, multiple sclerosis, Amyotrophic lateral sclerosis, Huntington's disease, mild cognitive impairment, amyloidosis, AIDS-related dementia, encephalitis, stroke, head trauma, epilepsy, mood disorders, and dementia.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following detailed description and claims.

DETAILED DESCRIPTION

Figure 1:
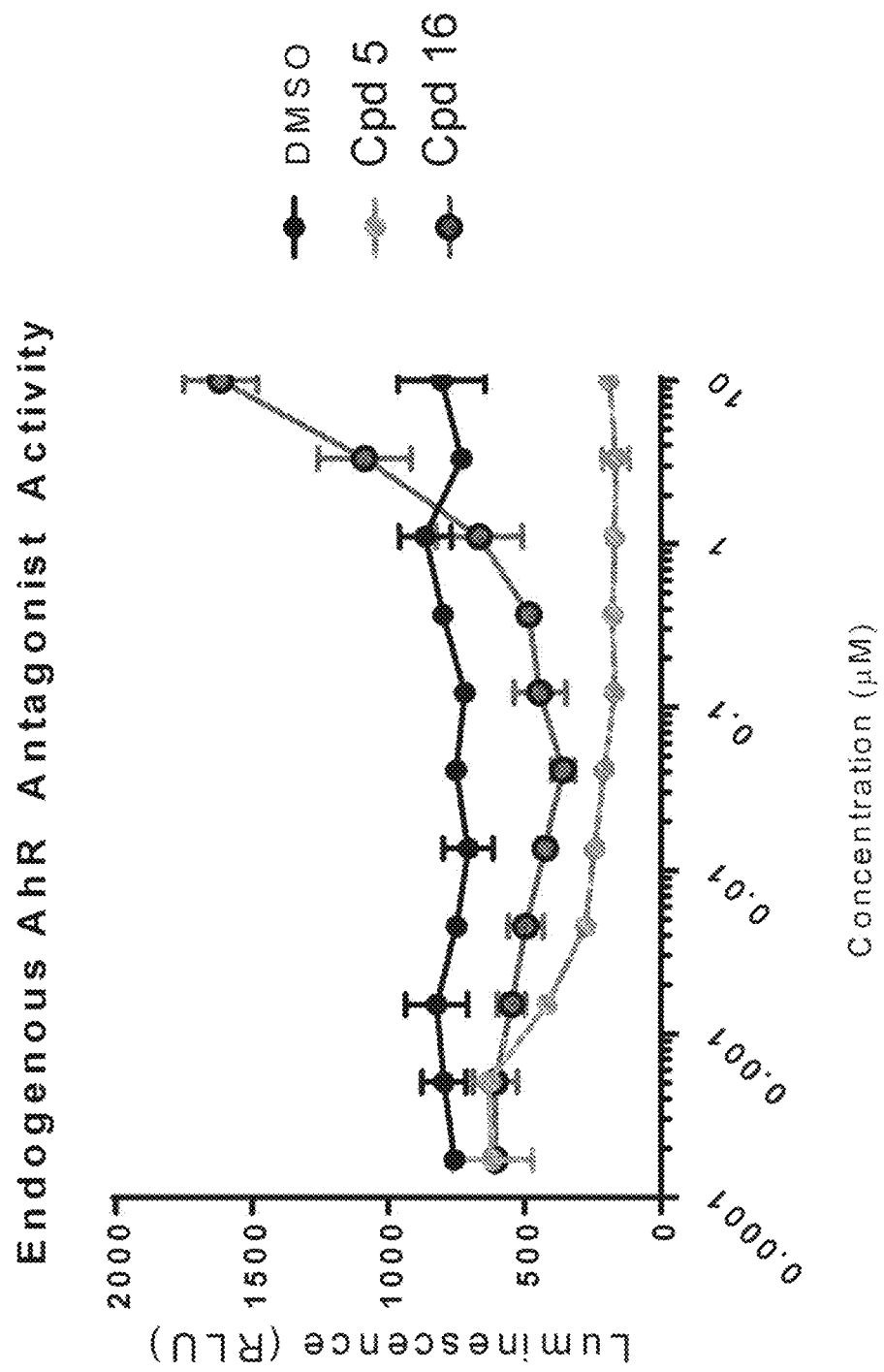
FIG. 1 is a graph demonstrating the effect of compound (5) and compound (16) on the aryl hydrocarbon receptor-driven expression of luciferase in the absence of the aryl hydrocarbon receptor agonist VAF347 in transiently transfected HepG2 cells in vitro. Experimental details for this experiment are reported in Example 3, below.

The compositions and methods described herein provide tools for expanding hematopoietic stem cells, for instance, by culturing hematopoietic stem cells ex vivo in the presence of an aryl hydrocarbon receptor antagonist represented by formula (I) or (II) described herein. It has presently been discovered that aryl hydrocarbon receptor antagonists of the formula (I) or (II) described herein are capable of inducing the proliferation of hematopoietic stem cells while maintaining the hematopoietic stem cell functional potential of the ensuing cells. As hematopoietic stem cells exhibit the ability to differentiate into a multitude of cell types within the hematopoietic lineage, the aryl hydrocarbon receptor antagonists described herein can be used to amplify a population of hematopoietic stem cells prior to transplantation of the hematopoietic stem cells to a patient in need thereof. Exemplary patients in need of a hematopoietic stem cell transplant are those suffering from a hemoglobinopathy, immunodeficiency, or metabolic disease, such as one of the various pathologies described herein.

Despite the promise of hematopoietic stem cell transplant therapy, methods of expanding hematopoietic stem cells ex vivo to produce quantities sufficient for transplantation has been challenging due to the propensity of hematopoietic stem cells to differentiate upon proliferation. The aryl hydrocarbon receptor antagonists described herein represent a solution to this long-standing difficulty, as the compounds set forth herein are capable of inducing the expansion of hematopoietic stem cells while preserving their capacity for reconstituting various populations of cells in the hematopoietic family. The compositions described herein therefore provide useful tools for the proliferation of hematopoietic stem cells prior to hematopoietic stem cell transplant therapy, and thus constitute methods of treating a variety of hematopoietic conditions, such as sickle cell anemia, thalassemia, Fanconi anemia, Wiskott-Aldrich syndrome, adenosine deaminase deficiency-severe combined immunodeficiency, metachromatic leukodystrophy, Diamond-Blackfan anemia and Schwachman-Diamond syndrome, human immunodeficiency virus infection, and acquired immune deficiency syndrome, among others.

Definitions

Listed below are definitions of various terms used in this application. These definitions apply to terms as they are used throughout this specification and claims, unless otherwise limited in specific instances, either individually or as part of a larger group.

As used herein, the term "about" refers to a value that is within 10% above or below the value being described. For example, the term "about 5 nM" indicates a range of from 4.5 nM to 5.5 nM.

As used herein, the term "donor" refers to a human or animal from which one or more cells are isolated prior to administration of the cells, or progeny thereof, into a recipient. The one or more cells may be, for example, a population of hematopoietic stem cells.

As used herein, the term "endogenous" describes a substance, such as a molecule, cell, tissue, or organ (for example, a hematopoietic stem cell or a cell of hematopoietic lineage, such as a megakaryocyte, thrombocyte, platelet, erythrocyte, mast cell, myoblast, basophil, neutrophil, eosinophil, microglial cell, granulocyte, monocyte, osteoclast, antigen-presenting cell, macrophage, dendritic cell, natural killer cell, T-lymphocyte, or B-lymphocyte) that is found naturally in a particular organism, such as a human patient.

As used herein, the term "engraftment potential" is used to refer to the ability of hematopoietic stem and progenitor cells to repopulate a tissue, whether such cells are naturally circulating or are provided by transplantation. The term encompasses all events surrounding or leading up to engraftment, such as tissue homing of cells and colonization of cells within the tissue of interest. The engraftment efficiency or rate of engraftment can be evaluated or quantified using any clinically acceptable parameter as known to those of skill in the art and can include, for example, assessment of competitive repopulating units (CRU); incorporation or expression of a marker in tissue(s) into which stem cells have homed, colonized, or become engrafted; or by evaluation of the progress of a subject through disease progression, survival of hematopoietic stem and progenitor cells, or survival of a recipient. Engraftment can also be determined by measuring white blood cell counts in peripheral blood during a post-transplant period. Engraftment can also be assessed by measuring recovery of marrow cells by donor cells in a bone marrow aspirate sample.

As used herein, the term "exogenous" describes a substance, such as a molecule, cell, tissue, or organ (for example, a hematopoietic stem cell or a cell of hematopoietic lineage, such as a megakaryocyte, thrombocyte, platelet, erythrocyte, mast cell, myoblast, basophil, neutrophil, eosinophil, microglial cell, granulocyte, monocyte, osteoclast, antigen-presenting cell, macrophage, dendritic cell, natural killer cell, T-lymphocyte, or B-lymphocyte) that is not found naturally in a particular organism, such as a human patient. Exogenous substances include those that are provided from an external source to an organism or to cultured matter extracted therefrom.

As used herein, the term "expanding amount" refers to a quantity or concentration of an agent, such as an aryl hydrocarbon receptor antagonist described herein, sufficient to induce the proliferation of a population of CD34+ cells (e.g., a CD34+ CD90+ cells), for example, by from about 1.1-fold to about 1,000-fold, or more (e.g., about 1.1-fold, 1.2-fold, 1.3-fold, 1.4-fold, 1.5-fold, 1.6-fold, 1.7-fold, 1.8-fold, 1.9-fold, 2-fold, 2.1-fold, 2.2-fold, 2.3-fold, 2.4-fold, 2.5-fold, 2.6-fold, 2.7-fold, 2.8-fold, 2.9-fold, 3-fold, 3.1-fold, 3.2-fold, 3.3-fold, 3.4-fold, 3.5-fold, 3.6-fold, 3.7-fold, 3.8-fold, 3.9-fold, 4-fold, 4.1-fold, 4.2-fold, 4.3-fold, 4.4-fold, 4.5-fold, 4.6-fold, 4.7-fold, 4.8-fold, 4.9-fold, 5-fold, 5.1-fold, 5.2-fold, 5.3-fold, 5.4-fold, 5.5-fold, 5.6-fold, 5.7-fold, 5.8-fold, 5.9-fold, 6-fold, 6.1-fold, 6.2-fold, 6.3-fold, 6.4-fold, 6.5-fold, 6.6-fold, 6.7-fold, 6.8-fold, 6.9-fold, 7-fold, 7.1-fold, 7.2-fold, 7.3-fold, 7.4-fold, 7.5-fold, 7.6-fold, 7.7-fold, 7.8-fold, 7.9-fold, 8-fold, 8.1-fold, 8.2-fold, 8.3-fold, 8.4-fold, 8.5-fold, 8.6-fold, 8.7-fold, 8.8-fold, 8.9-fold, 9-fold, 9.1-fold, 9.2-fold, 9.3-fold, 9.4-fold, 9.5-fold, 9.6-fold, 9.7-fold, 9.8-fold, 9.9-fold, 10-fold, 50-fold, 100-fold, 200-fold, 300-fold, 400-fold, 500-fold, 600-fold, 700-fold, 800-fold, 900-fold, 1,000-fold, or more).

As used herein, the term "hematopoietic stem cells" ("HSCs") refers to immature blood cells having the capacity to self-renew and to differentiate into mature blood cells comprising diverse lineages including but not limited to granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells). Such cells may include CD34+ cells. CD34+ cells are immature cells that express the CD34 cell surface marker. In humans, CD34+ cells are believed to include a subpopulation of cells with the stem cell properties defined above, whereas in mice, HSCs are CD34−. In addition, HSCs also refer to long term repopulating HSCs (LT-HSC) and short term repopulating HSCs (ST-HSC). LT-HSCs and ST-HSCs are differentiated, based on functional potential and on cell surface marker expression. For example, human HSCs are CD34+, CD38−, CD45RA−, CD90+, CD49F+, and lin− (negative for mature lineage markers including CD2, CD3, CD4, CD7, CD8, CD10, CD11B, CD19, CD20, CD56, CD235A). In mice, bone marrow LT-HSCs are CD34−, SCA-1+, C-kit+, CD135−, Slamfl/CD150+, CD48−, and lin− (negative for mature lineage markers including Ter119, CD11 b, Gr1, CD3, CD4, CD8, B220, IL7ra), whereas ST-HSCs are CD34+, SCA-1+, C-kit+, CD135−, Slamfl/CD150+, and lin— (negative for mature lineage markers including Ter119, CD11b, Gr1, CD3, CD4, CD8, B220, IL7ra). In addition, ST-HSCs are less quiescent and more proliferative than LT-HSCs under homeostatic conditions. However, LT-HSC have greater self renewal potential (i.e., they survive throughout adulthood, and can be serially transplanted through successive recipients), whereas ST-HSCs have limited self renewal (i.e., they survive for only a limited period of time, and do not possess serial transplantation potential). Any of these HSCs can be used in the methods described herein. ST-HSCs are particularly useful because they are highly proliferative and thus, can more quickly give rise to differentiated progeny.

As used herein, the term "hematopoietic progenitor cells" includes pluripotent cells capable of differentiating into several cell types of the hematopoietic system, including, without limitation, granulocytes, monocytes, erythrocytes, megakaryocytes, B-cells and T-cells, among others. Hematopoietic progenitor cells are committed to the hematopoietic cell lineage and generally do not self-renew. Hematopoietic progenitor cells can be identified, for example, by expression patterns of cell surface antigens, and include cells having the following immunophenotype: CD34+ or CD34+ CD90−. Hematopoietic progenitor cells include short-term hematopoietic stem cells, multi-potent progenitor cells, common myeloid progenitor cells, granulocyte-monocyte progenitor cells, and megakaryocyte-erythrocyte progenitor cells. The presence of hematopoietic progenitor cells can be determined functionally, for instance, by detecting colony-forming unit cells, e.g., in complete methylcellulose assays, or phenotypically through the detection of cell surface markers using flow cytometry and cell sorting assays described herein and known in the art.

As used herein, the term "hematopoietic stem cell functional potential" refers to the functional properties of hematopoietic stem cells which include 1) multi-potency (which refers to the ability to differentiate into multiple different blood lineages including, but not limited to, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells), 2) self-renewal (which refers to the ability of hematopoietic stem cells to give rise to daughter cells that have equivalent potential as the mother cell, and further that this ability can repeatedly occur throughout the lifetime of an individual without exhaustion), and 3) the ability of hematopoietic stem cells or progeny thereof to be reintroduced into a transplant recipient whereupon they home to the hematopoietic stem cell niche and re-establish productive and sustained hematopoiesis.

As used herein, patients that are "in need of" a hematopoietic stem cell transplant include patients that exhibit a defect or deficiency in one or more blood cell types, as well as patients having a stem cell disorder. Hematopoietic stem cells generally exhibit 1) multi-potency, and can thus differentiate into multiple different blood lineages including, but not limited to, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells), 2) self-renewal, and can thus give rise to daughter cells that have equivalent potential as the mother cell, and 3) the ability to be reintroduced into a transplant recipient whereupon they home to the hematopoietic stem cell niche and re-establish productive and sustained hematopoiesis. Hematopoietic stem cells can thus be administered to a patient defective or deficient in one or more cell types of the hematopoietic lineage in order to re-constitute the defective or deficient population of cells in vivo. For example, the patient may be suffering from cancer, and the deficiency may be caused by administration of a chemotherapeutic agent or other medicament that depletes, either selectively or non-specifically, the cancerous cell population. Additionally or alternatively, the patient may be suffering from a non-malignant hemoglobinopathy, such as sickle cell anemia, thalassemia, Fanconi anemia, and Wiskott-Aldrich syndrome. The subject may be one that is suffering from adenosine deaminase severe combined immunodeficiency (ADA SCID), HIV/AIDS, metachromatic leukodystrophy, Diamond-Blackfan anemia, and Schwachman-Diamond syndrome. The subject may have or be affected by an inherited blood disorder (e.g., sickle cell anemia) or an autoimmune disorder. Additionally or alternatively, the subject may have or be affected by a malignancy, such as a malignancy selected from the group consisting of hematologic cancers (e.g., leukemia, lymphoma, multiple myeloma, or myelodysplastic syndrome) and neuroblastoma. In some embodiments, the subject has or is otherwise affected by a metabolic disorder. For example, the subject may suffer or otherwise be affected by a metabolic disorder selected from the group consisting of glycogen storage diseases, mucopolysaccharidoses, Gaucher's Disease, Hurlers Disease, sphingolipidoses, metachromatic leukodystrophy, or any other diseases or disorders which may benefit from the treatments and therapies disclosed herein and including, without limitation, severe combined immunodeficiency, Wiscott-Aldrich syndrome, hyper immunoglobulin M (IgM) syndrome, Chediak-Higashi disease, hereditary lymphohistiocytosis, osteopetrosis, osteogenesis imperfecta, storage diseases, thalassemia major, sickle cell disease, systemic sclerosis, systemic lupus erythematosus, multiple sclerosis, juvenile rheumatoid arthritis and those diseases, or disorders described in "Bone Marrow Transplantation for Non-Malignant Disease," ASH Education Book, 1:319-338 (2000), the disclosure of which is incorporated herein by reference in its entirety as it pertains to pathologies that may be treated by administration of hematopoietic stem cell transplant therapy. Additionally or alternatively, a patient "in need of" a hematopoietic stem cell transplant may one that is or is not suffering from one of the foregoing pathologies, but nonetheless exhibits a reduced level (e.g., as compared to that of an otherwise healthy subject) of one or more endogenous cell types within the hematopoietic lineage, such as megakaryocytes, thrombocytes, platelets, erythrocytes, mast cells, myoblasts, basophils, neutrophils, eosinophils, microglia, granulocytes, monocytes, osteoclasts, antigen-presenting cells, macrophages, dendritic cells, natural killer cells, T-lymphocytes, and B-lymphocytes. One of skill in the art can readily determine whether one's level of one or more of the foregoing cell types, or other blood cell type, is reduced with respect to an otherwise healthy subject, for instance, by way of flow cytometry and fluorescence activated cell sorting (FACS) methods, among other procedures, known in the art.

As used herein, the term "recipient" refers to a patient that receives a transplant, such as a transplant containing a population of hematopoietic stem cells. The transplanted cells administered to a recipient may be, e.g., autologous, syngeneic, or allogeneic cells.

As used herein, the term "sample" refers to a specimen (e.g., blood, blood component (e.g., serum or plasma), urine, saliva, amniotic fluid, cerebrospinal fluid, tissue (e.g., placental or dermal), pancreatic fluid, chorionic villus sample, and cells) taken from a subject.

As used herein, the terms "subject" and "patient" refer to an organism, such as a human, that receives treatment for a particular disease or condition as described herein. For instance, a patient, such as a human patient, that is in need of hematopoietic stem cell transplantation may receive treatment that includes a population of hematopoietic stem cells so as to treat a stem cell disorder, such as a cancer, autoimmune disease, or metabolic disorder described herein. For instance, a patient, such as a human patient suffering from a stem cell disorder, may receive treatment in the form of a population of hematopoietic stem cells, such as a population of from about $1 \times 10^6$ to about $1 \times 10^9$ hematopoietic stem cells.

As used herein, the phrase "stem cell disorder" broadly refers to any disease, disorder, or condition that may be treated or cured by engrafting or transplanting a population of hematopoietic stem or progenitor cells in a target tissue within a patient. For example, Type I diabetes has been shown to be cured by hematopoietic stem cell transplant, along with various other disorders. Diseases that can be treated by infusion of hematopoietic stem or progenitor cells into a patient include, sickle cell anemia, thalassemias, Fanconi anemia, aplastic anemia, Wiskott-Aldrich syndrome, ADA SCID, HIV/AIDS, metachromatic leukodystrophy, Diamond-Blackfan anemia, and Schwachman-Diamond syndrome. Additional diseases that may be treated by transplantation of hematopoietic stem and progenitor cells as described herein include blood disorders (e.g., sickle cell anemia) and autoimmune disorders, such as scleroderma, multiple sclerosis, ulcerative colitis, and Chrohn's disease. Additional diseases that may be treated using hematopoietic stem and progenitor cell transplant therapy include cancer, such as a cancer described herein. Stem cell disorders include a malignancy, such as a neuroblastoma or a hematologic cancers, such as leukemia, lymphoma, and myeloma. For instance, the cancer may be acute myeloid leukemia, acute lymphoid leukemia, chronic myeloid leukemia, chronic lymphoid leukemia, multiple myeloma, diffuse large B-cell lymphoma, or non-Hodgkin's lymphoma. Disorders that may be treated by transplanting a population of hematopoietic stem cells to a patient include neurological disorders, such as Parkinson's disease, Alzheimer's disease, multiple sclerosis, Amyotrophic lateral sclerosis, Huntington's disease, mild cognitive impairment, amyloidosis, AIDS-related dementia, encephalitis, stroke, head trauma, epilepsy, mood disorders, and dementia. As described herein, without being limited by mechanism, the ability of hematopoietic stem cell transplantation to treat such disorders may be due, in part, to the capacity of hematopoietic stem cells to migrate to the central nervous system and differentiate into microglial cells, thereby repopulating a hematopoietic cell line that may be damaged or deficient in patients having a neurological disorder. Additional diseases treatable using hematopoietic stem or progenitor cell transplant therapy include myelodysplastic syndrome. In some embodiments, the patient has or is otherwise affected by a metabolic storage disorder. For example, the patient may suffer or otherwise be affected by a metabolic disorder selected from the group consisting of glycogen storage diseases, mucopolysaccharidoses, Gaucher's Disease, Hurlers Disease, sphingolipidoses, metachromatic leukodystrophy, or any other diseases or disorders which may benefit from the treatments and therapies disclosed herein and including, without limitation, severe combined immunodeficiency, Wiscott-Aldrich syndrome, hyper immunoglobulin M (IgM) syndrome, Chediak-Higashi disease, hereditary lymphohistiocytosis, osteopetrosis, osteogenesis imperfecta, storage diseases, thalassemia major, sickle cell disease, systemic sclerosis, systemic lupus erythematosus, multiple sclerosis, juvenile rheumatoid arthritis and those diseases, or disorders described in "Bone Marrow Transplantation for Non-Malignant Disease," ASH Education Book, 1:319-338 (2000), the disclosure of which is incorporated herein by reference in its entirety as it pertains to pathologies that may be treated by administration of hematopoietic stem or progenitor cell transplant therapy.

As used herein, the terms "treat", "treating" or "treatment" refer to a method of alleviating or abating a disease and/or its attendant symptoms. As used herein, the terms "preventing" or "prevent" describes reducing or eliminating the onset of the symptoms or complications of the disease, condition, or disorder. As used herein, the terms "disease(s)", "disorder(s)", and "condition(s)" are used interchangeably, unless the context clearly dictates otherwise.

"Treating" may refer to therapeutic treatment, in which the object is to prevent or slow down (lessen) an undesired physiological change or disorder or to promote a beneficial phenotype in the patient being treated. Beneficial or desired clinical results include, but are not limited to, the observation of an increase in the cell count or relative concentration of hematopoietic stem cells in a patient in need of a hematopoietic stem cell transplant following administration of an exogenous hematopoietic stem cell graft to the patient. Beneficial results of therapy described herein may also include an increase in the cell count or relative concentration of one or more cells of hematopoietic lineage, such as a megakaryocyte, thrombocyte, platelet, erythrocyte, mast cell, myoblast, basophil, neutrophil, eosinophil, microglial cell, granulocyte, monocyte, osteoclast, antigen-presenting cell, macrophage, dendritic cell, natural killer cell, T-lymphocyte, or B-lymphocyte, following conditioning therapy and subsequent hematopoietic stem cell transplant therapy. Additional beneficial results may include the reduction in quantity of a disease-causing cell population, such as a population of cancer cells or auto-immune cells.

As used herein, the terms "variant" and "derivative" are used interchangeably and refer to naturally-occurring, synthetic, and semi-synthetic analogues of a compound, peptide, protein, or other substance described herein. A variant or derivative of a compound, peptide, protein, or other substance described herein may retain or improve upon the biological activity of the original material.

As used herein, the term "alkyl" refers to a straight- or branched-chain alkyl group having, for example, from 1 to 20 carbon atoms in the chain, or, in certain embodiments, from 1 to 6 carbon atoms in the chain. Examples of alkyl groups include, but are not limited to, methyl, ethyl, n-propyl, isopropyl, butyl, isobutyl, sec-butyl, tert-butyl, pentyl, isopentyl, tert-pentyl, neopentyl, isopentyl, tert-pentyl, hexyl, isohexyl, and the like.

As used herein, the term "alkylene" refers to a straight- or branched-chain divalent alkyl group. The divalent positions may be on the same or different atoms within the alkyl chain. Examples of alkylene include methylene, ethylene, propylene, isopropylene, and the like.

As used herein, the term "heteroalkyl" refers to a straight or branched-chain alkyl group having, for example, from 1 to 20 carbon atoms in the chain, and further containing one or more heteroatoms (e.g., oxygen, nitrogen, or sulfur, among others) in the chain.

As used herein, the term "heteroalkylene" refers to a straight- or branched-chain divalent heteroalkyl group. The divalent positions may be on the same or different atoms within the heteroalkyl chain. The divalent positions may be one or more heteroatoms.

As used herein, the term "alkenyl" refers to a straight- or branched-chain alkenyl group having, for example, from 2 to 20 carbon atoms in the chain. It denotes a monovalent group derived from a hydrocarbon moiety containing, for example, from two to six carbon atoms having at least one carbon-carbon double bond. The double bond may or may not be the point of attachment to another group. Examples of alkenyl groups include, but are not limited to, vinyl, propenyl, isopropenyl, butenyl, tert-butylenyl, 1-methyl-2-buten-1-yl, hexenyl, and the like.

As used herein, the term "alkenylene" refers to a straight- or branched-chain divalent alkenyl group. The divalent positions may be on the same or different atoms within the alkenyl chain. Examples of alkenylene include ethenylene, propenylene, isopropenylene, butenylene, and the like.

As used herein, the term "heteroalkenyl" refers to a straight- or branched-chain alkenyl group having, for example, from 2 to 20 carbon atoms in the chain, and further containing one or more heteroatoms (e.g., oxygen, nitrogen, or sulfur, among others) in the chain.

As used herein, the term "heteroalkenylene" refers to a straight- or branched-chain divalent heteroalkenyl group. The divalent positions may be on the same or different atoms within the heteroalkenyl chain. The divalent positions may be one or more heteroatoms.

As used herein, the term "alkynyl" refers to a straight- or branched-chain alkynyl group having, for example, from 2 to 20 carbon atoms in the chain and at least one carbon-carbon triple bond. Examples of alkynyl groups include, but are not limited to, propargyl, butynyl, pentynyl, hexynyl, and the like.

As used herein, the term "alkynylene" refers to a straight- or branched-chain divalent alkynyl group. The divalent positions may be on the same or different atoms within the alkynyl chain.

As used herein, the term "heteroalkynyl" refers to a straight- or branched-chain alkynyl group having, for example, from 2 to 20 carbon atoms in the chain, and further containing one or more heteroatoms (e.g., oxygen, nitrogen, or sulfur, among others) in the chain.

As used herein, the term "heteroalkynylene" refers to a straight- or branched-chain divalent heteroalkynyl group. The divalent positions may be on the same or different atoms within the heteroalkynyl chain. The divalent positions may be one or more heteroatoms.

As used herein, the term "cycloalkyl" refers to a monocyclic, or fused, bridged, or spiro polycyclic ring structure that is saturated and has, for example, from 3 to 12 carbon ring atoms. Examples of cycloalkyl groups include cyclopropyl, cyclobutyl, cyclopentyl, cyclohexyl, cycloheptyl, cyclooctyl, bicyclo[3.1.0]hexane, and the like. Also contemplated is a monovalent group derived from a monocyclic or polycyclic carbocyclic ring compound having at least one carbon-carbon double bond by the removal of at least one or two hydrogen atoms. Examples of such groups include, but are not limited to, cyclopropenyl, cyclobutenyl, cyclopentenyl, As used herein, the term "cycloalkylene" refers to a divalent cycloalkyl group. The divalent positions may be on the same or different atoms within the ring structure. Examples of cycloalkylene include cyclopropylene, cyclobutylene, cyclopentylene, cyclohexylene, and the like.

As used herein, the term "heterocyloalkyl" or "heterocyclyl" refers to a monocyclic, or fused, bridged, or spiro polycyclic ring structure that is saturated and has, for example, from 3 to 12 ring atoms per ring structure selected from carbon atoms and heteroatoms selected from, e.g., nitrogen, oxygen, and sulfur, among others. The ring structure may contain, for example, one or more oxo groups on carbon, nitrogen, or sulfur ring members. Exemplary heterocycloalkyl groups include, but are not limited to, [1,3] dioxolane, pyrrolidinyl, pyrazolinyl, pyrazolidinyl, imidazolinyl, imidazolidinyl, piperazinyl, piperidinyl, oxazolidinyl, isooxazolidinyl, morpholinyl, thiazololidinyl, isothiazolidinyl, and tetrahydrofuryl.

As used herein, the term "heterocycloalkylene" refers to a divalent heterocyclolalkyl group. The divalent positions may be on the same or different atoms within the ring structure.

As used herein, the term "aryl" refers to a monocyclic or multicyclic aromatic ring system containing, for example, from 6 to 19 carbon atoms. Aryl groups include, but are not limited to, phenyl, fluorenyl, naphthyl, tetrahydronaphthyl, indanyl, indenyl, and the like. The divalent positions may be one or more heteroatoms.

As used herein, the term "arylene" refers to a divalent aryl group. The divalent positions may be on the same or different atoms.

As used herein, the term "heteroaryl" refers to a monocyclic heteroaromatic, or a bicyclic or a tricyclic fused-ring heteroaromatic group. In certain embodiments, the heteroaryl group contains five to ten ring atoms of which one ring atom is selected from S, O, and N; zero, one, or two ring atoms are additional heteroatoms independently selected from S, O, and N; and the remaining ring atoms are carbon. Heteroaryl groups include, but are not limited to, pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadia-zolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl, benzoquinolyl, and the like.

As used herein, the term "heteroarylene" refers to a divalent heteroaryl group. The divalent positions may be on the same or different atoms. The divalent positions may be one or more heteroatoms.

Unless otherwise constrained by the definition of the individual substituent, the foregoing chemical moieties, such as "alkyl", "alkylene", "heteroalkyl", "heteroalkylene", "alkenyl", "alkenylene", "heteroalkenyl", "heteroalkenylene", "alkynyl", "alkynylene", "heteroalkynyl", "heteroalkynylene", "cycloalkyl", "cycloalkylene", "heterocyclolalkyl", "heterocycloalkylene", "aryl," "arylene", "heteroaryl", and "heteroarylene" groups can optionally be substituted. As used herein, the term "optionally substituted" refers to a compound or moiety containing one or more (for example, 1, 2, 3, 4, 5, 6, 7, 8, 9, 10, or more) substituents, as permitted by the valence of the compound or moiety or a site thereof, such as a substituent selected from the group consisting of alkyl, alkenyl, alkynyl, cycloalkyl, heterocycloalkyl, alkyl aryl, alkyl heteroaryl, alkyl cycloalkyl, alkyl heterocycloalkyl, amino, ammonium, acyl, acyloxy, acylamino, aminocarbonyl, alkoxycarbonyl, ureido, carbamate, aryl, heteroaryl, sulfinyl, sulfonyl, alkoxy, sulfanyl, halogen, carboxy, trihalomethyl, cyano, hydroxy, mercapto, nitro, and the like. The substitution may include situations in which neighboring substituents have undergone ring closure, such as ring closure of vicinal functional substituents, to form, for instance, lactams, lactones, cyclic anhydrides, acetals, hemiacetals, thioacetals, aminals, and hemiaminals, formed by ring closure, for example, to furnish a protecting group.

As used herein, the term "optionally substituted" refers to a chemical moiety that may have one or more chemical substituents, as valency permits, such as C1-4 alkyl, C1-4 alkenyl, C1-4 alkynyl, C2-10 cycloalkyl, C2-10 heterocyclolalkyl, C2-10 aryl, C2-10 alkylaryl, C2-10 heteroaryl, C2-10 alkylheteroaryl, amino, ammonium, acyl, acyloxy, acylamino, aminocarbonyl, alkoxycarbonyl, ureido, carbamate, sulfinyl, sulfonyl, alkoxy, sulfanyl, halogen, carboxy, trihalomethyl, cyano, hydroxy, mercapto, nitro, and the like. An optionally substituted chemical moiety may contain, e.g., neighboring substituents that have undergone ring closure, such as ring closure of vicinal functional substituents, thus forming, e.g., lactams, lactones, cyclic anhydrides, acetals, thioacetals, or aminals formed by ring closure, for instance, in order to generate protecting group.

In accordance with the application, any of the aryls, substituted aryls, heteroaryls and substituted heteroaryls described herein, can be any aromatic group.

The terms "hal," "halo," and "halogen," as used herein, refer to an atom selected from fluorine, chlorine, bromine and iodine.

As described herein, compounds of the application and moieties present in the compounds may optionally be substituted with one or more substituents, such as are illustrated generally above, or as exemplified by particular classes, subclasses, and species of the application. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. The terms "optionally substituted", "optionally substituted alkyl," "optionally substituted alkenyl," "optionally substituted alkynyl", "optionally substituted cycloalkyl," "optionally substituted cycloalkenyl," "optionally substituted aryl", "optionally substituted heteroaryl," "optionally substituted aralkyl", "optionally substituted heteroaralkyl," "optionally substituted heterocycloalkyl," and any other optionally substituted group as used herein, refer to groups that are substituted or unsubstituted by independent replacement of one, two, or three or more of the hydrogen atoms thereon with substituents including, but not limited to:

—F, —Cl, —Br, —I, —OH, protected hydroxy, —NO$_2$, —CN, —NH$_2$, protected amino, —NH—C$_1$-C$_{12}$-alkyl, —NH—C$_2$-C$_{12}$-alkenyl, —NH—C$_2$-C$_{12}$-alkenyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O—C$_2$-C$_{12}$-alkenyl, —O—C$_2$-C$_{12}$-alkenyl, —O—C3-C$_{12}$-cycloalkyl, —O-aryl, —O-heteroaryl, —O-heterocycloalkyl, —C(O)—C$_1$-C$_{12}$-alkyl, —C(O)—C$_2$-C$_{12}$-alkenyl, —C(O)—C$_2$-C$_{12}$-alkenyl, —C(O)—C$_3$-C$_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_{12}$-alkenyl, —CONH—C$_2$-C$_{12}$-alkenyl, —CONN—C$_3$-C$_{12}$-cycloalkyl, —CONN-aryl, —CONH-heteroaryl, —CONH-heterocycloalkyl, —OCO₂—C₁-C₁₂-alkyl, —OCO₂—C₂-C₁₂-alkenyl, —OCO₂—C₂-C₁₂-alkenyl, —OCO₂—C₃-C₁₂-cycloalkyl, —OCO₂-aryl, —OCO₂-heteroaryl, —OCO₂-heterocycloalkyl, —OCONH₂, —OCONH—C₁-C₁₂-alkyl, —OCONH—C₂-C₁₂-alkenyl, —OCONH—C₂-C₁₂-alkenyl, —OCONH—C₃-C₁₂-cycloalkyl, —OCONH-aryl, —OCONH-heteroaryl, —OCONH-heterocycloalkyl, —NHC(O)—C₁-C₁₂-alkyl, —NHC(O)—C₂-C₁₂-alkenyl, —NHC(O)—C₂-C₁₂-alkenyl, —NHC(O)—C₃-C₁₂-cycloalkyl, —NHC(O)-aryl, —NHC(O)-heteroaryl, —NHC(O)-heterocycloalkyl, —NHCO₂—C₁-C₁₂-alkyl, —NHCO₂—C₂-C₁₂-alkenyl, —NHCO₂—C₂-C₁₂-alkenyl, —NHCO₂—C₃-C₁₂-cycloalkyl, —NHCO₂-aryl, —NHCO₂-heteroaryl, —NHCO₂-heterocycloalkyl, NHC(O)NH₂, —NHC(O)NH—C₁-C₁₂-alkyl, —NHC(O)NH—C₂-C₁₂-alkenyl, —NHC(O)NH—C₂-C₁₂-alkenyl, —NHC(O)NH—C₃-C₁₂-cycloalkyl, —NHC(O)NH-aryl, —NHC(O)NH-heteroaryl, NHC(O)NH-heterocycloalkyl, —NHC(S)NH₂, —NHC(S)NH—C₁-C₁₂-alkyl, —NHC(S)NH—C₂-C₁₂-alkenyl, —NHC(S)NH—C₂-C₁₂-alkenyl, —NHC(S)NH—C₃-C₁₂-cycloalkyl, —NHC(S)NH-aryl, —NHC(S)NH-heteroaryl, —NHC(S)NH-heterocycloalkyl, —NHC(NH)NH₂, —NHC(NH)NH—C₁-C₁₂-alkyl, —NHC(NH)NH—C₂-C₁₂-alkenyl, —NHC(NH)NH—C₂-C₁₂-alkenyl, —NHC(NH)NH—C₃-C₁₂-cycloalkyl, —NHC(NH)NH-aryl, —NHC(NH)NH-heteroaryl, —NHC(NH)NHheterocycloalkyl, —NHC(NH)—C₁-C₁₂-alkyl, —NHC(NH)—C₂-C₁₂-alkenyl, —NHC(NH)—C₂-C₁₂-alkenyl, —NHC(NH)—C₃-C₁₂-cycloalkyl, —NHC(NH)-aryl, —NHC(NH)-heteroaryl, —NHC(NH)-heterocycloalkyl, —C(NH)NH—C₁-C₁₂-alkyl, —C(NH)NH—C₂-C₁₂-alkenyl, —C(NH)NH—C₂-C₁₂-alkenyl, C(NH)NH—C₃-C₁₂-cycloalkyl, —C(NH)NH-aryl, —C(NH)NH-heteroaryl, —C(NH)NHheterocycloalkyl, —S(O)—C₁-C₁₂-alkyl, —S(O)—C₂-C₁₂-alkenyl, —S(O)—C₂-C₁₂-alkenyl, —S(O)—C₃-C₁₂-cycloalkyl, —S(O)-aryl, —S(O)-heteroaryl, —S(O)-heterocycloalkyl —SO₂NH₂, —SO₂NH—C₁-C₁₂-alkyl, —SO₂NH—C₂-C₁₂-alkenyl, —SO₂NH—C₂-C₁₂-alkenyl, —SO₂NH—C₃-C₁₂-cycloalkyl, —SO₂NH-aryl, —SO₂NH-heteroaryl, —SO₂NH-heterocycloalkyl, —NHSO₂—C₁-C₁₂-alkyl, —NHSO₂—C₂-C₁₂-alkenyl, —NHSO₂—C₂-C₁₂-alkenyl, —NHSO₂—C₃-C₁₂-cycloalkyl, —NHSO₂-aryl, —NHSO₂-heteroaryl, —NHSO₂-heterocycloalkyl, —CH₂NH₂, —CH₂SO₂CH₃, -aryl, -alkylaryl, -heteroaryl, -heteroarylalkyl, -heterocycloalkyl, —C₃-C₁₂-cycloalkyl, polyalkoxyalkyl, polyalkoxy, -methoxymethoxy, -methoxyethoxy, —SH, —S—C₁-C₁₂-alkyl, —S—C₂-C₁₂-alkenyl, —S—C₂-C₁₂-alkenyl, —S—C₃-C₁₂-cycloalkyl, —S-aryl, —S-heteroaryl, —S-heterocycloalkyl, or methylthiomethyl.

Compounds of Formula (I) and Formula (II)

The aryl hydrocarbon receptor antagonists described herein include compounds represented by formula (I) or formula (II):

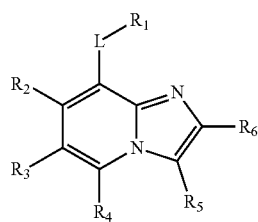

(I)

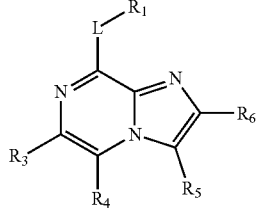

(II)

wherein L is a linker selected from the group consisting of —NR₇ₐ(CR₈ₐR₈ᵦ)ₙ—, —O(CR₈ₐR₈ᵦ)ₙ—, —C(O)(CR₈ₐR₈ᵦ)ₙ—, —C(S)(CR₈ₐR₈ᵦ)ₙ—, —S(O)₀₋₂(CR₈ₐR₈ᵦ)ₙ—, —(CR₈ₐR₈ᵦ)ₙ—, —NR₇ₐC(O)(CR₈ₐR₈ᵦ)ₙ—, —NR₇ₐC(S)(CR₈ₐR₈ᵦ)ₙ—, —OC(O)(CR₈ₐR₈ᵦ)ₙ—, —OC(S)(CR₈ₐR₈ᵦ)ₙ—, —C(O)NR₇ₐ(CR₈ₐR₈ᵦ)ₙ—, —C(S)NR₇ₐ(CR₈ₐR₈ᵦ)ₙ—, —C(O)O(CR₈ₐR₈ᵦ)ₙ—, —C(S)O(CR₈ₐR₈ᵦ)ₙ—, —S(O)₂NR₇ₐ(CR₈ₐR₈ᵦ)ₙ—, —NR₇ₐS(O)₂(CR₈ₐR₈ᵦ)ₙ—, —NR₇ₐC(O)NR₇ᵦ(CR₈ₐR₈ᵦ)ₙ—, and —NR₇ₐC(O)O(CR₈ₐR₈ᵦ)ₙ—, wherein R₇ₐ, R₇ᵦ, R₈ₐ, and R₈ᵦ are each independently selected from the group consisting of hydrogen and optionally substituted C1-4 alkyl, and each n is independently an integer from 2 to 6;

R₁ is selected from the group consisting of —S(O)₂NR₉ₐR₉ᵦ, —NR₉ₐC(O)R₉ᵦ, —NR₉ₐC(S)R₉ᵦ, —NR₉ₐC(O)NR₉ᵦR₉ᵧ, —C(O)R₉ₐ, —C(S)R₉ₐ, —S(O)₀₋₂R₉ₐ, —C(O)OR₉ₐ, —C(S)OR₉ₐ, —C(O)NR₉ₐR₉ᵦ, —C(S)NR₉ₐR₉ᵦ, —NR₉ₐS(O)₂R₉ᵦ, —NR₉ₐC(O)OR₉ᵦ, —OC(O)CR₉ₐR₉ᵦR₉ᵦ, —OC(S)CR₉ₐR₉ᵦR₉ᵦ, optionally substituted aryl, optionally substituted heteroaryl, optionally substituted cycloalkyl, and optionally substituted heterocycloalkyl, wherein R₉ₐ, R₉ᵦ, and R₉ᵦ are each independently selected from the group consisting of hydrogen, optionally substituted aryl, optionally substituted heteroaryl, optionally substituted alkyl, optionally substituted heteroalkyl, optionally substituted cycloalkyl, and optionally substituted heterocycloalkyl;

R₂ is selected from the group consisting of hydrogen and optionally substituted C1-4 alkyl;

R₃ is selected from the group consisting of optionally substituted aryl, optionally substituted heteroaryl, optionally substituted cycloalkyl, and optionally substituted heterocycloalkyl;

R₄ is selected from the group consisting of hydrogen and optionally substituted C1-4 alkyl;

R₅ is selected from the group consisting of optionally substituted aryl, optionally substituted heteroaryl, optionally substituted alkyl, optionally substituted heteroalkyl, optionally substituted cycloalkyl, and optionally substituted heterocycloalkyl; and R₆ is selected from the group consisting of hydrogen, optionally substituted aryl, optionally substituted heteroaryl, optionally substituted alkyl, optionally substituted heteroalkyl, optionally substituted cycloalkyl, and optionally substituted heterocycloalkyl;

or a salt thereof.

In some embodiments, R₁ is selected from the group consisting of —S(O)₂NR₉ₐR₉ᵦ, —NR₉ₐC(O)R₉ᵦ, —NR₉ₐC(S)R₉ᵦ, —NR₉ₐC(O)NR₉ᵦR₉ᵧ, —C(O)R₉ₐ, —C(S)R₉ₐ, —S(O)₀₋₂R₉ₐ, —C(O)OR₉ₐ, —C(S)OR₉ₐ, —C(O)NR₉ₐR₉ᵦ, —C(S)NR₉ₐR₉ᵦ, —NR₉ₐS(O)₂R₉ᵦ, —NR₉ₐC(O)OR₉ᵦ, —OC(O)CR₉ₐR₉ᵦR₉ᵦ, —OC(S)CR₉ₐR₉ᵦR₉ᵧ, phenyl, 1H-pyrrolopyridinyl, 1H-pyrrolopyridinyl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl, and 1H-indazolyl, wherein the phenyl, 1H-pyrrolopyridinyl, 1H-pyrrolopyridinyl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl, or 1H-indazolyl is optionally substituted, for example, with from 1 to 3 substituents independently selected from the group consisting of cyano, hydroxy, C1-4 alkyl, C1-4 alkoxy, halo, halo-substituted-C1-4 alkyl, halo-substituted-C1-4 alkoxy, amino, —O(CH$_2$)$_2$NR$_{10a}$R$_{10b}$, —S(O)$_2$NR$_{10a}$R$_{10b}$, —OS(O)$_2$NR$_{10a}$R$_{10b}$, and —NR$_{10a}$S(O)$_2$R$_{10b}$, wherein R$_{10a}$ and R$_{10b}$ are each independently selected from the group consisting of hydrogen, optionally substituted aryl, optionally substituted heteroaryl, optionally substituted alkyl, optionally substituted heteroalkyl, optionally substituted cycloalkyl, and optionally substituted heterocycloalkyl. For instance, R$_1$ may be selected from the group consisting of —S(O)$_2$NR$_{9a}$R$_{9b}$, —NR$_{9a}$C(O)R$_{9b}$, —NR$_{9a}$C(S)R$_{9b}$, —NR$_{9a}$C(O)NR$_{9b}$R$_{9c}$, —C(O)R$_{9a}$, —C(S)R$_{9a}$, —S(O)$_{0-2}$R$_{9a}$, —C(O)OR$_{9a}$, —C(S)OR$_{9a}$, —C(O)NR$_{9a}$R$_{9b}$, —C(S)NR$_{9a}$R$_{9b}$, —NR$_{9a}$S(O)$_2$R$_{9b}$, —NR$_{9a}$C(O)OR$_{9b}$, —OC(O)CR$_{9a}$R$_{9b}$R$_{9c}$, and —OC(S)CR$_{9a}$R$_{9b}$R$_{9c}$. R$_1$ may be selected from the group consisting of phenyl, 1H-pyrrolopyridinyl, 1H-pyrrolopyridinyl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl, and 1H-indazolyl, wherein the phenyl, 1H-pyrrolopyridinyl, 1H-pyrrolopyridinyl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl, or 1H-indazolyl is optionally substituted with from 1 to 3 substituents independently selected from the group consisting of cyano, hydroxy, C1-4 alkyl, C$_{1-4}$ alkoxy, halo, halo-substituted-C1-4 alkyl, halo-substituted-C1-4 alkoxy, amino, —O(CH$_2$)$_2$NR$_{10a}$R$_{10b}$, —S(O)$_2$NR$_{10a}$R$_{10b}$, —OS(O)$_2$NR$_{10a}$R$_{10b}$, and —NR$_{10a}$S(O)$_2$R$_{10b}$.

In some embodiments, R$_2$ is hydrogen.

In some embodiments, R$_3$ is selected from the group consisting of phenyl, thiophenyl, furanyl, 1H-benzoimidazolyl, quinolinyl, isoquinolinyl, imidazopyridinyl, benzothiophenyl, pyrimidinyl, pyridinyl, 1H-imidazolyl, pyrazinyl, pyridazinyl, 1H-pyrrolyl, and thiazolyl, wherein the phenyl, thiophenyl, furanyl, 1H-benzoimidazolyl, quinolinyl, isoquinolinyl, imidazopyridinyl, benzothiophenyl, pyrimidinyl, pyridinyl, 1H-imidazolyl, pyrazinyl, pyridazinyl, 1H-pyrrolyl, or thiazolyl is optionally substituted with from 1 to 3 substituents independently selected from the group consisting of cyano, hydroxy, C$_1$-4 alkyl, C1-4 alkenyl, C1-4 alkynyl, C2-6 cycloalkyl, C1-4 alkoxy, halo, halo-substituted-C1-4 alkyl, halo-substituted-C1-4 alkoxy, amino, —C(O)R$_{11a}$, —S(O)$_{0-2}$R$_{11a}$, —C(O)OR$_{11a}$, and —C(O)NR$_{11a}$R$_{11b}$, and wherein R$_{11a}$ and R$_{11b}$ are each independently selected from the group consisting of hydrogen and C$_{1-4}$ alkyl.

In some embodiments, R$_4$ is hydrogen.

In some embodiments, R$_5$ is selected from the group consisting of C1-10 alkyl, prop-1-en-2-yl, cyclohexyl, cyclopropyl, 2-(2-oxopyrrolidin-1-yl)ethyl, oxetan-2-yl, oxetan-3-yl, benzhydryl, tetrahydro-2H-pyran-2-yl, tetrahydro-2H-pyran-3-yl, phenyl, tetrahydrofuran-3-yl, benzyl, (4-pentylphenyl)(phenyl)methyl, and 1-(1-(2-oxo-6,9,12-trioxa-3-azatetradecan-14-yl)-1H-1,2,3-triazol-4-yl)ethyl, wherein the C1-10 alkyl, prop-1-en-2-yl, cyclohexyl, cyclopropyl, 2-(2-oxopyrrolidin-1-yl)ethyl, oxetan-2-yl, oxetan-3-yl, benzhydryl, tetrahydro-2H-pyran-2-yl, tetrahydro-2H-pyran-3-yl, phenyl, tetrahydrofuran-3-yl, benzyl, (4-pentylphenyl)(phenyl)methyl, or 1-(1-(2-oxo-6,9,12-trioxa-3-azatetradecan-14-yl)-1H-1,2,3-triazol-4-yl)ethyl is optionally substituted with from 1 to 3 substituents independently selected from the group consisting of hydroxy, C1-4 alkyl, and halo-substituted-C1-4alkyl.

In some embodiments, R$_5$ is selected from the group consisting of isopropyl, methyl, ethyl, prop-1-en-2-yl, isobutyl, cyclohexyl, sec-butyl, (S)-sec-butyl, (R)-sec-butyl, 1-hydroxypropan-2-yl, (S)-1-hydroxypropan-2-yl, (R)-1-hydroxypropan-2-yl, and nonan-2-yl.

In some embodiments, R$_5$ is (S)-1-hydroxypropan-2-yl.

In some embodiments, R$_5$ is (R)-1-hydroxpropan-2-yl.

In some embodiments, R$_5$ is (S)-sec-butyl.

In some embodiments, R$_5$ is (R)-sec-butyl.

In some embodiments, R$_5$ is selected from the group consisting of (i), (ii), (iii), (iv), and (v)

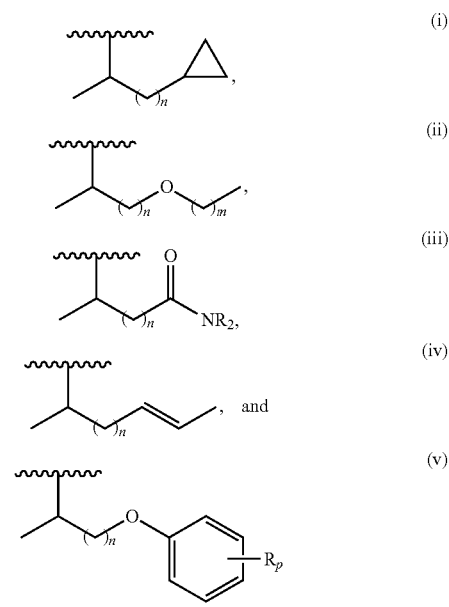

wherein n is an integer from 1 to 6, m is an integer from 0 to 6, p is an integer from 0 to 5, and each R is independently selected from the group consisting of cyano, hydroxy, C1-4 alkyl, C1-4 alkenyl, C1-4 alkynyl, C2-6 cycloalkyl, C1-4 alkoxy, halo, halo-substituted-C1-4 alkyl, halo-substituted-C1-4 alkoxy, amino, —C(O)R$_{12a}$, —S(O)$_{0-2}$R$_{12a}$, —C(O)OR$_{12a}$, and —C(O)NR$_{12a}$R$_{12b}$, and wherein R$_{12a}$ and R$_{12b}$ are each independently selected from the group consisting of hydrogen and C$_{1-4}$ alkyl.

In some embodiments, R$_5$ is selected from the group consisting of:

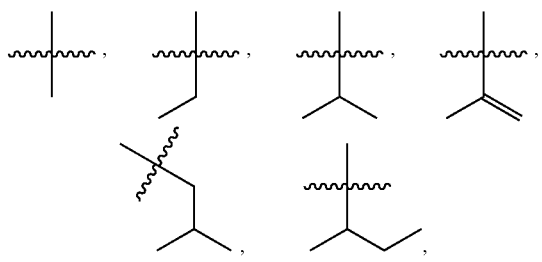

83

-continued

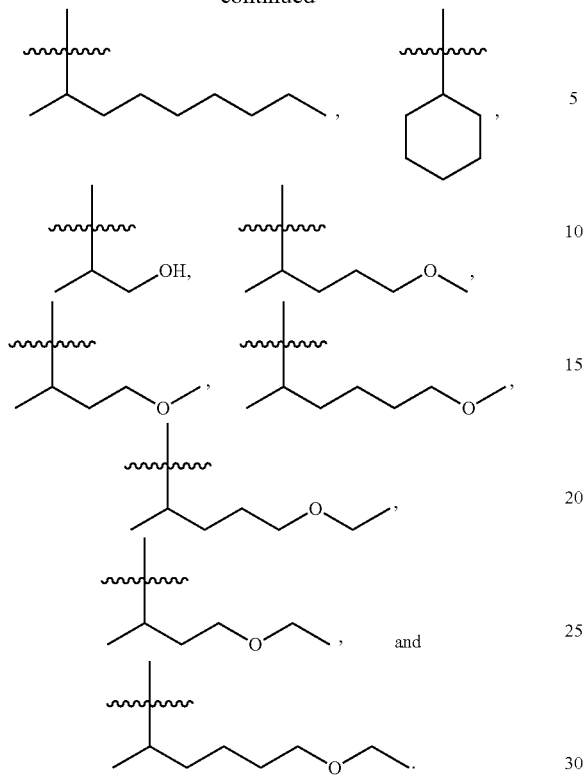

in some embodiments, R₅ is (ii);

In some embodiments, R₅ is selected from the group consisting of 4-methoxybutan-2-yl, (S)-4-methoxybutan-2-yl, (R)-4-methoxybutan-2-yl, 4-ethoxybutan-2-yl, (S)-4-ethoxybutan-2-yl, (R)-4-ethoxybutan-2-yl, 5-methoxypentan-2-yl, (S)-5-methoxypentan-2-yl, (R)-5-methoxypentan-2-yl, 5-ethoxypentan-2-yl, (S)-5-ethoxypentan-2-yl, (R)-5-ethoxypentan-2-yl, 6-methoxyhexan-2-yl, (S)-6-methoxyhexan-2-yl, (R)-6-methoxyhexan-2-yl, 6-ethoxyhexan-2-yl, (S)-6-ethoxyhexan-2-yl, and (R)-6-ethoxyhexan-2-yl.

In some embodiments, R₅ is (S)-4-methoxybutan-2-yl.
In some embodiments, R₅ is (R)-4-methoxybutan-2-yl.
In some embodiments, R₅ is (S)-5-methoxypentan-2-yl.
In some embodiments, R₅ is (R)-5-methoxypentan-2-yl.
In some embodiments, R₅ is (S)-4-ethoxybutan-2-yl.
In some embodiments, R₅ is (R)-4-ethoxybutan-2-yl.

Particular aryl hydrocarbon receptor antagonists described herein include:

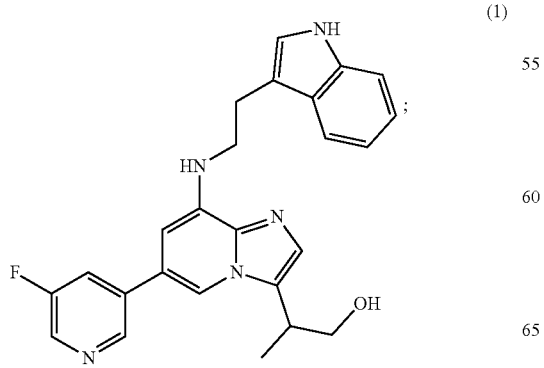

(1)

84

-continued

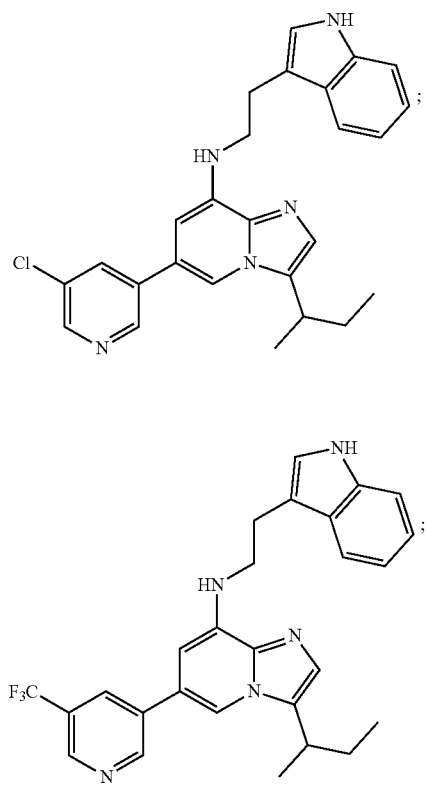

(2)

(3)

(4)

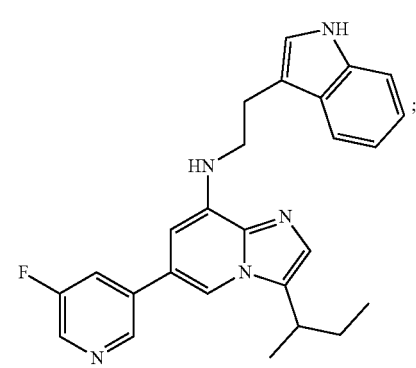

(5)

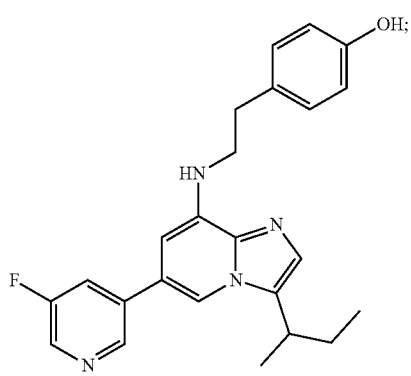
(6)
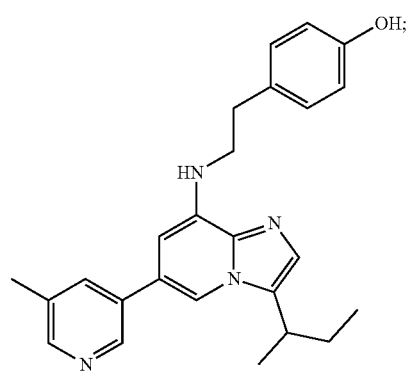
(7)
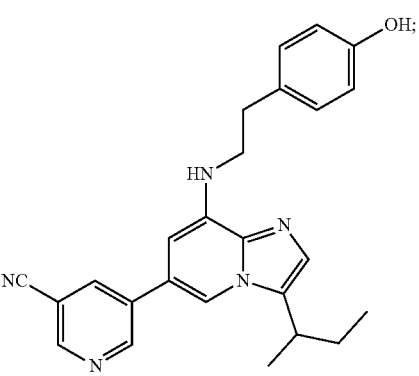
(8)
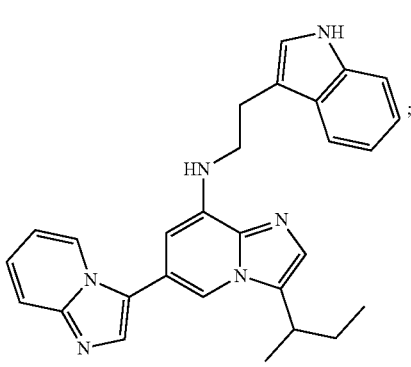
(9)
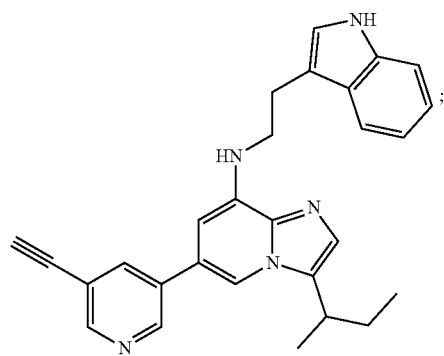
(10)
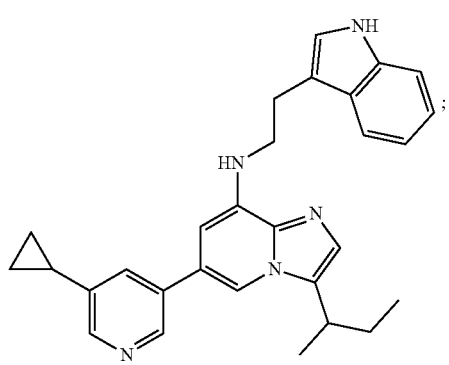
(11)
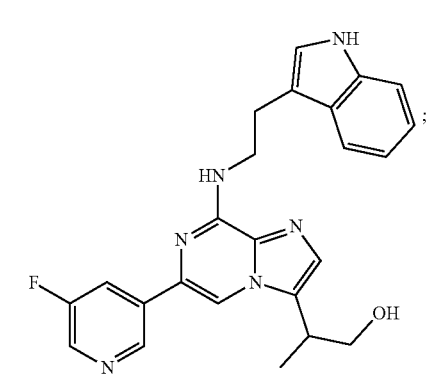
(12)
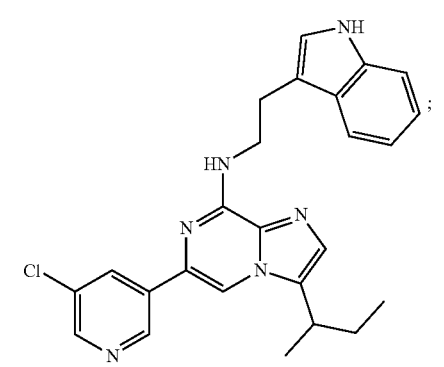
(13)

-continued
(14)
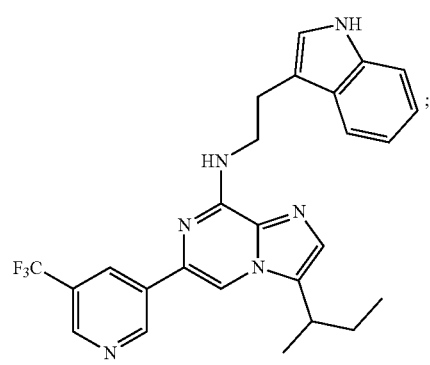
(15)
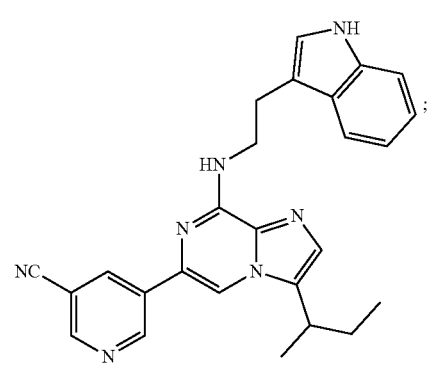
(16)
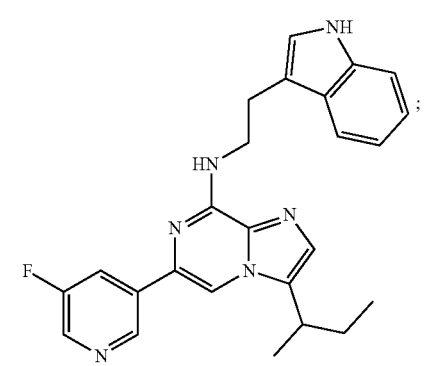
(17)
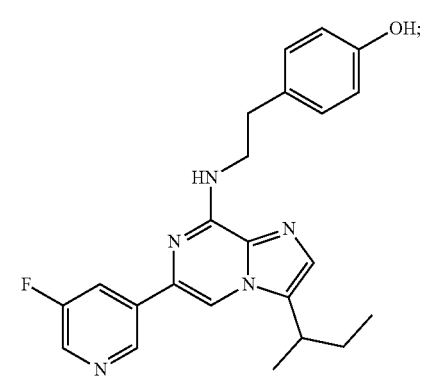
-continued
(18)
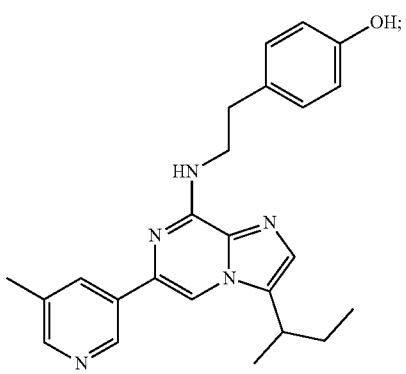
(19)
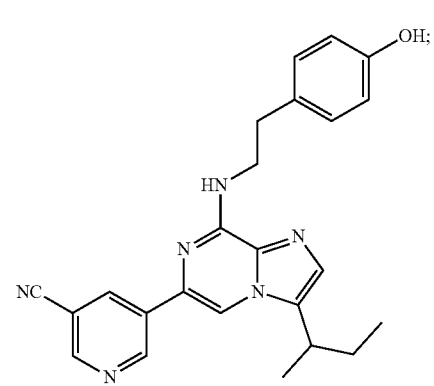
(20)
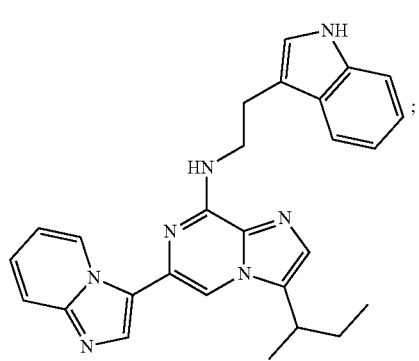
(21)
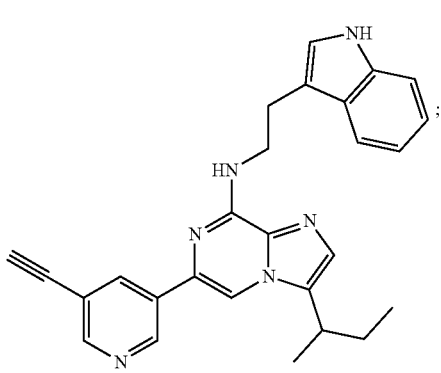

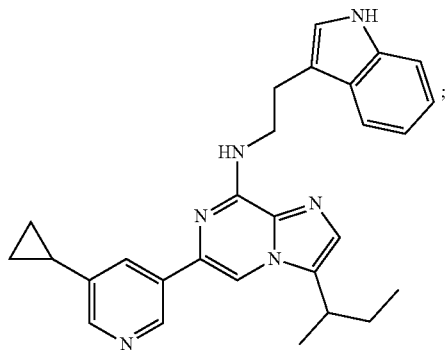

(22)

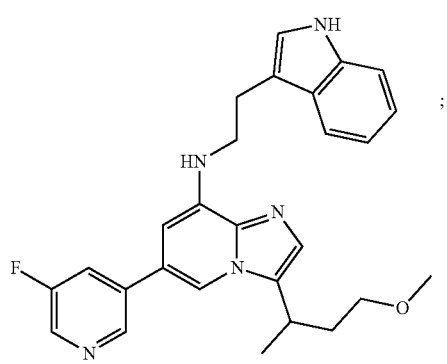

(23)

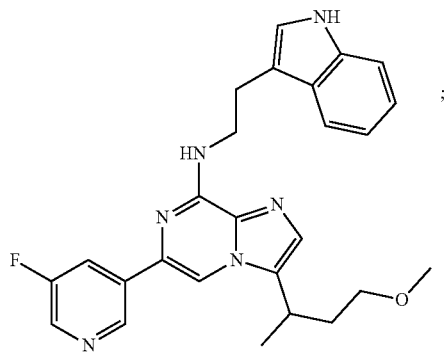

(24)

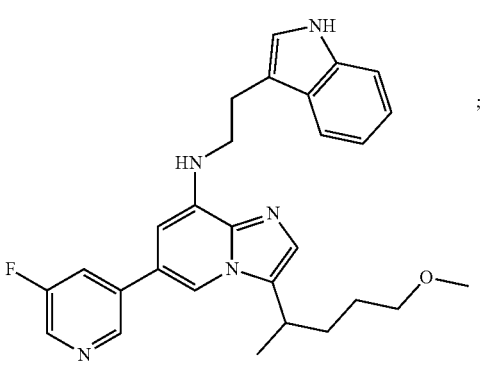

(25)

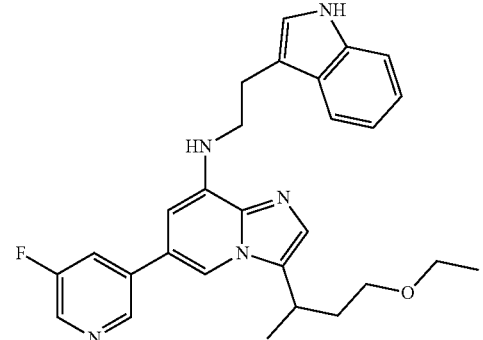

(26)

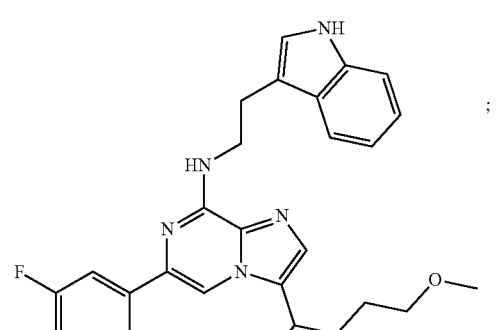

(27) ; and

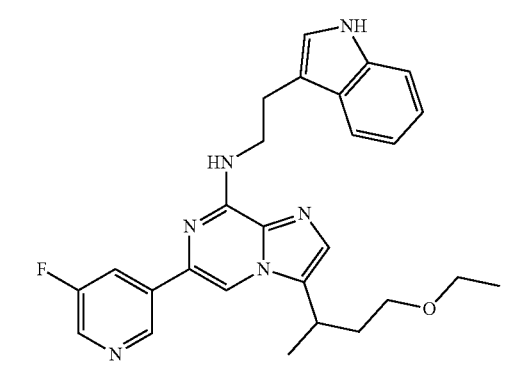

(28)

as well as salts thereof.

Where the number of any given substituent is not specified, there may be one or more substituents present. For example, "halo-substituted C1-4 alkyl" may include one or more of the same or different halogens.

When the compounds described herein contain olefinic double bonds or other centers of geometric asymmetry, and unless specified otherwise, it is intended that the compounds include both E and Z geometric isomers. Likewise, all tautomeric forms of carbonyl-containing compounds are also intended to be included.

It is to be understood that the compounds provided herein may contain chiral centers. Such chiral centers may be of either the (R) or (S) configuration, or may be a mixture thereof. Thus, the compounds provided herein may be enantiomerically pure, or may be stereoisomeric or diastereomeric mixtures. As such, one of skill in the art will recognize that administration of a compound in its (R) form is equivalent, for compounds that undergo epimerization in vivo, to administration of the compound in its (S) form.

Compounds described herein include, but are not limited to, those set forth above, as well as any of their isomers, such as diastereomers and enantiomers, as well as salts, esters, amides, thioesters, solvates, and polymorphs thereof, as well as racemic mixtures and pure isomers of the compounds set forth above.

Synthesis

Substituent Protecting Groups

The synthesis of aryl hydrocarbon receptor antagonists described herein may involve the selective protection and deprotection of alcohols, amines, ketones, sulfhydryls or carboxyl functional groups of a precursor. For example, commonly used protecting groups for amines include carbamates, such as tert-butyl, benzyl, 2,2,2-trichloroethyl, 2-trimethylsilylethyl, 9-fluorenylmethyl, allyl, and m-nitrophenyl. Other commonly used protecting groups for amines include amides, such as formamides, acetamides, trifluoroacetamides, sulfonamides, trifluoromethanesulfonyl amides, trimethylsilylethanesulfonamides, and tert-butylsulfonyl amides. Examples of commonly used protecting groups for carboxyls include esters, such as methyl, ethyl, tert-butyl, 9-fluorenylmethyl, 2-(trimethylsilyl)ethoxy methyl, benzyl, diphenylmethyl, O-nitrobenzyl, ortho-esters, and halo-esters. Examples of commonly used protecting groups for alcohols include ethers, such as methyl, methoxymethyl, methoxyethoxymethyl, methylthiomethyl, benzyloxymethyl, tetrahydropyranyl, ethoxyethyl, benzyl, 2-napthylmethyl, O-nitrobenzyl, P-nitrobenzyl, P-methoxybenzyl, 9-phenylxanthyl, trityl (including methoxy-trityls), and silyl ethers. Examples of commonly used protecting groups for sulfhydryls include many of the same protecting groups used for hydroxyls. In addition, sulfhydryls can be protected in a reduced form (e.g., as disulfides) or an oxidized form (e.g., as sulfonic acids, sulfonic esters, or sulfonic amides). Protecting groups can be chosen such that selective conditions (e.g., acidic conditions, basic conditions, catalysis by a nucleophile, catalysis by a Lewis acid, or hydrogenation) are required to remove each, exclusive of other protecting groups in a compound. The conditions required for the addition of protecting groups to amine, alcohol, sulfhydryl, and carboxyl functionalities and the conditions required for their removal are provided in detail, for example, in T. W. Green and P. G. M. Wuts, Protective Groups in Organic Synthesis ($2^{nd}$ Ed.), John Wiley & Sons, 1991 and P. J. Kocienski, Protecting Groups, Georg Thieme Verlag, 1994.

Exemplary Synthetic Methods

Aryl hydrocarbon receptor antagonists represented by formula (I) or (II) may be synthesized, for instance, by way of a palladium-catalyzed coupling reaction, such as a process depicted in Scheme 1, below.

Scheme 1. Pd-catalyzed coupling of halogenated imidazopyridine and imidazopyrazine precursors with amines, alcohols, alkynes, boronic esters and other L — $R_1$, $R_3$, and/or $R_5$ synthons

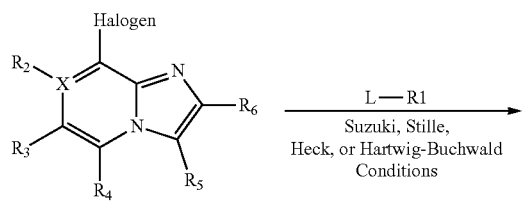

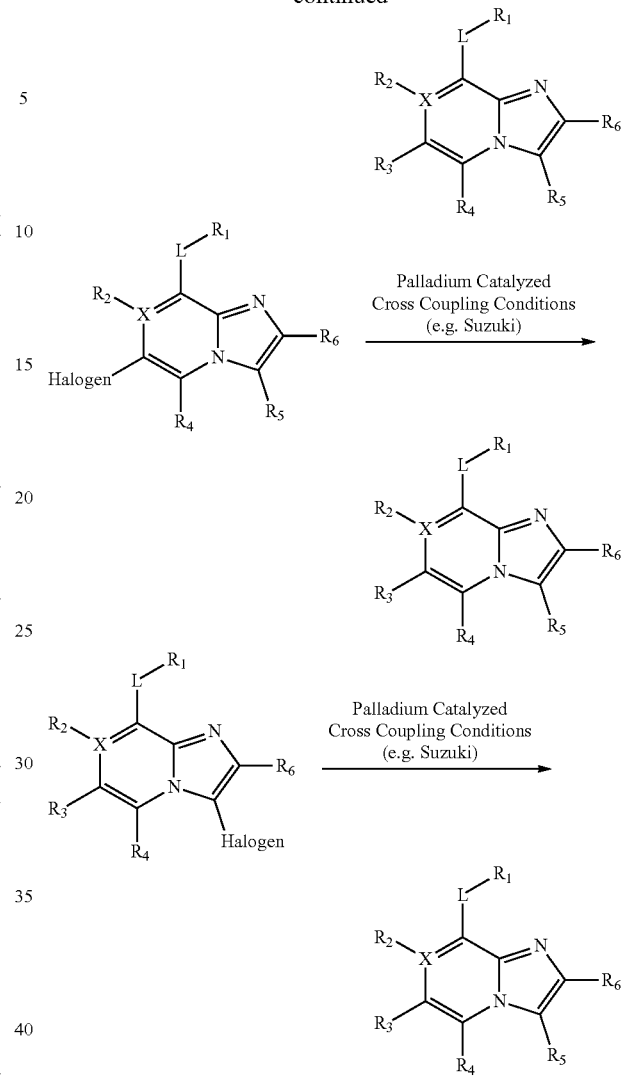

wherein X is C or N, with the proviso that $R_2$ is absent when X is N;

L is selected from the group consisting of —$NR_{7a}$(CR$_{8a}$R$_{8b}$)$_n$—, —O(CR$_{8a}$R$_{8b}$)$_n$—, —S(O)$_{0-2}$(CR$_{8a}$R$_{8b}$)$_n$—, and —(CR$_{8a}$R$_{8b}$)$_n$—, wherein $R_{7a}$, $R_{8a}$, and $R_{8b}$ are each independently selected from the group consisting of hydrogen and optionally substituted C1-4 alkyl, and each n is independently an integer from 2 to 6;

$R_1$ is selected from the group consisting of —S(O)$_2$NR$_{9a}$R$_{9b}$, —NR$_{9a}$C(O)R$_{9b}$, —NR$_{9a}$C(S)R$_{9b}$, —NR$_{9a}$C(O)NR$_{9b}$R$_{9c}$, —C(O)R$_{9a}$, —C(S)R$_{9a}$, —S(O)$_{0-2}$R$_{9a}$, —C(O)OR$_{9a}$, —C(S)OR$_{9a}$, —C(O)NR$_{9a}$R$_{9b}$, —C(S)NR$_{9a}$R$_{9b}$, —NR$_{9a}$S(O)$_2$R$_{9b}$, —NR$_{9a}$C(O)OR$_{9b}$, —OC(O)CR$_{9a}$R$_{9b}$R$_{9c}$, —OC(S)CR$_{9a}$R$_{9b}$R$_{9c}$, optionally substituted aryl, optionally substituted heteroaryl, optionally substituted cycloalkyl, and optionally substituted heterocycloalkyl, wherein $R_{9a}$, $R_{9b}$, and $R_{9c}$ are each independently selected from the group consisting of hydrogen, optionally substituted aryl, optionally substituted heteroaryl, optionally substituted alkyl, optionally substituted heteroalkyl, optionally substituted cycloalkyl, and optionally substituted heterocycloalkyl;

$R_2$ is selected from the group consisting of hydrogen and optionally substituted C1-4 alkyl;

$R_3$ is selected from the group consisting of optionally substituted aryl, optionally substituted heteroaryl, optionally substituted cycloalkyl, and optionally substituted heterocycloalkyl;

$R_4$ is selected from the group consisting of hydrogen and optionally substituted C1-4 alkyl;

$R_5$ is selected from the group consisting of optionally substituted aryl, optionally substituted heteroaryl, optionally substituted alkyl, optionally substituted heteroalkyl, optionally substituted cycloalkyl, and optionally substituted heterocycloalkyl; and $R_6$ is selected from the group consisting of hydrogen, optionally substituted aryl, optionally substituted heteroaryl, optionally substituted alkyl, optionally substituted heteroalkyl, optionally substituted cycloalkyl, and optionally substituted heterocycloalkyl.

For instance, when an organoboron species is employed as a synthon such as, for example, $R_3$—B(pin) and/or $R_5$—B(pin), Suzuki or Suzuki-Miyaura reaction conditions may be used to join the halogenated imidazopyridine or imidazopyrazine precursor with the organoboron $R_3$ or $R_5$ synthon species in the presence of a Pd catalyst, such as, for example $Pd(dppf)Cl_2$.

For instance, when L is an amino- or hydroxy-containing linker, Hartwig-Buchwald conditions may be used to join the halogenated precursor with the amine or alcohol in the presence of a Pd catalyst, as shown in Scheme 2, below.

Scheme 2.

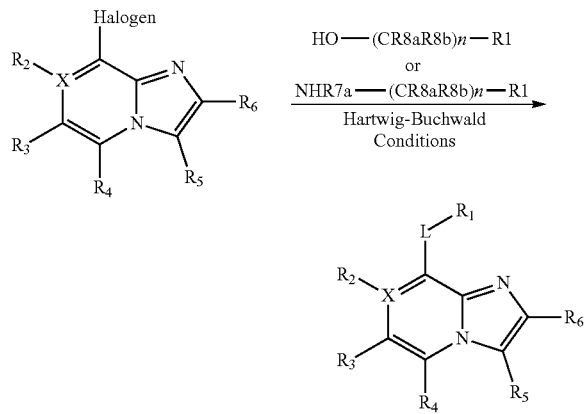

Exemplary Hartwig-Buchwald conditions include the use of a Pd catalyst, such as $Pd_2(dba)_3$, in the presence of dicyclohexylphosphino-2'-(N,N-dimethylamino)biphenyl, tBuONa, dioxane, 120° C., microwave irradiation. Hartwig-Buchwald reaction conditions are known in the art and are described, for instance, in Bailey et al., Bioorganic and Medicinal Chemistry Letters 19:3602-3606 (2009), the disclosure of which is incorporated herein by reference as it pertains to conditions useful for the Hartwig-Buchwald amination or etherification.

When L is a thiol, nucleophilic aromatic substitution conditions may be employed to join the linker to a halogenated precursor, as shown in Scheme 3, below.

Scheme 3.

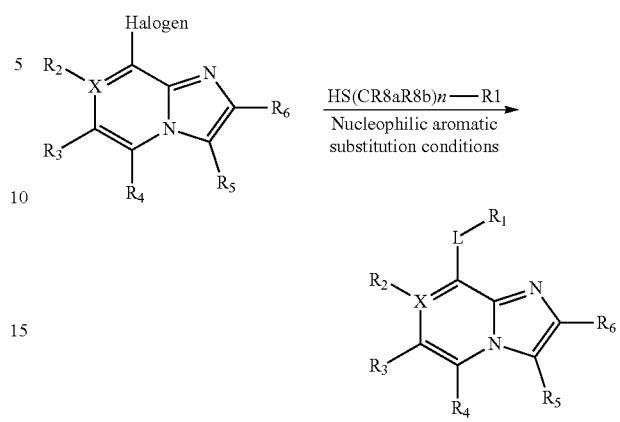

Nucleophilic aromatic substitution conditions include the use of a base to deprotonate the thiol shown in the above linker-$R_1$ pair. This reactive modality is particularly useful when the halogenated aryl precursor is activated by the presence of one or more electron-withdrawing substituents, (such as nitro, cyano, trifluoromethyl, trichloromethyl, and the like) and/or when X is nitrogen.

Additional amine, hydroxyl, and thiol arylation techniques that may be used to produce the compounds described herein include those described in Burke, A. J. and Marques, C. S. (eds) (2014) Amine, Phenol, Alcohol, and Thiol Arylation, in Catalytic Arylation Methods: From the Academic Lab to Industrial Processes, Wiley-VCH Verlag GmbH & Co. KGaA, Weinheim, Germany, the disclosure of which is incorporated herein by reference as it pertains to processes for chemical synthesis.

A Pd-catalyzed Heck reaction can be used to join olefinic linkers to a halogenated aryl precursor, as shown in Scheme 4, below.

Scheme 4.

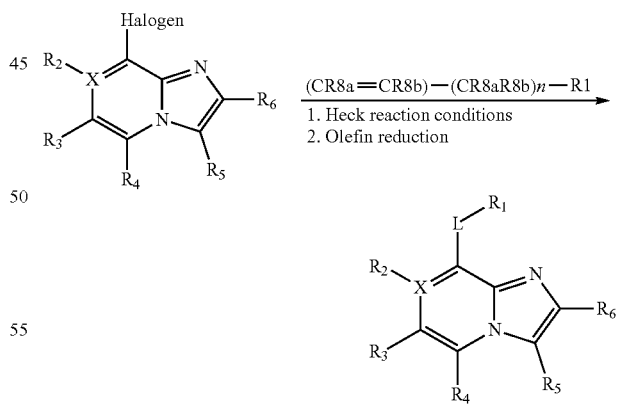

wherein "═" denotes a carbon-carbon double bond, which can subsequently be reduced to yield a saturated alkylene linker using olefin reduction methods known in the art.

For instances in which L is selected from the group consisting of —C(O)(CR$_{8a}$R$_{8b}$)$_n$—, —C(S)(CR$_{8a}$R$_{8b}$)$_n$—, —NR$_{7a}$C(O)(CR$_{8a}$R$_{8b}$)$_n$—, —NR$_{7a}$C(S)(CR$_{8a}$R$_{8b}$)$_n$—, —OC(O)(CR$_{8a}$R$_{8b}$)$_n$—, —OC(S)(CR$_{8a}$R$_{8b}$)$_n$—, —C(O)

$-NR_{7a}(CR_{8a}R_{8b})_n-$, $-C(S)NR_{7a}(CR_{8a}R_{8b})_n-$, $-C(O)O(CR_{8a}R_{8b})_n-$, $-C(S)O(CR_{8a}R_{8b})_n-$, $-S(O)_2NR_{7a}(CR_{8a}R_{8b})_n-$, $-NR_{7a}S(O)_2(CR_{8a}R_{8b})_n-$, $-NR_{7a}C(O)NR_{7b}(CR_{8a}R_{8b})_n-$, and $-NR_{7a}C(O)O(CR_{8a}R_{8b})_n-$, techniques such as acylation, sulfonamidation, and thionation reactions can be employed in order to produce compounds represented by formulas (I) and (II). Exemplary acylation, sulfonamidation, and thionation processes that may be used to synthesize the aryl hydrocarbon receptor antagonists described herein are depicted in Schemes 5-7, below.

Scheme 5.

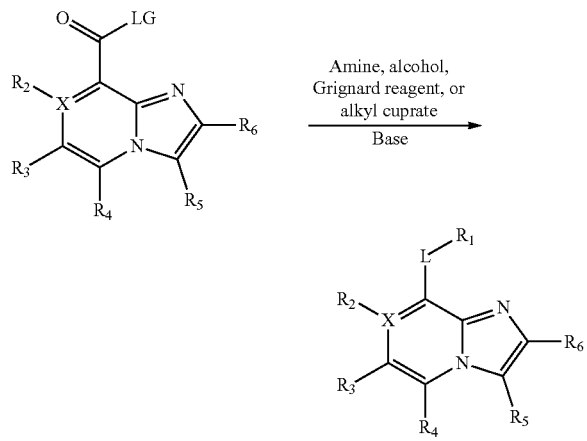

In Scheme 5, LG denotes a nucleofugal leaving group, such as a halogen (for instance, chlorine or bromine), a sulfonate (for instance, tosylate, brosylate, triflate, mesylate, and the like), and other leaving groups known in the art. In this way, linkers ("L") containing an amide, ester, ketone, urea, carbamate, or the like in which the carbonyl carbon is bound directly to the imidazopyridine or imiadzopyrazine ring system can be synthesized.

Similarly, to linkers ("L") containing a thioketone, thioamide, thioester, and the like can be synthesized by reacting the corresponding ketone, amide, or ester with a thionating reagent, as shown in Scheme 6, below.

Scheme 6.

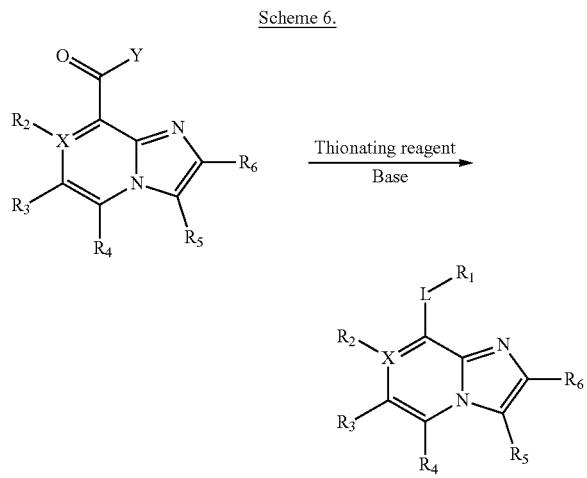

wherein C(O)Y denotes an amide, ester, ketone, or the like.

Exemplary thionating reagents are known in the art and include, for instance, Lawesson's reagent, which is described, for example, Jesberger, et al., Synthesis 13:1929-1258 (2003), the disclosure of which is incorporated herein by reference as it pertains to thionation techniques.

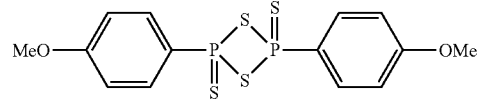

Lawesson's Reagent

When the linker ("L") contains a sulfonamide moiety bound to the imidazopyridine or imadazopyrazine ring system, for instance, at the sulfur or nitrogen of the sulfonamide functionality, sulfonamidation techniques known in the art can be used to produce the corresponding compound of formula (I) or (II). An exemplary sulfonamidation process is depicted in Scheme 7, below.

Scheme 7.

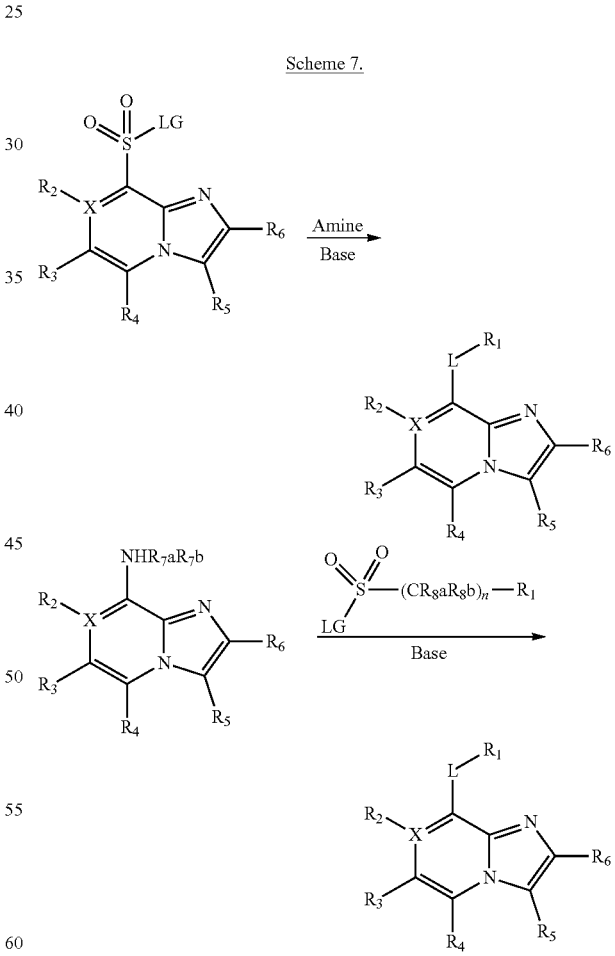

In Scheme 7, LG denotes a nucleofugal leaving group, such as a halogen (for instance, chlorine or bromine), a sulfonate (for instance, tosylate, brosylate, triflate, mesylate, and the like), and other leaving groups known in the art. In this way, linkers ("L") containing a sulfonamide in which the sulfur or nitrogen of the sulfonamide moiety is bound directly to the imidazopyridine or imiadzopyrazine ring system can be synthesized.

Stem Cells

In some embodiments, the stem cells of which the population is modified (e.g., expanded) with the compositions and methods described are capable of being expanded upon contacting the aryl hydrocarbon receptor antagonist. In some embodiments, the stem cells are not genetically modified stem cells.

In some embodiments, the stem cells are empbryonic stem cells or adult stem cells. In some embodiments, the stem cells are totipotentent stem cells, pluripotent stem cells, multipoteltent stem cells, oligopotent stem cells, or unipotent stem cells. In some embodiments, the stem cells are tissue-specific stem cells.

In some embodiments, the stem cells are hematopoietic stem cells, intestinal stem cells, osteoblastic stem cells, mesenchymal stem cells (i.e., lung mesenchymal stem cells, bone marrow-derived mesenchymal stromal cells, or bone marrow stromal cells), neural stem cells (i.e., neuronal dopaminergic stem cells or motor-neuronal stem cells), epithelial stem cells (i.e., lung epithelial stem cells, breast epithelial stem cells, vascular epithelial stem cells, or intestinal epithelial stem cells), cardiac myocyte progenitor stem cells, skin stem cells (i.e., epidermal stem cells or follicular stem cells (hair follicle stem cells)), skeletal muscle stem cells, adipose stem cells, liver stem cells, induced pluripotent stem cells, umbilical cord stem cells, amniotic fluid stem cells, limbal stem cells, dental pulp stem cells, placental stem cells, myoblasts, endothelial progenitor cells, exfoliated teeth derived stem cells, or hair follicle stem cells.

In some embodiments, the stem cells are hematopoietic stem cells.

In some embodiments, the stem cells are primary stem cells. For example, the stem cells are obtained from bone marrow, adipose tissue, or blood. In some embodiments, the the stem cells are cultured stem cells.

In some embodiments, the stem cells are CD34+ cells. In some embodiments, the stem cells are CD90+ cells. In some embodiments, the stem cells are CD45RA− cells. In some embodiments, the stem cells are CD34+CD90+ cells. In some embodiments, the stem cells are CD34+CD45RA− cells. In some embodiments, the stem cells are CD90+CD45RA− cells. In some embodiments, the stem cells are CD34+CD90+CD45RA− cells.

In some embodiments, the hematopoietic stem cells are extracted from the bone marrow, mobilized into the peripheral blood and then collected by apheresis, or isolated from umbilical cord blood units.

In some embodiments, the hematopoietic stem cells are CD34+ hematopoietic stem cells. In some embodiments, the hematopoietic stem cells are CD90+ hematopoietic stem cells. In some embodiments, the hematopoietic stem cells are CD45RA− hematopoietic stem cells. In some embodiments, the hematopoietic stem cells are CD34+CD90+ hematopoietic stem cells. In some embodiments, the hematopoietic stem cells are CD34+CD45RA− hematopoietic stem cells. In some embodiments, the hematopoietic stem cells are CD90+CD45RA− hematopoietic stem cells. In some embodiments, the hematopoietic stem cells are CD34+CD90+CD45RA− hematopoietic stem cells.

Methods for Expanding Hematopoietic Stem Cells

In another aspect, the disclosure features a method of producing an expanded population of hematopoietic stem cells ex vivo, the method including contacting a population of hematopoietic stem cells with the compound of any one of the above aspects or embodiments in an amount sufficient to produce an expanded population of hematopoietic stem cells.

In another aspect, the disclosure features a method of enriching a population of cells with hematopoietic stem cells ex vivo, the method including contacting a population of hematopoietic stem cells with the compound of any one of the above aspects or embodiments in an amount sufficient to produce a population of cells enriched with hematopoietic stem cells.

In another aspect, the disclosure features a method of maintaining the hematopoietic stem cell functional potential of a population of hematopoietic stem cells ex vivo for two or more days, the method including contacting a first population of hematopoietic stem cells with the compound of any one of the above aspects or embodiments, wherein the first population of hematopoietic stem cells exhibits a hematopoietic stem cell functional potential after two or more days that is greater than that of a control population of hematopoietic stem cells cultured under the same conditions and for the same time as the first population of hematopoietic stem cells but not contacted with the compound.

In one embodiment, said method for expanding hematopoietic stem cells, comprises (a) providing a starting cell population comprising hematopoietic stem cells and (b) culturing said starting cell population ex vivo in the presence of an AHR antagonist agent compound of any one of the above aspects or embodiments.

The starting cell population comprising hematopoietic stem cells will be selected by the person skilled in the art depending on the envisaged use. Various sources of cells comprising hematopoietic stem cells have been described in the art, including bone marrow, peripheral blood, neonatal umbilical cord blood, placenta or other sources such as liver, particularly fetal liver.

The cell population may first be subjected to enrichment or purification steps, including negative and/or positive selection of cells based on specific cellular markers in order to provide the starting cell population. Methods for isolating said starting cell population based on specific cellular markers may use fluorescent activated cell sorting (FACS) technology also called flow cytometry or solid or insoluble substrate to which is bound antibodies or ligands that interact with specific cell surface markers. For example, cells may be contacted with a solid substrate (e.g., column of beads, flasks, magnetic particles) containing the antibodies and any unbound cells are removed. When a solid substrate comprising magnetic or paramagnetic beads is used, cells bound to the beads can be readily isolated by a magnetic separator.

In one embodiment, said starting cell population is enriched in a desirable cell marker phenotype (e.g., CD34+, CD133+, CD90+) or based on efflux of dyes such as rhodamine, Hoechst or aldehyde dehydrogenase activity. In one specific embodiment, said starting cell population is enriched in CD34+ cells. Methods for enriching blood cell population in CD34+ cells include kits commercialized by Miltenyi Biotec (CD34+ direct isolation kit, Miltenyi Biotec, Bergisch, Gladbach, Germany) or by Baxter (Isolex 3000).

In some embodiments, the hematopoietic stem cells are CD34+ hematopoietic stem cells. In some embodiments, the hematopoietic stem cells are CD90+ hematopoietic stem cells. In some embodiments, the hematopoietic stem cells are CD45RA− hematopoietic stem cells. In some embodiments, the hematopoietic stem cells are CD34+CD90+ hematopoietic stem cells. In some embodiments, the hematopoietic stem cells are CD34+CD45RA− hematopoietic stem cells. In some embodiments, the hematopoietic stem cells are CD90+CD45RA− hematopoietic stem cells. In some embodiments, the hematopoietic stem cells are CD34+CD90+CD45RA− hematopoietic stem cells.

In some embodiments, the hematopoietic stem cells are mammalian cells, such as human cells. In some embodiments, the human cells are CD34+ cells, such as CD34+ cells are CD34+, CD34+CD38−, CD34+CD38−CD90+, CD34+CD38−CD90+CD45RA−, CD34+CD38−CD90+CD45RA−CD49F+, or CD34+CD90+CD45RA− cells.

In some embodiments, the hematopoietic stem cells are obtained from human cord blood, mobilized human peripheral blood, or human bone marrow. The hematopoietic stem cells may, for example, be freshly isolated from the human or may have been previously cryopreserved.

The amount of cord blood from a single birth is often inadequate to treat an adult or an older child. One advantage of the expansion methods using the compounds of the invention, or an agent capable of down-regulating the activity and/or expression of aryl hydrocarbon receptor and/or a down-stream effector of aryl hydrocarbon receptor pathway, is that it enables the production of a sufficient amount of hematopoietic stem cells from only one cord blood unit.

Accordingly, in one embodiment, the starting cell population is derived from neonatal umbilical cord blood cells which have been enriched in CD34+ cells. In one related embodiment, said starting cell population is derived from one or two umbilical cord blood Units.

In another embodiment, the starting cell population is derived from human mobilized peripheral blood cells which have been enriched in CD34+ cells. In one related embodiment, said starting cell population is derived from human mobilized peripheral blood cells isolated from only one patient.

Said starting cell population enriched in CD34+ cells may preferably contain at least about 50% CD34+ cells, in some embodiments, more than about 90% CD34+ cells, and may comprise between $10^5$ and $10^9$ nucleated cells.

The starting cell population may be used directly for expansion or frozen and stored for use at a later date.

Conditions for culturing the starting cell population for hematopoietic stem cell expansion will vary depending, inter alia, on the starting cell population, the desired final number of cells, and desired final proportion of HSCs.

In one embodiment, the culturing conditions comprises the use of other cytokines and growth factors, generally known in the art for hematopoietic stem cell expansion. Such cytokines and growth factors include without limitation IL-1, IL-3, IL-6, IL-11, G-CSF, GM-CSF, SCF, FlT3-L, thrombopoietin (TPO), erythropoeitin, and analogs thereof. As used herein, "analogs" include any structural variants of the cytokines and growth factors having the biological activity as the naturally occurring forms, including without limitation, variants with enhanced or decreased biological activity when compared to the naturally occurring forms or cytokine receptor agonists such as an agonist antibody against the TPO receptor (for example, VB22B sc(Fv)2 as detailed in patent publication WO 2007/145227, and the like). Cytokine and growth factor combinations are chosen to expand HSC and progenitor cells while limiting the production of terminally differentiated cells. In one specific embodiment, one or more cytokines and growth factors are selected from the group consisting of SCF, Flt3-L and TPO. In one specific embodiment, at least TPO is used in a serum-free medium under suitable conditions for HSC expansion. In one related embodiment, a mixture of IL6, SCF, Flt3-L and TPO is used in the method for expanding HSCs in combination with the compound of the present disclosure.

The expansion of HSC may be carried out in a basal medium, which may be supplemented with mixtures of cytokines and growth factors. A basal medium typically comprises amino acids, carbon sources, vitamins, serum proteins (e.g. albumin), inorganic salts, divalent cations, buffers and any other element suitable for use in expansion of HSC. Examples of such basal medium appropriate for a method of expanding HSC include, without limitation, StemSpan® SFEM—Serum-Free Expansion Medium (StemCell Technologies, Vancouver, Canada), StemSpan® H3000—Defined Medium (StemCell Technologies, Vancouver, Canada), CellGro® SCGM (CellGenix, Freiburg Germany), StemPro®-34 SFM (Invitrogen).

In one embodiment, the compound of the present disclosure is administered during the expansion method of said starting cell population under a concentration appropriate for HSC expansion. In one specific embodiment, said compound or AHR modulating agent is administered at a concentration comprised between 1 pM and 100 µM, for example between 10 pM and 10 µM, or between 100 pM and 1 µM.

In one embodiment where starting cell population essentially consists of CD34+ enriched cells from one or two cord blood units, the cells are grown under conditions for HSC expansion from about 3 days to about 90 days, for example between 7 and 2 days and/or until the indicated fold expansion and the characteristic cell populations are obtained. In one specific embodiment, the cells are grown under conditions for HSC expansion not more than 21 days, 14 days or 7 days.

In one embodiment, the starting cell population is cultured during a time sufficient to reach an absolute number of CD34+ cells of at least $10^5$, $10^6$, $10^7$, $10^8$ or $10^9$ cells. In another embodiment, said starting cell population is cultured during a time sufficient for a 10 to 50000 fold expansion of CD34+ cells, for example between 100 and 10000 fold expansion, for examples between 50 and 1000 fold expansion.

The cell population obtained after the expansion method may be used without further purification or may be subject to further purification or selection steps.

The cell population may then be washed to remove the compound of the present disclosure and/or any other components of the cell culture and resuspended in an appropriate cell suspension medium for short term use or in a long-term storage medium, for example a medium suitable for cryopreservation.

Cell Population with Expanded Hematopoietic Stem Cells as Obtained by the Expansion Method and Therapeutic Compositions In another aspect, the disclosure features a composition comprising a population of hematopoietic stem cells, wherein the hematopoietic stem cells or progenitors thereof have been contacted with the compound of any one of the above aspects or embodiments, thereby expanding the hematopoietic stem cells or progenitors thereof.

The invention further provides a cell population with expanded hemapoetic stem cells obtainable or obtained by the expansion method described above. In one embodiment, such cell population is resuspended in a pharmaceutically acceptable medium suitable for administration to a mammalian host, thereby providing a therapeutic composition.

The compound as defined in the present disclosure enables the expansion of HSCs, for example from only one or two cord blood units, to provide a cell population quantitatively and qualitatively appropriate for efficient short and long term engraftment in a human patient in need thereof. In one embodiment, the present disclosure relates to a therapeutic composition comprising a cell population with expanded HSCs derived from not more than one or two cord blood units. In one embodiment, the present disclosure relates to a therapeutic composition containing a total amount of cells of at least about $10^5$, at least about $10^6$, at least about $10^7$, at least about $10^8$ or at least about $10^9$ cells with about 20% to about 100%, for example between about 43% to about 80%, of total cells being CD34+ cells. In certain embodiments, said composition contains between 20-100%, for example between 43-80%, of total cells being CD34+CD90+CD45RA−.

In some embodiments, the hematopoietic stem cells are CD34+ hematopoietic stem cells. In some embodiments, the hematopoietic stem cells are CD90+ hematopoietic stem cells. In some embodiments, the hematopoietic stem cells are CD45RA− hematopoietic stem cells. In some embodiments, the hematopoietic stem cells are CD34+CD90+ hematopoietic stem cells. In some embodiments, the hematopoietic stem cells are CD34+CD45RA− hematopoietic stem cells. In some embodiments, the hematopoietic stem cells are CD90+CD45RA− hematopoietic stem cells. In some embodiments, the hematopoietic stem cells are CD34+CD90+CD45RA− hematopoietic stem cells.

In some embodiments, the hematopoietic stem cells of the therapeutic composition are mammalian cells, such as human cells. In some embodiments, the human cells are CD34+ cells, such as CD34+ cells are CD34+, CD34+ CD38−, CD34+CD38−CD90+, CD34+CD38-CD90+ CD45RA−, CD34+CD38−CD90+CD45RA−CD49F+, or CD34+CD90+CD45RA− cells.

In some embodiments, the hematopoietic stem cells of the therapeutic composition are obtained from human cord blood, mobilized human peripheral blood, or human bone marrow. The hematopoietic stem cells may, for example, be freshly isolated from the human or may have been previously cryopreserved.

Methods of Treatment

As described herein, hematopoietic stem cell transplant therapy can be administered to a subject in need of treatment so as to populate or repopulate one or more blood cell types, such as a blood cell lineage that is deficient or defective in a patient suffering from a stem cell disorder. Hematopoietic stem and progenitor cells exhibit multi-potency, and can thus differentiate into multiple different blood lineages including, but not limited to, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells). Hematopoietic stem cells are additionally capable of self-renewal, and can thus give rise to daughter cells that have equivalent potential as the mother cell, and also feature the capacity to be reintroduced into a transplant recipient whereupon they home to the hematopoietic stem cell niche and re-establish productive and sustained hematopoiesis. Thus, hematopoietic stem and progenitor cells represent a useful therapeutic modality for the treatment of a wide array of disorders in which a patient has a deficiency or defect in a cell type of the hematopoietic lineage. The deficiency or defect may be caused, for example, by depletion of a population of endogenous cells of the hematopoietic system due to administration of a chemotherapeutic agent (e.g., in the case of a patient suffering from a cancer, such as a hematologic cancer described herein). The deficiency or defect may be caused, for example, by depletion of a population of endogenous hematopoietic cells due to the activity of self-reactive immune cells, such as T lymphocytes or B lymphocytes that cross-react with self antigens (e.g., in the case of a patient suffering from an autoimmune disorder, such as an autoimmune disorder described herein). Additionally or alternatively, the deficiency or defect in cellular activity may be caused by aberrant expression of an enzyme (e.g., in the case of a patient suffering from various metabolic disorders, such as a metabolic disorder described herein).

Thus, hematopoietic stem cells can be administered to a patient defective or deficient in one or more cell types of the hematopoietic lineage in order to re-constitute the defective or deficient population of cells in vivo, thereby treating the pathology associated with the defect or depletion in the endogenous blood cell population. Hematopoietic stem and progenitor cells can be used to treat, e.g., a non-malignant hemoglobinopathy (e.g., a hemoglobinopathy selected from the group consisting of sickle cell anemia, thalassemia, Fanconi anemia, aplastic anemia, and Wiskott-Aldrich syndrome). In these cases, for example, a population of hematopoietic stem cells may be expanded ex vivo by culturing the cells in the presence of an aryl hydrocarbon receptor antagonist described herein. The hematopoietic stem cells thus expanded may then be administered to a patient, where the cells may home to a hematopoietic stem cell niche and re-constitute a population of cells that are damaged or deficient in the patient.

Hematopoietic stem or progenitor cells mobilized to the peripheral blood of a subject may be withdrawn (e.g., harvested or collected) from the subject by any suitable technique. For example, the hematopoietic stem or progenitor cells may be withdrawn by a blood draw. In some embodiments, hematopoietic stem or progenitor cells mobilized to a subject's peripheral blood as contemplated herein may be harvested (i.e., collected) using apheresis. In some embodiments, apheresis may be used to enrich a donor's blood with mobilized hematopoietic stem or progenitor cells.

Additionally or alternatively, hematopoietic stem and progenitor cells can be used to treat an immunodeficiency, such as a congenital immunodeficiency. Additionally or alternatively, the compositions and methods described herein can be used to treat an acquired immunodeficiency (e.g., an acquired immunodeficiency selected from the group consisting of HIV and AIDS). In these cases, for example, a population of hematopoietic stem cells may be expanded ex vivo by culturing the cells in the presence of an aryl hydrocarbon receptor antagonist described herein. The hematopoietic stem cells thus expanded may then be administered to a patient, where the cells may home to a hematopoietic stem cell niche and re-constitute a population of immune cells (e.g., T lymphocytes, B lymphocytes, NK cells, or other immune cells) that are damaged or deficient in the patient.

Hematopoietic stem and progenitor cells can also be used to treat a metabolic disorder (e.g., a metabolic disorder selected from the group consisting of glycogen storage diseases, mucopolysaccharidoses, Gaucher's Disease, Hurlers Disease, sphingolipidoses, Sly Syndrome, alpha-Mannosidosis, X-ALD, Aspartylglucosaminuria, Wolman Disease, late infantile metachromatic leukodystrophy, Niemann Pick Type C disease, Niemann Pick Type B disease, Juvenile Tay Sachs, Infantile Tay Sachs, Juvenile Sandhoff, Infantile Sandhoff, GM1 gangliosidosis, MPSIV (Morquio), Presymptomatic or milder forms of globoid cell leukodystrophy, infantile Krabbe when newborn and asymptomatic, early diagnosis fucosidosis, Fabry, MPSIS, MPSIH/S, MPSII, MPSVI in conjunction with ERT or where alloantibodies attenuate efficacy of ERT, Pompe where alloantibodies attenuate efficacy of ERT, Mucolipidosis II, and metachromatic leukodystrophy). In these cases, for example, a population of hematopoietic stem cells may be expanded ex vivo by culturing the cells in the presence of an aryl hydrocarbon receptor antagonist described herein. The hematopoietic stem cells thus expanded may then be administered to a patient, where the cells may home to a hematopoietic stem cell niche and re-constitute a population of hematopoietic cells that are damaged or deficient in the patient.

Additionally or alternatively, hematopoietic stem or progenitor cells can be used to treat a malignancy or proliferative disorder, such as a hematologic cancer or myeloproliferative disease. In the case of cancer treatment, for example, a population of hematopoietic stem cells may be expanded ex vivo by culturing the cells in the presence of an aryl hydrocarbon receptor antagonist described herein. The hematopoietic stem cells thus expanded may then be administered to a patient, where the cells may home to a hematopoietic stem cell niche and re-constitute a population of cells that are damaged or deficient in the patient, such as a population of hematopoietic cells that is damaged or deficient due to the administration of one or more chemotherapeutic agents to the patient. In some embodiments, hematopoietic stem or progenitor cells may be infused into a patient in order to repopulate a population of cells depleted during cancer cell eradication, such as during systemic chemotherapy. Exemplary hematological cancers that can be treated by way of administration of hematopoietic stem and progenitor cells in accordance with the compositions and methods described herein are acute myeloid leukemia, acute lymphoid leukemia, chronic myeloid leukemia, chronic lymphoid leukemia, multiple myeloma, diffuse large B-cell lymphoma, and non-Hodgkin's lymphoma, as well as other cancerous conditions, including neuroblastoma.

Additional diseases that can be treated by the administration of hematopoietic stem and progenitor cells to a patient include, without limitation, adenosine deaminase deficiency and severe combined immunodeficiency, hyper immunoglobulin M syndrome, Chediak-Higashi disease, hereditary lymphohistiocytosis, osteopetrosis, osteogenesis imperfecta, storage diseases, thalassemia major, systemic sclerosis, systemic lupus erythematosus, multiple sclerosis, and juvenile rheumatoid arthritis.

In addition, administration of hematopoietic stem and progenitor cells can be used to treat autoimmune disorders. In some embodiments, upon infusion into a patient, transplanted hematopoietic stem and progenitor cells may home to a stem cell niche, such as the bone marrow, and establish productive hematopoiesis. This, in turn, can re-constitute a population of cells depleted during autoimmune cell eradication, which may occur due to the activity of self-reactive lymphocytes (e.g., self-reactive T lymphocytes and/or self-reactive B lymphocytes). Autoimmune diseases that can be treated by way of administering hematopoietic stem and progenitor cells to a patient include, without limitation, psoriasis, psoriatic arthritis, Type 1 diabetes mellitus (Type 1 diabetes), rheumatoid arthritis (RA), human systemic lupus (SLE), multiple sclerosis (MS), inflammatory bowel disease (IBD), lymphocytic colitis, acute disseminated encephalomyelitis (ADEM), Addison's disease, alopecia universalis, ankylosing spondylitisis, antiphospholipid antibody syndrome (APS), aplastic anemia, autoimmune hemolytic anemia, autoimmune hepatitis, autoimmune inner ear disease (AIED), autoimmune lymphoproliferative syndrome (ALPS), autoimmune oophoritis, Balo disease, Behcet's disease, bullous pemphigoid, cardiomyopathy, Chagas' disease, chronic fatigue immune dysfunction syndrome (CFIDS), chronic inflammatory demyelinating polyneuropathy, Crohn's disease, cicatrical pemphigoid, coeliac sprue-dermatitis herpetiformis, cold agglutinin disease, CREST syndrome, Degos disease, discoid lupus, dysautonomia, endometriosis, essential mixed cryoglobulinemia, fibromyalgia-fibromyositis, Goodpasture's syndrome, Grave's disease, Guillain-Barre syndrome (GBS), Hashimoto's thyroiditis, Hidradenitis suppurativa, idiopathic and/or acute thrombocytopenic purpura, idiopathic pulmonary fibrosis, IgA neuropathy, interstitial cystitis, juvenile arthritis, Kawasaki's disease, lichen planus, Lyme disease, Meniere disease, mixed connective tissue disease (MCTD), myasthenia gravis, neuromyotonia, opsoclonus myoclonus syndrome (OMS), optic neuritis, Ord's thyroiditis, pemphigus vulgaris, pernicious anemia, polychondritis, polymyositis and dermatomyositis, primary biliary cirrhosis, polyarteritis nodosa, polyglandular syndromes, polymyalgia rheumatica, primary agammaglobulinemia, Raynaud phenomenon, Reiter s syndrome, rheumatic fever, sarcoidosis, scleroderma, Sjögren's syndrome, stiff person syndrome, Takayasu's arteritis, temporal arteritis (also known as "giant cell arteritis"), ulcerative colitis, collagenous colitis, uveitis, vasculitis, vitiligo, vulvodynia ("vulvar vestibulitis"), and Wegener s granulomatosis.

Hematopoietic stem cell transplant therapy may additionally be used to treat neurological disorders, such as Parkinson's disease, Alzheimer's disease, multiple sclerosis, Amyotrophic lateral sclerosis, Huntington's disease, mild cognitive impairment, amyloidosis, AIDS-related dementia, encephalitis, stroke, head trauma, epilepsy, mood disorders, and dementia. As described herein, upon transplantation into a patient, hematopoietic stem cells may migrate to the central nervous system and differentiate into, for example, microglial cells, thereby re-constituting a population of cells that may be damaged or deficient in a patient suffering from a neurological disorder. In these cases, for example, a population of hematopoietic stem cells may be expanded ex vivo by culturing the cells in the presence of an aryl hydrocarbon receptor antagonist described herein. The hematopoietic stem cells thus expanded may then be administered to a patient suffering from a neurological disorder, where the cells may home to the central nervous system, such as the brain of the patient, and re-constitute a population of hematopoietic cells (e.g., microglial cells) that are damaged or deficient in the patient.

As described herein, hematopoietic stem cell transplant therapy can be administered to a subject in need of treatment so as to populate or repopulate one or more blood cell types, such as a blood cell lineage that is deficient or defective in a patient suffering from a stem cell disorder. Hematopoietic stem and progenitor cells exhibit multi-potency, and can thus differentiate into multiple different blood lineages including, in one embodiment, microglia.

The methods disclosed herein for treating disorders in a subject in need thereof comprise the administration of an expanded population of hematopoietic stem cells to a subject in need thereof. In one embodiment, the number of expanded hematopoietic stem cells administered to the subject is equal to or greater than the amount of hematopoietic stem cells needed to achieve a therapeutic benefit. In one embodiment, the number of expanded hematopoietic stem cells administered to the subject is greater than the amount of hematopoietic stem cells needed to achieve a therapeutic benefit. In one embodiment, the therapeutic benefit achieved is proportional to the number of expanded hematopoietic stem cells that are administered.

A dose of the expanded hematopoietic stem cell composition of the disclosure is deemed to have achieved a therapeutic benefit if it alleviates a sign or a symptom of the disease. The sign or symptom of the disease may comprise one or more biomarkers associated with the disease, or one or more clinical symptoms of the disease.

For example, administration of the expanded hematopoietic stem cell composition may result in the reduction of a biomarker that is elevated in individuals suffering from the disease, or elevate the level of a biomarker that is reduced in individuals suffering from the disease.

For example, administering the expanded hematopoietic stem cell composition of the disclosure may elevate the level of an enzyme that is reduced in an individual suffering from a metabolic disorder. This change in biomarker level may be partial, or the level of the biomarker may return to levels normally seen in healthy individuals.

Selection of Donors and Patients

In some embodiments, the patient is the donor. In such cases, withdrawn hematopoietic stem or progenitor cells may be re-infused into the patient, such that the cells may subsequently home hematopoietic tissue and establish productive hematopoiesis, thereby populating or repopulating a line of cells that is defective or deficient in the patient (e.g., a population of megakaryocytes, thrombocytes, platelets, erythrocytes, mast cells, myeoblasts, basophils, neutrophils, eosinophils, microglia, granulocytes, monocytes, osteoclasts, antigen-presenting cells, macrophages, dendritic cells, natural killer cells, T-lymphocytes, and B-lymphocytes). In this scenario, the transplanted hematopoietic stem or progenitor cells are least likely to undergo graft rejection, as the infused cells are derived from the patient and express the same HLA class I and class II antigens as expressed by the patient.

Alternatively, the patient and the donor may be distinct. In some embodiments, the patient and the donor are related, and may, for example, be HLA-matched. As described herein, HLA-matched donor-recipient pairs have a decreased risk of graft rejection, as endogenous T cells and NK cells within the transplant recipient are less likely to recognize the incoming hematopoietic stem or progenitor cell graft as foreign, and are thus less likely to mount an immune response against the transplant. Exemplary HLA-matched donor-recipient pairs are donors and recipients that are genetically related, such as familial donor-recipient pairs (e.g., sibling donor-recipient pairs).

In some embodiments, the patient and the donor are HLA-mismatched, which occurs when at least one HLA antigen, in particular with respect to HLA-A, HLA-B and HLA-DR, is mismatched between the donor and recipient. To reduce the likelihood of graft rejection, for example, one haplotype may be matched between the donor and recipient, and the other may be mismatched.

Administration and Dosing of Hematopoietic Stem or Progenitor Cells

Hematopoietic stem and progenitor cells described herein may be administered to a subject, such as a mammalian subject (e.g., a human subject) suffering from a disease, condition, or disorder described herein, by one or more routes of administration. For instance, hematopoietic stem cells described herein may be administered to a subject by intravenous infusion. Hematopoietic stem cells may be administered at any suitable dosage. Non-limiting examples of dosages include about $1 \times 10^5$ CD34+ cells/kg of recipient to about $1 \times 10^8$ CD34+ cells/kg (e.g., from about $2 \times 10^5$ CD34+ cells/kg to about $9 \times 10^7$ CD34+ cells/kg, from about $3 \times 10^5$ CD34+ cells/kg to about $8 \times 10^7$ CD34+ cells/kg, from about $4 \times 10^5$ CD34+ cells/kg to about $7 \times 10^7$ CD34+ cells/kg, from about $5 \times 10^5$ CD34+ cells/kg to about $6 \times 10^7$ CD34+ cells/kg, from about $5 \times 10^5$ CD34+ cells/kg to about $1 \times 10^8$ CD34+ cells/kg, from about $6 \times 10^5$ CD34+ cells/kg to about $1 \times 10^8$ CD34+ cells/kg, from about $7 \times 10^5$ CD34+ cells/kg to about $1 \times 10^8$ CD34+ cells/kg, from about $8 \times 10^5$ CD34+ cells/kg to about $1 \times 10^8$ CD34+ cells/kg, from about $9 \times 10^5$ CD34+ cells/kg to about $1 \times 10^8$ CD34+ cells/kg, from about $1 \times 10^7$ CD34+ cells/kg to about $1 \times 10^8$ CD34+ cells/kg, or from about $1 \times 10^6$ CD34+ cells/kg to about $1 \times 10^7$ CD34+ cells/kg, among others).

Hematopoietic stem or progenitor cells and pharmaceutical compositions described herein may be administered to a subject in one or more doses. When multiple doses are administered, subsequent doses may be provided one or more days, weeks, months, or years following the initial dose.

EXAMPLES

The following examples are put forth so as to provide those of ordinary skill in the art with a description of how the compositions and methods described herein may be used, made, and evaluated, and are intended to be purely exemplary and are not intended to limit the scope of what the inventors regard as their invention.

Example 1. Synthesis of Compound (5)

Compound (5) can be synthesized, for example, using a Hartwig-Buchwald amination process that includes coupling a halogenated imidazopyridine precursor to a protected 2-aminoethyl indole, as shown in Scheme 8, below.

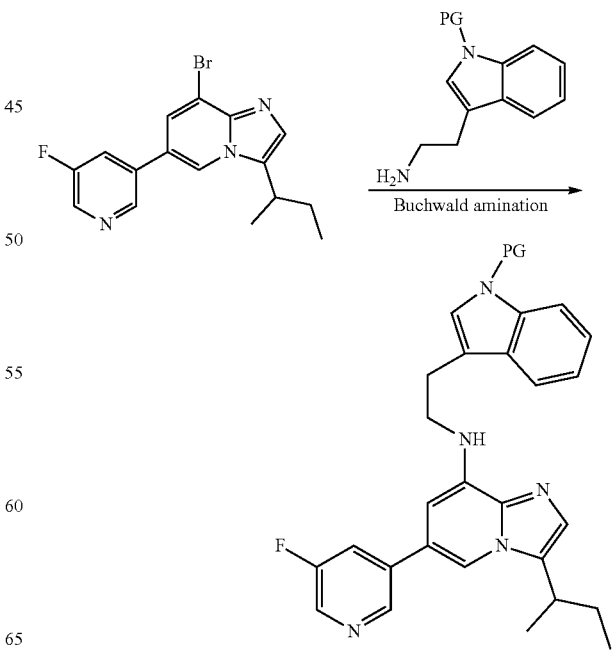

Scheme 8.

Deprotection of the ensuing adduct, for instance, using conventional deprotection methods known in the art, can yield compound (5).

Alternatively, the tandem amination-hydrolysis procedure outline in Scheme 9, below, may be used to synthesize compound (5).

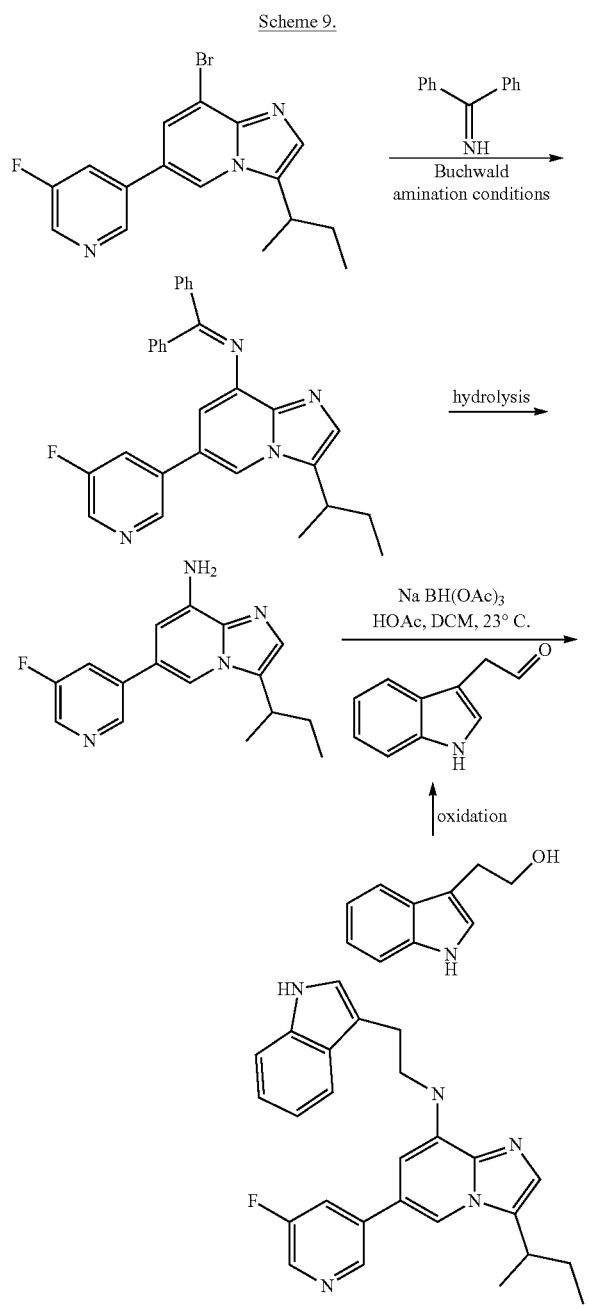

Example 2. Synthesis of Compound (16)

In a manner similar to that described in Example 1, compound (16) can be synthesized by way of a Hartwig-Buchwald process, followed by a Suzuki coupling and indole deprotection, as shown in Scheme 10, below.

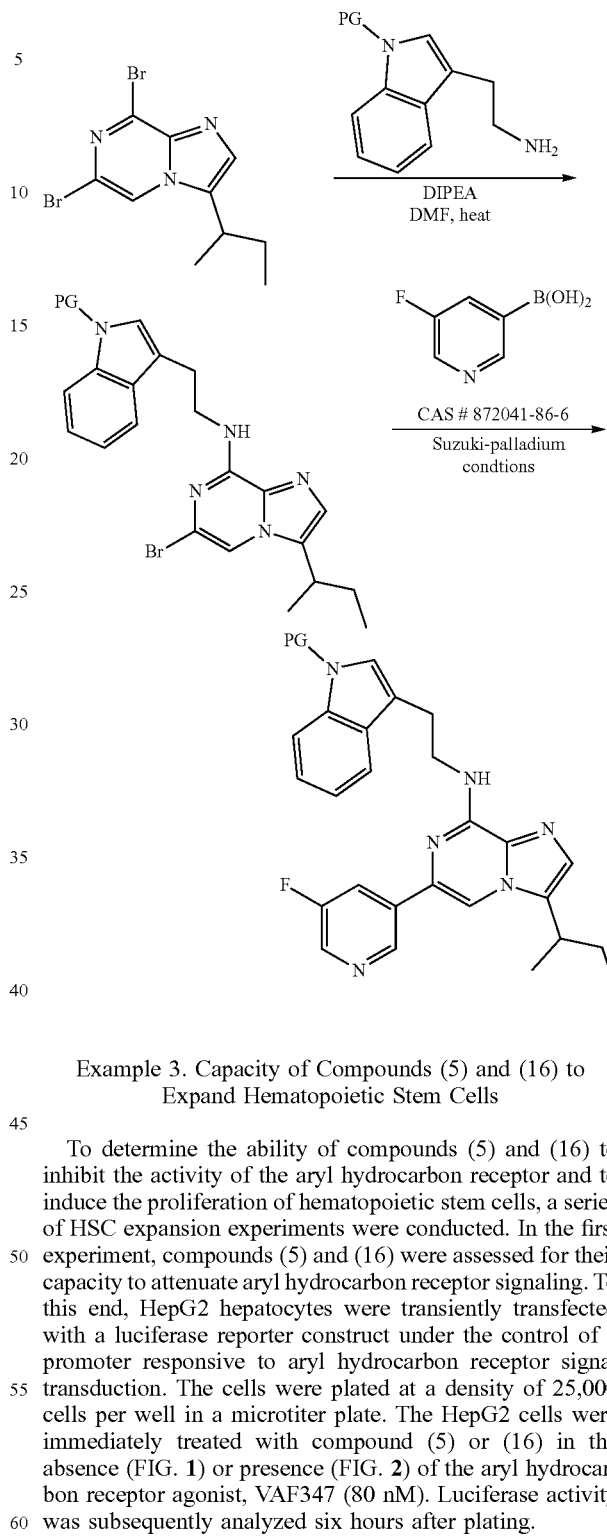

Example 3. Capacity of Compounds (5) and (16) to Expand Hematopoietic Stem Cells To determine the ability of compounds (5) and (16) to inhibit the activity of the aryl hydrocarbon receptor and to induce the proliferation of hematopoietic stem cells, a series of HSC expansion experiments were conducted. In the first experiment, compounds (5) and (16) were assessed for their capacity to attenuate aryl hydrocarbon receptor signaling. To this end, HepG2 hepatocytes were transiently transfected with a luciferase reporter construct under the control of a promoter responsive to aryl hydrocarbon receptor signal transduction. The cells were plated at a density of 25,000 cells per well in a microtiter plate. The HepG2 cells were immediately treated with compound (5) or (16) in the absence (FIG. 1) or presence (FIG. 2) of the aryl hydrocarbon receptor agonist, VAF347 (80 nM). Luciferase activity was subsequently analyzed six hours after plating.

Figure 2:
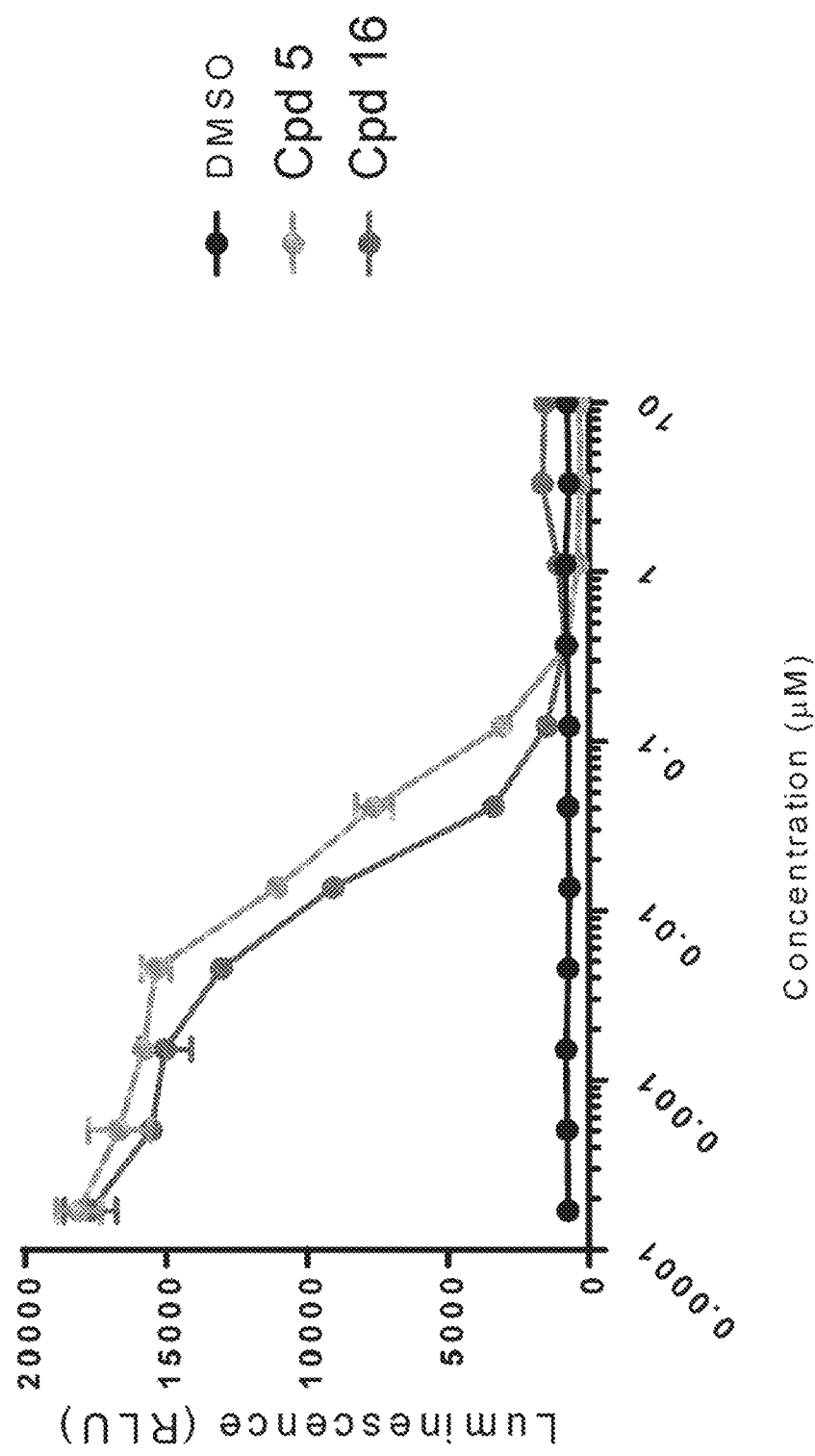
FIG. 2 is a graph demonstrating the effect of compound (5) and compound (16) on the aryl hydrocarbon receptor-driven expression of luciferase in the presence of the aryl hydrocarbon receptor agonist VAF347 in transiently transfected HepG2 cells in vitro. Experimental details for this experiment are reported in Example 3, below.

As shown in FIGS. 1 and 2, compounds (5) and (16) were capable of suppressing aryl hydrocarbon receptor activity even in the presence of the activator VAF347.

Figure 3:
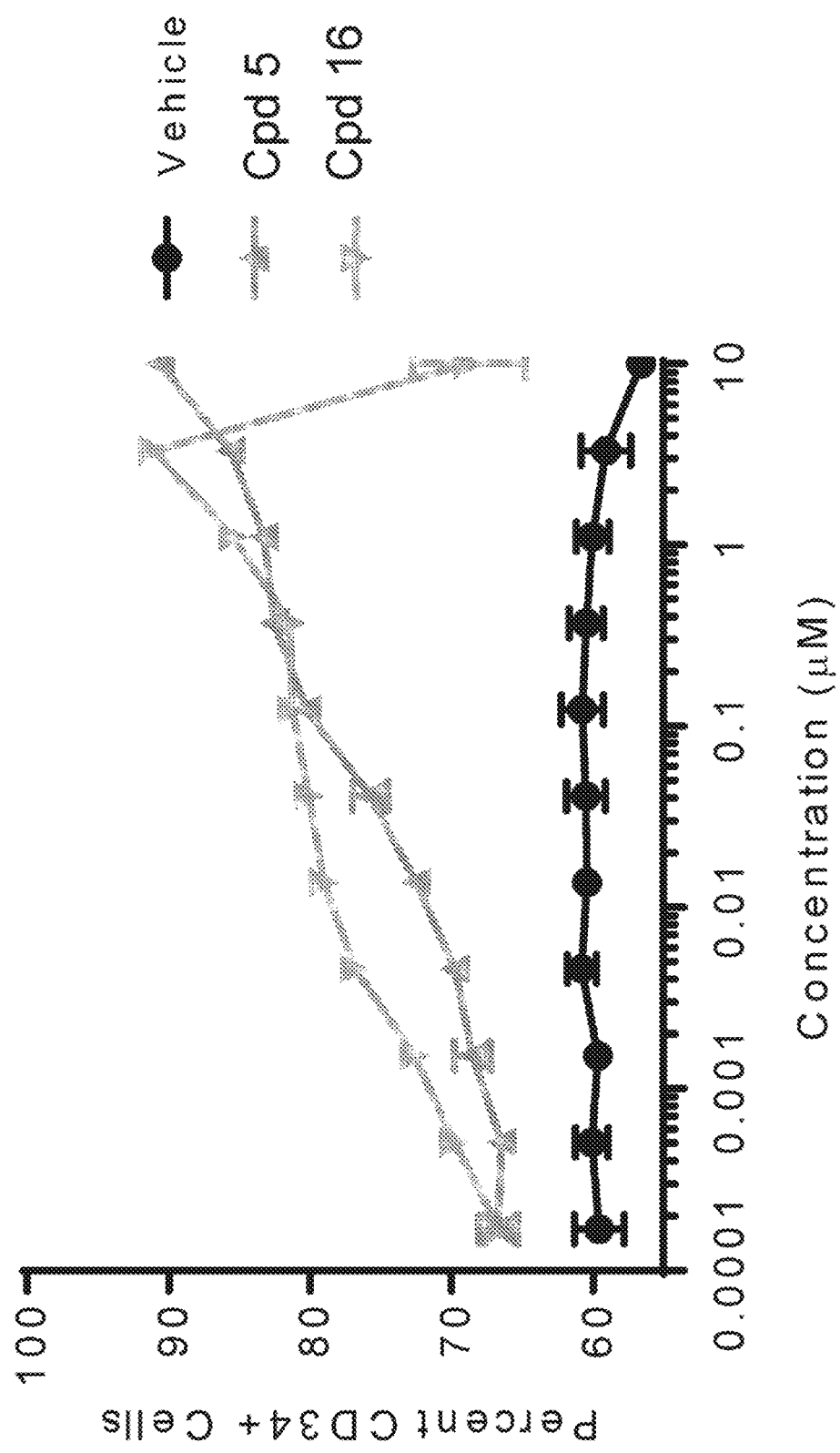
FIG. 3 is a graph demonstrating the effect of compound (5) and compound (16) on the quantity of CD34+ cells in a hematopoietic stem cell population over the course of a seven-day experiment. Experimental details for this experiment are reported in Example 3, below.

To assess the ability of compounds (5) and (16) to induce the proliferation of hematopoietic stem cells, a population of mononuclear peripheral blood cells enriched in CD34+ cells were plated at a density of 2,350 cells per well (50 µL) in a microtiter plate in the presence of each compound. The percentage of CD34+ hematopoietic stem cells was assessed seven days following the initial plating. The results of this experiment are reported in FIG. 3. As shown therein, compounds (5) and (16) were capable of potentiating hematopoietic stem cell growth in a dose-dependent manner. The compounds of formula (I) and (II) described herein can thus be used to expand hematopoietic stem cells ex vivo in order to obtain sufficient quantities of such cells for in vivo applications.

Surprisingly, compounds (5) and (16) were capable of promoting hematopoietic stem cell expansion with a potency greater than that reported for StemReganinl (SR1), which is described, for example, in U.S. Pat. No. 8,927,281, which is incorporated herein by reference. This difference in biological activity is expected to have a significant clinical benefit, as a reduced quantity of aryl hydrocarbon receptor antagonists according to formulas (I) and (II) described herein relative to SR1 may be used to prepare an amplified population of hematopoietic stem cells suitable for transplantation to a patient in need thereof (for instance, as described in Example 4, below).

Example 4. Administration of Hematopoietic Stem Cells to a Human Patient in Need Thereof Using the methods disclosed herein, a population of hematopoietic stem cells that have been expanded ex vivo using the aryl hydrocarbon receptor antagonists of formula (I) or (II) can be administered to a human patient in need of hematopoietic stem cell transplant therapy. Prior to the transplantation, a population of hematopoietic stem cells may be cultured in the presence of the aryl hydrocarbon receptor antagonist for one or more days (e.g., for one, two, three, four, five, six, seven, eight, nine, ten, or more days, replenishing culture medium as needed). The hematopoietic stem cell population may be expanded to $1\times10^6$ to $1\times10^{12}$ hematopoietic stem cells prior to infusion into the patient in need of transplant therapy.

Following the conclusion of the expansion process, the patient may receive an infusion (e.g., an intravenous infusion) of the expanded, exogenous hematopoietic stem cells, such as from a practitioner that performed the ex vivo expansion or from a different physician. The patient may then be administered an infusion of autologous, syngeneic, or allogeneic hematopoietic stem cells, for instance, at a dosage of from $1\times10^3$ to $1\times10^9$ hematopoietic stem cells/kg. The engraftment of the hematopoietic stem cell transplant may be monitored, for example, by detecting an increase in concentration of hematopoietic stem cells or cells of the hematopoietic lineage (such as megakaryocytes, thrombocytes, platelets, erythrocytes, mast cells, myoblasts, basophils, neutrophils, eosinophils, microglia, granulocytes, monocytes, osteoclasts, antigen-presenting cells, macrophages, dendritic cells, natural killer cells, T-lymphocytes, and B-lymphocytes) in a blood sample isolated from the patient following administration of the transplant. This analysis may be conducted, for example, from 1 hour to 6 months, or more, following hematopoietic stem cell transplant therapy (e.g., 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, or more). A finding that the concentration of hematopoietic stem cells or cells of the hematopoietic lineage has increased (e.g., by 1%, 2%, 3%, 4%, 5%, 6%, 7%, 8%, 9%, 10%, 20%, 30%, 40%, 50%, 60%, 70%, 80%, 90%, 100%, 200%, 500%, or more) following the transplant therapy relative to the concentration of the corresponding cell type prior to transplant therapy provides one indication that the transplantation therapy is successful.

Figure 4:
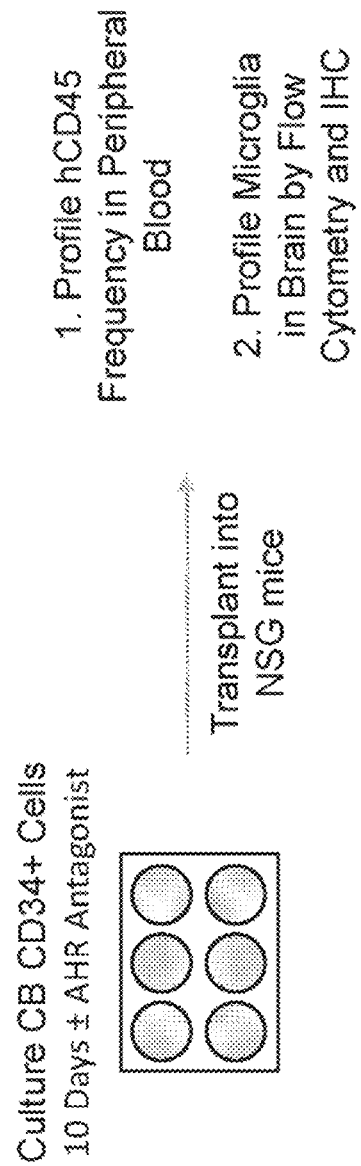
FIG. 4 is a scheme showing the design of experiments, described in Example 5, below, aimed at examining the ability of hematopoietic stem cells to migrate to central nervous system tissue and promote the engraftment of microglial cells in the brain.

Example 5. Engraftment of Microglial Cells in the Central Nervous System Following Hematopoietic Stem Cell Transplant To investigate the ability of hematopoietic stem cells to differentiate into microglial cells and subsequently engraft in central nervous system tissue, such as the brain of a hematopoietic stem cell transplant recipient, a series of experiments were conducted in which human hematopoietic stem cells were first expanded ex vivo in the presence of an aryl hydrocarbon receptor antagonist (compound (16) or compound (24)) and were subsequently transplanted into NSG mice, in accordance with the scheme shown in FIG. 4. The frequency of human CD45+ cells in the peripheral blood of the mice was then determined, as well as the profile of microglial cells in the brain tissue using flow cytometry and immunohistochemistry techniques.

Figure 5A:
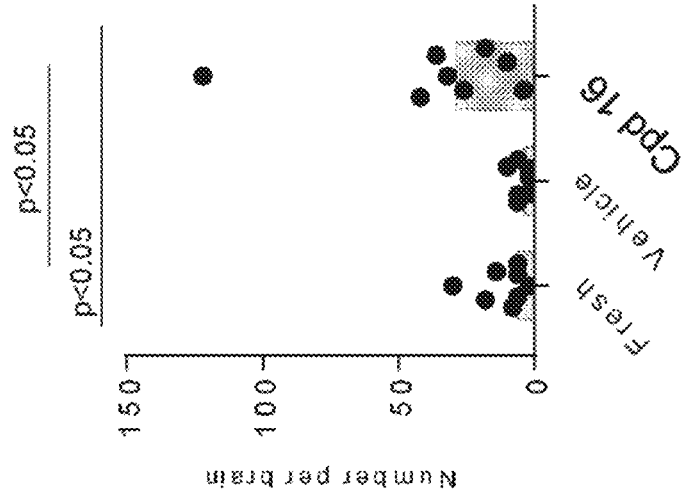
FIGS. 5A and 5B are graphs showing the ability of hematopoietic stem cells expanded, ex vivo, in the presence of compound (16) to increase the frequency of CD45+ cells in peripheral blood of NSG mice, and to promote the engraftment of microglial cells in the brains of NSG mice. Each bar graph shows the median value obtained upon examination of n=8 NSG mice.
Figure 5B:
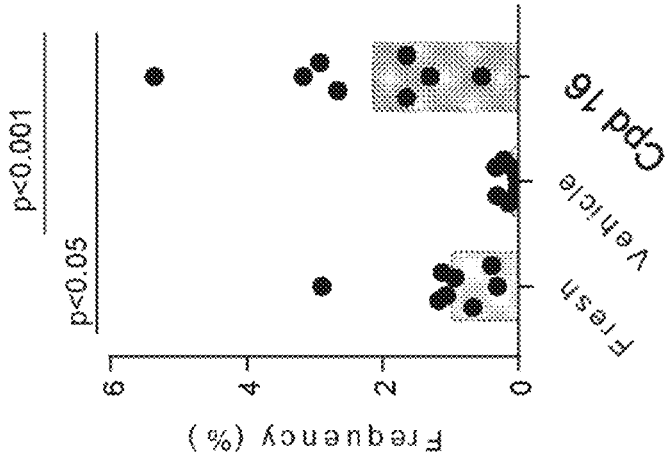
Figure 6B:
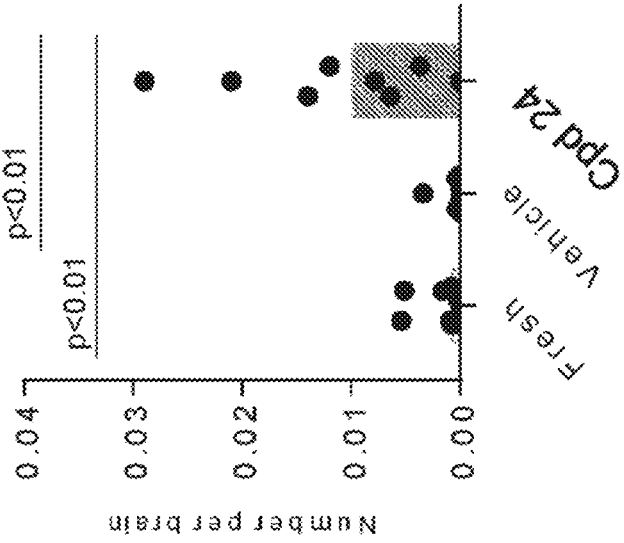
FIGS. 6A and 6B are graphs showing the ability of hematopoietic stem cells expanded, ex vivo, in the presence of compound (24) to increase the frequency of CD45+ cells in peripheral blood of NSG mice, and to promote the engraftment of microglial cells in the brains of NSG mice. Each bar graph shows the median value obtained upon examination of n=6-8 NSG mice.
Figure 6A:
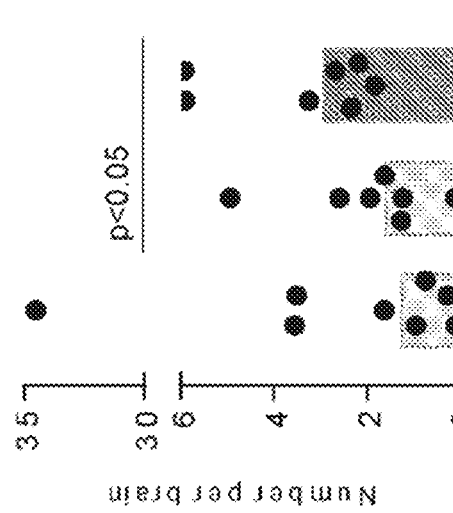

As shown in FIGS. 5A and 5B, upon transplantation of hematopoietic stem cells expanded ex vivo in the presence of compound (16), NSG mice exhibited an increased frequency of hCD45+ cells in peripheral blood, as well as an increased engraftment of hCD45+CD11b+ microglial cells in the brain. Similar results were obtained upon transplantation of hematopoietic stem cells expanded ex vivo in the presence of compound (24), as shown in FIGS. 6A and 6B.

Collectively, these data demonstrate the ability of hematopoietic stem cells expanded in the presence of aryl hydrocarbon receptor antagonists described herein to promote the engraftment of microglial cells in central nervous system tissue of a hematopoietic stem cells transplant recipient. These findings provide further evidence that hematopoietic stem cell transplantation can be used to treat a wide array of neurological disorders, including Parkinson's disease, Alzheimer's disease, multiple sclerosis, Amyotrophic lateral sclerosis, Huntington's disease, mild cognitive impairment, amyloidosis, AIDS-related dementia, encephalitis, stroke, head trauma, epilepsy, mood disorders, and dementia, among others.

Materials and Methods

Cord Blood Expansion and Transplantation

Approximately 60,000 cord blood CD34+ cells were seeded in T25 flasks at a final volume of 12 mL in HSC growth media (SFEM supplemented with Pen/Strep, 50 ng/mL FLT3L, TPO, SCF, and IL-6). Flasks were incubated for 10 days at 37° C./5% $CO_2$. Cells were cultured in the presence of 500 nM of AHR antagonist, where indicated. Cells were transferred to a larger flask when needed to maintain cells at a density less than $1\times10^6$ cells/mL throughout the culture period.

At the time of thaw, an equal number of cells to the starting cell cultures were injected into NSG mice, sublethally irradiated (200 cGy) 24 hours prior to injection. After 10 days of culture, the entire progeny of the cultures was injected into NSG mice. Peripheral blood was harvested by retro-orbital bleeding at approximately weeks 4 and 8 or by cardiac puncture at week 12 and chimerism was assessed by flow cytometry using antibodies against hCD45, mCD45, hCD33, hCD19, hCD3 and a viability dye.

Brain Harvesting and Processing

At 3 months, brains were harvested. 1 hemisphere was fixed in formalin, embedded, and used for immunohistochemistry. The other hemisphere was crushed in Dounce buffer (15 mM HEPES/0.5% glucose in phenol red-free HBSS) and filtered through a 40 μM filter to create a single cell suspension and resuspended in 900 μL 0.5% BSA/PBS. Myelin was depleted from brain samples, per manufacturer's instructions, by incubating with 100 μL myelin removal beads (Miltenyi Biotec), incubating for 15 minutes at 4° C., washing with PBS, and resuspending in 1 mL MACS Buffer prior to deletion on an AutoMACs Pro.

Flow Cytometric Detection of Microglia

Myelin-depleted samples were resuspended in 100 μL PBS and stained with antibodies against hCD45, mCD45, CD11b, CD19, CD3, and 7-AAD viability dye. Cells were washed once in PBS and resuspended in 300 μL final volume. The entire sample was acquired by flow cytometry (BD Celesta) to quantitate the number of microglia per brain hemisphere.

Immunohistochemical Detection of Microglia

Embedded brains were sectioned at approximately 5 microns and stained with Ku80 (brown) and Iba-1 (red) primary antibodies). Mouse brains were analyzed from each transplanted mouse and five levels were analyzed each. Glass slides were scanned at 20× using an Aperio AT2 whole slide scanner. Image analysis was performed on the digital slide images using Visiopharm software.

Example 6. Synthesis of Compound (24)

In a manner similar to that described in Example 1 and Example 2, compound (24) can be synthesized by way of an arene iodination and Hartwig-Buchwald process, followed by a first Suzuki coupling, a second Suzuki coupling and alkene reduction by catalytic hydrogenation over palladium as shown in Scheme 11, below.

Figure 7:
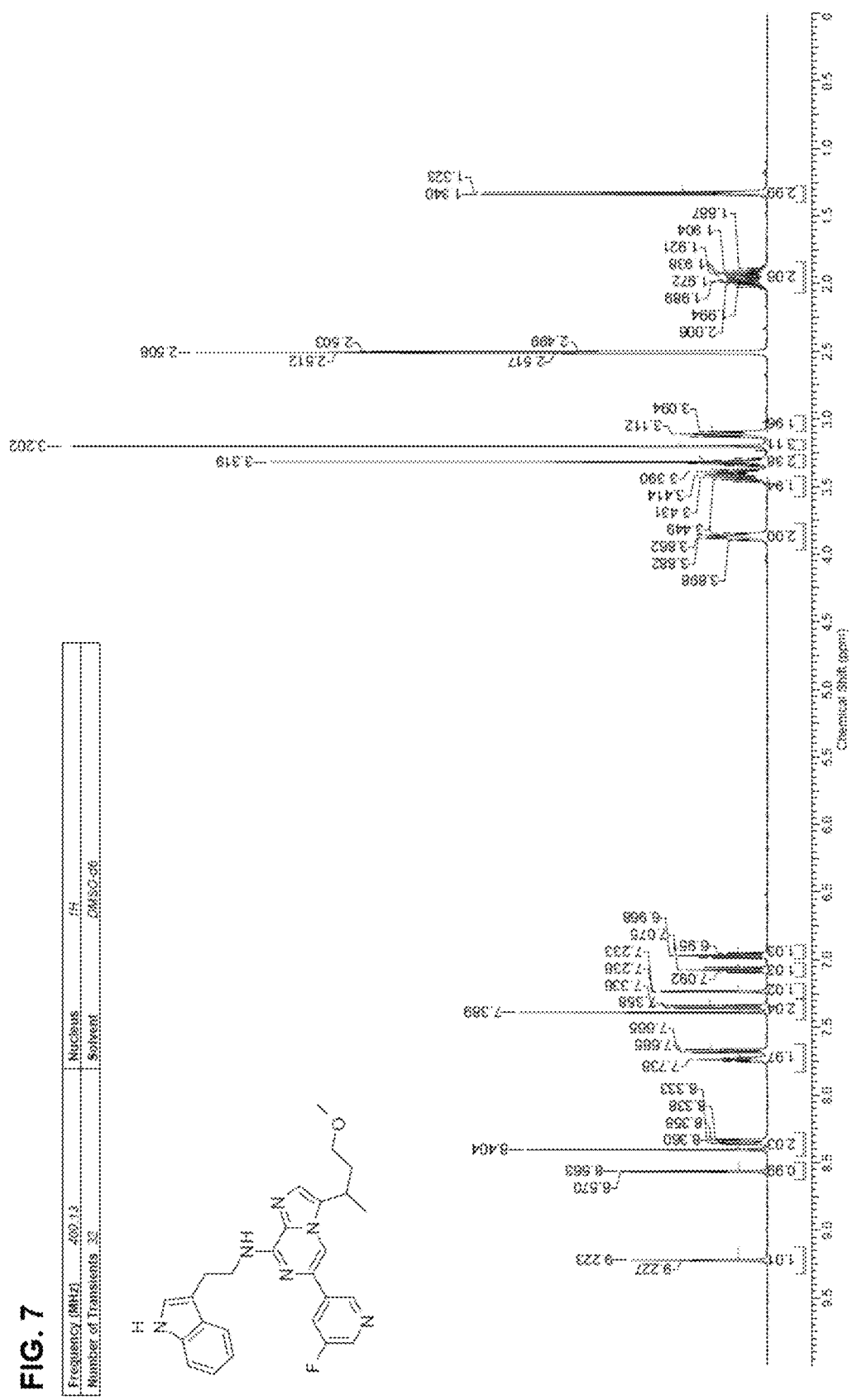
FIG. 7 sets forth a $^1$H-NMR spectra of compound (24) in DMSO-d6.

6-(5-fluoropyridin-3-yl)-N-[2-(1H-indol-3-yl)ethyl]-3-(3-methoxy-1-methylpropyl)imidazo[1,2-a]pyrazin-8-amine, Compound (24) was isolated as a white solid. FIG. 7 sets forth a $^1$H-NMR spectrum (d6-DMSO) consistent with the structure. HPLC analysis gave 97.93% Area at 254 nm and 97.65% Area at 210 nm; Retention time: 3.765 min; HPLC conditions: Agilent 1100 HPLC. Zorbax Eclipse XDBC18 50×4.6 mm 1.8 micron column. Solvent A: Water (0.1% TFA); Solvent B: Acetonitrile (0.07% TFA). Gradient: 95% A to 95% B over 5 min; hold for 1 min; recycle over 1 min; 30 s hold. UV Detection: 210 and 254 nm with no reference. Column temperature: 30° C. Mass spectrum was consistent with structure MS (ESI+) for $C_{26}H_{27}FN_6O$ m/z 459.1 (M+H)+; MS (ESI−) for $C_{26}H_{27}FN_6O$ m/z 457.2 (M−H)−.

Figure 8:
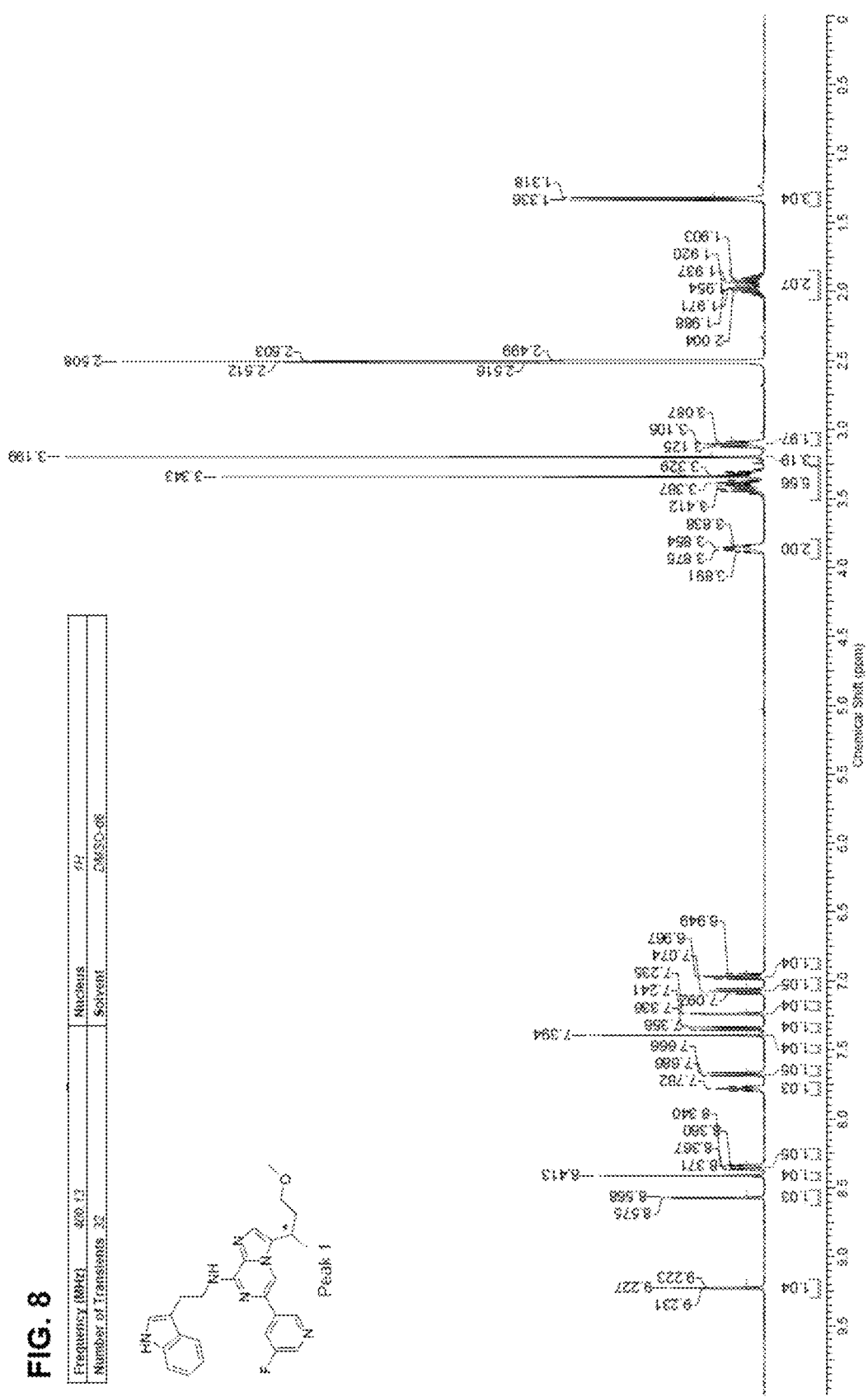
FIG. 8 sets forth a $^1$H-NMR spectra of an isolated compound (24) enantiomer peak in DMSO-d6.

Preparative HPLC AD-H (2×25 cm) 25% methanol/$CO_2$, 100 bar, 65 mL/min, 220 nm, inj vol.: 0.5 mL, 20 mg/mL methanol:DCM and analytical HPLC AD-H (25×0.46 cm) 35% methanol/$CO_2$, 100 bar 3 mL/min, 220, 254 and 280 nm allowed for the resolution of distinct enatiomeric peaks for Compound (24). FIG. 8 sets forth a $^1$H-NMR spectrum (d6-DMSO) consistent with the structure isolated as peak 1.

Figure 9:
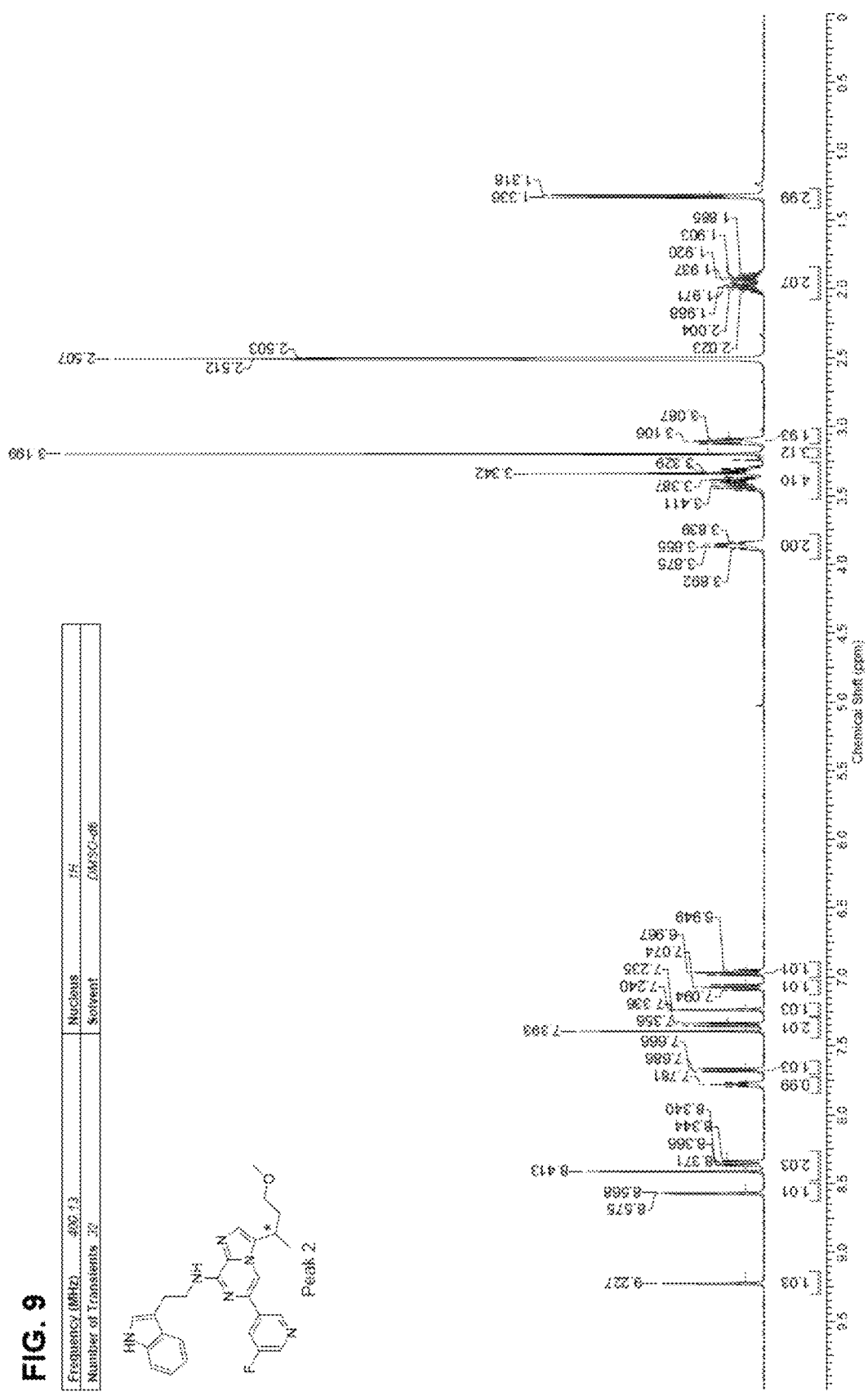
FIG. 9 sets forth a $^1$H-NMR spectra of an isolated compound (24) enantiomer peak in DMSO-d6.

FIG. 9 sets forth a $^1$H-NMR spectrum (d6-DMSO) consistent with the structure isolated as peak 2.

Scheme 11.

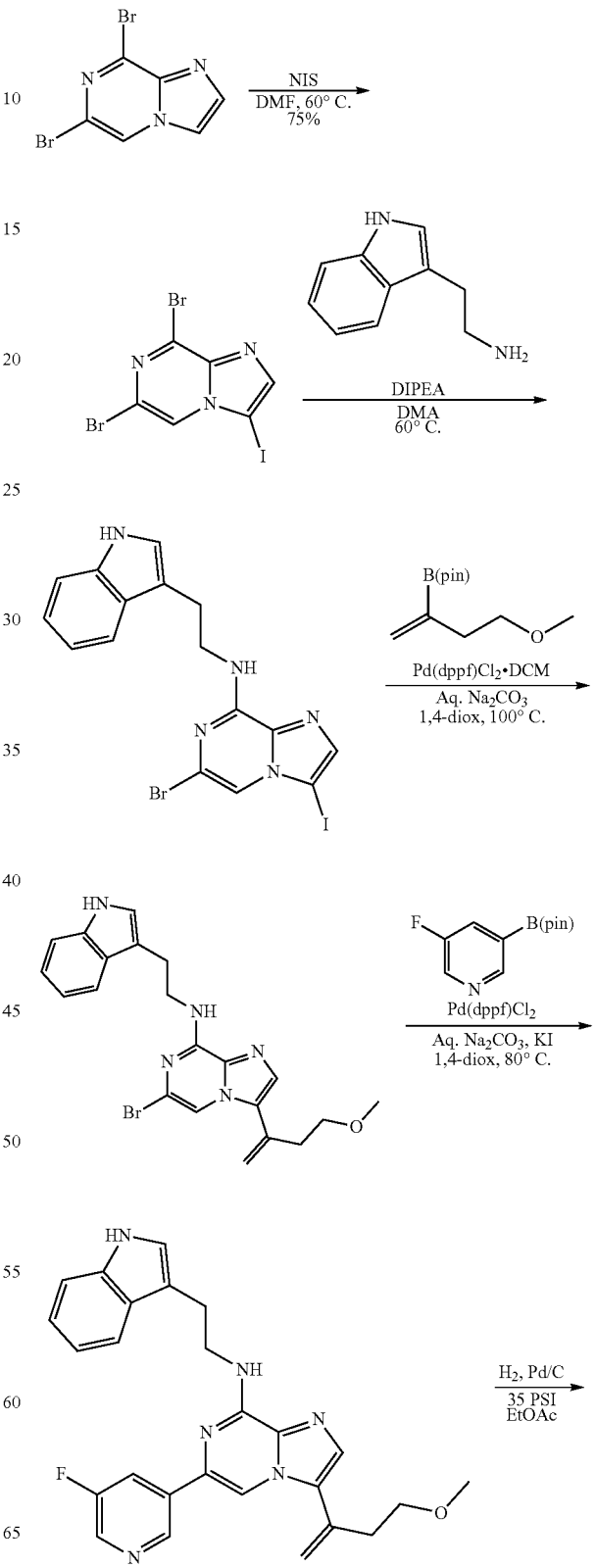

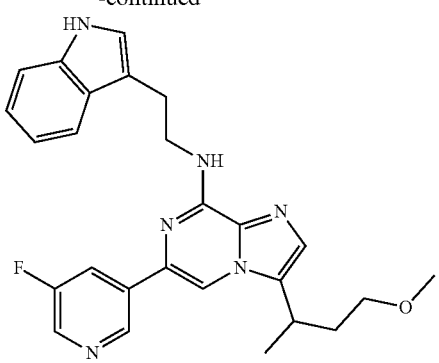

Example 7. Synthesis of Compound (27)

In a manner similar to that described in Example 6, compound (27) can be synthesized by way of a first Suzuki coupling, and second Suzuki coupling and alkene reduction by catalytic hydrogenation over palladium as shown in Scheme 12, below.

Figure 10:
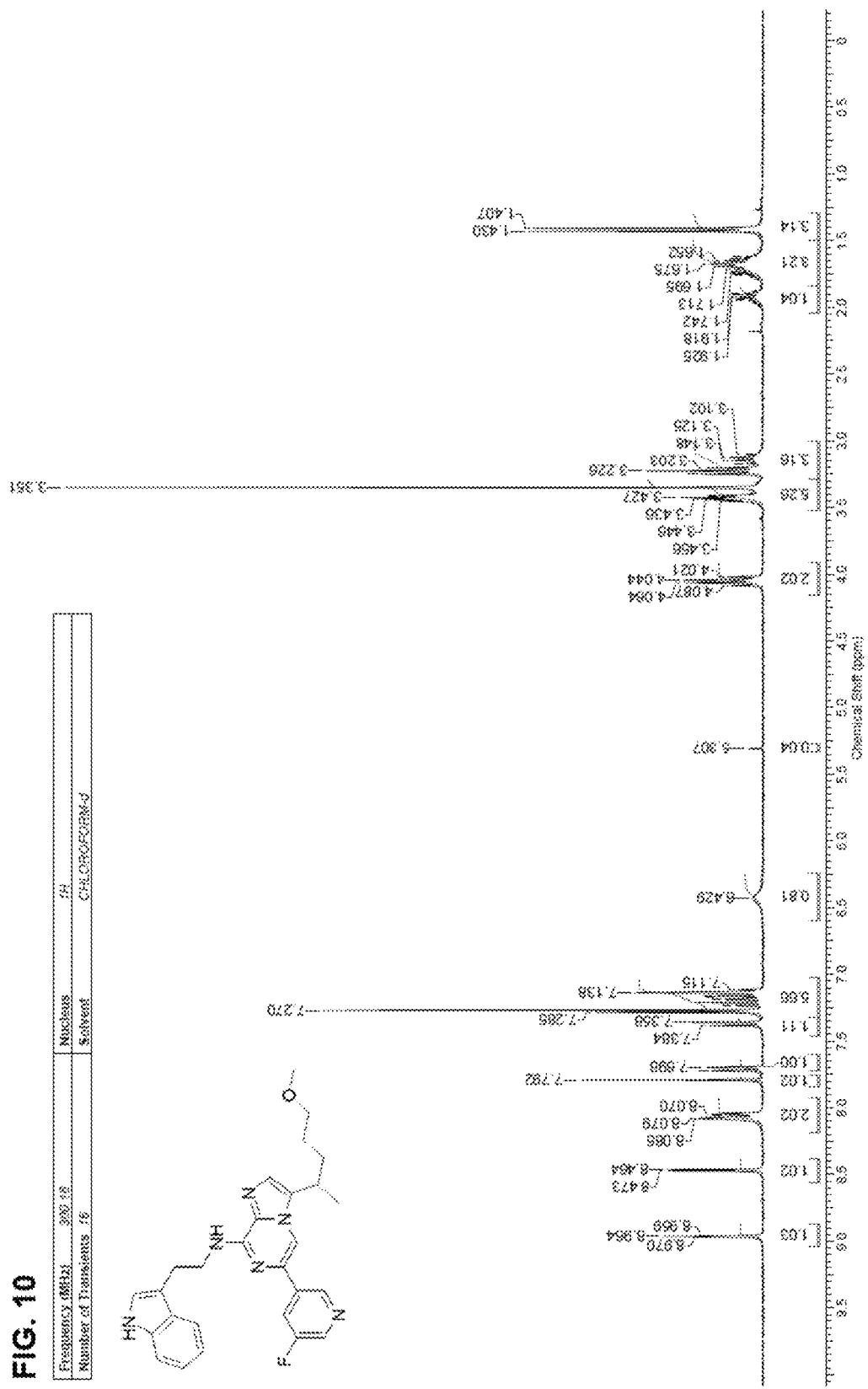
FIG. 10 sets forth a $^1$H-NMR spectra of compound (27) in chloroform-d.

6-(5-fluoropyridin-3-yl)-N-[2-(1H-indol-3-yl)ethyl]-3-(4-methoxy-1-methylbutyl)imidazo[1,2-a]pyrazin-8-amine, Compound (27) was isolated as a white solid. FIG. 10 sets forth a $^1$H-NMR spectrum (CDCl$_3$) consistent with the structure. HPLC analysis gave 98.0% Area at 254 nm and 97.2% Area at 210 nm; Retention time: 3.670 min; HPLC conditions: Agilent 1100 HPLC. Zorbax Eclipse XDBC18; 50×4.6 mm 1.8 micron column. Solvent A: Water (0.1% TFA); Solvent B: Acetonitrile (0.07% TFA). Gradient: 95% A to 95% B over 5 min; hold for 1 min; recycle over 1 min; 30 s hold. UV Detection: 210 and 254 nm with no reference. Column temperature: 30° C. Mass Spectrum was consistent with structure MS (ESI+) for C$_{27}$H$_{29}$FN$_6$O m/z 473.1 (M+H)+; MS (ESI−) for C$_{27}$H$_{29}$FN$_6$O m/z 471.2 (M−H)−.

Scheme 12.

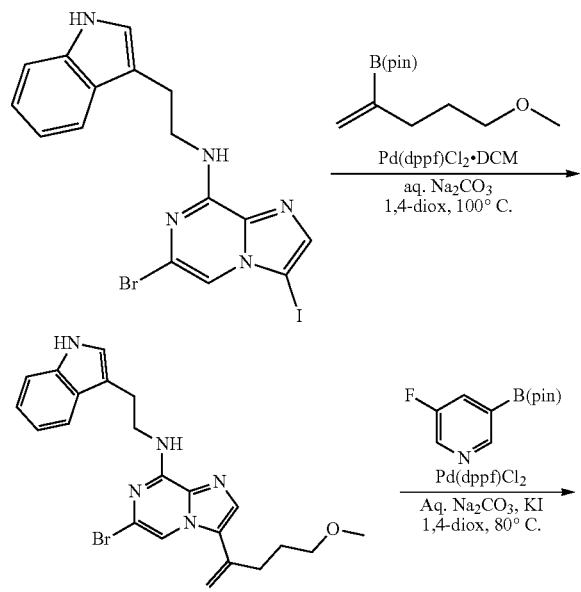

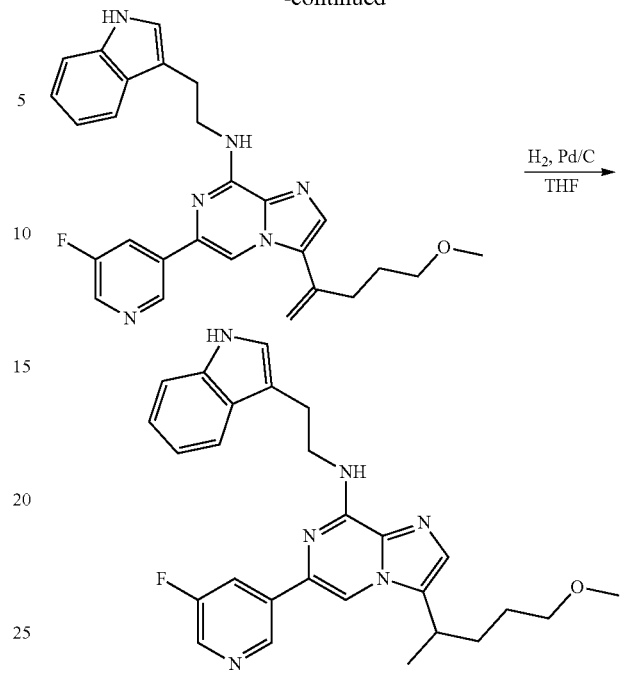

Example 8. Synthesis of Compound (28)

In a manner similar to that described in Example 6 and Example 7, compound (28) can be synthesized by way of a first Suzuki coupling, and second Suzuki coupling and alkene reduction by catalytic hydrogenation over palladium as shown in Scheme 13, below.

Figure 11:
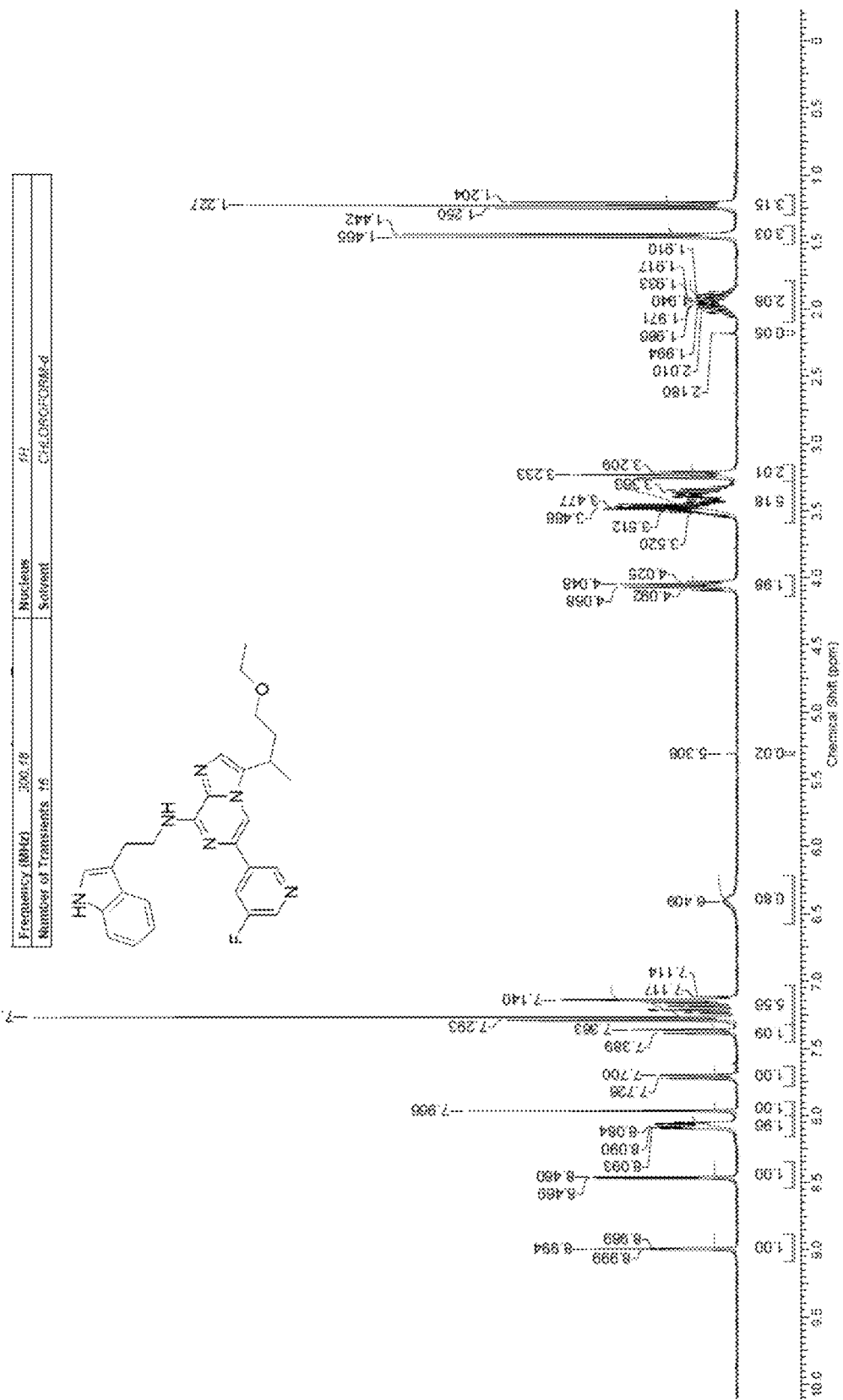
FIG. 11 sets forth a $^1$H-NMR spectra of compound (28) in chloroform-d.
Figure 12:
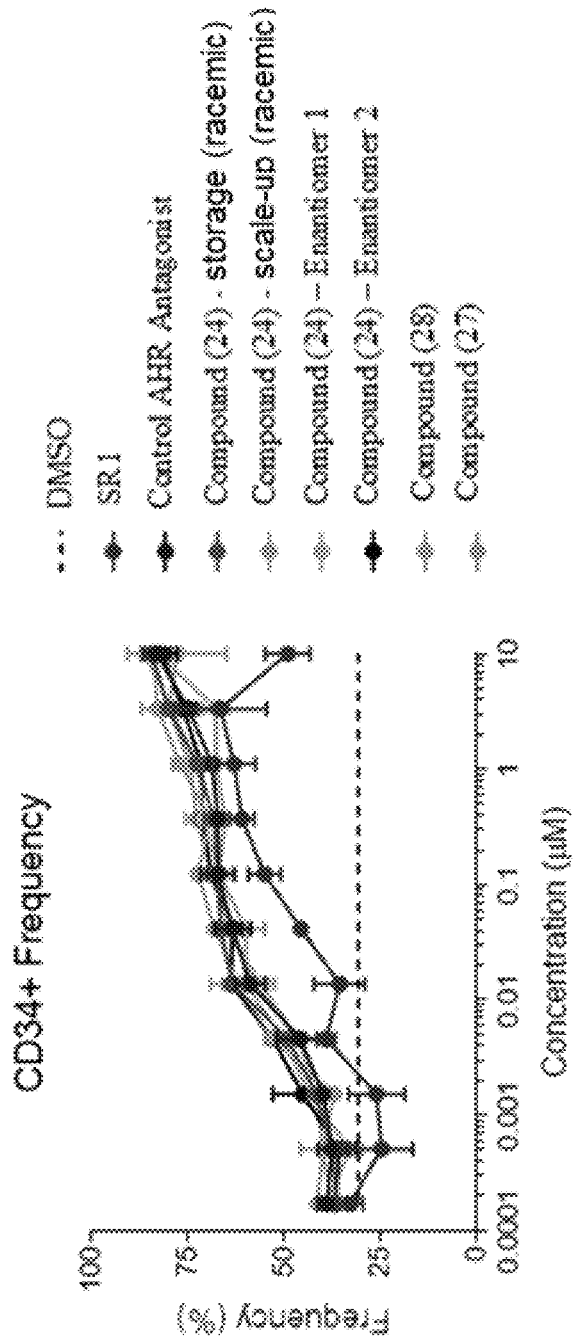
FIG. 12 is a graph demonstrating expansion capabilities of AHR antagonists in terms of CD34+ frequency. Experimental details for this experiment are reported in Example 9, below.
Figure 13:
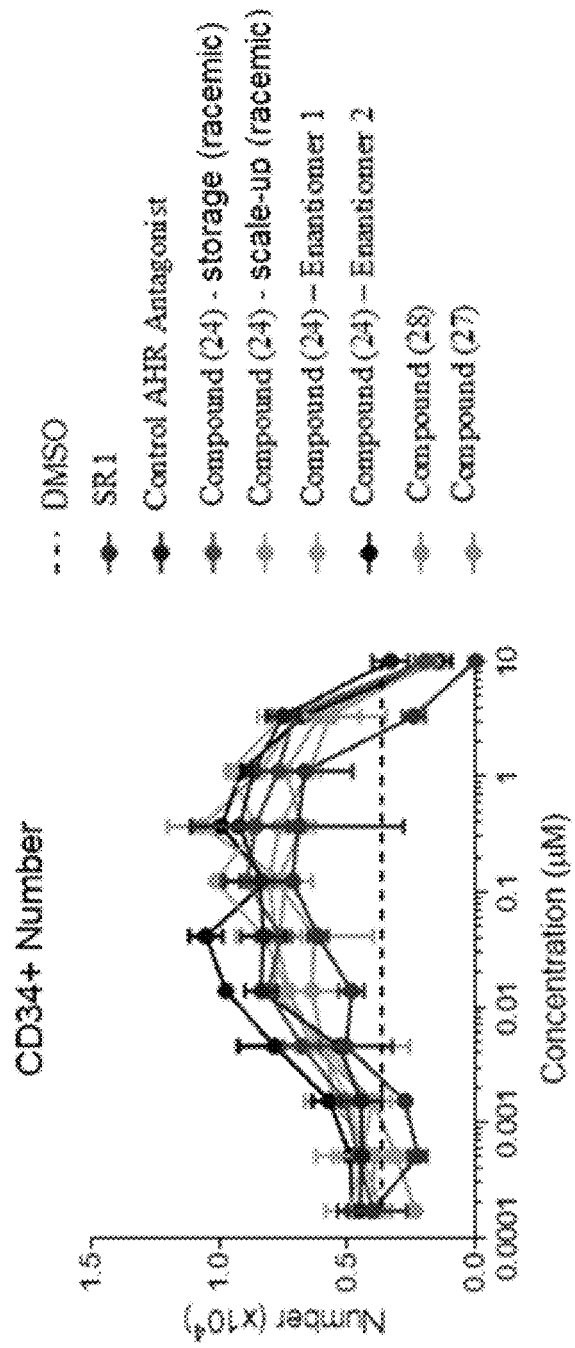
FIG. 13 is a graph demonstrating expansion capabilities of AHR antagonists in terms of CD34+ number. Experimental details for this experiment are reported in Example 9, below.

3-(3-ethoxy-1-methylpropyl)-6-(5-fluoropyridin-3-yl)-N-[2-(1H-indol-3-yl)ethyl]imidazo[1,2-a]pyrazin-8-amine, Compound (28) was isolated as an off-white solid. FIG. 11 sets forth a $^1$H-NMR spectrum (CDCl$_3$) consistent with the structure. HPLC analysis gave 99.3% Area at 254 nm and 99.0% Area at 210 nm; Retention time: 3.757 min; HPLC conditions: Agilent 1100 HPLC. Zorbax Eclipse XDBC18; 50×4.6 mm 1.8 micron column. Solvent A: Water (0.1% TFA); Solvent B: Acetonitrile (0.07% TFA). Gradient: 95% A to 95% B over 5 min; hold for 1 min; recycle over 1 min; 30 s hold. UV Detection: 210 and 254 nm with no reference. Column temperature: 30° C. Mass spectrum was consistent with structure MS (ESI+) for C$_{27}$H$_{29}$FN$_6$O m/z 473.1 (M+H)+; MS (ESI−) for C$_{27}$H$_{29}$FN$_6$O m/z 471.2 (M−H)−.

Scheme 13.

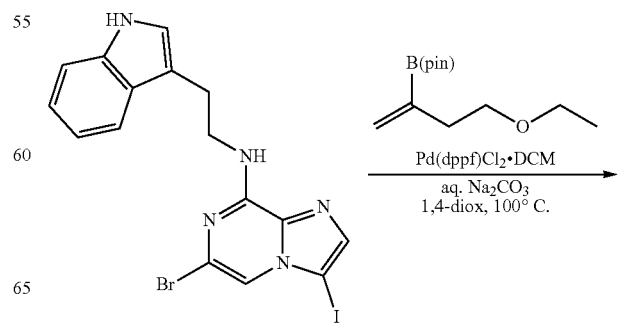

-continued

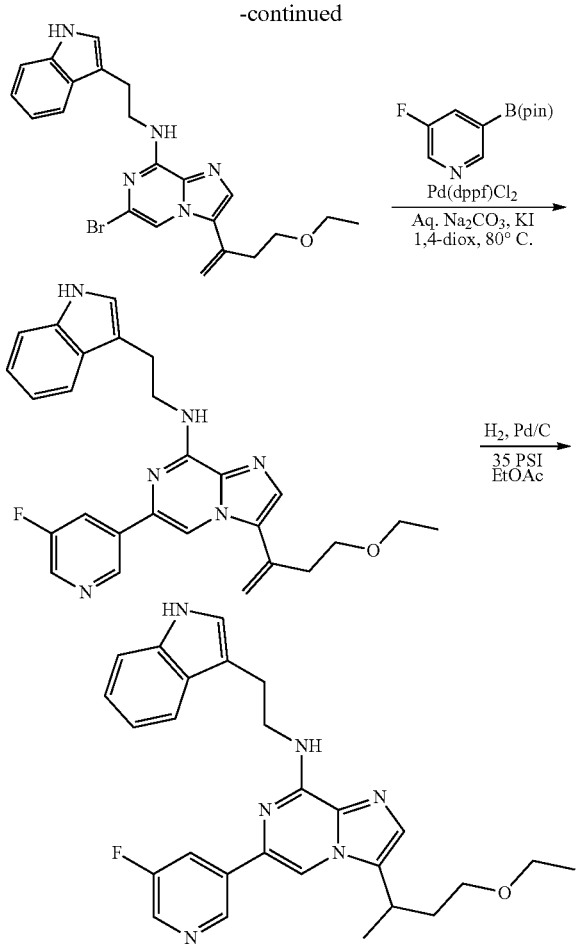

Suitable substrates may be provided for the first Suzuki coupling in the synthesis of compound (24), compound (27), and compound (28) in Example 6, Example 7, and Example 8, respectively, by alkylation of a suitable alkynyl alcohol and borylation of the alkyne as shown in Scheme 14, below.

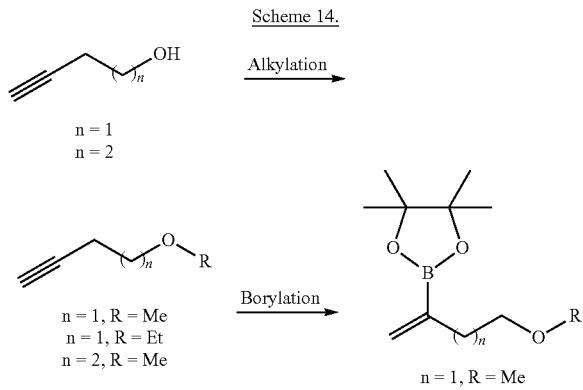

Example 9. Evaluation of AHR Antagonists

To determine the activity of a scale-up batch of Compound (24), individual enantiomers, and two derivatives Compound (27) and Compound (28) were evaluated for i) the ability to expand CD34+ hematopoietic stem/progenitor cells and ii) AHR antagonist activity. The compounds were compared to control AHR antagonist SR1, an additional control AHR antagonist, and stored sample of Compound (24)

CD34+ Frequency and Number

Methods—mobilized peripheral blood CD34+ cells were cultured in the presence of compound, in dose response beginning at 10 μM. CD34+ cell frequency and number was assessed at day 7 by flow cytometry. All synthesized compounds show equivalent expansion capabilities if not greater than SR1.

TABLE 1

CD34+ Frequency and Number

| Compound | EC50 (μM) |
| --- | --- |
| SR1 | 0.112 |
| Control AHR Antagonist | 0.001 |
| Compound (24) - storage (racemic) | 0.007 |
| Compound (24) - scale-up (racemic) | 0.007 |
| Compound (24) - Enantiomer Peak 1 | 0.011 |
| Compound (24) - Enantiomer Peak 2 | 0.004 |
| Compound (28) | 0.010 |
| Compound (27) | 0.008 |

AHR Antagonist Assay

Figure 14:
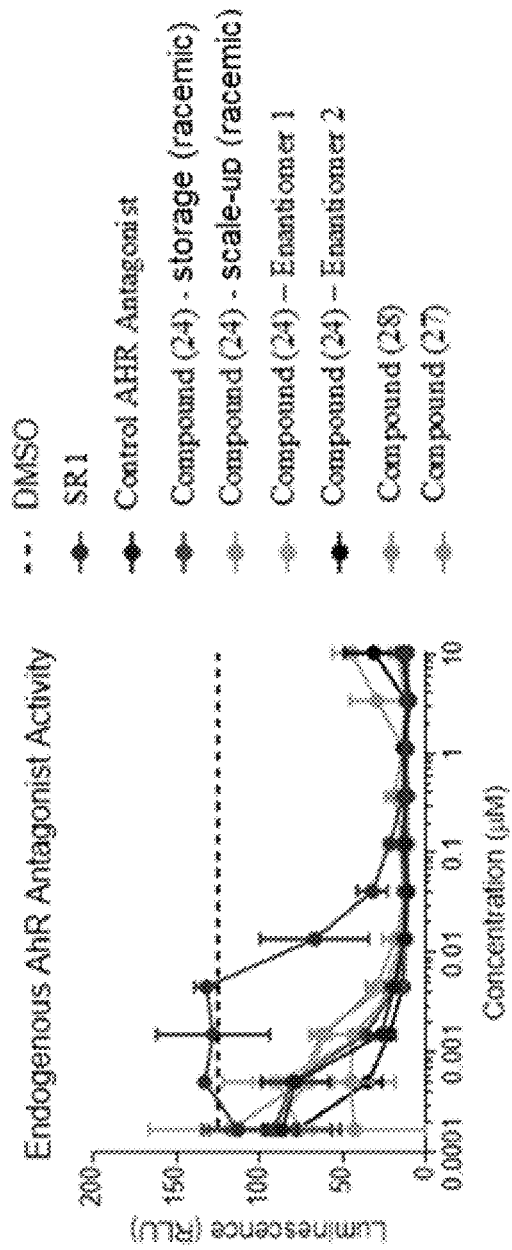
FIG. 14 is a graph demonstrating endogeneous AHR antagonist activity. Experimental details for this experiment are reported in Example 9, below.
Figure 15:
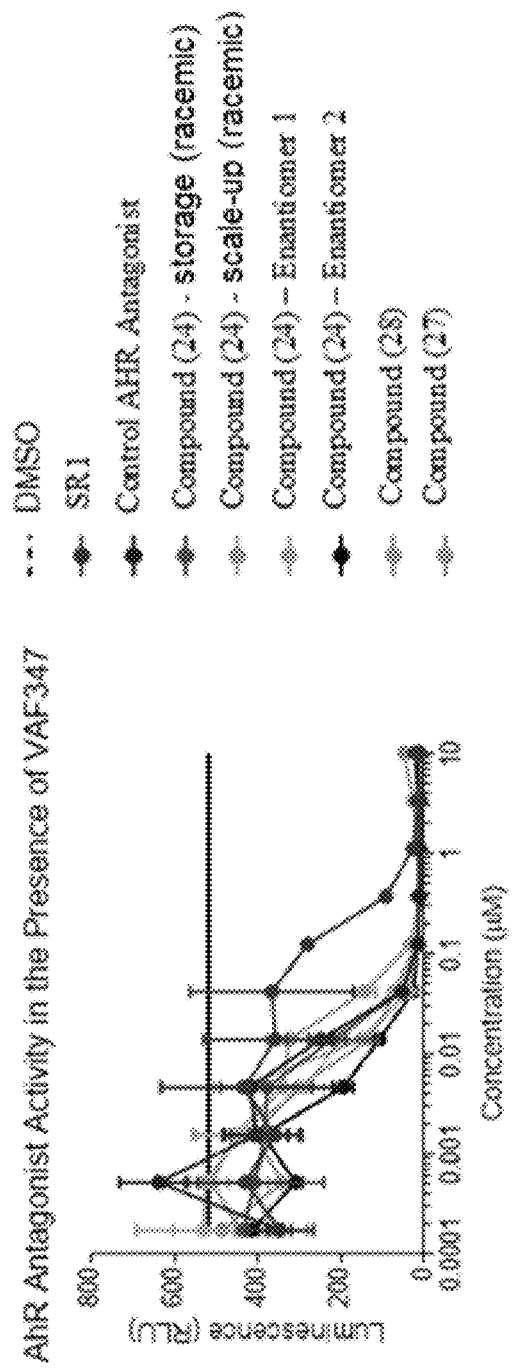
FIG. 15 is a graph demonstrating AHR antagonist activity in the presence of VAF347. Experimental details for this experiment are reported in Example 9, below.

Methods—HepG2 cells transiently transfected with the pGudLuc6.1 plasmid were thawed and 25,000 cells were plated per well and immediately treated the AHR agonist VAF347 (fixed at 40 nM) and/or the indicated AHR antagonists. Luciferase activity was measured 24 hours post-culture, corresponding to endogenous AHR antagonist activity (without VAF347, FIG. 14) or in the presence of VAF347 (FIG. 15). All synthesized compounds show equivalent AHR antagonist activity if not greater than SR1.

TABLE 2

Endogenous AHR Antagonist Activity

| Compound | EC50 (μM) |
| --- | --- |
| SR1 | 0.033 |
| Control AHR Antagonist | 0.0009 |
| Compound (24) - storage (racemic) | 0.001 |
| Compound (24) - scale-up (racemic) | ND |
| Compound (24) - Enantiomer Peak 1 | 0.001 |
| Compound (24) - Enantiomer Peak 2 | 0.0004 |
| Compound (28) | 0.002 |
| Compound (27) | 0.002 |

TABLE 3

AHR Antagonist Activity in the Presence of VAF347

| Compound | EC50 (μM) |
| --- | --- |
| SR1 | 0.193 |
| Control AHR Antagonist | 0.014 |
| Compound (24) - storage (racemic) | 0.013 |
| Compound (24) - scale-up (racemic) | 0.011 |
| Compound (24) - Enantiomer Peak 1 | 0.012 |
| Compound (24) - Enantiomer Peak 2 | 0.006 |
| Compound (28) | 0.030 |
| Compound (27) | 0.009 |

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

The invention claimed is:

1. A method of producing an expanded population of hematopoietic stem cells ex vivo, comprising contacting a population of hematopoietic stem cells with a compound represented by formula (I) or (II):

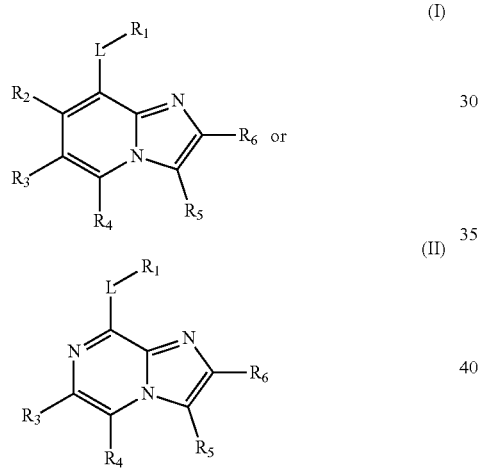

wherein L is selected from the group consisting of —$NR_{7a}(CR_{8a}R_{8b})_n$—, —$O(CR_{8a}R_{8b})_n$—, —$C(O)(CR_{8a}R_{8b})_n$—, —$C(S)(CR_{8a}R_{8b})_n$—, —$S(O)_{0-2}(CR_{8a}R_{8b})_n$—, —$(CR_{8a}R_{8b})_n$—, —$NR_{7a}C(O)(CR_{8a}R_{8b})_n$—, —$NR_{7a}C(S)(CR_{8a}R_{8b})_n$—, —$OC(O)(CR_{8a}R_{8b})_n$—, —$OC(S)(CR_{8a}R_{8b})_n$—, —$C(O)NR_{7a}(CR_{8a}R_{8b})_n$—, —$C(S)NR_{7a}(CR_{8a}R_{8b})_n$—, —$C(O)O(CR_{8a}R_{8b})_n$—, —$C(S)O(CR_{8a}R_{8b})_n$—, —$S(O)_2NR_{7a}(CR_{8a}R_{8b})_n$—, —$NR_{7a}S(O)_2(CR_{8a}R_{8b})_n$—, —$NR_{7a}C(O)NR_{7b}(CR_{8a}R_{8b})_n$—, and —$NR_{7a}C(O)O(CR_{8a}R_{8b})_n$—, wherein $R_{7a}$, $R_{7b}$, $R_{8a}$, and $R_{8b}$ are each independently selected from the group consisting of hydrogen and optionally substituted C1-4 alkyl, and each n is independently an integer from 2 to 6;

$R_1$ is selected from the group consisting of —$S(O)_2NR_{9a}R_{9b}$, —$NR_{9a}C(O)R_{9b}$, —$NR_{9a}C(S)R_{9b}$, —$NR_{9a}C(O)NR_{9b}R_{9c}$, —$C(O)R_{9a}$, —$C(S)R_{9a}$, —$S(O)_{0-2}R_{9a}$, —$C(O)OR_{9a}$, —$C(S)OR_{9a}$, —$C(O)NR_{9a}R_{9b}$, —$C(S)NR_{9a}R_{9b}$, —$NR_{9a}S(O)_2R_{9b}$, —$NR_{9a}C(O)OR_{9b}$, —$OC(O)CR_{9a}R_{9b}R_{9c}$, —$OC(S)CR_{9a}R_{9b}R_{9c}$, optionally substituted aryl, optionally substituted heteroaryl, optionally substituted cycloalkyl, and optionally substituted heterocycloalkyl, wherein $R_{9a}$, $R_{9b}$, and $R_{9c}$ are each independently selected from the group consisting of hydrogen, optionally substituted aryl, optionally substituted heteroaryl, optionally substituted alkyl, optionally substituted heteroalkyl, optionally substituted cycloalkyl, and optionally substituted heterocycloalkyl;

$R_2$ is selected from the group consisting of hydrogen and optionally substituted C1-4 alkyl;

$R_3$ is selected from the group consisting of optionally substituted aryl, optionally substituted heteroaryl, optionally substituted cycloalkyl, and optionally substituted heterocycloalkyl;

$R_4$ is selected from the group consisting of hydrogen and optionally substituted C1-4 alkyl;

$R_5$ is selected from the group consisting of optionally substituted aryl, optionally substituted heteroaryl, optionally substituted alkyl, optionally substituted heteroalkyl, optionally substituted cycloalkyl, and optionally substituted heterocycloalkyl; and $R_6$ is selected from the group consisting of hydrogen, optionally substituted aryl, optionally substituted heteroaryl, optionally substituted alkyl, optionally substituted heteroalkyl, optionally substituted cycloalkyl, and optionally substituted heterocycloalkyl;

or a salt thereof.

2. The method of claim 1, wherein said compound is represented by formula (I-e) or (II-e)

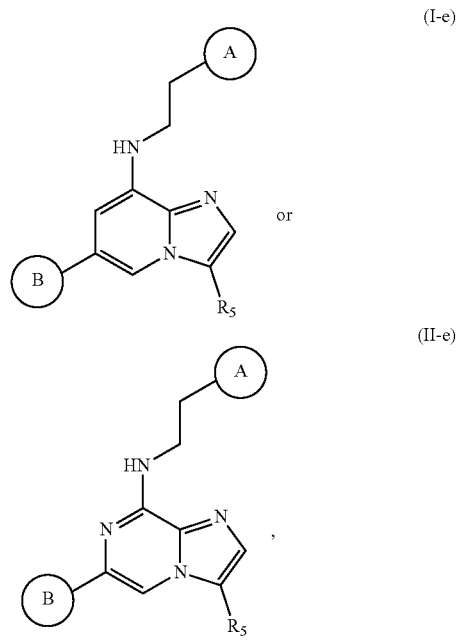

wherein A is an optionally substituted ring system selected from the group consisting of phenyl, 1H-indol-2-yl, 1H-indol-3-yl, thiophen-3-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, and 2-oxo-2,3-dihydro-1H-benzo[d]imidazol-5-yl, wherein the phenyl, 1H-indol-2-yl, 1H-indol-3-yl, thiophen-3-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, or 2-oxo-2,3-dihydro-1H-benzo[d]

imidazol-5-yl is optionally substituted with from 1 to 3 substituents independently selected from the group consisting of cyano, hydroxy, C1-4 alkyl, C1-4 alkoxy, halo, halo-substituted-C1-4 alkyl, halo-substituted-C1-4 alkoxy, amino, —O(CH$_2$)$_2$NR$_{10a}$R$_{10b}$, —S(O)$_2$NR$_{10a}$R$_{10b}$, —OS(O)$_2$NR$_{10a}$R$_{10b}$, and —NR$_{10a}$S(O)$_2$R$_{10b}$, wherein R$_{10a}$ and R$_{10b}$ are each independently selected from the group consisting of hydrogen, optionally substituted aryl, optionally substituted heteroaryl, optionally substituted alkyl, optionally substituted heteroalkyl, optionally substituted cycloalkyl, and optionally substituted heterocycloalkyl;

B is an optionally substituted ring system selected from the group consisting of thiophen-2-yl, thiophen-3-yl, furan-3-yl, 1H-benzo[d]imidazol-1-yl, isoquinolin-4-yl, 1H-imidazo[4,5-b]pyridin-1-yl, imidazo[1,2-a]pyridin-3-yl, benzo[b]thiophen-3-yl, pyrimidin-5-yl, pyridin-2-yl, pyridin-3-yl, pyridin-4-yl, 1H-imidazol-1-yl, pyrazin-2-yl, pyridazin-4-yl, 1H-pyrrol-2-yl and thiazol-5-yl, wherein the thiophen-2-yl, thiophen-3-yl, furan-3-yl, 1H-benzo[d]imidazol-1-yl, isoquinolin-4-yl, 1H-imidazo[4,5-b]pyridin-1-yl, benzo[b]thiophen-3-yl, pyrimidin-5-yl, pyridin-2-yl, pyridin-3-yl, pyridin-4-yl, 1H-imidazol-1-yl, pyrazin-2-yl, pyridazin-4-yl, 1H-pyrrol-2-yl, or thiazol-5-yl is optionally substituted with from 1 to 3 substituents independently selected from the group consisting of cyano, hydroxy, C$_1$-4 alkyl, C2-4 alkenyl, C2-4 alkynyl, C3-6 cycloalkyl, C1-4 alkoxy, halo, halo-substituted-C1-4 alkyl, halo-substituted-C1-4 alkoxy, amino, —C(O)R$_{11a}$, —S(O)$_{0-2}$R$_{11a}$, —C(O)OR$_{11a}$, and —C(O)NR$_{11a}$R$_{11b}$, wherein R$_{11a}$ and R$_{11b}$ are each independently selected from the group consisting of hydrogen and C1-4 alkyl; and R$_5$ is selected from the group consisting of C1-10 alkyl, prop-1-en-2-yl, cyclohexyl, cyclopropyl, 2-(2-oxopyrrolidin-1-yl)ethyl, oxetan-2-yl, oxetan-3-yl, benzhydryl, tetrahydro-2H-pyran-2-yl, tetrahydro-2H-pyran-3-yl, phenyl, tetrahydrofuran-3-yl, benzyl, (4-pentylphenyl)(phenyl)methyl, and 1-(1-(2-oxo-6,9,12-trioxa-3-azatetradecan-14-yl)-1H-1,2,3-triazol-4-yl)ethyl, wherein the C1-10 alkyl, prop-1-en-2-yl, cyclohexyl, cyclopropyl, 2-(2-oxopyrrolidin-1-yl)ethyl, oxetan-2-yl, oxetan-3-yl, benzhydryl, tetrahydro-2H-pyran-2-yl, tetrahydro-2H-pyran-3-yl, phenyl, tetrahydrofuran-3-yl, benzyl, (4-pentylphenyl)(phenyl)methyl, or 1-(1-(2-oxo-6,9,12-trioxa-3-azatetradecan-14-yl)-1H-1,2,3-triazol-4-yl)ethyl is optionally substituted with from 1 to 3 substituents independently selected from the group consisting of hydroxy, C1-4 alkyl, and halo-substituted-C1-4alkyl, or R$_5$ is selected from the group consisting of (i), (ii), (iii), (iv), and (v)

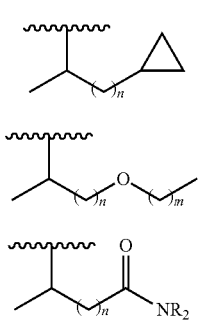

(i)

(ii)

(iii)

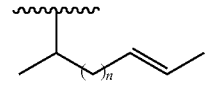

(iv)

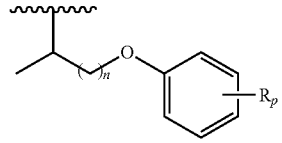

(v)

wherein n is an integer from 1 to 6, m is an integer from 0 to 6, p is an integer from 0 to 5, and each R is independently selected from the group consisting of cyano, hydroxy, C1-4 alkyl, C2-4 alkenyl, C2-4 alkynyl, C3-6 cycloalkyl, C1-4 alkoxy, halo, halo-substituted-C1-4 alkyl, halo-substituted-C1-4 alkoxy, amino, —C(O)R$_{12a}$, —S(O)$_{0-2}$R$_{12a}$, —C(O)OR$_{12a}$, and —C(O)NR$_{12a}$R$_{11b}$, and wherein R$_{12a}$ and R$_{12b}$ are each independently selected from the group consisting of hydrogen and C1-4 alkyl;

or a salt thereof.

3. The method of claim 1, wherein said compound is represented by formula (I-f), (II-f), (I-g), or (II-g)

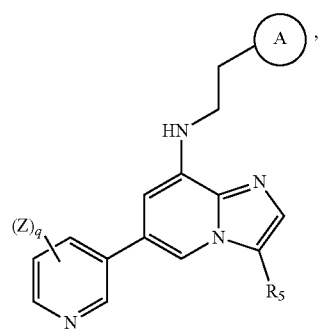

(I-f)

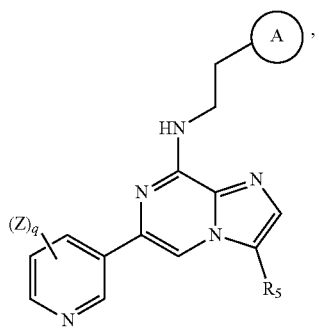

(II-f)

-continued (I-g)

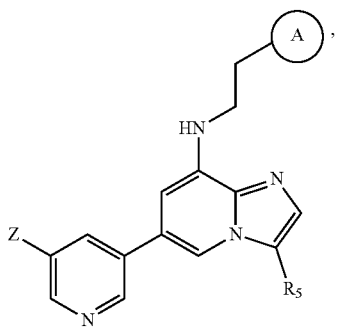

(II-g)

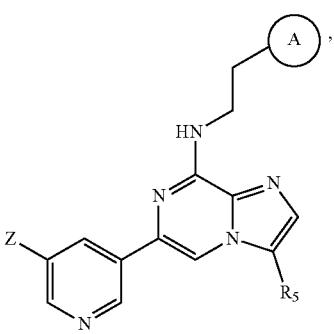

wherein A is an optionally substituted ring system selected from the group consisting of phenol-4-yl and 1H-indol-3-yl;

q is an integer from 0 to 4;

each Z is independently a substituent selected from the group consisting of C1-4 alkyl, halo, halo-substituted-C1-4 alkyl, C2-4 alkenyl, C2-4 alkynyl, C3-6 cycloalkyl, C1-4 alkoxy, cyano, amino, $C(O)R_{11a}$, $-S(O)_{0-2}R_{11a}$, $-C(O)OR_{11a}$, and $-C(O)NR_{11a}R_{11b}$, wherein $R_{11a}$ and $R_{11b}$ are each independently selected from the group consisting of hydrogen and C1-4 alkyl; and $R_5$ is selected from the group consisting of isopropyl, methyl, ethyl, prop-1-en-2-yl, isobutyl, cyclohexyl, sec-butyl, (S)-sec-butyl, (R)-sec-butyl, 1-hydroxypropan-2-yl, (S)-1-hydroxypropan-2-yl, (R)-1-hydroxypropan-2-yl, and nonan-2-yl, or $R_5$ is selected from the group consisting of (i), (ii), (iii), (iv), and (v)

(i)

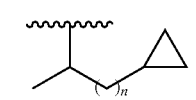

(ii)

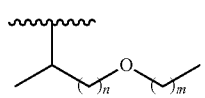

(iii)

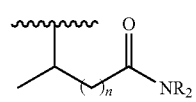

(iv)

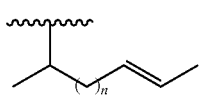

(v)

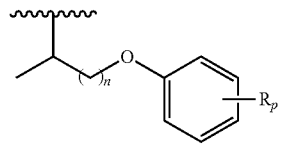

wherein n is an integer from 1 to 6, m is an integer from 0 to 6, p is an integer from 0 to 5, and each R is independently selected from the group consisting of cyano, hydroxy, C1-4 alkyl, C2-4 alkenyl, C2-4 alkynyl, C3-6 cycloalkyl, C1-4 alkoxy, halo, halo-substituted-C1-4 alkyl, halo-substituted-C1-4 alkoxy, amino, $-C(O)R_{12a}$, $-S(O)_{0-2}R_{12a}$, $-C(O)OR_{12a}$, and $-C(O)NR_{12a}R_{12b}$, and wherein $R_{12a}$ and $R_{11b}$ are each independently selected from the group consisting of hydrogen and C1-4 alkyl;

or a salt thereof.

4. The method of claim 1, wherein said compound is represented by-formula (I-h), (II-h), (I-i), (II-i), (I-j), (II-j), (I-k), or (II-k)

(I-h)

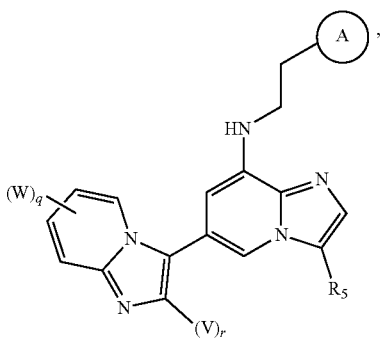

(II-h)

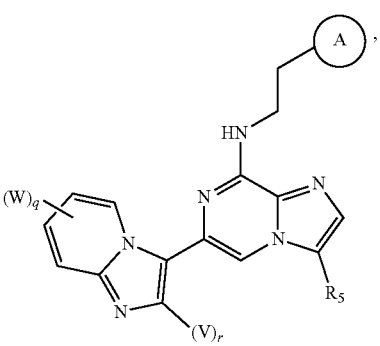

(I-i)

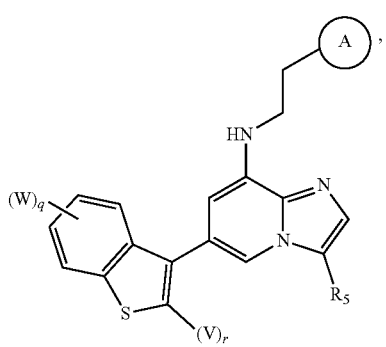

-continued (II-i)
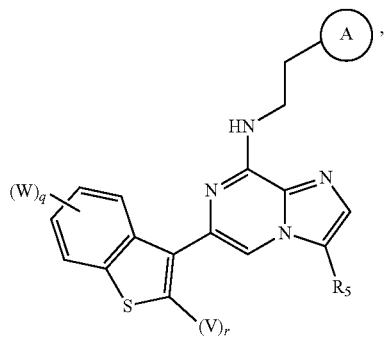

(I-j)
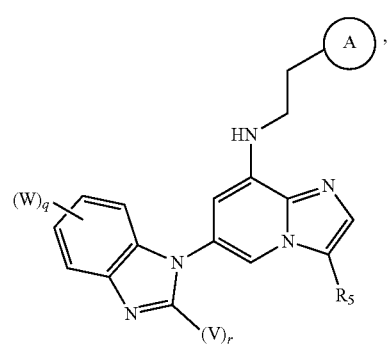

(II-j)
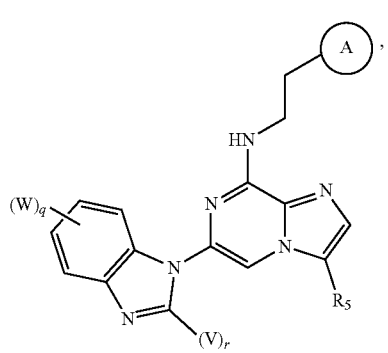

(I-k)
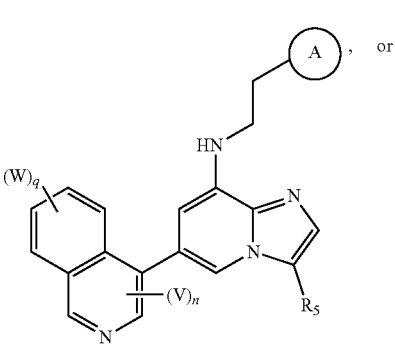

or

-continued (II-k)
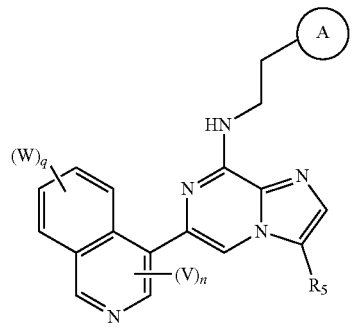

wherein A is an optionally substituted ring system selected from the group consisting of phenol-4-yl and 1H-indol-3-yl;

q is an integer from 0 to 4;

r is 0 or 1;

W and V are each independently a substituent selected from the group consisting of C1-4 alkyl, halo, halo-substituted-C1-4 alkyl, C2-4 alkenyl, C2-4 alkynyl, C3-6 cycloalkyl, C1-4 alkoxy, cyano, amino, C(O)$R_{11a}$, —S(O)$_{0-2}R_{11a}$, —C(O)O$R_{11a}$, and —C(O)N$R_{11a}R_{11b}$ wherein $R_{11a}$ and $R_{11b}$ are each independently selected from the group consisting of hydrogen and C1-4 alkyl; and $R_5$ is selected from the group consisting of C1-10 alkyl, prop-1-en-2-yl, cyclohexyl, cyclopropyl, 2-(2-oxopyrrolidin-1-yl)ethyl, oxetan-2-yl, oxetan-3-yl, benzhydryl, tetrahydro-2H-pyran-2-yl, tetrahydro-2H-pyran-3-yl, phenyl, tetrahydrofuran-3-yl, benzyl, (4-pentylphenyl)(phenyl)methyl, and 1-(1-(2-oxo-6,9,12-trioxa-3-azatetradecan-14-yl)-1H-1,2,3-triazol-4-yl)ethyl, wherein the C1-10 alkyl, prop-1-en-2-yl, cyclohexyl, cyclopropyl, 2-(2-oxopyrrolidin-1-yl)ethyl, oxetan-2-yl, oxetan-3-yl, benzhydryl, tetrahydro-2H-pyran-2-yl, tetrahydro-2H-pyran-3-yl, phenyl, tetrahydrofuran-3-yl, benzyl, (4-pentylphenyl)(phenyl)methyl, and 1-(1-(2-oxo-6,9,12-trioxa-3-azatetradecan-14-yl)-1H-1,2,3-triazol-4-yl)ethyl is optionally substituted with from 1 to 3 substituents independently selected from the group consisting of hydroxy, C1-4 alkyl, and halo-substituted-C1-4alkyl, or $R_5$ is selected from the group consisting of (i), (ii), (iii), (iv), and (v)

(i)
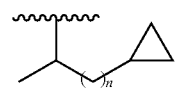

(ii)
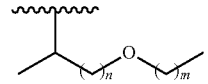

(iii)
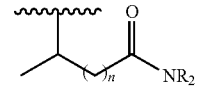

(iv)
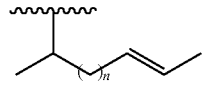

-continued

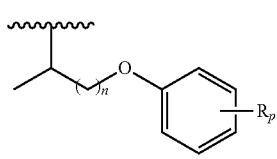
(v)

wherein n is an integer from 1 to 6, m is an integer from 0 to 6, p is an integer from 0 to 5, and each R is independently selected from the group consisting of cyano, hydroxy, $C_{1-4}$ alkyl, C2-4 alkenyl, C2-4 alkynyl, C3-6 cycloalkyl, C1-4 alkoxy, halo, halo-substituted-C1-4 alkyl, halo-substituted-C1-4 alkoxy, amino, —C(O)$R_{12a}$, —S(O)$_{0-2}R_{12a}$, —C(O)O$R_{12a}$, and —C(O)N$R_{12a}R_{11b}$, and wherein $R_{12a}$ and $R_{12b}$ are each independently selected from the group consisting of hydrogen and $C_{1-4}$ alkyl;

or a salt thereof.

5. The method of claim 3, wherein said compound is represented by formula (II-f)

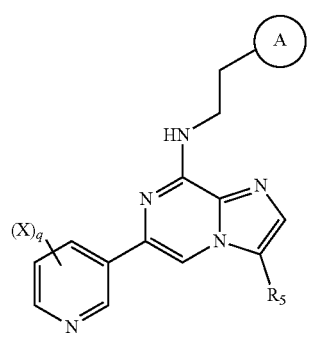
(II-f)

wherein A is an optionally substituted ring system selected from the group consisting of phenol-4-yl and 1H-indol-3-yl;

q is an integer from 0 to 4;

each Z is independently a substituent selected from the group consisting of C1-4 alkyl, halo, halo-substituted-C1-4 alkyl, C2-4 alkenyl, C2-4 alkynyl, C3-6 cycloalkyl, C1-4 alkoxy, cyano, amino, C(O)$R_{11a}$, —S(O)$_{0-2}R_{11a}$, —C(O)O$R_{11a}$, and —C(O)N$R_{11a}R_{11b}$, wherein $R_{11a}$ and $R_{11b}$ are each independently selected from the group consisting of hydrogen and C1-4 alkyl; and $R_5$ is selected from the group consisting of isopropyl, methyl, ethyl, prop-1-en-2-yl, isobutyl, cyclohexyl, sec-butyl, (S)-sec-butyl, (R)-sec-butyl, 1-hydroxypropan-2-yl, (S)-1-hydroxypropan-2-yl, (R)-1-hydroxypropan-2-yl, and nonan-2-yl, or $R_5$ is selected from the group consisting of (i), (ii), (iii), (iv), and (v)

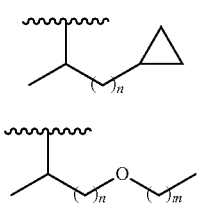
(i)

(ii)

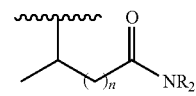
(iii)

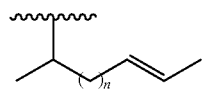
(iv)

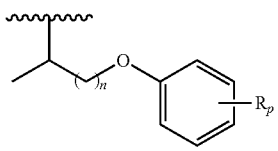
(v)

wherein n is an integer from 1 to 6, m is an integer from 0 to 6, p is an integer from 0 to 5, and each R is independently selected from the group consisting of cyano, hydroxy, C1-4 alkyl, C2-4 alkenyl, C2-4 alkynyl, C3-6 cycloalkyl, C1-4 alkoxy, halo, halo-substituted-C1-4 alkyl, halo-substituted-C1-4 alkoxy, amino, —C(O)$R_{12a}$, —S(O)$_{0-2}R_{12a}$, —C(O)O$R_{12a}$, and —C(O)N$R_{12a}R_{11b}$, and wherein $R_{12a}$ and $R_{12b}$ are each independently selected from the group consisting of hydrogen and C1-4 alkyl;

or a salt thereof.

6. The method of claim 3, wherein said compound is represented by formula (II-g)

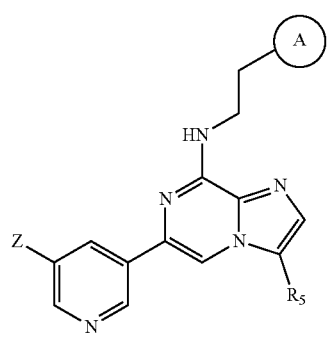
(II-g)

wherein A is an optionally substituted ring system selected from the group consisting of phenol-4-yl and 1H-indol-3-yl;

Z is a substituent selected from the group consisting of C1-4 alkyl, halo, halo-substituted-C1-4 alkyl, C2-4 alkenyl, C2-4 alkynyl, C3-6 cycloalkyl, C1-4 alkoxy, cyano, amino, C(O)$R_{11a}$, —S(O)$_{0-2}R_{11a}$, —C(O)O$R_{11a}$, and —C(O)N$R_{11a}R_{11b}$, wherein $R_{11a}$ and $R_{11b}$ are each independently selected from the group consisting of hydrogen and C1-4 alkyl; and $R_5$ is selected from the group consisting of isopropyl, methyl, ethyl, prop-1-en-2-yl, isobutyl, cyclohexyl, sec-butyl, (S)-sec-butyl, (R)-sec-butyl, 1-hydroxypropan-2-yl, (S)-1-hydroxypropan-2-yl, (R)-1-hydroxypropan-2-yl, and nonan-2-yl, or $R_5$ is selected from the group consisting of (i), (ii), (iii), (iv), and (v)

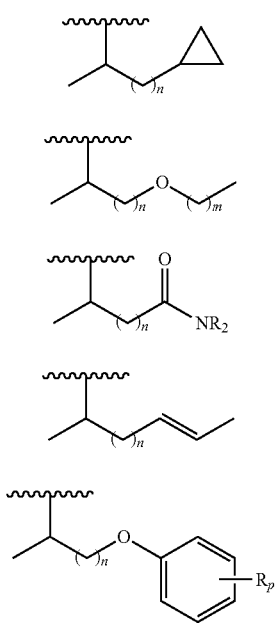

wherein n is an integer from 1 to 6, m is an integer from 0 to 6, p is an integer from 0 to 5, and each R is independently selected from the group consisting of cyano, hydroxy, C1-4 alkyl, C2-4 alkenyl, C2-4 alkynyl, C3-6 cycloalkyl, C1-4 alkoxy, halo, halo-substituted-C1-4 alkyl, halo-substituted-C1-4 alkoxy, amino, —C(O)R$_{12a}$, —S(O)$_{0-2}$R$_{12a}$, —C(O)OR$_{12a}$, and —C(O)NR$_{12a}$R$_{12b}$, and wherein R$_{12a}$ and R$_{12b}$ are each independently selected from the group consisting of hydrogen and C1-4 alkyl;

or a salt thereof.

7. The method of claim 5, wherein A is phenol-4-yl.

8. The method of claim 5, wherein A is 1H-indol-3-yl.

9. The method of claim 5, wherein R$_5$ is selected from the group consisting of isopropyl, methyl, ethyl, isobutyl, cyclohexyl, hydroxypropan-2-yl, sec-butyl, 3-ethoxy-1-methylpropyl, 1-methoxy-4-pentyl, and 1-methoxy-3-butyl.

10. The method of claim 5, wherein each Z is independently selected from the group consisting of methyl, ethynyl, cyclopropyl, fluoro, chloro, trifluoromethyl, and cyano.

11. The method of claim 6, wherein R$_5$ is selected from the group consisting of isopropyl, methyl, ethyl, isobutyl, cyclohexyl, hydroxypropan-2-yl, sec-butyl, 3-ethoxy-1-methylpropyl, 1-methoxy-4-pentyl, and 1-methoxy-3-butyl.

12. The method of claim 6, wherein Z is selected from the group consisting of methyl, ethynyl, cyclopropyl, fluoro, chloro, trifluoromethyl, and cyano.

13. The method of claim 6, wherein

A is 1H-indol-3-yl;

R$_5$ is selected from the group consisting of isopropyl, methyl, ethyl, isobutyl, cyclohexyl, hydroxypropan-2-yl, sec-butyl, 3-ethoxy-1-methylpropyl, 1-methoxy-4-pentyl, and 1-methoxy-3-butyl; and Z is selected from the group consisting of methyl, ethynyl, cyclopropyl, fluoro, chloro, trifluoromethyl, and cyano.

14. The method of claim 1, wherein said compound is selected from the group consisting of

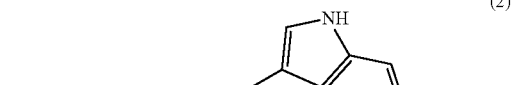

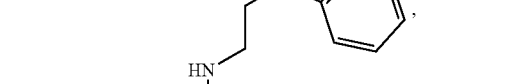

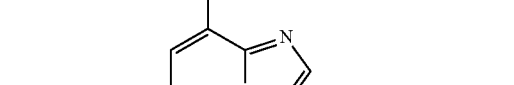

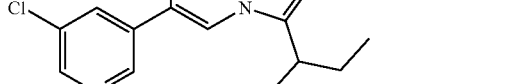

-continued
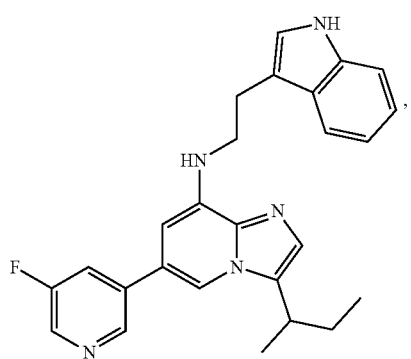 (5)
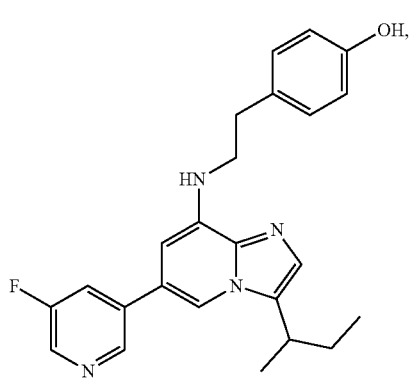 (6)
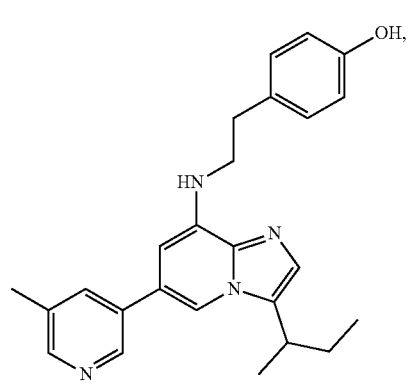 (7)
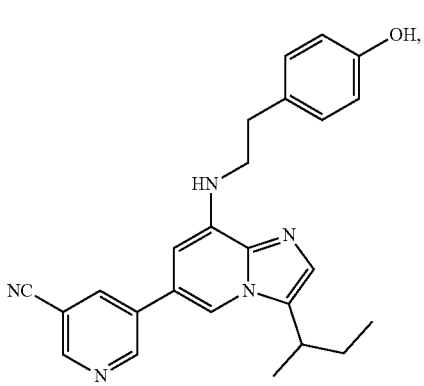 (8)
-continued
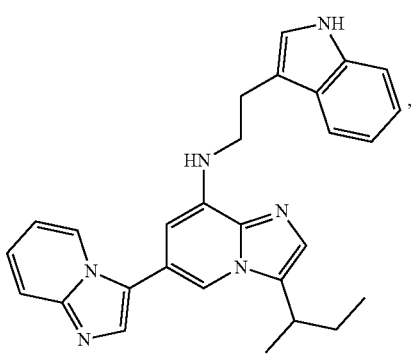 (9)
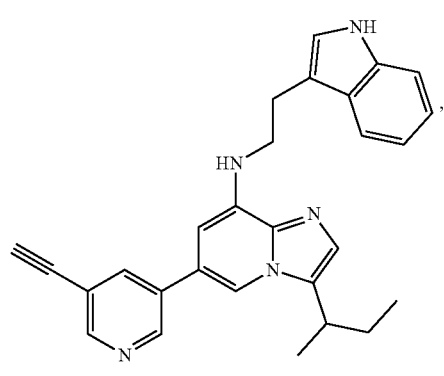 (10)
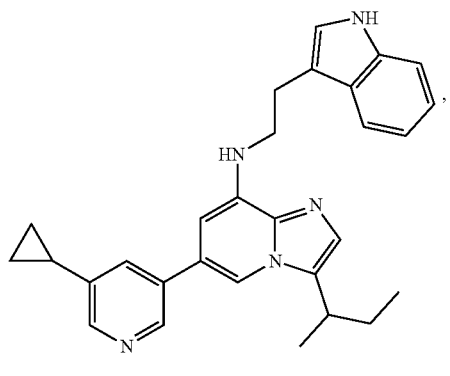 (11)
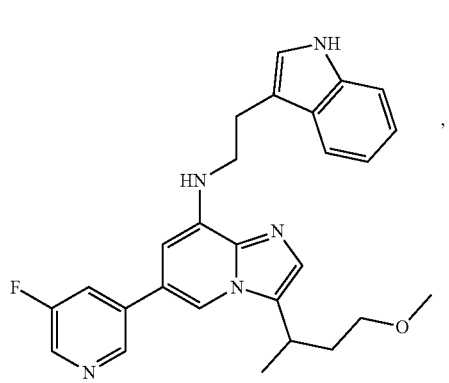 (23)

-continued
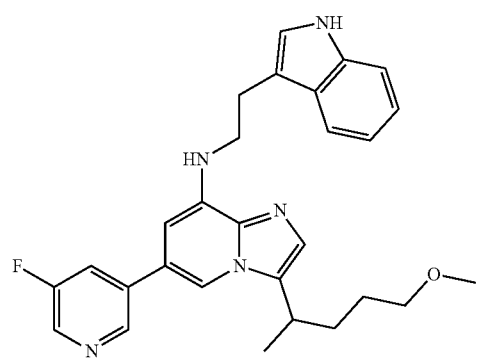
(25)
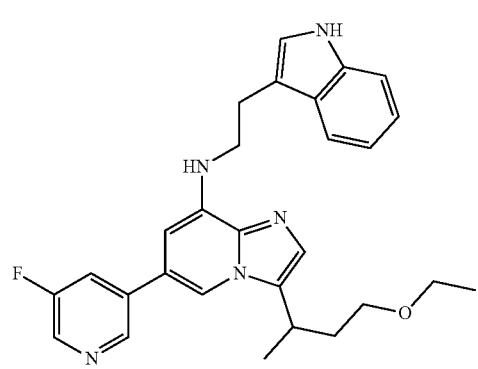
(26)
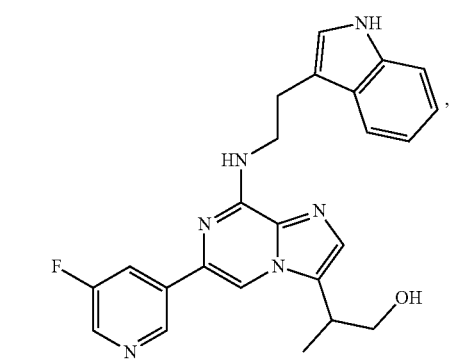
(12)
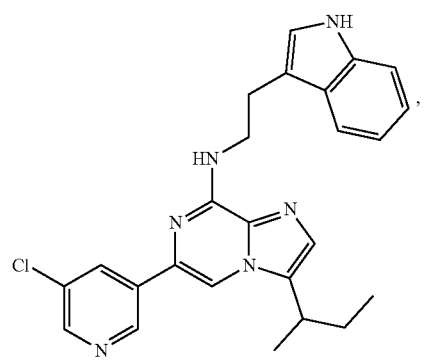
(13)
-continued
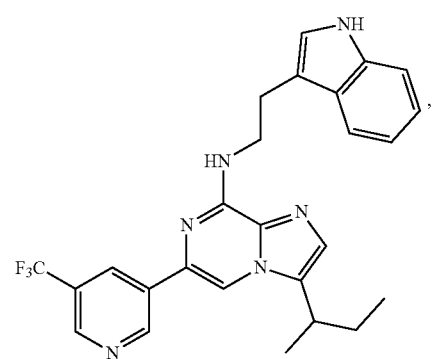
(14)
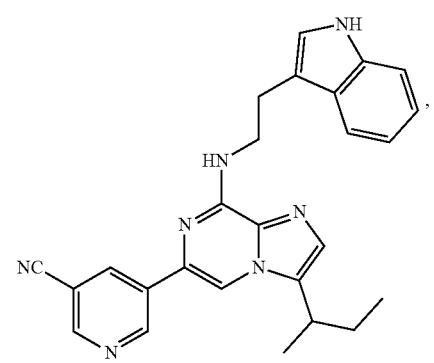
(15)
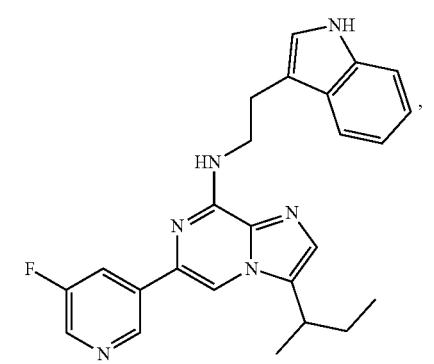
(16)
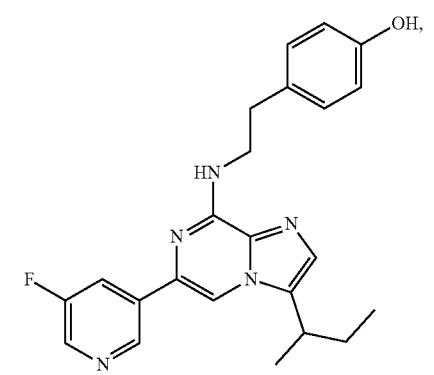
(17)

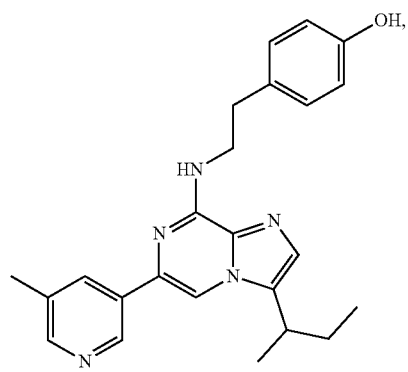 (18)
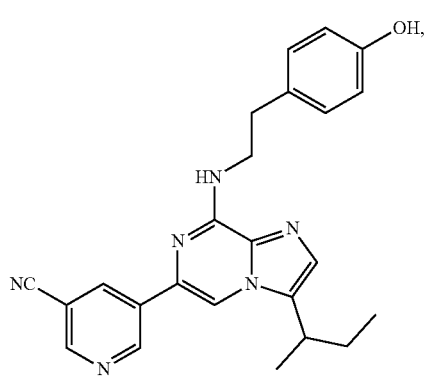 (19)
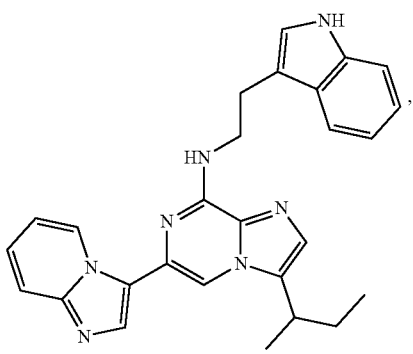 (20)
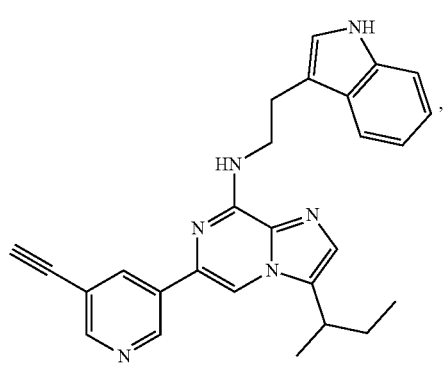 (21)
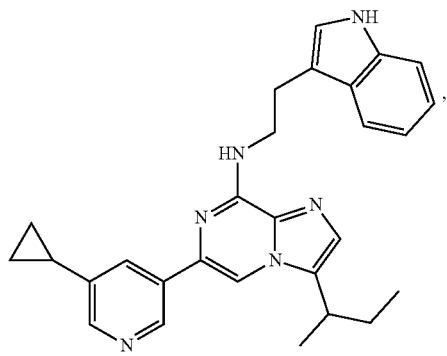 (22)
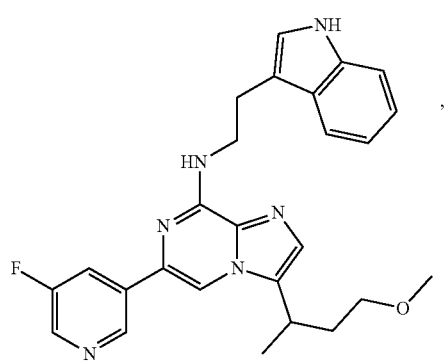 (24)
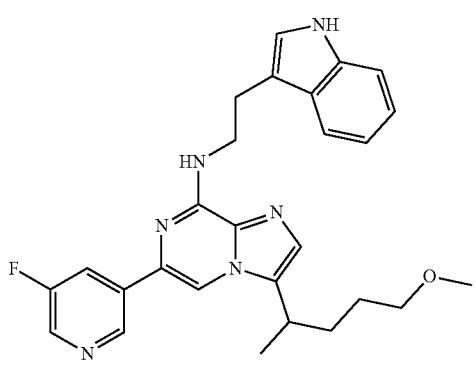 (27)
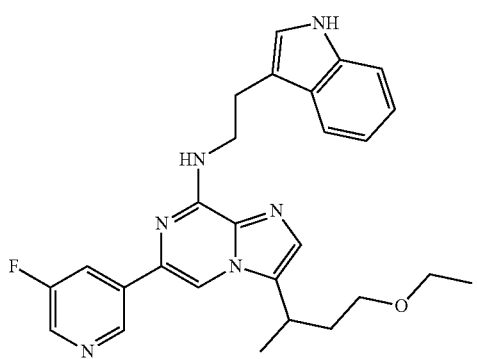 (28)
and salts thereof.

15. The method of claim 5, wherein said compound is a compound selected from the group consisting of
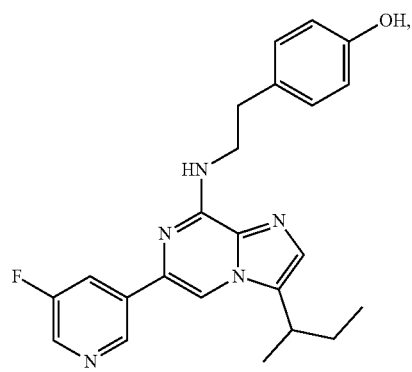 (17)
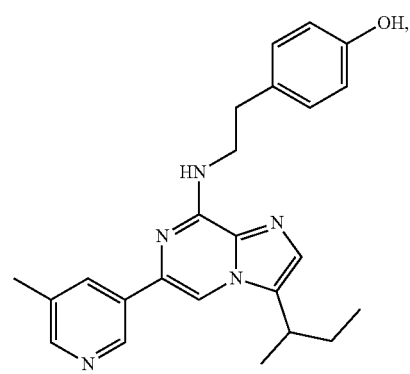 (18)
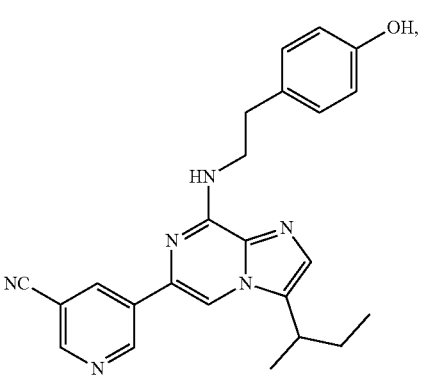 (19)
and salts thereof.
16. The method of claim 3, wherein said compound is selected from the group consisting of
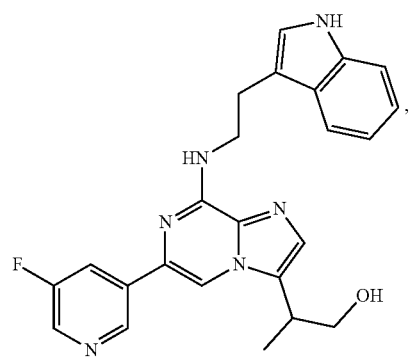 (12)
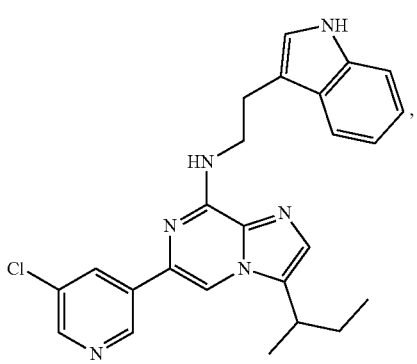 (13)
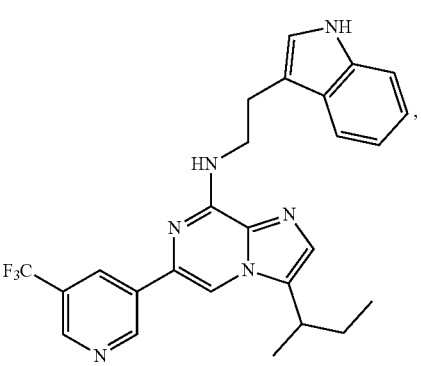 (14)

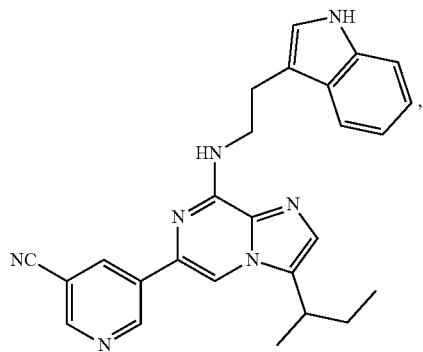
(15)
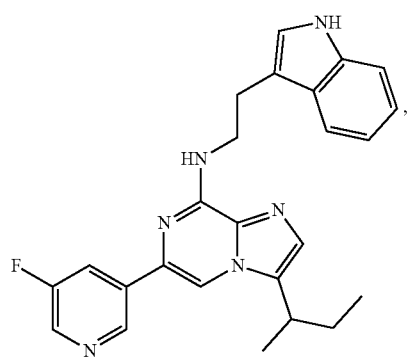
(16)
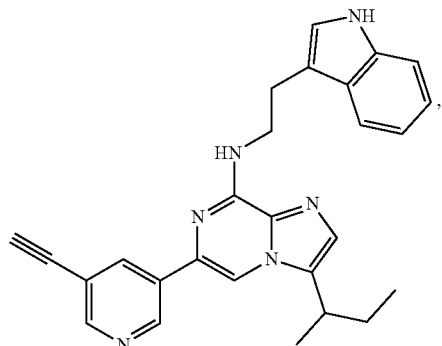
(21)
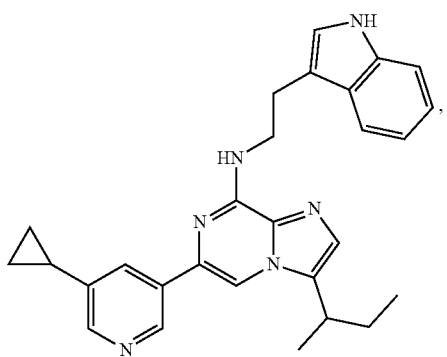
(22)
and salts thereof.
* * * * *

UNITED STATES PATENT AND TRADEMARK OFFICE
CERTIFICATE OF CORRECTION

PATENT NO.         : 10,919,900 B2
APPLICATION NO.    : 16/570045
DATED              : February 16, 2021
INVENTOR(S)        : Arthur Glenn Romero Page 1 of 3

It is certified that error appears in the above-identified patent and that said Letters Patent is hereby corrected as shown below:

In the Claims

At Column 120, Claim number 2, Line number 25, replace:
"—C(O)NR$_{12a}$R$_{11b}$, and wherein R$_{12a}$ and R$_{12b}$ are each"
With:
-- —C(O)NR$_{12a}$R$_{12b}$, and wherein R$_{12a}$ and R$_{12b}$ are each--

At Column 122, Claim number 3, Line number 17, replace:
"—C(O)NR$_{12a}$R$_{12b}$, and wherein R$_{12a}$ and R$_{11b}$ are each"
With:
-- —C(O)NR$_{12a}$R$_{12b}$, and wherein R$_{12a}$ and R$_{12b}$ are each--

At Column 123, Claim number 4, Lines 20-33, replace:

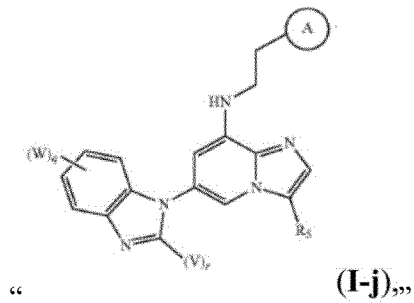

" (I-j),"
With:

Signed and Sealed this
Twentieth Day of July, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,919,900 B2

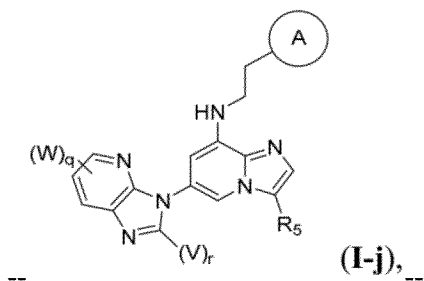

-- (I-j), --

At Column 123, Claim number 4, Lines 37-50, replace:

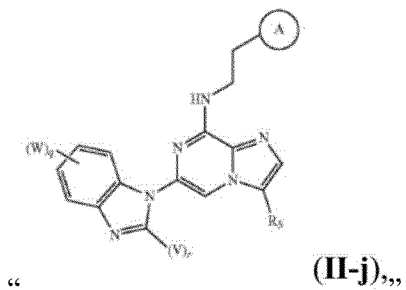

" (II-j),,,

With:

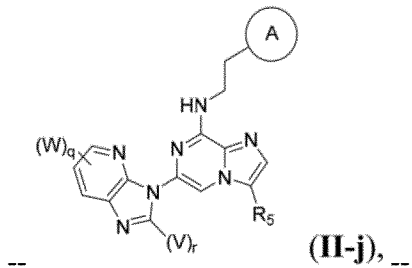

-- (II-j), --

At Column 125, Claim number 4, Line number 17, replace:
"C(O)NR$_{12a}$R$_{11b}$, and wherein R$_{12a}$ and R$_{12b}$ are each"
With:
--C(O)NR$_{12a}$R$_{12b}$, and wherein R$_{12a}$ and R$_{12b}$ are each--

At Column 125, Claim number 5, Lines 25-36, replace:

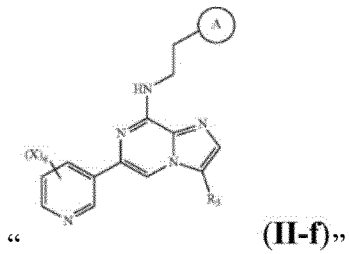

" (II-f),,

With:

CERTIFICATE OF CORRECTION (continued)
U.S. Pat. No. 10,919,900 B2

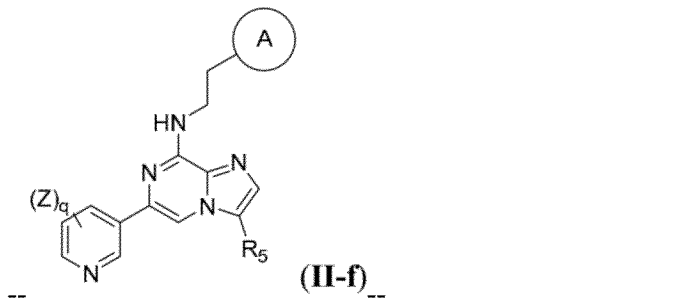

-- (II-f) --

At Column 126, Claim number 5, Line 27, replace:
"—C(O)NR$_{12a}$R$_{11b}$, and wherein R$_{12a}$ and R$_{11b}$ are each"
With:
-- —C(O)NR$_{12a}$R$_{12b}$, and wherein R$_{12a}$ and R$_{12b}$ are each--